(12) United States Patent
Tets et al.

(10) Patent No.: US 12,274,720 B2
(45) Date of Patent: Apr. 15, 2025

(54) METHODS FOR TREATING AND PREVENTING DISEASES

(71) Applicants: Viktor Veniaminovich Tets, New York, NY (US); Georgy Viktorovich Tets, New York, NY (US)

(72) Inventors: Viktor Veniaminovich Tets, New York, NY (US); Georgy Viktorovich Tets, New York, NY (US)

(73) Assignees: Viktor Veniaminovich Tets, New York, NY (US); Georgy Viktorovich Tets, New York, NY (US)

( * ) Notice: Subject to any disclaimer, the term of this patent is extended or adjusted under 35 U.S.C. 154(b) by 1033 days.

(21) Appl. No.: 16/616,231

(22) PCT Filed: Apr. 20, 2018

(86) PCT No.: PCT/US2018/028640
§ 371 (c)(1),
(2) Date: Nov. 22, 2019

(87) PCT Pub. No.: WO2018/217351
PCT Pub. Date: Nov. 29, 2018

(65) Prior Publication Data
US 2020/0215131 A1 Jul. 9, 2020

Related U.S. Application Data

(60) Provisional application No. 62/581,552, filed on Nov. 3, 2017, provisional application No. 62/537,316, filed
(Continued)

(51) Int. Cl.
A61K 35/76 (2015.01)
A61K 31/785 (2006.01)
(Continued)

(52) U.S. Cl.
CPC ............ *A61K 35/76* (2013.01); *A61K 31/785* (2013.01); *A61P 1/00* (2018.01); *C12Q 1/6883* (2013.01)

(58) Field of Classification Search
None
See application file for complete search history.

(56) References Cited

U.S. PATENT DOCUMENTS

| 5,955,287 A | 9/1999 | Fernandez-Pol |
| 6,201,104 B1 | 3/2001 | MacDonald et al. |
| (Continued) | | |

FOREIGN PATENT DOCUMENTS

| CA | 2628552 A1 | 5/2007 |
| HU | 0100159 A2 | 5/2001 |
| (Continued) | | |

OTHER PUBLICATIONS

Dupon et al., Eur. J. Clin. Pharmacol. 45: 529-534 (1993).*
(Continued)

*Primary Examiner* — Erin M. Bowers
(74) *Attorney, Agent, or Firm* — Troutman Pepper Locke LLP

(57) ABSTRACT

Provided herein are methods for preventing or treating diseases, said methods comprising (i) inhibiting entry of bacteriophages and/or component(s) thereof into microbiota, bodily fluid(s) or tissue(s) of the mammals and/or (ii) inactivating or modifying bacteriophages and/or component(s) thereof present in microbiota, bodily fluid(s) or tissues of the mammals and/or (iii) inactivating or modifying bacteriophages and/or component(s) thereof in one or more of food, drinking water, water for washing, water for air humidification, air, or habitat object of the mammals.

5 Claims, 88 Drawing Sheets

Specification includes a Sequence Listing.

Related U.S. Application Data on Jul. 26, 2017, provisional application No. 62/510,549, filed on May 24, 2017.

(51) Int. Cl.
*A61P 1/00* (2006.01)
*C12Q 1/6883* (2018.01)

(56) References Cited

U.S. PATENT DOCUMENTS

| | | | |
|---|---|---|---|
| 6,528,269 | B1 | 3/2003 | Sy et al. |
| 9,063,141 | B2 | 6/2015 | Grallert et al. |
| 2002/0012927 | A1 | 1/2002 | Bummer et al. |
| 2005/0124794 | A1 | 6/2005 | McCrae et al. |
| 2006/0233780 | A1 | 10/2006 | Genkin et al. |
| 2006/0263767 | A1 | 11/2006 | Castrillon et al. |
| 2007/0221559 | A1 | 9/2007 | Wang |
| 2013/0183284 | A1 | 7/2013 | Genkin et al. |
| 2013/0203849 | A1 | 8/2013 | Ben Yehuda |
| 2014/0234260 | A1 | 8/2014 | Borody |
| 2014/0271701 | A1 | 9/2014 | Sechi et al. |
| 2017/0020937 | A1 | 1/2017 | Mattey et al. |

FOREIGN PATENT DOCUMENTS

| | | | |
|---|---|---|---|
| WO | 2016190780 | A1 | 12/2016 |
| WO | 2017042831 | A2 | 3/2017 |
| WO | 2017118924 | A1 | 7/2017 |
| WO | 2019028456 | A1 | 2/2019 |

OTHER PUBLICATIONS

Anderson et al., Bacteriophage 1(2): 86-93 (2011).*
Bille et al., PLoS One: 3(12): e3885 (2008).*
Bille, E. et al., "Association of a Bacteriophage with Meningococcal Disease in Young Adults" PLoS One (2008) vol. 3, Issue 12, 6 pages total.
De Paepe, M. et al., "Bacteriophages: An Underestimated Role in Human and Animal Health?" Frontiers in Cellular and Infection Microbiology (2014) vol. 4, Article 39, 11 pages total.
European Communication (pursuant to Rule 164(1) EPC) issued by the European Patent Office in European Application No. 18805942.2 dated Jan. 22, 2021, 19 pages total.
Lepage, P. et al., "Dysbiosis in Inflammatory Bowel Disease: A Role for Bacteriophages?" Gut Microbiota (2008) vol. 57, No. 3, pp. 424-425.
Santiago-Rodriguez, T.M. et al., "Transcriptorne Analysis of Bacteriophage Communities in Periodontal Health and Disease" BMC Genomics (2015) vol. 16, No. 549, 9 pages total.
Tetz, G. et al., "Bacteriophages as Potential New Mammalian Pathogens" Scientific Reports (2017) vol. 7, No. 7043, 9 pages total.
Tetz, G. et al., "Parkinson's Disease and Bacteriophages as its Overlooked Contributors" Scientific Reports (2018) vol. 8, No. 10812, 11 pages total.
Wagner, J. et al., "Bacteriophages in Gut Samples from Pediatric Crohn's Disease Patients: Metagenomic Analysis Using 454 Pyrosequencing" HHS Public Access Author Manuscript (2013) vol. 19, No. 8, pp. 1598-1608.
Office Action issued Mar. 30, 2023 in connection with U.S. Appl. No. 17/256,428.
Google patent translation of HU0100159A2 (Year: 2001).
Office Action issued Jun. 29, 2023 in connection with U.S. Appl. No. 17/257,389.
Palma et al., "Dietary water affects human skin hydration and biomechanics", Clinical Cosmetic and Investigational Dermatology, 2015, 413-421.
Aviv, O. et al., "Poly(hexamethylene guanidine)-poly(ethylene glycol) Solid Blend for Water Microbial Deactivation" Polymer Degradation and Stability (2016) vol. 129, pp. 1-21.

Communication (International Preliminary Report on Patentability) issued by the International Searching Authority in International Application No. PCT/US2018/028640 dated Nov. 26, 2019, 19 pages total.
Communication (International Search Report) issued by the International Searching Authority in International Application No. PCT/US2018/028640 dated Sep. 4, 2018, 8 pages total.
Communication (Written Opinion) issued by the International Searching Authority in International Application No. PCT/US2018/028640 dated Sep. 4, 2018, 18 pages total.
Costa, L. et al., "Photodynamic Inactivation of Mammalian Viruses and Bacteriophages" Viruses (2012) vol. 4, pp. 1034-1075.
De Haard, HJ et al., "Llama Antibodies Against a Lactococcal Protein Located at the Tip of the Phage Tail Prevent Phage Infection" Journal of Bacteriology (2005) vol. 187, No. 13, pp. 4531-4541.
Findley, K. et al., "The Skin Microbiome: A Focus on Pathogens and Their Association with Skin Disease" PLoS One (2014) vol. 10, No. 10, pp. 1-3.
Galtier, M. et al., "Bacteriophages to Reduce Gut Carriage of Antibiotic Resistant Uropathogens with Low Impact on Microbiota Composition" Environmental Microbiology (2016) vol. 18, No. 7, pp. 2237-2245.
Garneau, JE et al., "The CRISPR/Cas Bacterial immune System Cleaves Bacteriophage and Plasmid DNA" Nature (2010) vol. 468, No. 7320, pp. 67-71.
Horwich, A. et al., "Protein aggregation in disease: a role for folding intermediates forming specific multimeric interactions" Journal of Clinical Investigation, Nov. 2002, vol. 110, No. 9, pp. 1221-1232.
Mirzaei, MK et al., "Isolation of Phages for Phage Therapy: A Comparison of Spot Tests and Efficiency of Plating Analyses for Determination of Host Range and Efficacy" PLoS One (2015) vol. 10, No. 3, pp. 1-13.
Shukla, GS et al., "Intravenous Infusion of Phage-Displayed Antibody Library in Human Cancer Patients: Enrichment and Cancer-Specificity of Tumor-Homing Phage-Antibodies" Cancer Immunology, Immunotherapy (2013) vol. 62, No. 8, pp. 1-14.
Tetz, G. et al., "Bacteriophage Infections of Microbiota can Lead to Leaky Gut in an Experiemntal Rodent Model" Gut Pathogens (2016) vol. 8, No. 33, pp. 1-4.
Zaczek, M. et al., "Antibody Production in Response to Staphylococcal MS-1 Phage Cocktail in Patients Undergoing Phage Therapy" Frontiers in Microbiology (2016) vol. 7, No. 1681, pp. 1-14.
Office Action issued Dec. 14, 2023 in connection with U.S. Appl. No. 17/051,598.
Matsumoto T, et al. (1998) J. Med. Microbiol. 47:303-308.
Leitner WW, et al. (Dec. 10, 1999) Vaccine. 18(9-10): 765-777.
Meemon K and Sabhon P (2015) Parasitol Res. 114:2807-2813. (DOI 10.1007/s00436-015-4589-6).
European Communication (Extended European Search Report) issued by the European Patent Office in European Application No. 18805942.2 dated Apr. 22, 2021, 13 pages total.
Communication (International Preliminary Report on Patentability) mailed in International Application No. PCT/US19/39732 mailed Dec. 29, 2020, 10 pages total.
Elena Biagi et al, "Gut Microbiota and Extreme Longevity", Current Biology, GB, (Jun. 1, 2016), vol. 26, No. 11. doi:10.1016/j.cub.2016.04.016, ISSN 0960-9822, pp. 1480-1485, XP055683144.
Communication (International Search Report) mailed in International Application No. PCT/US19/39732 mailed Nov. 6, 2019, 5 pages total.
Communication (Written Opinion) mailed in International Application No. PCT/US19/39732 mailed Nov. 6, 2019, 9 pages total.
Gallo, P.M. et al., "Amyloid-DNA Composites of Bacterial Biofilms Stimulate Autoimmunity" Immunity (2015) vol. 42, No. 6, pp. 1171-1184.
Newby, B.N., "Type 1 Inteferons Promote a Diabetogenic Microenvironment in Type 1 Diabetes" (2017) University of Florida, 150 pages total.
Tetz, G. et al., "Bacteriophages as New Human Viral Pathogens" Microrganisms (2018) vol. 6, No. 2, 12 pages total.

(56) References Cited

OTHER PUBLICATIONS

Tetz, G. et al., "Type 1 Diabetes: an Association Between Autoimmunity, the Dynamics of Gut Amyloid-producing *E. coli* and Their Phages" bioRxiv (2018) 433110, doi: https://doi.org/10.1101/433110, 31 pages total.

Tetz, G. et al., "Type 1 Diabetes: an Association Between Autoimmunity, the Dynamics of Gut Amyloid-producing *E. coli* and Their Phages" Scientific Reports (2019) vol. 9, No. 9685, 11 pages total.

Tursi, S.A. et al., "Bacterial Amyloid Curli Acts as a Carrier for DNA to Elicit an Autoimmune Response via TLR2 and TLR9" PLoS Pathogens (2017) vol. 13, No. 4, 25 pages total.

Zaccone, P. et al., "*Salmonella typhimurium* Infection Halts Developmen of Type 1 Diabetes in NOD Mice, Inflammation and Innate Immunity" Eur. J. Immunol. (2004) vol. 34, No. 11, pp. 3246-3256.

Supplementary European Search Report issued Feb. 9, 2022 in connection with EP Application No. 19826448.

Gianchecchi E. et al., "On the pathogenesis of insulin-dependent diabetes mellitus: the role of microbiota", Immunologic Research, Humana Press, Inc. US, vol. 65, No. 1, Jul. 16, 2016, pp. 242-256.

Vaarala O. et al., "The Perfect Storm" for Type 1 Diabetes: The Complex Interplay Between Intestinal Microbiota, Gut Permeability, and Mucosal Immunity, Diabetes, vol. 57, No. 10, Sep. 26, 2008, pp. 2555-2562.

Kosiewicz M. et al., "Relationship between gut microbiota and development of T cell associated disease", Febs Letters, Elsevier Amsterdam, NL, vol. 588, No. 22, Mar. 26, 2014, pp. 4195-4206.

Communication (International Preliminary Report on Patentability) mailed in International Application No. PCT/US19/40524 mailed Jan. 14, 2021, 12 pages total.

Biagi, E. et al., "Through Ageing and Beyond: Gut Microbiota and Inflammatory Status in Seniors and Centenarians" (2010) PLoS One vol. 5, Issue 5, pp. 1-14.

Claesson, M.J. et al., "Gut Microbiota Composition Correlates with Diet and Health in the Elderly" Nature (2012) vol. 488, No. 7410, pp. 178-184.

Communication (International Search Report) mailed in International Application No. PCT/US19/40524 mailed Nov. 18, 2019, 9 pages total.

Communication (Written Opinion) mailed in International Application No. PCT/US19/40524 mailed Nov. 18, 2019, 10 pages total.

Juge, R. et al., "Shift in Skin Microbiota of Western European Women Across Aging" Journal of Applied Microbiology (2018) vol. 125, No. 3, pp. 907-916.

Jylhava, J. et al., "Biological Age Predictors" EBioMedicine (2017) vol. 21, pp. 29-36.

O'Toole, P.W. et al., "Gut Microbiota and Aging" Science (2015) vol. 350, No. 6265, pp. 1214-1215, XP055669176.

Petrascheck, M. et al., "Computational Analysis of Lifespan Experiment Reproducibility" Frontiers in Genetics (2017) vol. 8, No. 92, pp. 1-11, XP055669171.

Tetz, G. et al., "Tet's Theory and Law of Longevity" Theory in Biosciences (2018) vol. 137, No. 2, pp. 145-154.

European Communication (Extended European Search Report) issued by the European Patent Office in European Application No. 19830501.3 dated Mar. 10, 2022, 11 pages total.

Jonas Zierer et al., "Integration of "omics"data in aging research: from biomarkers to systems biology", Aging Cell, vol. 14, No. 6, Aug. 30, 2015, pp. 933-944, XP055766774, gb issn: 1474-9718, DOI: 10.1111/acel.12386.

Garagnani P. et al., "The Three Genetics (Nuclear DNA, Mitochondrial DNA, and Gut Microbiome) of Longevity in Humans Considered as Metaorganisms", Biomed Research Int, vol. 2014, (Jan. 1, 2014), pp. 1-14, XP055896304, ISSN: 2314-6133, DOI: 10.1155/2014/560340.

Dato Serena et al., "The genetics of human longevity: an intricacy of genes, environment, culture and microbiome", Mechanisms of Ageing and Development, (Jul. 1, 2017), vol. 165, doi: 10.1016/J.MAD.2017.03.011, ISSN 0047-6374, pp. 147-155, XP085162845.

Xian Xia et al., "Molecular and phenotypic biomarkers of aging", F1000RESEARCH, (Jan. 1, 2017), vol. 6, doi: 10.12688/f1000research.10692.1, p. 860, XP055388474.

Santoro Aurelia et al., "Gut microbiota changes in the extreme decades of human life: a focus on centenarians", CMLS Cellular and Molecular Life Sciences, Birkhauser Verlag, Heidelberg, DE, vol. 75, No. 1, doi:10.1007/S00018-017-2674-Y, ISSN 1420-682X, (Oct. 14, 2017), pp. 129-148, (Oct. 14, 2017), XP036389430.

Pitchaimani, M. et al., "Maximum Life Span Predictions Using the Gompertz Tumour Growth Model" IOSR Journal of Mathematics (2014) vol. 10, Issue 6, pp. 55-62, XP055669182.

Castilla et al., "In Vitro Generation of Infectious Scrapie Prions," Cell, Apr. 22, 2005, vol. 121, pp. 195-206.

Cordeiro et al., "DNA Converts Cellular Prion Protein in the β-Sheet Conformation and Inhibits Prion Peptide Aggregation," The Journal of Biological Chemistry, Dec. 28, 2001, vol. 276, No. 52, pp. 49400-49409.

Prusiner S. "Biology and Genetics of Prions Causing Neurodegeneration," Annual Review of Genetics, Nov. 23, 2013, vol. 47, pp. 601-623.

Kipkorir et al., "Highly Infectious CJD Particles Lack Prion Protein but Contain Many Viral-Linked Peptides by LC-MS/MS," Journal of Cellular Biochemistry, Jun. 16, 2014, vol. 115, No. 11, pp. 2012-2221.

Tetz et al., "Prion-like Domains in Eukaryotic Viruses," Scientific Reports, Jun. 12, 2018, vol. 8, pp. 1-10.

Tetz et al., "Bacterial DNA Induces the Formation of Heat-Resistant Disease-Associated 'Tezt-Proteins' in Human Plasma," bioRxiv, Apr. 9, 2019, pp. 1-24.

Tetz et al., "Effect of Deoxyribonuclease I Treatment for Dementia in End-Stage Alzheimer's Disease: a Case Report," Journal of Medical Case Reports, May 28, 2016, vol. 10, No. 1, pp. 1-3.

Written Opinion dated Jul. 23, 2019, issued in connection with international Application No. PCT/US2019/026272, 18 pages total.

International Search Report dated Jul. 23, 2019, issued in connection with international Application No. PCT/US2019/026272, 6 pages total.

International Report on Patentability dated Nov. 3, 2020, issued in connection with international Application No. PCT/US2019/026272, 19 pages total.

Supplementary Partial European Search Report issued Feb. 2, 2022 in connection with EP Application No. 19796997.

March Z. M. et al., "Prion-like domains as epigenetic regulators, scaffolds for subcellular organization, and drivers of neurodegenerative disease", Brain Research, Elsevier, Amsterdam, NL, vol. 1647, Mar. 19, 2016, pp. 9-18.

Stefanov K. P. et al., "Distinct modulatory role of RNA in the aggregation of the tumor suppressor protein p53 core domain", Journal of Biological Chemistry, vol. 292, No. 22, Apr. 18, 2017, pp. 9345-9357.

Janeway C. A. et al., "The complement system and innate immunity—Immunology—NCBI Bookshelf" In: "Immunobiology: The Immune System in Health and Disease", Jan. 1, 2001, Garland Science, New York, pp. 1-14.

Sim et al., "Nucleophilic compounds acting on C3 and C4", Activators and Inhibitors of Complement, Springer Netherlands, Dordrecht, pp. 107-125, Oct. 31, 1992.

Fernandez-Pol Alberto J. et al., "Genomics, Proteomics and Cancer: Specific Ribosomal, Mitochondrial, and Tumor Reactive Proteins Can Be Used as Biomarkers for Early Detection of Breast Cancer in Serum", Cancer Genomics & Proteomics, vol. 2, No. 1, Jan. 1, 2005, pp. 1-24.

\* cited by examiner

| | | |
|---|---|---|
| All families | Correlation Coefficient Spearman's rho | .159 |
| | Sig. (2-tailed) | .040 |
| | N | 168 |
| Bicaudaviridae | Correlation Coefficient Spearman's rho | -.866 |
| | Sig. (2-tailed) | .333 |
| | N | 3 |
| Inoviridae | Correlation Coefficient Spearman's rho | |
| | Sig. (2-tailed) | . |
| | N | 2 |
| Leviviridae | Correlation Coefficient Spearman's rho | |
| | Sig. (2-tailed) | . |
| | N | 2 |
| Myoviridae | Correlation Coefficient Spearman's rho | .067 |
| | Sig. (2-tailed) | .433 |
| | N | 137 |
| Podoviridae | Correlation Coefficient Spearman's rho | .050 |
| | Sig. (2-tailed) | .870 |
| | N | 13 |
| Siphoviridae | Correlation Coefficient Spearman's rho | -.183 |
| | Sig. (2-tailed) | .638 |
| | N | 9 |
| Tectiviridae | Correlation Coefficient Spearman's rho | |
| | Sig. (2-tailed) | |
| | N | 1 |
| Undef | Correlation Coefficient Spearman's rho | |

METHODS FOR TREATING AND PREVENTING DISEASES

CROSS-REFERENCE TO RELATED APPLICATIONS

This application is a U.S. National Phase of International Patent Application No. PCT/US2018/028640, filed on Apr. 20, 2018, which published as WO 2018/217351 A1 on Nov. 29, 2018, and claims priority to U.S. Provisional Application No. 62/510,549, filed on May 24, 2017, U.S. Provisional Application No. 62/537,316, filed on Jul. 26, 2017, and U.S. Provisional Application No. 62/581,552, filed on Nov. 3, 2017, all of which are herein incorporated by reference in their entireties.

FIELD OF THE INVENTION

Provided herein are methods for preventing or treating diseases, said methods comprising (i) inhibiting entry of bacteriophages and/or component(s) thereof into microbiota, bodily fluid(s) or tissue(s) of the mammals and/or (ii) inactivating or modifying bacteriophages and/or component(s) thereof present in microbiota, bodily fluid(s) or tissue(s) of the mammals and/or (iii) inactivating or modifying bacteriophages and/or component(s) thereof in one or more of food, drinking water, water for washing, water for air humidification, air, or habitat object of the mammals.

BACKGROUND OF THE INVENTION

The microbiota of the human intestinal tract is comprised of bacteria, fungi, and viruses, including bacteriophages. This highly diverse and complex ecosystem is characterised by dynamic stability of each of its components in the context of the host organism. The human gut contains approximately $10^{15}$ bacteriophages, which >10 times of the number of bacterial cells and 100 times of the number of human cells (Dalmasso, M. et al., 2014).

Growing evidence suggests that alterations of the intestinal microbiota are critical pathogenic factors that trigger various polyaetiological diseases associated with increased intestinal permeability and chronic inflammation (Natividad, J. et al., 2013; Sommer, F. et al., 2013; Ashida, H. et al., 2011).

Intestinal barrier dysfunction or disruption, known as "leaky gut" syndrome, is characterized by the translocation of macromolecules, bacteria or their toxins to the lamina propria, which is implicated in the pathogenesis of numerous diseases (Maes M. et al., 2012). Abnormally permeable mucosal barrier is associated with various pathologies including inflammatory bowel disease, Crohn's disease, neurodegenerative diseases, diabetes type 1, some types of cancers, cardiovascular disorders, rheumatoid arthritis, etc. (Tlaskalova-Hogenová H. et al., 2011; Berk, M. et al., 2013; Anderson, G. et al., 2015). The altered microbiota composition and dysfunctional intestinal barrier have emerged as potential triggers of the growing incidence of chronic diseases (Natividad, J. et al., 2013).

Until recently, bacteriophages have been considered not to be harmful to humans since they selectively interact with bacteria do not affect eukaryotic cells. Therefore, bacteriophages were used in a number of experimental and clinical therapeutic studies (Sulakvelidze, A. et al., 2001; Wittebole, X. et al., 2013).

Prions are molecules characterized by self-propagation, which can undergo a conformational switch leading to the creation of new prions. Prion proteins have originally been associated with the development of mammalian pathologies; however, recently they have been shown to contribute to the environmental adaptation in a variety of prokaryotic and eukaryotic organisms. Bacteriophages are widespread and represent the important regulators of microbiota homeostasis and have been shown to be diverse across various bacterial families. Here, the inventors examined whether bacteriophages contain prion-like proteins and whether these prion-like protein domains are involved in the regulation of homeostasis.

In bacteria, PrPs were shown to play important roles in molecular transport, secretion, cell wall development, and other processes (Blanco et al., 2012; Yuan et al., 2014).

Parkinson's disease (PD) is the second most common neurodegenerative disease and is characterized by motor disturbances such as resting tremor, rigidity, postural instability, gait problems, and gastrointestinal dysfunction (Lee, A. & Gilbert, R., 2016; Edwards, L. et al., 1991; Jankovic, J. et al., 2012) These motor symptoms are mainly related to the depletion of dopamine in the striatum as a result of a complicated multifactorial process (Agid, Y. et al., 1991). One of the pathways implicated in PD is a loss of dopaminergic neurons in the substantia nigra pars compacta due to accumulation of fibrils of insoluble misfolded α-synuclein (Furukawa, Y. et al., 1998, Cookson, M. et al., 2009 and Olanow, C. et al., 2013).

Normally, α-synuclein plays a role in the regulation of vesicular release and is highly expressed in presynaptic neuronal terminals. The reasons why this protein adopts a β-sheet structure and forms aggregates are not completely understood. The insoluble synuclein fibrils referred to as Lewy bodies are a hallmark of PD and are toxic for neurons (Volpicelli-Daley, L. et al., 2011). In the Western world, the incidence of the disease is on the rise, with a higher prevalence in white men (Klingelhoefer, L. et al., 2015). While genetic risk factors of PD, such as SNCA and INPP5F genes encoding α-synuclein and inositol polyphosphate-5-phosphatase, respectively, have been identified, most PD cases can be attributed to environmental and epigenetic factors (Nalls, M., 2014, Kalia, L. et al., 2015 and Ritz, B. eta al., 2015). These include the gastrointestinal microbiota (GI), with a possible role of a microbiota-gut-brain axis in PD development (Sampson, T. et al., 2016 and Sharon, G. et al., 2016).

Although phagobiota are important regulators of microbial community composition in the GI and, as such, can influence the gut-brain axis, there are no data on the role of bacteriophages in neurodegenerative diseases, and the causal relationship between the microbiota changes and PD pathogenesis has never been addressed. In the past, the study of bacteriophages in humans has been limited by the lack of systematic approaches and insufficient research on phage diversity.

SUMMARY OF THE INVENTION

As specified in the Background Section, there is a great need in the art to develop methods for maintaining the stability and diversity of animal microbiota and for treatment of various diseases. The present invention addresses this and other needs by providing methods and compositions for reducing the exposure of microbiota, bodily fluid(s) and/or tissue(s) to bacteriophages.

In one aspect, the invention provides a method for preventing or treating a microbiota disease or consequences thereof in a mammal in need thereof, said method comprising (i) inhibiting entry of bacteriophages and/or component(s) thereof (e.g., bacteriophage protein(s) and/or nucleic acid(s)) into microbiota of the mammal and/or (ii) inactivating or modifying bacteriophages and/or component(s) thereof present in microbiota of the mammal and/or (iii) inactivating or modifying bacteriophages and/or component(s) thereof in one or more of food, probiotic compositions, prebiotic compositions, drinking water, water for washing, water for air humidification, air, or habitat object of the mammal. In a related aspect, the invention provides a method for preventing or treating an increase in a barrier permeability (e.g., mucosal permeability, intestinal permeability, blood-spinal barrier permeability, placenta permeability, cord barrier permeability, or blood-brain barrier permeability) in a mammal in need thereof, wherein said increase in the barrier permeability is caused by entry of a bacteriophage or a component thereof into microbiota, bodily fluid(s) and/or tissue(s) of the mammal, said method comprising (i) inhibiting entry of bacteriophages and/or component(s) thereof (e.g., bacteriophage protein(s) and/or nucleic acid(s)) into microbiota, bodily fluid(s) and/or tissue(s) of the mammal and/or (ii) inactivating or modifying bacteriophages and/or component(s) thereof present in microbiota, bodily fluid(s) and/or tissue(s) of the mammal and/or (iii) inactivating or modifying bacteriophages and/or component(s) thereof in one or more of food, probiotic compositions, prebiotic compositions, drinking water, water for washing, water for air humidification, air, or habitat object of the mammal.

In a further related aspect, the invention provides a method for preventing or treating a disease in a mammal in need thereof, said method comprising (i) inhibiting entry of bacteriophages and/or component(s) thereof (e.g., bacteriophage protein(s) and/or nucleic acid(s)) into microbiota, bodily fluid(s) and/or tissue(s) of the mammal and/or (ii) inactivating or modifying bacteriophages and/or component(s) thereof present in microbiota, bodily fluid(s) and/or tissue(s) of the mammal and/or (iii) inactivating or modifying bacteriophages and/or component(s) thereof in one or more of food, probiotic compositions, prebiotic compositions, drinking water, water for washing, water for air humidification, air, or habitat object of the mammal.

In one embodiment of the above aspect, the microbiota comprise eukaryotic cells and the bacteriophages are prevented from entering the eukaryotic cells. In another embodiment of the above aspect, the eukaryotic cells are present in one or more of food, probiotic compositions, prebiotic compositions, drinking water, water for washing, water for air humidification, air, or habitat object of the mammal and the bacteriophages are prevented from entering the eukaryotic cells.

In one embodiment of the above aspect, the disease is endotoxemia, oncological diseases, obesity, irritable bowel syndrome (IBS), non-specific ulcerative colitis, celiac disease, diabetes, rheumatoid arthritis, multiple sclerosis, CADASIL Syndrome, stroke, psoriasis, age-related changes of skin, vaginosis, Sudden arrhythmic death syndrome, Crohn's disease, atopic dermatitis, ankylosing spondylitis, systemic lupus erythematosus (SLE), scleroderma, liver failure, liver cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, primary biliary cirrhosis, primary sclerosing cholangitis, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia), Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, asthma, bipolar disorder, schizophrenia, depressive disorder, autism, autism spectrum disorders, Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD), Amyotrophic Lateral Sclerosis (ALS), Huntington's disease, a disease associated with the formation of a misfolded protein, Alzheimer's disease, Parkinson's disease, Spinal muscular atrophy, other neurodegenerative diseases, vaginitis, skin diseases, intestinal disorders, ulcerative colitis, inflammatory bowel diseases crohn's disease, Psoriasis, atopic dermatitis, asthma, cystic fibrosis, chronic obstructive pulmonary disease, and pathologies of the oral cavity.

In one embodiment of the above aspect, the oncological disease is a cancer. In one embodiment of the above aspect, the oncological disease is a malignancy.

In one embodiment of the above aspect, the disease is an amyloidosis.

In one embodiment of the above aspect, the disease is a disease associated with the formation of a misfolded protein.

In yet another aspect, the invention provides a method for increasing longevity and/or decreasing aging in a mammal in need thereof, said method comprising (i) inhibiting entry of bacteriophages and/or component(s) thereof (e.g., bacteriophage protein(s) and/or nucleic acid(s)) into microbiota, bodily fluid(s) and/or tissue(s) of the mammal and/or (ii) inactivating or modifying bacteriophages and/or component(s) thereof present in microbiota, bodily fluid(s) and/or tissue(s) of the mammal and/or (iii) inactivating or modifying bacteriophages and/or component(s) thereof in one or more of food, probiotic compositions, prebiotic compositions, drinking water, water for washing, water for air humidification, air, or habitat object of the mammal. In one specific embodiment, the aging is skin aging.

In one embodiments of the above methods, the method of (ii) inactivating or modifying bacteriophages and/or component(s) thereof present in microbiota, bodily fluid(s) and/or tissue(s) of the mammal comprises treating said microbiota, bodily fluid(s) and/or tissue(s) with an antibacteriophagal agent, an antifungal agent or a gene-editing nuclease.

In one embodiment of the above methods, the antibacteriophagal agent is effective to inhibit replication of bacteriophage. In one embodiment of the above methods, the antifungal agent is effective to inhibit replication of bacteriophage.

Non-limiting examples of an antibacteriophagal agent include reverse-transcriptase inhibitors, such as analog reverse-transcriptase inhibitors; Nucleotide analog reverse-transcriptase inhibitors; Non-nucleoside reverse-transcriptase inhibitors; Portmanteau inhibitors (Zidovudine, Didanosine, Zalcitabine, Stavudine, Lamivudine, Abacavir, Emtricitabine, Entecavir, Tenofovir, Adefovir, Hepsera, Thymidine analogues: zidovudine and stavudine; Cytidine analogues: zalcitabine (ddC), lamivudine (3TC), and emtricitabine (FTC) Guanosine analogues: abacavir (ABC) and entecavir (ETV) Adenosine analogues: didanosine (ddI), tenofovir (TDF), and adefovir (ADV) Efavirenz, Nevirapine, Delavirdine, Etravirine, Rilpivirine, acyclovir and derivatives (e.g. ganciclovir, Valganciclovir, Valaciclovir Penciclovir Famciclovir) 2,8-dithioxo-1H-pyrano[2,3d 6,5-d']dipyrimidyne and 10-aza-analogue; (2,6-dichlorophenyl) amide salt of carbopentoxysulfanilic acid., Bacteriophage entry inhibitors (Maraviroc and enfuvirtide); Penetration inhibitors (Amantadine and rimantadine, Pleconaril), integrase inhibitors (raltegravir, elvitegravir and dolutegravir), protease inhibitors (lopinavir, indinavir, nelfinavir, amprenavir, ritonavir, darunavir, bevirimat and vivecon), translation and transcription inhibitors, protease inhibitors, assembly inhibitors (rifampicin), release inhibitors (zanamivir and oseltamivir), blockers of phage release by blocking viral progeny interaction with bacterial cell including lysozyme enzyme inhibition; interferon and its inducers; Rintatolimod, Atazanavir, Atripla; Cidofovir, Docosanol, Edoxudine, Ecoliever, Fomivirsen, Fosamprenavir, Foscarnet, Ibacitabine, Imunovir, Idoxuridine, Imiquimod, Inosine, Loviride, Moroxydine, Methisazone, Nelfinavir, Nevirapine, Nexavir, Nitazoxanide, Ritonavir, Peginterferon alfa-2a, Peramivir, Podophyllotoxin, Pyramidine, Saquinavir, Sofosbuvir, Telaprevir, Tipranavir, Trizivir, Tromantadine, Truvada, Vicriviroc, Vidarabine, Viramidine.

In one embodiment of the above methods, the antibacteriophagal agent is selected from the group consisting of phlepmycin, glycopeptide antibiotics, esterified milk proteins, Rifampcin, and polymerase inhibitors. In one embodiment of the above methods, the antifungal agent is selected from the group consisting of phlepmycin, glycopeptide antibiotics, esterified milk proteins, Rifampcin, and polymerase inhibitors.

In one embodiment of the above methods, the glycopeptide antibiotic is selected from the group consisting of vancomycin, teicoplanin, telavancin, ramoplanin, decaplanin, and bleomycin.

In one embodiment of the above methods, the polymerase inhibitor is selected from the group consisting of ribavirin, ribamidil, favipiravir, azidothymidine, and umifenovirum.

In one embodiment of the above methods, the gene editing nuclease is capable of cleaving sequence from the bacteriophage present in the genome of the bacteria, and optionally wherein the bacteriophage is a temperate bacteriophage.

In one embodiment of the above methods, the antibody is specific to bacteria comprising a temperate bacteriophage.

In one embodiment of the above methods, the antibody is an anti-phage neutralizing antibody.

In one embodiment of the above aspect, the class of antibody is IgG or IgM.

In one embodiment of the above aspect, the antibody is prepared by a process comprising use of phage display to select for an antibody that is specific to the bacteriophage and/or component thereof.

In one embodiment of the above aspect, the agent is effective to stimulate a humoral immune response to the bacteriophage or to stimulate phagocytosis of the bacteriophage.

In one embodiment of any of the above methods of the invention, the inhibition of entry of bacteriophages and/or component(s) thereof (e.g., bacteriophage protein(s) and/or nucleic acid(s)) into the microbiota, bodily fluid(s) and/or tissue(s) of the mammal comprises treating said microbiota, bodily fluid(s) and/or tissue(s) with an agent selected from the group consisting of an antibody, an antibacteriophagal agent, an inactivated bacteriophage, an agent inactivating a bacteriophage receptor within said microbiota, and a bacteriophage receptor or a derivative thereof, wherein said agent is able to interact with bacteria in said microbiota, bodily fluid(s) and/or tissue(s) in a way to prevent the entry of bacteriophages and/or component(s) thereof (but in the case of microbiota does not inhibit growth and activity of bacteria within said microbiota).

In one embodiment of any of the above methods of the invention, the inhibition of entry of bacteriophages and/or component(s) thereof into the microbiota of the mammal comprises administering a probiotic composition or a microbiota transplant, wherein said administration results in populating said microbiota with one or more bacterial variants not susceptible to bacteriophage infection. In one specific embodiment, said one or more bacterial variants lack bacteriophage receptor(s). In one specific embodiment, said probiotic composition comprises one or more components selected from the group consisting of live bacterial cells, spores, conditionally lethal bacterial cells, and recombinant carrier strains.

In one embodiment of any of the above methods of the invention, the inhibition of entry of bacteriophages and/or component(s) thereof into the microbiota, bodily fluid(s) and/or tissue(s) of the mammal comprises treating said bacteriophages and/or component(s) thereof with an antibody or an antibacteriophagal agent. In some embodiments, the antibody is a synthetic antibody. In some embodiments, the antibody is a single domain antibody. In some embodiments, the antibody is a mini-antibody.

In one embodiment of any of the above methods of the invention, the inhibition of entry of bacteriophages and/or component(s) thereof into the microbiota, bodily fluid(s) and/or tissue(s) of the mammal comprises administering to the mammal one or more components of a bacterial or fungal biofilm matrix. Non-limiting examples of components of biofilm matrices which can be used in the methods of the present invention include, e.g., polysaccharides (e.g., sucrose-derived glucans, cellulose, curdlan, dextran, alginate, emulsan, gellan, xanthan, β-1,3 glucan), extracellular DNA, extracellular RNA, proteins (e.g., an amyloid [including, e.g., a bacterial amyloid, a human amyloid, a synthetic amyloid], lectins, enzymes), lipids (e.g., lysophospholipids, cardiolipin, glycerolipids), etc. See, e.g., Flemming, H. C., & Wingender, J. (2010). The biofilm matrix. Nature Reviews Microbiology, 8(9), 623-633; Mitchell, K. F., Zarnowski, R., & Andes, D. R. (2016). Fungal Super Glue: The Biofilm Matrix and Its Composition, Assembly, and Functions. PLoS Pathog, 12(9), e1005828.

In one embodiment of any of the above methods of the invention, the tissue is skin or a mucosal surface, and the bacteriophage inactivation in the microbiota and/or tissue comprises treating the microbiota and/or tissue with an agent selected from the group consisting of polyhexamethylene guanidine derivatives, ozone, a peroxide, a metal, an antibody, an antibacteriophagal agent, free radicals, halogen-containing compounds, cationic compounds, glycolytic enzymes, lysozyme, and nisin.

In one embodiment of any of the above methods of the invention, the bacteriophage inactivation in one or more of food, probiotic compositions, prebiotic compositions, drinking water, water for washing, water for air humidification, air, or habitat object of the mammal comprises treating said food, probiotic compositions, prebiotic compositions, drinking water, water for washing, water for air humidification, habitat object, or bacteriophages isolated therefrom, and/or component(s) of bacteriophages isolated therefrom with an agent selected from the group consisting of "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, ozone, a peroxide (e.g., $H_2O_2$), a metal, an antibody, and an antibacteriophagal agent.

In one embodiment of any of the above methods of the invention, the bacteriophage inactivation in one or more of food, probiotic compositions, prebiotic compositions, drinking water, water for washing, water for air humidification, air, or habitat object of the mammal comprises subjecting said food, probiotic compositions, prebiotic compositions, drinking water, water for washing, water for air humidification, air, habitat object, or bacteriophages isolated therefrom, and/or component(s) of bacteriophages isolated therefrom to a treatment selected from the group consisting of filtration, pascalization, heat treatment, gamma radiation, UV radiation, electron flow, microwave radiation, capsid-targeted viral inactivation, photocatalytic inactivation, differential exposure, and centrifugation.

In one embodiment of any of the above methods of the invention, the bacteriophage inactivation in said microbiota, bodily fluid(s) and/or tissue(s) comprises treating said microbiota, bodily fluid(s) and/or tissue(s) with an agent selected from the group consisting of "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, ozone, a peroxide (e.g., $H_2O_2$), a metal, an antibody, and an antibacteriophagal agent.

In one embodiment of any of the above methods of the invention, the bacteriophage inactivation in said microbiota, bodily fluid(s) and/or tissue(s) comprises subjecting said microbiota, bodily fluid(s) and/or tissue(s) to a treatment selected from the group consisting of filtration, pascalization, heat treatment, gamma radiation, UV radiation, electron flow, microwave radiation, capsid-targeted viral inactivation, photocatalytic inactivation, differential exposure, and centrifugation.

In another aspect, the invention provides a method for decreasing negative side-effects of a microbiota transplant in a mammal, comprising treating said microbiota transplant prior to its administration to the mammal to inactivate, remove or modify bacteriophages and/or component(s) thereof contained in the transplant. In one specific embodiment, the microbiota transplant is a fecal transplant. In another specific embodiment, the microbiota transplant is a non-fecal transplant. In various embodiments of this aspect, the microbiota transplant is treated with an agent selected from the group consisting of "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, ozone, a peroxide (e.g., $H_2O_2$), a metal, an antibody, and an antibacteriophagal agent. In another embodiment, the microbiota transplant is subjected to a treatment selected from the group consisting of filtration, pascalization, heat treatment, gamma radiation, UV radiation, electron flow, microwave radiation, capsid-targeted viral inactivation, photocatalytic inactivation, differential exposure, and centrifugation.

In yet another aspect, the invention provides a method for decreasing negative side-effects of an organ transplant or blood transfusion in a mammal, comprising treating said organ transplant or blood transfusion prior to its administration to the mammal to inactivate, remove or modify bacteriophages and/or component(s) thereof contained in the transplant.

In one embodiment of the above aspects of decreasing negative side-effects of a microbiota transplant in a mammal, the bacteriophage inactivation comprises treating said transplant with an agent selected from the group consisting of "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, ozone, a peroxide (e.g., $H_2O_2$), a metal, an antibody, an antibacteriophagal agent, free radicals, halogen-containing compounds, cationic compounds, glycolytic enzymes, and nisin.

In another embodiment of the above aspects of decreasing negative side-effects of a microbiota transplant in a mammal, the bacteriophage inactivation comprises subjecting said transplant to a treatment selected from the group consisting of filtration, pascalization, heat treatment, gamma radiation, UV radiation, electron flow, microwave radiation, capsid-targeted viral inactivation, photocatalytic inactivation, differential exposure, and centrifugation.

In a related aspect, the invention provides a method for administering a microbiota transplant to a mammal, comprising treating said transplant to inactivate or modify bacteriophages and/or component(s) thereof (e.g., bacteriophage protein(s) and/or nucleic acid(s)) contained in the transplant in accordance with any of the above-identified methods prior to the administration of said transplant to the mammal. In one embodiment, the microbiota transplant is a fecal transplant. In another embodiment, the microbiota transplant is a non-fecal transplant. In another embodiment, the method further comprises determining quantitative and/or qualitative bacteriophage composition of the microbiota of the mammal before and/or after the transplant.

In another aspect, the invention provides a method for administering an organ transplant or blood to a mammal, comprising treating said organ transplant or blood to inactivate or modify bacteriophages and/or component(s) thereof (e.g., bacteriophage protein(s) and/or nucleic acid(s)) contained in the transplant in accordance with any of the above-identified methods prior to the administration of said transplant or blood to the mammal. In one embodiment, the method further comprises determining quantitative and/or qualitative bacteriophage composition in the microbiota of the organ or blood of the mammal before and/or after the transplant or transfusion.

In one embodiment of the above methods involving administering an organ transplant or blood, the method further comprises detecting the presence of a bacteriophage or a component thereof in the blood, plasma, or serum of a donor and/or a recipient before, during or after the blood transfusion.

In one embodiment of the above methods involving administering an organ transplant or blood, the method further comprises detecting the presence of a mammalian host protein or a bacterial host protein in the blood, plasma, or serum of a donor and/or a recipient before, during or after the organ transplant or the blood transfusion, wherein the mammalian host protein or the bacterial host protein appears as a result of the presence of a bacteriophage in the blood, the plasma, or the serum of the donor and/or the recipient during the organ transplant or the blood transfusion.

In one embodiment of the above methods involving a habitat object, the habitat object is selected from the group consisting of furniture, dishes, bath, sink, toilet bowl, and container for packaging and/or storage of food products and/or water. In one embodiment of the above methods involving a habitat object, the habitat object is selected from the group consisting of a room, a motor vehicle, a train, an airplane, a surface vessel, a submarine vessel, and a spacecraft.

In one embodiment of the above methods involving administering an agent or a component of a biofilm matrix, the agent or the component of biofilm matrix is in a form selected from the group consisting of a liquid, a tablet, a capsule, drops, a lozenge, a gel, an ointment, a suppository, a chewing gum, and a candy. In one embodiment of the above methods involving administering an agent or a component of a biofilm matrix, the agent or the component of biofilm matrix is administered in combination with at least one other compound that increases the activity of said agent or component. In specific embodiments, the agent or the component of biofilm matrix is contained in a composition further comprising a pharmaceutically acceptable carrier or excipient.

In one embodiment of any of the above methods, the microbiota is selected from the group consisting of gastrointestinal (GI) microbiota, mucosal microbiota, skin microbiota, microbiota of respiratory system, microbiota of otorhinolaryngology, and microbiota of urinary tract.

In one embodiment of any of the above methods, the method further comprises determining quantitative and/or qualitative bacteriophage composition of the microbiota, bodily fluid(s) and/or tissue(s) of the mammal.

In one embodiment of any of the above methods related to microbiota transplants or organ transplants or blood transfusions, the method further comprises determining quantitative and/or qualitative bacteriophage composition of the microbiota of the transplant.

In another aspect, the invention provides a method for determining a likelihood of a microbiota disease or consequences thereof in a mammal, said method comprising quantitative and/or qualitative analysis of (i) bacteriophages and/or component(s) thereof (e.g., bacteriophage protein(s) and/or nucleic acid(s)) present in microbiota, bodily fluid(s) or tissue(s) of the mammal and/or (ii) bacteriophages and/or component(s) thereof present in one or more of food, probiotic compositions, prebiotic compositions, drinking water, water for washing, water for air humidification, air, habitat object of the mammal, and/or (iii) bacteriophages and/or component(s) thereof present in microbiota transplant, organ transplant or blood before administering it to the mammal.

In a further aspect, the invention provides a method for determining a likelihood of an increase in a barrier permeability (e.g., mucosal permeability, intestinal permeability, blood-spinal barrier permeability, placenta permeability, cord barrier permeability, or blood-brain barrier permeability) in a mammal, wherein said increase in the barrier permeability is caused by entry of a bacteriophage and/or component(s) thereof into microbiota, bodily fluid(s) and/or tissue(s) of the mammal, said method comprising quantitative and/or qualitative analysis of (i) bacteriophages and/or component(s) thereof (e.g., bacteriophage protein(s) and/or nucleic acid(s)) present in microbiota, bodily fluid(s) and/or tissue(s) of the mammal and/or (ii) bacteriophages and/or component(s) thereof present in one or more of food, probiotic compositions, prebiotic compositions, drinking water, water for washing, water for air humidification, air, habitat object of the mammal, and/or (iii) bacteriophages and/or component(s) thereof present in microbiota transplant, organ transplant or blood before administering it to the mammal.

In one embodiment, the method comprises isolating the phage using a method comprising heating, filtering a probe, or the use of a chemical agent to isolate the bacteriophage. Heating may be conducted at a temperature from 80° C. to 300° C. and from 1 minute to 48 hours. The probe may be filtered mechanically through a 0.22 or 0.17 nm Millipore filter. The chemical agent may be chloroform.

In yet another aspect, the invention provides a method for diagnosing a disease or determining a likelihood of a disease in a mammal, said method comprising quantitative and/or qualitative analysis of (i) bacteriophages and/or component(s) thereof (e.g., bacteriophage protein(s) and/or nucleic acid(s)) present in microbiota, bodily fluid(s) and/or tissue(s) of the mammal and/or (ii) bacteriophages and/or component(s) thereof present in one or more of food, probiotic compositions, prebiotic compositions, drinking water, water for washing, water for air humidification, air, habitat object of the mammal, and/or (iii) bacteriophages and/or component(s) thereof present in microbiota transplant, organ transplant or blood before administering it to the mammal. Non-limiting examples of encompassed diseases include, e.g., endotoxemia, oncological diseases, obesity, irritable bowel syndrome (IBS), non-specific ulcerative colitis, celiac disease, diabetes, rheumatoid arthritis, multiple sclerosis, CADASIL Syndrome, stroke, psoriasis, age-related changes of skin, vaginosis, Sudden arrhythmic death syndrome, Crohn's disease, atopic dermatitis, ankylosing spondylitis, systemic lupus erythematosus (SLE), scleroderma, liver failure, liver cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, primary biliary cirrhosis, primary sclerosing cholangitis, asthma, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia) Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, bipolar disorder, schizophrenia, depressive disorder, autism, autism spectrum disorders, Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD), Amyotrophic Lateral Sclerosis (ALS), Huntington's disease, a disease associated with the formation of a misfolded protein, Alzheimer's disease, Parkinson's disease, other neurodegenerative diseases, vaginitis, skin diseases, intestinal disorders, ulcerative colitis, inflammatory bowel diseases crohn's disease, Psoriasis, atopic dermatitis, asthma, cystic fibrosis, chronic obstructive pulmonary disease, and pathologies of the oral cavity.

In one embodiment, the method comprises isolating the phage using a method comprising heating or filtering a probe used to isolate the bacteriophage.

In another aspect, the invention provides a method for determining a likelihood of aging in a mammal in need thereof, said method comprising quantitative and/or qualitative analysis of (i) bacteriophages and/or component(s) thereof (e.g., bacteriophage protein(s) and/or nucleic acid(s)) present in microbiota, bodily fluid(s) and/or tissue(s) of the mammal and/or (ii) bacteriophages and/or component(s) thereof present in one or more of food, probiotic compositions, prebiotic compositions, drinking water, water for washing, water for air humidification, air, habitat object of the mammal, and/or (iii) bacteriophages and/or component(s) thereof present in microbiota transplant, organ transplant or blood before administering it to the mammal.

In one embodiment of any of the above methods for determining likelihood, the microbiota is selected from the group consisting of gastrointestinal (GI) microbiota, mucosal microbiota, skin microbiota, microbiota of respiratory system, microbiota of otorhinolaryngology, microbiota of urinary tract.

In one embodiment of any of the above methods for determining likelihood, the quantitative and/or qualitative analysis of bacteriophages is performed by assaying for alterations in the host organism. Exemplary alterations may indicate the presence of, or a likelihood of, endotoxemia, oncological diseases, obesity, irritable bowel syndrome (IBS), non-specific ulcerative colitis, celiac disease, diabetes, rheumatoid arthritis, multiple sclerosis, CADASIL Syndrome, stroke, psoriasis, age-related changes of skin, vaginosis, Sudden arrhythmic death syndrome, Crohn's disease, atopic dermatitis, ankylosing spondylitis, systemic lupus erythematosus (SLE), scleroderma, liver failure, liver cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, primary biliary cirrhosis, primary sclerosing cholangitis, asthma, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia) Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, bipolar disorder, schizophrenia, depressive disorder, autism, autism spectrum disorders, Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD), Amyotrophic Lateral Sclerosis (ALS), Huntington's disease, a disease associated with the formation of a misfolded protein, Alzheimer's disease, Parkinson's disease, other neurodegenerative diseases, vaginitis, skin diseases, intestinal disorders, ulcerative colitis, inflammatory bowel diseases crohn's disease, Psoriasis, atopic dermatitis, asthma, cystic fibrosis, chronic obstructive pulmonary disease, and pathologies of the oral cavity.

In one embodiment of any of the above methods for determining likelihood, the assay is selected from an assay for detecting the appearance of a protein or a nucleic acid that is present in response to entry of a bacteriophage into the host organism or bacteriophage-mediated lysis of infected bacteria. Exemplary proteins include core proteins and surface proteins.

In one embodiment of any of the above methods for determining likelihood, the bacteriophage comprises a protein with a prion-like domain and the assay comprises analyzing the folding of a human protein or a bacterial protein.

In one embodiment of any of the above methods for determining likelihood, the protein present in response to entry of a bacteriophage into the host organism is a receptor on the bacterial surface, an antibody specific to an epitope of the bacteriophage, or a phage-specific immunoglobulin.

In one embodiment of any of the above methods for determining likelihood, the epitope is present on a portion of the bacteriophage viron required to infect a host cell.

In one embodiment of any of the above methods for determining likelihood, the antibody specific to the epitope of the bacteriophage is a neutralizing antibody or wherein the phage-specific immunoglobulin is an IgM or an IgG.

In some embodiments, the analysis of bacteriophages and/or component(s) thereof is combined with the bacterial abundance analysis (e.g., as the analysis of bacteriophage/bacterial host ratio) and/or the analysis of the genetic susceptibility of the host to the disease.

Non-limiting examples of the methods which can be used for the quantitative and/or qualitative analysis of bacteriophages and/or component(s) thereof in any of the above methods for determining likelihood include, e.g., cultural microbiology methods (including those used for isolation and cultivation phages), Western blotting, ELISA, liquid biopsy methods, liquid chromatography and mass spectrometry (LC/MS) analysis, genetic methods (e.g., DNA or RNA sequencing, including high-throughput methods such as, e.g., Sanger sequencing, single-molecule real-time sequencing, ion semiconductor sequencing, sequencing by synthesis, sequencing by ligation, nanopore sequencing, pyrosequencing, large-scale sequencing, whole genome sequencing, DNA nanoball sequencing, Heliscope single molecule sequencing, single molecule real time (SMRT) sequencing, Tunnelling currents DNA sequencing, sequencing by hybridization, sequencing with mass spectrometry, microfluidic Sanger sequencing, microscopy-based techniques, RNAP sequencing, in vitro virus high-throughput sequencing), proteomic methods (e.g., determining amino acid composition, identification by mass spectrometry, predicting from DNA/RNA sequences, transcriptome analysis), metagenomic methods (e.g., Shotgun metagenomics, high-throughput sequencing, bioinformatics), computational modeling and simulation methods (e.g., metabolic modeling due to the availability of genome-scale metabolic models, software tools for automatically generating models from metagenomic data, flux balance analysis, dynamic modeling of the intestinal microbiota, Lotka-Volterra equations, multi-species modeling approaches, Computational Modeling of Intestinal Host-Microbiota Interactome), data analysis (e.g., principal coordinate analysis, community metabolism, meta-transcriptomics, analysis of viromes), simple simulation, and any combination thereof as well as mathematical models used to describe biological systems (e.g., Next-generation Sequencing Simulator for Metagenomics (NeSSM), combining complete genomes currently available, a community composition table, and sequencing parameters, [Jia, B., Xuan, L., Cai, K., Hu, Z., Ma, L., & Wei, C. (2013) PLoS One, 8(10), e75448]; SParse InversE Covariance Estimation for Ecological Association Inference [SPIEC-EASI]; R package dealing with microbiome association [OmiSA]; Parallel-META 3; MethaPIAn. In some embodiments, the computational modeling and simulation methods are those used for determining predisposition of the alterations of microbiota following a specific challenge.

In one embodiment of any of the above methods involving preventing entry or inactivation or modification of bacteriophages and/or component(s) thereof in a bodily fluid of a mammal, the bodily fluid is blood (e.g., whole blood, serum, or plasma), cerebrospinal fluid (CSF) or amniotic fluid.

In one embodiment of any of the above methods involving preventing entry or inactivation or modification of bacteriophages and/or component(s) thereof in a tissue of a mammal, the tissue is a nervous tissue, a liver tissue or placenta. In some embodiments, the bacteriophage are prevented from entering a human cell, modified in a human cell, or are inactivated in a human cell.

In one embodiment of any of the above methods involving preventing entry or inactivation or modification of bacteriophages and/or component(s) thereof, the methods specifically target bacteriophages comprising prion-like domains (PrDs) (e.g., using antibodies targeting bacteriophage proteins comprising PrDs). In one embodiment of any of the above methods involving preventing entry or inactivation or modification of bacteriophages and/or component(s) thereof, the methods specifically target a PrD of a bacteriophage. In some embodiments, proteins comprising PrDs comprise glutamine/asparagine (Q/N) enriched PrDs. In some embodiments, PrDs are determined using protein analysis (e.g., Western blot, ELISA) and/or algorithms (e.g., PLAAC algorithm or PrionW). Non-limiting examples of bacteriophage proteins comprising PrDs targeted by the methods of the invention include, e.g., proteins involved in interactions between bacteriophages and host cells such as, e.g., proteins associated with attachment and/or penetration (e.g., Tail protein, Baseplate wedge protein, Putative tail lysin, Collagen triple helix repeat protein, Tape measure protein, Central tail fiber, PblA-like tail protein, Gp36, Gp17, Gp22, Gp7, Gp25, Gp54, Gp4, TmpC) and proteins associated with release (e.g., D-ala-D-ala carboxypeptidase, Putative endolysin, Hydrolase, Amidase). Additional non-limiting examples of such proteins are provided in Examples 14-16 and the accompanying tables and figures.

In one embodiment of any of the above methods involving preventing entry or inactivation or modification of bacteriophages, the methods specifically target bacteriophages not comprising PrDs (e.g., using antibodies targeting bacteriophage proteins not comprising PrDs). Non-limiting examples of such proteins are provided in Examples 14-16 and the accompanying tables and figures.

In one embodiment of any of the above methods involving preventing entry or inactivation or modification of bacteriophages, the methods specifically target bacteriophages using antibodies or antibodies targeting synthetic bacteriophages or genetically-modified bacteriophages.

In one embodiment of any of the above methods involving preventing entry or inactivation or modification of bacteriophages and/or component(s) thereof, the methods specifically target bacteriophages contained in food products and/or water. In some embodiments, such bacteriophages comprise prion-like domains (PrDs). In some embodiments, such bacteriophages do not comprise PrDs. In some embodiments, the bacteriopage(s) are active against *E. coli, Salmonella* spp., *Shigella* spp., *Staphylococcus* spp., and/or *Listeria* spp. In some embodiments, the food product is milk and the bacteriopage(s) are active against lactic acid bacteria (LAB) (e.g., *Lactococcus, Lactobacillus, Leuconostoc, Pediococcus, Streptococcus*). Non-limiting examples of such bacteriopage(s) active against *E. coli, Salmonella* spp., *Shigella* spp., *Staphylococcus* spp., *Listeria* spp., and/or LAB include *Caudovirales* and *Ligamenvirales* as well as currently unclassified bacteriophages of Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, or Tectiviridae families. The bacteriophages may be from another family besides the Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae families.

In one embodiment of any of the above methods, the bacteriophage or the component thereof comprises a polypeptide with a prion-like domain. In another aspect, the invention provides a method for preventing the growth of bacteria in a product (e.g., a food product) comprising contacting said product with an effective amount of a composition comprising bacteriophages not comprising prion-like domains (PrDs). In a related aspect, the invention provides a method for packaging a product (e.g., a food product), comprising packaging the product with a packaging material comprising an effective amount of a composition comprising bacteriophages not comprising PrDs. In some embodiments, such bacteriophage compositions do not comprise any bacteriophages with PrDs.

In another aspect, the invention provides a method for preventing the growth of bacteria in a product (e.g., a food product) comprising contacting said product with an effective amount of a composition comprising bacteriophages comprising PrDs. In a related aspect, the invention provides a method for packaging a product (e.g., a food product), comprising packaging the product with a packaging material comprising an effective amount of a composition comprising bacteriophages comprising PrDs. Non-limiting examples of such bacteriopage(s) include *Caudovirales* and *Ligamenvirales* as well as currently unclassified bacteriophages of Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, or Tectiviridae families. The bacteriophages may be from another family besides the Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae families.

In some embodiments, bacteriophages comprising PrDs comprise glutamine/asparagine (Q/N) enriched PrDs. In some embodiments, PrDs are determined using protein analysis (e.g., Western blot, ELISA) and/or algorithms (e.g., PLAAC algorithm or PrionW). Non-limiting examples of bacteriophage proteins comprising PrDs include, e.g., proteins involved in interactions between bacteriophages and host cells such as, e.g., proteins associated with attachment and/or penetration (e.g., Tail protein, Baseplate wedge protein, Putative tail lysin, Collagen triple helix repeat protein, Tape measure protein, Central tail fiber, PblA-like tail protein, Gp36, Gp17, Gp22, Gp7, Gp25, Gp54, Gp4, TmpC) and proteins associated with release (e.g., D-ala-D-ala carboxypeptidase, Putative endolysin, Hydrolase, Amidase). Additional non-limiting examples of such proteins are provided in Examples 14-16 and the accompanying tables and figures. In some embodiments, PrD contained in the bacteriophage compositions of the invention are inactivated (e.g., using PrD-specific antibodies).

In some of the embodiments of the above methods of preventing bacterial growth in a product, the product and/or packaging is treated with the bacteriophage composition for at least a fraction of a second.

In any of the above methods of preventing bacterial growth in a product, non-limiting examples of bacteria which growth can be prevented include, e.g., *E. coli, Staphylococcus* spp., *Shigella* spp., *Listeria* spp., *Salmonella* spp. (e.g., *S. typhimurium, S. enteritidis, S. schwarzengrund*), lactic acid bacteria (LAB) (e.g., *Lactococcus, Lactobacillus, Leuconostoc, Pediococcus, Streptococcus*), and antibiotic-resistant bacteria (e.g., vancomycin-resistant enterococci (VRE), multi-drug resistant *Staphylococcus aureus* (MDRSA)).

Treatment with bacteriophage compositions of the invention can be combined with another anti-microbial treatment, such as, e.g., treatment with an antibiotic, a disinfectant, a detergent, or a surfactant.

The efficacy of bacteriophage treatment to reduce bacterial growth may be determined by any method known in the art, including, e.g., quantitating bacteria periodically in samples taken from the treated product and compared to an untreated control (e.g., sample from the same product before the beginning of the treatment) or by evaluation of phage plaques on host bacterial culture. In one embodiment, this may be performed daily. In one embodiment, bacterial growth reduction is considered effective if bacterial colonization is reduced by at least 1 log.

According to some embodiments of the present invention, bacteriophages may be used for food and agriculture sanitation (including meats, fruits and vegetable sanitation), hospital sanitation, home sanitation, military sanitation (including anti-bioterrorism applications and military vehicle and equipment sanitation), industrial sanitation, etc. Other applications not specifically mentioned are within the contemplation of the present invention.

In a related aspect, the invention provides bacteriophage compositions which can be used, e.g., in the above methods of preventing bacterial growth in a product. Such compositions can comprise, for example, a single bacteriophage, multiple bacteriophages, such as a bacteriophage cocktail, and mixtures of a bacteriophage(s) with an additional anti-microbial agent, such as, e.g., an antibiotic, a disinfectant, a detergent, a surfactant, etc. In some embodiments, such compositions do not comprise any bacteriophages with PrDs. In some embodiments, such compositions do not comprise any bacteriophages with PrDs and the product is food or water. In some embodiments, such compositions comprise bacteriophages with PrDs. Non-limiting examples of such bacteriopage(s) include, e.g., bacteriophages which can infect *E. coli, Staphylococcus* spp., *Shigella* spp., *Listeria* spp., *Salmonella* spp. (e.g., *S. typhimurium, S. enteritidis, S. schwarzengrund*), lactic acid bacteria (LAB) (e.g., *Lactococcus, Lactobacillus, Leuconostoc, Pediococcus, Streptococcus*), and antibiotic-resistant bacteria (e.g., vancomycin-resistant enterococci (VRE), multi-drug resistant *Staphylococcus aureus* (MDRSA)). Further non-limiting examples of such bacteriophages include, e.g., *Caudovirales* and *Ligamenvirales* and currently unclassified bacteriophages of Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, or Tectiviridae families. The bacteriophages may be from another family besides the Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and Tectiviridae families.

In some embodiments, the bacteriophages may be one or more of the following listed bacteriophages that comprise at least one PrD: Acholeplasma_phage_MV-L1, Achromobacter_phage_JWAlpha, Achromobacter_phage_JWDelta, Achromobacter_phage_JWF, Achromobacter_phage_phiAxp-1, Achromobacter_phage_phiAxp-2, Achromobacter_phage_phiAxp-3, Acidianus_bottle-shaped_virus, Acidianus_bottle-shaped_virus_2, Acidianus_filamentous_virus_2, Acidianus_filamentous_virus_7, Acidianus_rod-shaped_virus_1, Acidianus_rod-shaped_virus_2, Acidianus_spindle-shaped_virus_1, Acidianus_tailed_spindle_virus, Acidianus_two-tailed_virus, Acinetobacter_bacteriophage_AP22, Acinetobacter_phage_AB1, Acinetobacter_phage_AB3, Acinetobacter_phage_Abp1, Acinetobacter_phage_Ac42, Acinetobacter_phage_Acj61, Acinetobacter_phage_Acj9, Acinetobacter_phage_Fri 1, Acinetobacter_phage_I ME_AB3, Acinetobacter_phage_ME-AB2, Acinetobacter_phage_LZ35, Acinetobacter_phage_Petty, Acinetobacter_phage_phiAB1, Acinetobacter_phage_phiAB6, Acinetobacter_phage_Presley, Acinetobacter_phage_vB_AbaM_Acibel004, Acinetobacter_phage_vB_AbaM_IME200, Acinetobacter_phage_vB_AbaM_phiAbaA1, Acinetobacter_phage_vB_AbaP_Acibel007, Acinetobacter_phage_vB_AbaP_PD-6A3, Acinetobacter_phage_vB_AbaP_PD-AB9, Acinetobacter_phage_YMC11/12/R2315, Acinetobacter_phage_YMC13/03/R2096, Acinetobacter_phage_ZZ1, Acinetobacter_virus_AbC62, Actinomyces_virus_Av1, Actinoplanes_phage_phiAsp2, Aeromonas_phage_CC2, Aeromonas_phage_phiAS5, Aeromonas_phage_PX29, Aeromonas_phage_vB_AsaM-56, Aeromonas_virus_25, Aeromonas_virus_31, Aeromonas_virus_44RR2, Aeromonas_virus_65, Aeromonas_virus_Aehl, Aeromonas_virus_Aesl2, Aeromonas_virus_Aes508, Aeromonas_virus_AS4, Agrobacterium_phage_7-7-1, Alteromonas_phage_vB_AmaP_AD45-P, Alteromonas_phage_vB_AmaP_AD45-P1, Alteromonas_phage_vB_AmaP_AD45-P3, Alteromonas_phage_vB_AmaP_AD45-P4, Anabaena_phage_A-4L, Archaeal_BJ1_virus, Arthrobacter_phage_BarretLemon, Arthrobacter_phage_Mudcat, Arthrobacter_phage_vB_ArS-ArV2, Arthrobacter_phage_vB_ArtM-ArV1, Azospirillum_phage_Cd, Bacillus_phage_0305phi8-36, Bacillus_phage_AR9, Bacillus_phage_Aurora, Bacillus_phage_AvesoBmore, Bacillus_phage_Basilisk, Bacillus_phage_BCD7, Bacillus_phage_BCJA1 c, Bacillus_ phage_Bcp1, Bacillus_phage_BCP78, Bacillus_phage_BCP8-2, Bacillus_phage_BCU4, Bacillus_phage_Belinda, Bacillus_phage_BM5, Bacillus_phage_Bp8p-T, Bacillus_phage_BPS10C, Bacillus_phage_BPS13, Bacillus_phage_CampHawk, Bacillus_phage_Cherry, Bacillus_ phage_Deep_Blue, Bacillus_phage_DIGNKC, Bacillus_phage_DirtyBetty, Bacillus_phage_Eldridge, Bacillus_phage_Evoli, Bacillus_phage_Eyuki, Bacillus_phage_Fah, Bacillus_phage_Gamma, Bacillus_phage_Gamma isolate d'Herelle, Bacillus_phage_Hakuna, Bacillus_phage_Hoody_T, Bacillus_phage_JBP901, Bacillus_phage_Kida, Bacillus_phage_Mater, Bacillus_phage_Megatron, Bacillus_phage_MG-B1, Bacillus_phage_Moonbeam, Bacillus_phage_Nemo, Bacillus_phage_Nigalana, Bacillus_phage_NotTheCreek, Bacillus_phage_Pavlov, Bacillus_ phage_PBC1, Bacillus_phage_PfEFR-5, Bacillus_phage_phi105, Bacillus_phage_phi3T, Bacillus_phage_Phrodo, Bacillus_phage_PM1, Bacillus_phage_SageFayge, Bacillus_phage_SalinJah, Bacillus_phage_SF6, Bacillus_ phage_Shbhl, Bacillus_phage_SP-10, Bacillus_phage_SP-15, Bacillus_phage_SPP1, Bacillus_phage_TP21-L, Bacillus_phage_TsarBomba, Bacillus_phage_vB_BanS-Tsamsa, Bacillus_phage_vB_BceM-Bc431 v3, Bacillus_ phage_VMY22, Bacillus_phage_Zuko, Bacillus_virus_1, Bacillus_virus_250, Bacillus_virus_Agate, Bacillus_virus_ Andromeda, Bacillus_virus_B103, Bacillus_virus_B4, Bacillus_virus_B5S, Bacillus_virus_Bastille, Bacillus_virus_Bigbertha, Bacillus_virus_Blastoid, Bacillus_virus_BMBtp2, Bacillus_virus_Bobb, Bacillus_virus_Bp8pC, Bacillus_virus_CAM003, Bacillus_virus_CP51, Bacillus_ virus_Curly, Bacillus_virus_Eoghan, Bacillus_virus_G, Bacillus_virus_GA1, Bacillus_virus_Gemini, Bacillus_virus_Glittering, Bacillus_virus_Grass, Bacillus_virus_IEBH, Bacillus_virus_JL, Bacillus_virus_NIT1, Bacillus_virus_ Page, Bacillus_virus_Palmer, Bacillus_virus_Pascal, Bacillus_virus_Pony, Bacillus_virus_Pookie, Bacillus_virus_ poppyseed, Bacillus_virus_Riggi, Bacillus_virus_Riley, Bacillus_virus_Shanette, Bacillus_virus_Slash, Bacillus_virus_SPbeta, Bacillus_virus_SPO1, Bacillus_virus_Spock, Bacillus_virus_Stahl, Bacillus_virus_Staley, Bacillus_virus_Stills, Bacillus_virus_Taylor, Bacillus_virus_Troll, Bacillus_virus_Wbeta, Bacillus_virus_WPh, Bacteriophage_APSE-2, Bacteroides_phage_B124-14, Bdellovibrio_phage_phi1402, Bordetella_virus_BPP1, Brevibacillus_phage_Abouo, Brevibacillus_phage_Davies, Brevibacillus_phage_Jenst, Brevibacillus_phage_Osiris, Brochothrix_phage_A9, Brochothrix_phage_BL3, Brochothrix_phage_NF5, Brucella_phage_Bk, Brucella_phage_F1, Brucella_phage_fZ, Brucella_phage_Pr, Brucella_phage_R/C, Brucella_phage_S708, Brucella_phage_Tb, Brucella_phage_Wb, Burkholderia virus Bcep781, Burkholderia_phage_AH2, Burkholderia_phage_BcepB1A, Burkholderia_phage_BcepGomr, Burkholderia_phage_Bp-AMP1, Burkholderia_phage_Bp-AMP2, Burkholderia_phage_Bp-AMP4, Burkholderia_phage_JG068, Burkholderia_virus_Bcepl, Burkholderia_virus_Bcep22, Burkholderia_virus_Bcep43, Burkholderia_virus_BcepF1, Burkholderia_virus_Bcepil02, Burkholderia_virus_Bcepmigl, Burkholderia_virus_BcepNY3, Burkholderia_virus_DC1, Burkholderia_virus_KL1, Burkholderia_virus_ phi6442, Burkholderia_virus_phiE125, Campylobacter_phage_CP30A, Campylobacter_phage_PC14, Campylobacter_virus_CP21, Campylobacter_virus_CP220, Campylobacter_virus_CP8, Campylobacter_virus_CP81, Campylobacter_virus_CPt10, Campylobacter_virus_CPX, Campylobacter_virus_BB35, Campylobacter_virus_ NCTC12673, Caulobacter_phage_CcrColossus, Caulobacter_phage_Cr30, Caulobacter_phage_Percy, Caulobacter_virus_Karma, Caulobacter_virus_Magneto, Caulobacter_virus_phiCbK, Caulobacter_virus_Rogue, Caulobacter_virus_Swift, Cellulophaga phage phi13:1, Cellulophaga phage phi19:2, Cellulophaga phage phi3:1, Cellulophaga phage phi38:2, Cellulophaga phage phi3ST:2, Cellulophaga phage phi47:1, Cellulophaga_phage_phi10:1, Cellulophaga_phage_phi12:2, Cellulophaga_phage_phi12a:1, Cellulophaga_phage_phi13:2, Cellulophaga_phage_phi14:2, Cellulophaga_phage_phi18:3, Cellulophaga_phage_phi19:3, Cellulophaga_phage_phi39:1, Cellulophaga_phi46:1, Cellulophaga_phage_phi46:3, Cellulophaga_phage_phi48:1, Cellulophaga_phage_phiSM, Cellulophaga_virus_Cba12:1, Cellulophaga_virus_Cba12:3, Cellulophaga_virus_Cba121, Cellulophaga_virus_Cba171, Cellulophaga_virus_Cba172, Cellulophaga_virus_Cba18:1, Cellulophaga_virus_Cba18:2, Cellulophaga_virus_Cba181, Cellulophaga_virus_Cba41, Cellulophaga_virus_phi_ST, Cellulophaga_virus_phiST, Cellulophaga_virus_ST, Chimpanzee_faeces_associated_microphage_2, Citrobacter_phage_CVT22, Citrobacter_phage_IME-CF2, Citrobacter_phage_Margaery, Citrobacter_phage_Merlin, Citrobacter_phage_Michonne, Citrobacter_phage_Miller, Citrobacter_phage_Moogle, Citrobacter_phage_Moon, Citrobacter_phage_phiCFP-1, Citrobacter_phage_SH1, Citrobacter_phage_SH2, Citrobacter_phage_Stevie, Citrobacter_phage_vB_CfrM_CfP1, Clavibacter_phage_CMP1, Clostridium_phage_CDMH1, Clostridium_phage_c-st, Clostridium_phage_phi24R, Clostridium_phage_phiCD146, Clostridium_phage_phiCD211, Clostridium_phage_phiCD24-1, Clostridium_phage_phiCD38-2, Clostridium_phage_phiCD505, Clostridium_phage_phiCD6356, Clostridium_phage_phiCP130, Clostridium_phage_phiCP26F, Clostridium_phage_phiCP340, Clostridium_phage_phiCP39-O, Clostridium_phage_phiCP7R, Clostridium_phage_phiCPV4, Clostridium_phage_phiCTP1, Clostridium_phage_phiMMP01, Clostridium_phage_phiMMP02, Clostridium_phage_phiMMP03, Clostridium_phage_phiZP2, Clostridium_phage_vB_CpeS-CP51, Clostridium_virus_phiCD27, Corynebacterium_phage_BFK20, Croceibacter_phage_P2559S, Croceibacter_phage_P2559Y, Cronobacter_phage_CR5, Cronobacter_phage_Dev-CD-23823, Cronobacter_phage_ENT39118, Cronobacter_phage_ENT47670, Cronobacter_phage_PBES_02, Cronobacter_phage_phiES15, Cronobacter_phage_S13, Cronobacter_phage_vB_CsaM_GAP161, Cronobacter_phage_vB_CsaM_GAP32, Cronobacter_phage_vB_CsaP_GAP52, Cronobacter_phage_vB_CsaP_Ss1, Cronobacter_phage_vB_CskP_GAP227, Cronobacter_virus_CR3, Cronobacter_virus_CR8, Cronobacter_virus_ESP29491, Cronobacter_virus_GAP31, Cyanophage P-RSM3, Cyanophage S-SSM6a, Cyanophage_9515-10a, Cyanophage_NATL1A-7, Cyanophage_NATL2A-133, Cyanophage_PP, Cyanophage_P-RSM1, Cyanophage_P-RSM6, Cyanophage_PSS2, Cyanophage_P-SSP2, Cyanophage_P-TIM40, Cyanophage_S-RIM32, Cyanophage_S-RIM50, Cyanophage_SS120-1, Cyanophage_S-TIM5, Deftia_phage_phiW-14, Delftia_phage_lME-DE1, Delftia_phage_RG-2014, Dickeya_virus_Limestone, Dinoroseobacter_phage_DFL12phi1, Dinoroseobacter_phage_vBDshPR2C, Edwardsiella_phage_eiAU, Edwardsiella_phage_eiAU-183, Edwardsiella_phage_GF-2, Edwardsiella_phage_KF-1, Edwardsiella_phage_MSW-3, Edwardsiella_phage_PEi20, Eel_River_basin_pequenovirus, Enterobacter_phage_Arya, Enterobacter_phage_EcP1, Enterobacter_phage_Enc34, Enterobacter_phage_phiKDA1, Enterobacter_phage_Tyrion, Enterobacter_virus_CC31, Enterobacter_virus_PG7, Enterobacteria_phage_f1, Enterobacteria_phage_f1, Enterobacteria phage L17, Enterobacteria phage RB55, Enterobacteria phage RB59, Enterobacteria phage RB68, Enterobacteria_phage_13a, Enterobacteria_phage_alpha3, Enterobacteria_phage_cdt1, Enterobacteria_phage_CUS-3, Enterobacteria_phage_DT571/2, Enterobacteria_phage_DT57C, Enterobacteria_phage_EK99P-1, Enterobacteria_phage_ES 18, Enterobacteria_phage_f1, Enterobacteria_phage_f1, Enterobacteria_phage_fd, Enterobacteria_phage_GEC-3S, Enterobacteria_phage_HK106, Enterobacteria_phage_HK140, Enterobacteria_phage_HK225, Enterobacteria_phage_HK446, Enterobacteria_phage_HK542, Enterobacteria_phage_HK544, Enterobacteria_phage_ HK629, Enterobacteria_phage_HK630, Enterobacteria_phage_HK633, Enterobacteria_phage_D18_sensu_lato, Enterobacteria_phage_If1, Enterobacteria_phage_IME10, Enterobacteria_phage_J8-65, Enterobacteria_phage_JS, Enterobacteria_phage_JSE, Enterobacteria_phage_K3, Enterobacteria_phage_M1, Enterobacteria_phage_M13, Enterobacteria_phage_mEp043_c-1, Enterobacteria_phage_mEp235, Enterobacteria_phage_mEp237, Enterobacteria_phage_mEp460, Enterobacteria_phage_mEpX1, Enterobacteria_phage_mEpX2, Enterobacteria_phage_NJO1, Enterobacteria_phage_Phi1, Enterobacteria_phage_phi80, Enterobacteria_phage_phi92, Enterobacteria_phage_phiEcoM-GJ1, Enterobacteria_phage_phiJLA23, Enterobacteria_phage_phiK, Enterobacteria_phage_PR772, Enterobacteria_phage_PRD1, Enterobacteria_phage_PRD3, Enterobacteria_phage_RB10, Enterobacteria_phage_RB14, Enterobacteria_phage_RB16, Enterobacteria_phage_RB27, Enterobacteria_phage_RB3, Enterobacteria_phage_RB32, Enterobacteria_phage_RB33, Enterobacteria_phage_RB43, Enterobacteria_phage_RB49, Enterobacteria_phage_RB5, Enterobacteria_phage_RB51, Enterobacteria_phage_RB6, Enterobacteria_phage_RB68, Enterobacteria_phage_RB7, Enterobacteria_phage_RB9, Enterobacteria_phage_Sf101, Enterobacteria_phage_SfMu, Enterobacteria_phage_St-1, Enterobacteria_phage_ST104, Enterobacteria_phage_SV76, Enterobacteria_phage_T3, Enterobacteria_phage_T4_sensu_lato, Enterobacteria_phage_UAB_Phi20, Enterobacteria_phage_vB_EcoP_ACG-C91, Enterobacteria_phage_vB_EcoS_ACG-M12, Enterobacteria_phage_vB_EcoS_NBD2, Enterobacteria_phage_vB_KleM-RaK2, Enterobacterial_phage_mEp213, Enterobacterial_phage_mEp234, Enterobacterial_phage_mEp390, Enterobacterio_phage_MS2, Enterococcus_phage_BC611, Enterococcus_phage_ECP3, Enterococcus_phage_EfaCPT1, Enterococcus_phage_EFC-1, Enterococcus_phage_EFDG1, Enterococcus_phage_EFLK1, Enterococcus_phage_MEEF1, Enterococcus_phage_ME-EFm1, Enterococcus_phage_ME-EFm5, Enterococcus_phage_phiEf11, Enterococcus_phage_phiEF24C, Enterococcus_phage_phif11, Enterococcus_phage_phif11A, Enterococcus_phage_phiFL1B, Enterococcus_phage_phiFL1C, Enterococcus_phage_phif12, Enterococcus_phage_phif13, Enterococcus_phage_phiFL3A, Enterococcus_phage_phiFL3B, Enterococcus_phage_SAP6, Enterococcus_phage_vB_Efae230P-4, Enterococcus_phage_vB_EfaP_ME195, Enterococcus_phage_vB_EfaS_ME197, Enterococcus_phage_vB_EfaS_ME198, Erwinia_phage_phiEa104, Erwinia_phage_phiEa21-4, Erwinia_amylovora_phage_Era103, Erwinia_phage_Ea35-70, Erwinia_phage_Ea9-2, Erwinia_phage_ENT90, Erwinia_phage_PEp14, Erwinia_phage_phiEa100, Erwinia_phage_phiEa1H, Erwinia_phage_phiEa21-4, Erwinia_phage_phiEa2809, Erwinia_phage_PhiEaH1, Erwinia_phage_phiEaH2, Erwinia_phage_phiEt88, Erwinia_phage_vB_EamM_Asesino, Erwinia_phage_vB_EamM_ChrisDB, Erwinia_phage_vB_EamM_EarlPhillipIV, Erwinia_phage_vB_EamM_Huxley, Erwinia_phage_vB_EamM_Kwan, Erwinia_phage_vB_EamM_Phobos, Erwinia_phage_vB_EamM-Y2, Erwinia_phage_vB_EamP_Frozen, Erwinia_phage_vB_EamP-L1, Erwinia_phage_vB_EamP-S6, Escherichia phage bV_EcoS_AHP24, Escherichia phage vB_EcoS_AHS24, Escherichia_coli_O157_typing_phage_1, Escherichia_coli_O157_typing_phage_10, Escherichia_coli_O157_typing_phage_11, Escherichia_coli_O157_typing_phage_12, Escherichia_coli_O157_typing_phage_3, Escherichia_coli_O157_typing_phage_5, Escherichia_coli_O0157_typing_phage_6, Escherichia_phage_121 Q, Escherichia_phage_172-1, Escherichia_phage_64795_ec1, Escherichia_phage_Akfv33, Escherichia_phage_APCEc01, Escherichia_phage_Bf23, Escherichia_phage_Cba120, Escherichia_phage_D108, Escherichia_phage_EB49, Escherichia_phage_EC6, Escherichia_phage_ECBP2, Escherichia_phage_ECBP5, Escherichia_phage_ECML-117, Escherichia_phage_ECML-4, Escherichia_phage_HK639, Escherichia_phage_HK75, Escherichia_phage_HY01, Escherichia_phage_HY02, Escherichia_phage_HY03, Escherichia_phage_ID21, Escherichia_phage_lD32, Escherichia_phage_JH2, Escherichia_phage_Jk06, Escherichia_phage_K1-ind(3), Escherichia_phage_KBNP1711, Escherichia_phage_Lw1, Escherichia_phage_N4, Escherichia_phage_NC29, Escherichia_phage_NC35, Escherichia_phage_P483, Escherichia_phage_PBECO_4, Escherichia_phage_phAPEC8, Escherichia_phage_Phax1, Escherichia_phage_phiKT, Escherichia_phage_phiV10, Escherichia_phage_Pollock, Escherichia_phage_slur01, Escherichia_phage_slur02, Escherichia_phage_slur05, Escherichia_phage_slur07, Escherichia_phage_slur08, Escherichia_phage_slur09, Escherichia_phage_slur16, Escherichia_phage_SUSP1, Escherichia_phage_SUSP2, Escherichia_phage_T5, Escherichia_phage_TL-2011 b, Escherichia_phage_UFV-AREG 1, Escherichia_phage_vB_EcoM_Alf5, Escherichia_phage_vB_EcoM_AYO 145A, Escherichia_phage_vB_EcoM_PhAPEC2, Escherichia_phage_vB_EcoM-UFV13, Escherichia_phage_vB_EcoM-VpaE1, Escherichia_phage_vB_EcoS_FFH1, Escherichia_phage_wV7, Escherichia_phage_wV8, Escherichia_virus_4MG, Escherichia_virus_9g, Escherichia_virus_ADB2, Escherichia_virus_AHP42, Escherichia_virus_AHS24, Escherichia_virus AKS96, Escherichia_virus_APEC5, Escherichia_virus_APEC7, Escherichia_virus_AR1, Escherichia_virus_Bp4, Escherichia_virus_C40, Escherichia_virus_Cajan, Escherichia_virus_CVM10, Escherichia_virus_E112, Escherichia_virus_E41c, Escherichia_virus_EC1 UPM, Escherichia_virus_ECBP1, Escherichia_virus_ECML134, Escherichia_virus_FFH2, Escherichia_virus_FI, Escherichia_virus_FV3, Escherichia_virus_G7C, Escherichia_virus_HK022, Escherichia_virus_HK97, Escherichia_virus_ME08, Escherichia_virus_lme09, Escherichia_virus_lME11, Escherichia_virus_JenK1, Escherichia_virus_JenP1, Escherichia_virus_JenP2, Escherichia_virus_JES2013, Escherichia_virus_JL1, Escherichia_virus_JSO9, Escherichia_virus_JS10, Escherichia_virus_K1-5, Escherichia_virus_K1E, Escherichia_virus_K1G, Escherichia_virus_K1H, Escherichia_virus_K1 ind1, Escherichia_virus_K1 ind2, Escherichia_virus_KP26, Escherichia_virus_Lambda, Escherichia_virus_MS2, Escherichia_virus_Mu, Escherichia_virus_N15, Escherichia_virus_P1, Escherichia_virus_P2, Escherichia_virus_phiEco32, Escherichia_virus_Rogue1, Escherichia_virus_Rtp, Escherichia_virus_Seurat, Escherichia_virus_SV14, Escherichia_virus_T1, Escherichia_virus_TLS, Escherichia_virus_V5, Escherichia_virus_VR20, Escherichia_virus_VR25, Escherichia_virus_VR26, Escherichia_virus_VR5, Escherichia_virus_VR7, Flavobacterium_phage_11 b, Flavobacterium_phage_FCL-2, Flavobacterium_sp._phage_1/32, Geobacillus_phage_GBK2, Geobacillus_phage_GBSV1, Geobacillus_virus_E3, Gokushovirinae_Bog8989_22, Gokushovirinae_Fen672_31, Gokushovirinae_Fen7875_21, Gordonia_phage_Bantam, Gordonia_phage_BaxterFox, Gordonia_phage_BetterKatz, Gordonia_phage_BritBrat, Gordonia_phage_Emalyn, Gordonia_phage_GMA4, Gordonia_phage_GMA6, Gordonia_phage_GMA7, Gordonia_phage_Gmala1, Gordonia_phage_GordDuk1, Gordonia_phage_GordTnk2, Gordonia_phage_GTE2, Gordonia_phage_Hotorobo, Gordonia_phage_JSwag, Gordonia_phage_Jumbo, Gordonia_phage_Kvothe, Gordonia_phage_Monty, Gordonia_phage_Orchid, Gordonia_phage_Phinally, Gordonia_phage_Remus, Gordonia_phage_Splinter, Gordonia_phage_Vendetta, Gordonia_phage_Vivi2, Gordonia_phage_Wizard, Gordonia_phage_Woes, Gordonia_phage_Yvonnetastic, Haemophilus_phage_Aaphi23, Haemophilus_phage_HP1, Halocynthia_phage_JM-2012, Hamiltonella_virus_APSE1, Helicobacter_phage_1961P, Helicobacter_phage_KHP30, Helicobacter_phage_KHP40, lodobacteriophage_phiPLPE, Klebsiella_phage_0507-KN2-1, Klebsiella_phage_JD001, Klebsiella_phage_JD18, Klebsiella_phage_K5, Klebsiella_phage_K64-1, Klebsiella_phage_KLPN1, Klebsiella_phage_KP15, Klebsiella_phage_KP27, Klebsiella_phage_KP32, Klebsiella_phage_Matisse, Klebsiella_phage_phiKO2, Klebsiella_phage_PKO 111, Klebsiella_phage_PKP126, Klebsiella_phage_Sushi, Klebsiella_phage_vB_Kp2, Klebsiella_phage_vB_KpnM_KB57, Klebsiella_phage_vB_KpnM_KpV477, Klebsiella_virus_1513, Klebsiella_virus_F19, Klebsiella_virus_KP34, Klebsiella_virus_KP36, Klebsiella_virus_SU552A, Lactobacillus_phage_A2, Lactobacillus_phage_ATCC_8014-B2, Lactobacillus_phage_ATCC8014, Lactobacillus_phage_c5, Lactobacillus_phage_CL1, Lactobacillus_phage_CL2, Lactobacillus_phage_iLpl308, Lactobacillus_phage_iLp84, Lactobacillus_phage_J-1, Lactobacillus_phage_JCL1032, Lactobacillus_phage_Lb338-1, Lactobacillus_phage_LBR48, Lactobacillus_phage_Lc-Nu, Lactobacillus_ phage_Ld17, Lactobacillus_phage_Ld25A, Lactobacillus_ phage_Ld3, Lactobacillus_phage_Ldl1, Lactobacillus_ phage_LF1, Lactobacillus_phage_Lfelnf, Lactobacillus_ phage_LfeSau, Lactobacillus_phage_LL-H, Lactobacillus_ phage_LLKu, Lactobacillus_phage_LP65, Lactobacillus_ phage_Lrml, Lactobacillus_phage_Lv-1, Lactobacillus_ phage_phijlb1, Lactobacillus_phage_phiadh, Lactobacillus_ phage_phiAQ113, Lactobacillus_phage_phig1e, Lactobacillus_phage_phiLdb, Lactobacillus_phage_phiPYB5, Lactobacillus_phage_PL-1, Lactobacillus_phage_PLE3, Lactobacillus_phage_Shal, Lactobacillus_prophage_Lj928, Lactobacillus_prophage_Lj965, Lactoccocus_phage_WP-2, Lactococcus_phage_1358, Lactococcus_phage_1706, Lactococcus_phage_340, Lactococcus_phage_50101, Lactococcus_phage_63301, Lactococcus_phage_712, Lactococcus_phage_936_sensu_ato, Lactococcus_phage_949, Lactococcus_phage_98201, Lactococcus_Phage_ASCC273, Lactococcus_Phage_ASCC281, Lactococcus_phage_ASCC284, Lactococcus_phage_ASCC287, Lactococcus_phage_ASCC310, Lactococcus_phage_ASCC324, Lactococcus_phage_ASCC337, Lactococcus_phage_ASCC356, Lactococcus_phage_ASCC358, Lactococcus_phage_ASCC368, Lactococcus_phage_ASCC395, Lactococcus_phage_ASCC397, Lactococcus_phage_ASCC406, Lactococcus_phage_ASCC454, Lactococcus_phage_ASCC460, Lactococcus_Phage_ASCC465, Lactococcus_phage_ASCC473, Lactococcus_phage_ASCC476, Lactococcus_phage_ASCC489, Lactococcus_phage_ASCC497, Lactococcus_phage_ASCC502, Lactococcus_phage_ASCC506, Lactococcus_phage_ASCC527, Lactococcus_phage_ASCC531, Lactococcus_Phage_ASCC532, Lactococcus_phage_ASCC544, Lactococcus_phage_asccphi28, Lactococcus_phage_bIL170, Lactococcus_phage_bIL286, Lactococcus_phage_bIL309, Lactococcus_phage_BK5-T, Lactococcus_phage_BM13, Lactococcus_phage_CB13, Lactococcus_phage_CB14, Lactococcus_phage_CB19, Lactococcus_phage_CB20, Lactococcus_phage_H9EEP4, Lactococcus_phagejm2, Lactococcus_phagejm3, Lactococcus_phage_KSY1, Lactococcus_phage_P008, Lactococcus_ phage_P78, Lactococcus_phage_P87, Lactococcus_phage_P92, Lactococcus_phage_P118, Lactococcus_phage_P162, Lactococcus_phage_P335_sensu_lato, Lactococcus_phage_P680, Lactococcus_phage_phiL47, Lactococcus_phage_phiLC3, Lactococcus_phage_PLgT-1, Lactococcus_phage_SL4, Lactococcus_phage_TP901-1, Lactococcus_phage_Tuc2009, Lactococcus_phage_ul36, Lactococcus_phage_WRP3, Lelliottia_phage_phD2B, Leuconostoc_phage_Lmdl, Leuconostoc_phage_P793, Leuconostoc_phage_phiLN03, Leuconostoc_phage_phiLN04, Leuconostoc_phage_phiLN12, Leuconostoc_phage_phiLN25, Leuconostoc_phage_phiLN6B, Liberibacter_phage_SC2, Listeria_phage_A118, Listeria_phage_A500, Listeria_phage_B025, Listeria_phage_B054, Listeria_phage_List-36, Listeria_phage_LMSP-25, Listeria_phage_LMTA-148, Listeria_phage_LMTA-57, Listeria_phage_LMTA-94, Listeria_phage_LP-030-3, Listeria_phage_LP-048, Listeria_phage_vB_LmoM_AG20, Listeria_phage_vB_LmoS_293, Listeria_virus_LP-124, Listeria_virus_A511, Listeria_virus_LMTA-34, Listeria_virus_LP-083-2, Listeria_virus_LP-125, Listeria_virus_P100, Mannheimia_phage_vB_MhM_3927AP2, Mannheimia_phage_vB_MhS_535AP2, Mannheimia_phage_ vB_MhS_587AP2, Mesorhizobium_phage_vB_MIoP_Lo5R7ANS, Methanobacterium_phage_psiM2, Microbacterium_phage_vB_MoxS-ISF9, Microcystis_aeruginosa_phage_MaLMM01, Microcystis_phage_MaMV-DC, Microviridae_Bog1249_12, Microviridae_Bog5275_51, Microviridae_Bog9017_22, Microviridae_Fen2266_11, Microviridae_Fen418_41, Microviridae_Fen4707_41, Microviridae_Fen685_11, Microviridae_Fen7786_21, Microviridae_Fen7895_21, Microviridae_Fen7918_21, Microviridae_phiCA82, Morganella_phage_vB_MmoM_MP1, Mycobacteriophage_ElTiger69, Mycobacterium phage Ares, Mycobacterium phage LRRHood, Mycobacterium_phage_244, Mycobacterium_phage_32HC, Mycobacterium_phage_39HC, Mycobacterium_phage_ABCat, Mycobacterium_phage_Abrogate, Mycobacterium_phage_Acadian, Mycobacterium_phage_Adawi, Mycobacterium_phage_Adjutor, Mycobacterium_phage_Adler, Mycobacterium_phage_Adler_F1725, Mycobacterium_phage_Adzzy, Mycobacterium_phage_Airmid, Mycobacterium_phage_Akoma, Mycobacterium_phage_Alex, Mycobacterium_phage_Alice, Mycobacterium_phage_Alma, Mycobacterium_phage_Alsfro, Mycobacterium_phage_Alvin, Mycobacterium_phage_Angelica, Mycobacterium_phage_AnnaL29, Mycobacterium_phage_Anubis, Mycobacterium_phage_Apizium, Mycobacterium_phage_Arbiter, Mycobacterium_ phage_ArcherNM, Mycobacterium_phage_ArcherS7, Mycobacterium_phage_Archie, Mycobacterium_phage_Ardmore, Mycobacterium_phage_Ariel, Mycobacterium_phage_Artemis2UCLA, Mycobacterium_phage_Arturo, Mycobacterium_phage_Astraea, Mycobacterium_phage_Astro, Mycobacterium_phage_Athena, Mycobacterium_phage_Audrey, Mycobacterium_phage_Ava3, Mycobacterium_phage_Avani, Mycobacterium_phage_Babsiella, Mycobacterium_phage_Bactobuster, Mycobacterium_phage_Badfish, Mycobacterium_phage_Baee, Mycobacterium_phage_Baka, Mycobacterium_phage_Bane1, Mycobacterium_phage_Bane2, Mycobacterium_phage_Barnyard, Mycobacterium_phage_BarrelRoll, Mycobacterium_phage_Barriga, Mycobacterium_phage_Bask21, Mycobacterium_ phage_BBPiebs31, Mycobacterium_phage_BellusTerra, Mycobacterium_phage_Benedict, Mycobacterium_phage_Bernall3, Mycobacterium_phage_Bernardo, Mycobacterium_ phage_Bethlehem, Mycobacterium_phage_BigNuz, Mycobacterium_phage_BillKnuckles, Mycobacterium_phage_Bipolar, Mycobacterium_phage_Bipper, Mycobacterium_phage_Blue7, Mycobacterium_phage_Bobi, Mycobacterium_phage_Boomer, Mycobacterium_phage_Breeniome, Mycobacterium_phage_Breezona, Mycobacterium_phage_Brocalys, Mycobacterium_phage_bron, Mycobacterium_phage_BrownCNA, Mycobacterium_phage_Bruin, Mycobacterium_phage_Brujita, Mycobacterium_phage_Bruns, Mycobacterium_phage_Brusacoram, Mycobacterium_phage_BTCU-1, Mycobacterium_phage_Butters, Mycobacterium_phage_Butterscotch, Mycobacterium_phage_BuzzLyseyear, Mycobacterium_phage_Bxb1, Mycobacterium_phage_Bxz1, Mycobacterium_phage_Bxz2, Mycobacterium_phage_Cabrinians, Mycobacterium_phage_Cali, Mycobacterium_phage_Cambiare, Mycobacterium_phage_CaptainTrips, Mycobacterium_phage_Carcharodon, Mycobacterium_phage_Catalina, Mycobacterium_phage_Catdawg, Mycobacterium_phage_Catera, Mycobacterium_phage_Cerasum, Mycobacterium_phage_Chadwick, Mycobacterium_phage_Chah, Mycobacterium_phage_Chandler, Mycobacterium_phage_Charlie, Mycobacterium_phage_Chel2, Mycobacterium_phage_Che8, Mycobacterium_phage_Che9c, Mycobacterium_phage_Che9d, Mycobacterium_phage_Cheetobro, Mycobacterium_phage_Cjw 1, Mycobacterium_phage_CloudWang3, Mycobacterium_phage_Colbert, Mycobacterium_phage_Conspiracy, Mycobacterium_phage_Contagion, Mycobacterium_phage_Cooper, Mycobacterium_phage_Corndog, Mycobacterium_phage_Cosmo, Mycobacterium_phage_Courthouse, Mycobacterium_phage_CrimD, Mycobacterium_phage_Crossroads, Mycobacterium_phage_Daenerys, Mycobacterium_phage_DaHudson, Mycobacterium_phage_Dandelion, Mycobacterium_phage_Dante, Mycobacterium_phage_DaVinci, Mycobacterium_phage_DD5, Mycobacterium_phage_DeadP, Mycobacterium_phage_Dhanush, Mycobacterium_phage_DLane, Mycobacterium_phage_Donovan, Mycobacterium_phage_Dori, Mycobacterium_phage_Dorothy, Mycobacterium_phage_DotProduct, Mycobacterium_phage_Drago, Mycobacterium_phage_DrDrey, Mycobacterium_phage_Dreamboat, Mycobacterium_phage_DS6A, Mycobacterium_phage_Dumbo, Mycobacterium_phage_Dusk, Mycobacterium_phage_Dylan, Mycobacterium_phage_Eagle, Mycobacterium_phage_EagleEye, Mycobacterium_phage_Edtherson, Mycobacterium_phage_Elphl0, Mycobacterium_phage_Emerson, Mycobacterium_phage_EmpTee, Mycobacterium_phage_Enkosi, Mycobacterium_phage_Equemiohl3, Mycobacterium_phage_Eremos, Mycobacterium_phage_EricB, Mycobacterium_phage_Estave 1, Mycobacterium_phage_ET08, Mycobacterium_phage_Euphoria, Mycobacterium_phage_Eureka, Mycobacterium_phage_Faith 1, Mycobacterium_phage_Fang, Mycobacterium_phage_Farber, Mycobacterium_phage_Fezzik, Mycobacterium_phage_fionn, Mycobacterium_phage_Firecracker, Mycobacterium_phage_Fishburne, Mycobacterium_phage_FlagStaff, Mycobacterium_phage_Florinda, Mycobacterium_phage_FluffyNinja, Mycobacterium_phage_Flux, Mycobacterium_phage_Fredward, Mycobacterium_phage_Fruitloop, Mycobacterium_phage_G1DIQ3, Mycobacterium_phage_Gadjet, Mycobacterium_phage_Gadost, Mycobacterium_phage_Gaia, Mycobacterium_phage_Gardann, Mycobacterium_phage_Gengar, Mycobacterium_phage_Giles, Mycobacterium_phage_Gizmo, Mycobacterium_phage_Goku, Mycobacterium_phage_Gompeii16, Mycobacterium_phage_Goose, Mycobacterium_phage_Graduation, Mycobacterium_phage_Gumball, Mycobacterium_phage_GUmbie, Mycobacterium_phage_Gyarad, Mycobacterium_phage_Hades, Mycobacterium_phage_Hammer, Mycobacterium_phage_HamSlice, Mycobacterium_phage_Hamulus, Mycobacterium_phage_Harvey, Mycobacterium_phage_Heathcliff, Mycobacterium_phage_Hedgerow, Mycobacterium_phage_HelDan, Mycobacterium_phage_Hertubise, Mycobacterium_phage_Hosp, Mycobacterium_phage_H ufflyPuff, Mycobacterium_phage_HyRo, Mycobacterium_phage_lbhubesi, Mycobacterium_phage_ICleared, Mycobacterium_phage_lnventum, Mycobacterium_phage_lracema64, Mycobacterium_phage_lsaacEli, Mycobacterium_phage_Jabbawokkie, Mycobacterium_phage_JacAttac, Mycobacterium_phage_JAMaL, Mycobacterium_phage_Jasper, Mycobacterium_phagejaws, Mycobacterium_phage_JC27, Mycobacterium_phage_Jebeks, Mycobacterium_phage_Jeffabunny, Mycobacterium_phage_Job42, Mycobacterium_phage_Jobu08, Mycobacterium_phage_Joliel, Mycobacterium_phage_Kamiyu, Mycobacterium_phage_Kampy, Mycobacterium_phage_KayaCho, Mycobacterium_phage_KBG, Mycobacterium_phage_Kikipoo, Mycobacterium_phage_Kimberlium, Mycobacterium_phage_KingVeveve, Mycobacterium_phage_KLucky39, Mycobacterium_phage_Kostya, Mycobacterium_phage_KSSJEB, Mycobacterium_phage_Kugel, Mycobacterium_phage_L5, Mycobacterium_phage_LadyBird, Mycobacterium_phage_Laminal3, Mycobacterium_phage_Lasso, Mycobacterium_phage_Lesedi, Mycobacterium_phage_LHTSCC, Mycobacterium_phage_Lilac, Mycobacterium_phage_LinStu, Mycobacterium_phage_LittleE, Mycobacterium_phage_Llama, Mycobacterium_phage_Llij, Mycobacterium_phage_Lockley, Mycobacterium_phage_Lolly9, Mycobacterium_phage_Loser, Mycobacterium_phage_LRRHood, Mycobacterium_phage_Luchador, Mycobacterium_phage_macncheese, Mycobacterium_phage_Makemake, Mycobacterium_phage_Malithi, Mycobacterium_phage_Manad, Mycobacterium_phage_Marcell, Mycobacterium_phage_MarQuardt, Mycobacterium_phage_Medusa, Mycobacterium_phage_MeeZee, Mycobacterium_phage_Melvin, Mycobacterium_phage_MiaZeal, Mycobacterium_phage_MichelleMyBell, Mycobacterium_phage_Milly, Mycobacterium_phage_Mindy, Mycobacterium_phage_Minerva, Mycobacterium_phage_MoMoMixon, Mycobacterium_phage_MOOREtheMARYer, Mycobacterium_phage_Morgushi, Mycobacterium_phage_Mosby, Mycobacterium_phage_MosMoris, Mycobacterium_phage_Mozy, Mycobacterium_phage_MrGordo, Mycobacterium_phage_Mulciber, Mycobacterium_phage_Murdoc, Mycobacterium_phage_Murphy, Mycobacterium_phage_Murucutumbu, Mycobacterium_phage_Museum, Mycobacterium_phage_Mutaforma13, Mycobacterium_phage_Myrna, Mycobacterium_phage_Nacho, Mycobacterium_phage_Nala, Mycobacterium_phage_Nappy, Mycobacterium_phage_NelitzaMV, Mycobacterium_phage_Nepal, Mycobacterium_phage_Nerujay, Mycobacterium_phage_Newman, Mycobacterium_phage_Nhonho, Mycobacterium_phage_Nigel, Mycobacterium_phage_Nova, Mycobacterium_phage_Nyxis, Mycobacterium_phage_Oaker, Mycobacterium_phage_Obamal2, Mycobacterium_phage_Odin, Mycobacterium_phage_OkiRoe, Mycobacterium_phage_Oline, Mycobacterium_phage_Omega, Mycobacterium_phage_Oosterbaan, Mycobacterium_phage_Optimus, Mycobacterium_phage_Orion, Mycobacterium_phage_OSmaximus, Mycobacterium_phage_Ovechkin, Mycobacterium_phage_Pacc40, Mycobacterium_phage_Panchino, Mycobacterium_phage_Papez, Mycobacterium_phage_Pari, Mycobacterium_phage_PattyP, Mycobacterium_phage_PBI1, Mycobacterium_phage_Peaches, Mycobacterium_phage_Perseus, Mycobacterium_phage_PG1, Mycobacterium_phage_Phaedrus, Mycobacterium_phage_Phantastic, Mycobacterium_phage_PhatBacter, Mycobacterium_phage_Phatniss, Mycobacterium_phage_Phaux, Mycobacterium_phage_Phayonce, Mycobacterium_phage_Phelemich, Mycobacterium_phage_Phipps, Mycobacterium_phage_Phlei, Mycobacterium_phage_Phlyer, Mycobacterium_phage_Phoxy, Mycobacterium_phage_Phrann, Mycobacterium_phage_PhrostyMug, Mycobacterium_phage_Phrux, Mycobacterium_phage_Piglet, Mycobacterium_phage_Pinto, Mycobacterium_phage_Pio, Mycobacterium_phage_Pipefish, Mycobacterium_phage_Pipsqueak, Mycobacterium_phage_Piro94, Mycobacterium_phage_Pleione, Mycobacterium_phage_PLot, Mycobacterium_phage_PMC, Mycobacterium_phage_Pops, Mycobacterium_phage_PopTart, Mycobacterium_phage_Porky, Mycobacterium_phage_Predator, Mycobacterium_phage_Puhltonio, Mycobacterium_phage_Pumpkin, Mycobacterium_phage_Quico, Mycobacterium_phage_Quink, Mycobacterium_phage_QuinnKiro, Mycobacterium_phage_Qyrzula, Mycobacterium_phage_Rakim, Mycobacterium_phage_Ramsey, Mycobacterium_phage_Rebeuca, Mycobacterium_phage_Redi, Mycobacterium_phage_Redno2, Mycobacterium_phage_RedRock, Mycobacterium_phage_Reprobate, Mycobacterium_phage_Rey, Mycobacterium_phage_RhynO, Mycobacterium_phage_RidgeCB, Mycobacterium_phage_Rizal, Mycobacterium_phage_RonRayGun, Mycobacterium_phage_Rosebush, Mycobacterium_phage_Rufus, Mycobacterium_phage_Rumpelstiltskin, Mycobacterium_phage_Saal, Mycobacterium_phage_Sabertooth, Mycobacterium_phage_Saintus, Mycobacterium_phage_Sarfire, Mycobacterium_phage_Sbash, Mycobacterium_phage_Scoot17C, Mycobacterium_phage_ScottMcG, Mycobacterium_phage_SDcharge11, Mycobacterium_phage_Seabiscuit, Mycobacterium_phage_Seagreen, Mycobacterium_phage_Sebata, Mycobacterium_phage_Serendipity, Mycobacterium_phage_Serenity, Mycobacterium_phage_Serpentine, Mycobacterium_phage_Severus, Mycobacterium_phage_SG4, Mycobacterium_phage_Shaka, Mycobacterium_phage_Shauna1, Mycobacterium_phage_ShedlockHolmes, Mycobacterium_phage_Sheen, Mycobacterium_phage_ShiLan, Mycobacterium_phage_Shipwreck, Mycobacterium_phage_ShiVal, Mycobacterium_phage_Shrimp, Mycobacterium_phage_Sigman, Mycobacterium_phage_SirDuracell, Mycobacterium_phage_SirHarley, Mycobacterium_phage_SiSi, Mycobacterium_phage_SkiPole, Mycobacterium_phage_Smeadley, Mycobacterium_phage_Snenia, Mycobacterium_phage_Solon, Mycobacterium_phage_Sparkdehlily, Mycobacterium_phage_Sparky, Mycobacterium_phage_Spartacus, Mycobacterium_phage_Spike509, Mycobacterium_phage_Spud, Mycobacterium_phage_Squirty, Mycobacterium_phage_Stinger, Mycobacterium_phage_Suffolk, Mycobacterium_phage_Swish, Mycobacterium_phage_Switzer, Mycobacterium_phage_SWU1, Mycobacterium_phage_Taj, Mycobacterium_phage_TallGRassMM, Mycobacterium_phage_Tasp14, Mycobacterium_phage_Theia, Mycobacterium_phage_TheloniousMonk, Mycobacterium_phage_Thibault, Mycobacterium_phage_Thor, Mycobacterium_phage_Thora, Mycobacterium_phage_ThreeOh3D2, Mycobacterium_phage_Tiffany, Mycobacterium_phage_Tiger, Mycobacterium_phage_Timshel, Mycobacterium_phage_TiroTheta9, Mycobacterium_phage_TM4, Mycobacterium_phage_Tonenili, Mycobacterium_phage_Toto, Mycobacterium_phage_Treddle, Mycobacterium_phage_Trike, Mycobacterium_phage_Trixie, Mycobacterium_phage_Troll4, Mycobacterium_phage_Trouble, Mycobacterium_phage_Tweety, Mycobacterium_phage_Twister, Mycobacterium_phage_U2, Mycobacterium_phage_UncleHowie, Mycobacterium_phage_UnionJack, Mycobacterium_phage_Velveteen, Mycobacterium_phage_Vincenzo, Mycobacterium_phage_Violet, Mycobacterium_phage_Vista, Mycobacterium_phage_Vivaldi, Mycobacterium_phage_VohminGhazi, Mycobacterium_phage_Vortex, Mycobacterium_phage_Wally, Mycobacterium_phage_Wanda, Mycobacterium_phage_Wee, Mycobacterium_phage_Wheeler, Mycobacterium_phage_Whirlwind, Mycobacterium_phage_Wildcat, Mycobacterium_phage_Wile, Mycobacterium_phage_Willis, Mycobacterium_phage_Winky, Mycobacterium_phage_WIVsmall, Mycobacterium_phage_Xeno, Mycobacterium_phage_X-Factor, Mycobacterium_phage_Yoshand, Mycobacterium_phage_YungJamal, Mycobacterium_phage_Zaka, Mycobacterium_phage_Zapner, Mycobacterium_phage_Zonia, Mycobacterium_virus_Ff47, Mycoplasma_virus_P1, Myxococcus_phage_Mx8, Nitratiruptor_phage_NrS-1, Paenibacillus_phage_Harrison, Paenibacillus_phage_Vegas, Pantoea_phage_LIMElight, Pantoea_phage_LIMEzero, Parabacteroides_phage_YZ-2015a, Parabacteroides_phage_YZ-2015b, Paracoccus_phage_vB_PmaS_IMEP1, Pasteurella_phage_F108, Pectobacterium_bacteriophage_PM2, Pectobacterium_phage_My1, Pectobacterium_phage_Peat1, Pectobacterium_phage_phiTE, Pectobacterium_phage_PM1, Pectobacterium_phage_PP1, Pectobacterium_phage_PP16, Pectobacterium_phage_PP90, Pectobacterium_phage_ZF40, Pediococcus_phage_cIP1, Pelagibacter_phage_HTVC008M, Pelagibacter_phage_HTVC010P, Pelagibacter_phage_HTVC011 P, Pelagibacter_phage_HTVC019P, Persicivirga_phage_P12024L, Persicivirga_phage_ P12024S, Phage_phiJL001, Phage_vB_EcoP_SU10, Phormidium_phage_Pf-WMP3, Phormidium_phage_Pf-WMP4, Prochlorococcus phage P-SSM5, Prochlorococcus_phage_P-SSM5, Prochlorococcus_phage_MED4-184, Prochlorococcus_phage_MED4-213, Prochlorococcus_phage_P-HM1, Prochlorococcus_phage_P-HM2, Prochlorococcus_phage_P-RPM4, Prochlorococcus_phage_P-RSM3, Prochlorococcus_phage_P-RSM4, Prochlorococcus_phage_P-SSM2, Prochlorococcus_phage_P-SSM3, Prochlorococcus_phage_P-SSM4, Prochlorococcus_phage_P-SSM5, Prochlorococcus_phage_P-SSM7, Prochlorococcus_phage_P-SSP10, Prochlorococcus_phage_P-SSP7, Prochlorococcus_phage_P-TIM68, Prochlorococcus_phage_Syn1, Prochlorococcus_phage_Syn33, Propionibacterium_phage_P101A, Propionibacterium_phage_P9.1, Propionibacterium_phage_PA6, Propionibacterium_phage_PHL009, Proteus_phage_PM_75, Proteus_phage_PM_85, Proteus_phage_PM_93, Proteus_phage_PM16, Proteus_phage_pPM_01, Proteus_phage_vB_PmiM_Pm5461, Proteus_phage_vB_PmiP_Pm5460, Providencia_phage_Redjac, Pseudoalteromonas_phage_H101, Pseudoalteromonas_phage_H105/1, Pseudoalteromonas_phage_PM2, Pseudoalteromonas_phage_Pq0, Pseudoalteromonas_phage_pYD6-A, Pseudoalteromonas_phage_RIO-1, Pseudoalteromonas_phage_TW1, Pseudomonad_phage_gh-1, Pseudomonas phage CHA_P1, Pseudomonas phage P3_CHA, Pseudomonas phage PAK_P5, Pseudomonas phage PB1, Pseudomonas phage vB_PaeP_p2-10_Or1, Pseudomonas_phage_14-1, Pseudomonas_phage_201 phi2-1, Pseudomonas_phage_AF, Pseudomonas_phage_Andromeda, Pseudomonas_phage_B3, Pseudomonas_phage_Bf7, Pseudomonas_phage_D3112, Pseudomonas_phage_DL54, Pseudomonas_phage_DL60, Pseudomonas_phage_DL62, Pseudomonas_phage_DL68, Pseudomonas_phage_EL, Pseudomonas_ phage_F116, Pseudomonas_phage_F8, Pseudomonas_phage_FHA0480, Pseudomonas_phage_H66, Pseudomonas_phage_JBD18, Pseudomonas_phage_JBD30, Pseudomonas_phage_JBD5, Pseudomonas_phage_JBD69, Pseudomonas_phage_JBD88a, Pseudomonas_phage_JD024, Pseudomonas_phage_JG024, Pseudomonas_phage_KPP12, Pseudomonas_phage_KPP22, Pseudomonas_phage_KPP25, Pseudomonas_phage_LBL3, Pseudomonas_phage_LKD16, Pseudomonas_phage_LMA2, Pseudomonas_phage_Lu 11, Pseudomonas_phage_LUZ19, Pseudomonas_phage_LUZ24, Pseudomonas_phage_MD8, Pseudomonas_phage_MP22, Pseudomonas_phage_MP29, Pseudomonas_phage_MP38, Pseudomonas_phage_MP48, Pseudomonas_phage_MPK6, Pseudomonas_phage_MPK7, Pseudomonas_phage_MR299-2, Pseudomonas_phage_NH-4, Pseudomonas_phage_NP1, Pseudomonas_phage_OBP, Pseudomonas_phage_PA1 phi, Pseudomonas_phage_PaBG, Pseudomonas_phage_PAE1, Pseudomonas_phage_PaMx11, Pseudomonas_phage_PaMx25, Pseudomonas_phage_PaMx42, Pseudomonas_phage_PaMx74, Pseudomonas_phage_PaP2, Pseudomonas_phage_PaP3, Pseudomonas_phage_Pf1, Pseudomonas_phage_Pf-10, Pseudomonas_phage_phi2, Pseudomonas_phage_phi-2, Pseudomonas_phage_PhiCHU, Pseudomonas_phage_phiCTX, Pseudomonas_phage_philBB-PAA2, Pseudomonas_phage_phikF77, Pseudomonas_phage_phiKMV, Pseudomonas_phage_phiKZ, Pseudomonas_phage_PhiPA3, Pseudomonas_phage_phiPSA1, Pseudomonas_phage_phiPSA2, Pseudomonas_phage_phiPsa374, Pseudomonas_phage_PPPL-1, Pseudomonas_phage_PPpW-3, Pseudomonas_phage_PT2, Pseudomonas_phage_PT5, Pseudomonas_phage_SN, Pseudomonas_phage_tf, Pseudomonas_phage_TL, Pseudomonas_phage_UFV-P2, Pseudomonas_phage_vB_Pae_PS44, Pseudomonas_phage_vB_Pae-Kakheti25, Pseudomonas_phage_vB_PaeM_PAO 1_Ab27, Pseudomonas_phage_vB_PaeM_PS24, Pseudomonas_phage_vB_PaeP_C2-10_Ab22, Pseudomonas_phage_vB_PaeP_MAG4, Pseudomonas_phage_vB_PaeP_PAO 1_Ab05, Pseudomonas_phage_vB_PaeP_PPA-ABTNL, Pseudomonas_phage_vB_PaeS_SCH_Ab26, Pseudomonas_phage_vB_Pae-TbilisiM32, Pseudomonas_phage_vB_PsyM_KIL1, Pseudomonas_phage_VCM, Pseudomonas_virus_Ab03, Pseudomonas_virus_KPP10, Pseudomonas_virus_PAKP3, Psychrobacter_phage_pOW20-A, Puniceispirillum_phage_HMO-2011, Ralstonia phage phiRSL1, Ralstonia_phage_PE226, Ralstonia_phage_RS603, Ralstonia_phage_RSB1, Ralstonia_phage_RSB3, Ralstonia_phage_RSF1, Ralstonia_phage_RSJ2, Ralstonia_phage_RSJ5, Ralstonia_phage_RSK1, Ralstonia_phage_RSL2, Ralstonia_phage_RSM1, Ralstonia_phage_RSM3, Ralstonia_phage_RSMSuper, Ralstonia_phage_RSP15, Rhizobium_phage_RHE, Rhizobium_phage_RHEph01, Rhizobium_phage_vB_RglS_P106B, Rhizobium_phage_vB_RleM_P10VF, Rhizobium_phage_vB_RIeS_L338C, Rhizobium_virus_RHEph4, Rhodobacter_phage_RC1, Rhodobacter_phage_RcapMu, Rhodobacter_phage_RcTitan, Rhodococcus_phage_E3, Rhodococcus_phage_REQ 1, Rhodococcus_phage_ReqiPepy6, Rhodococcus_phage_ReqiPine5, Rhodococcus_phage_ReqiPoco6, Rhodococcus_phage_RGL3, Rhodoferax_phage_P26218, Rhodovulum_phage_RS1, Riemerella_phage_RAP44, Roseobacter_phage_RDJL_Phi_1, Roseobacter_phage_SIO1, Salinivibrio_phage_CW02, Salmonella phage SPC32H, Salmonella phage SPC32N, Salmonella_phage_100268_sal2, Salmonella_Phage_103203_sal5, Salmonella_phage_1118970_ sal1, Salmonella_phage_118970_sal2, Salmonella_ phage_118970_sal4, Salmonella_phage_36, Salmonella_phage_37, Salmonella_phage_38, Salmonella_phage_7-11, Salmonella_phage_BP12C, Salmonella_ phage_BP63, Salmonella_phage_BPS15Q2, Salmonella_phage_Chi, Salmonella_phage_Det7, Salmonella_phage_epsilon15, Salmonella_phage_epsilon34, Salmonella_phage_FelixO1, Salmonella_phage_FSL_SP-058, Salmonella_phage_FSL_SP-076, Salmonella_phage_g341c, Salmonella_phage_GG32, Salmonella_phage_HB-2014, Salmonella_phage_HK620, Salmonella_phage_iEPS5, Salmonella_phage_IME207, Salmonella_phage_Marshall, Salmonella_phage_Maynard, Salmonella_phage_NRO1, Salmonella_phage_phiSG-JL2, Salmonella_phage_PhiSH19, Salmonella_phage_phSE-2, Salmonella_phage_SE1, Salmonella_phage_SEN22, Salmonella_phage_SEN34, Salmonella_phage_SEN4, Salmonella_phage_SEN5, Salmonella_phage_SFP10, Salmonella_phage_Shivani, Salmonella_phage_SJ46, Salmonella_phage_SKML-39, Salmonella_phage_SPC32H, Salmonella_phage_SPC32N, Salmonella_phage_Spc35, Salmonella_phage_SPN19, Salmonella_phage_SPN1S, Salmonella_phage_SPN3US, Salmonella_phage_SPN9CC, Salmonella_phage_SPN9TCW, Salmonella_phage_SSU5, Salmonella_phage_ST160, Salmonella_phage_ST64T, Salmonella_phage_Stitch, Salmonella_phage_STP4-a, Salmonella_phage_vB_SalM_PM10, Salmonella_phage_vB_SalM_SJ2, Salmonella_phage_vB_SalM_SJ3, Salmonella_phage_vB_SemP_Emek, Salmonella_phage_vB_SnwM_CGG4-1, Salmonella_phage_Vi_II-E1, Salmonella_phage_Vi06, Salmonella_phage_Vil, Salmonella_virus_9NA, Salmonella_virus_P22, Salmonella_virus_S16, Salmonella_virus_SE1, Salmonella_virus_SP31, Salmonella_virus_SSE121, Salmonella_virus_STML198, Serratia_phage_Eta, Serratia_phage_phiMAM1, Serratia_phage_PS2, Shewanella_phage_Spp001, Shewanella_sp._phage_1/4, Shewanella_sp._phage_1/40, Shewanella_sp._phage_1/41, Shewanella_sp._phage_1/44, Shigella_phage_Ag3, Shigella_phage_POCJ13, Shigella_phage_pSf-1, Shigella_phage_Sf6, Shigella_phage_SHBML-50-1, Shigella_phage_SHFML-11, Shigella_phage_SHFML-26, Shigella_phage_SHSML-45, Shigella_phage_SHSML-52-1, Shigella_virus_PSf2, Shigella_virus_Pssl, Shigella_virus_Sbl, Shigella_virus_Shfl1, Shigella_virus_Shf12, Shigella_virus_SP18, Silicibacter_phage_DSS3phi2, Sinorhizobium_phage_PBC5, Sinorhizobium_phage_phiLM21, Sinorhizobium_phage_phiM9, Sodalis_phage_SO1, Sphingomonas_phage_PAU, Spiroplasma_kunkelii_virus_SkV1_CR2-3x, Spiroplasma_phage_1-C74, Spiroplasma_phage_4, Spiroplasma_phage_SVTS2, Staphylococcus phage S13', Staphylococcus_phage_13, Staphylococcus_phage_187, Staphylococcus_phage_23MRA, Staphylococcus_phage_2638A, Staphylococcus_phage_37, Staphylococcus_phage_3A, Staphylococcus_phage_42E, Staphylococcus_phage_44AHJD, Staphylococcus_phage_47, Staphylococcus_phage_ 52A, Staphylococcus_phage_53, Staphylococcus_phage_55, Staphylococcus_phage_66, Staphylococcus_phage_69, Staphylococcus_phage_71, Staphylococcus_phage_77, Staphylococcus_phage_80, Staphylococcus_phage_ 80alpha, Staphylococcus_phage_812, Staphylococcus_phage_85, Staphylococcus_phage_88, Staphylococcus_ phage_92, Staphylococcus_phage_96, Staphylococcus_phage_B166, Staphylococcus_phage_B236, Staphylococcus_phage_BP39, Staphylococcus_phage_CNPH82, Staphylococcus_phage_CNPx, Staphylococcus_ phage_DW2, Staphylococcus_phage_EW, Staphylococcus_phage_GRCS, Staphylococcus_phage_IME-SA4, Staphylococcus_phage_lpla35, Staphylococcus_phage_lpla5, Staphylococcus_phage_lpla7, Staphylococcus_phage_l pla88, Staphylococcus_phage_JS01, Staphylococcus_phage_LH1, Staphylococcus_phage_P68, Staphylococcus_phage_P954, Staphylococcus_phage_PH15, Staphylococcus_phage_Phil2, Staphylococcus_phage_phi5967PVL, Staphylococcus_phage_phi7247PVL, Staphylococcus_phage_phi724PVL, Staphylococcus_phage_phi7401 PVL, Staphylococcus_phage_phiBU01, Staphylococcus_phage_phiETA, Staphylococcus_phage_phiETA2, Staphylococcus_ phage_phiETA3, Staphylococcus_phage_philBB-SEP1, Staphylococcus_phage_philPLA-C1C, Staphylococcus_phage_philPLA-RODI, Staphylococcus_phage_phiJB, Staphylococcus_phage_phiMR11, Staphylococcus_phage_phiMR25, Staphylococcus_phage_phinm1, Staphylococcus_phage_phinm2, Staphylococcus_phage_phiNM3, Staphylococcus_phage_phinm4, Staphylococcus_phage_phiRS7, Staphylococcus_phage_phiSa1119, Staphylococcus_phage_PVL, Staphylococcus_phage_Pvl108, Staphylococcus_phage_ROSA, Staphylococcus_phage_S13, Staphylococcus_phage_S24-1, Staphylococcus_phage_S25-4, Staphylococcus_phage_SA1, Staphylococcus_phage_SA12, Staphylococcus_phage_SA13, Staphylococcus_phage_SAP-2, Staphylococcus_phage_Sap26, Staphylococcus_phage_Sb-1, Staphylococcus_ phage_SLPW, Staphylococcus_phage_St, Staphylococcus_phage_SMSAP5, Staphylococcus_phage_SP5, Staphylococcus_phage_SP6, Staphylococcus_phage_SPbeta-like, Staphylococcus_phage_Stau2, Staphylococcus_phage_S-tauST398-1, Staphylococcus_phage_StauST398-2, Staphylococcus_phage_StauST398-3, Staphylococcus_phage_S-tauST398-4, Staphylococcus_phage_StauST398-5, Staphylococcus_phage_StB12, Staphylococcus_ phage_StB20, Staphylococcus_phage_StB20-like, Staphylococcus_phage_StB27, Staphylococcus_phage_TEM 123, Staphylococcus_phage_tp310-2, Staphylococcus_phage_T-wort, Staphylococcus_phage_vB_SauM_Remus, Staphylococcus_phage_vB_SauM_Romulus, Staphylococcus_phage_vB_SauS_phi2, Staphylococcus_phage_YMC/09/04/R1988, Staphylococcus_prophage_phiPV83, Staphylococcus_virus_Fi200W, Staphylococcus_virus_676Z, Staphylococcus_virus_A3R, Staphylococcus_virus_A5W, Staphylococcus_virus_Fi200W, Staphylococcus_virus_G1, Staphylococcus_virus_G15, Staphylococcus_virus_ME-SA1, Staphylococcus_virus_ME-SA2, Staphylococcus_virus_ISP, Staphylococcus_virus_JD7, Staphylococcus_virus_K, Staphylococcus_virus_MCE2014, Staphylococcus_virus_MSA6, Staphylococcus_virus_P108, Staphylococcus_virus_P4W, Staphylococcus_virus_S253, Staphylococcus_virus_SA11, Staphylococcus_virus_SA12, Staphylococcus_virus_SA5, Staphylococcus_virus_SEP9, Staphylococcus_virus_Sextaec, Staphylococcus_virus_Staph 1N, Staphylococcus_virus_Team 1, Stenotrophomonas_phage_vB_SmaS-DLP, Stenotrophomonas_virus_ME13, Streptococcus_phage_2972, Streptococcus_ phage_5093, Streptococcus_phage_7201, Streptococcus_phage_858, Streptococcus_phage_A25, Streptococcus_phage_Abc2, Streptococcus_phage_Alq 132, Streptococcus_phage_APCM01, Streptococcus_phage_C1, Streptococcus_phage_Cp-1, Streptococcus_phage_Dp-1, Streptococcus_phage_DT1, Streptococcus_phage_EJ-1, Streptococcus_phage_M102, Streptococcus_phage_MM1, Streptococcus_phage_MM1_1998, Streptococcus_phage_O1205, Streptococcus_phage_P9, Streptococcus_phage_ phi3396, Streptococcus_phage_phi7917, Streptococcus_phage_phi891591, Streptococcus_phage_phiARl0468-4, Streptococcus_phage_phiARl0746, Streptococcus_phage_phiARl0923, Streptococcus_phage_phiNJ2, Streptococcus_phage_phiSS12, Streptococcus_phage_phiST 1, Streptococcus_phage_Sfi11, Streptococcus_ phage_Sfi19, Streptococcus_phage_Sfi21, Streptococcus_ phage_SMP, Streptococcus_phage_SOCP, Streptococcus_phage_SPQS1, Streptococcus_phage_SpSL1, Streptococcus_phage_Str-PAP-1, Streptococcus_phage_T12, Streptococcus_phage_TP-778L, Streptococcus_phage_TP-J34, Streptococcus_phage_YMC-2011, Streptococcus_virus_9871, Streptococcus_virus_9872, Streptococcus_virus_9874, Streptomyces_phage_Caliburn, Streptomyces_phage_Jay2Jay, Streptomyces_phage_mu1/6, Streptomyces_ phage_phiSAJS1, Streptomyces_phage_phiSASD 1, Streptomyces_phage_TP1604, Stx2-converting_phage_86, Stygiolobus_rod-shaped_virus, Sulfitobacter_phage_EE36phi1, Sulfitobacter_phage_phiCB2047-B, Sulfolobales_Mexican_ fusellovirus_1, Sulfolobales_Mexican_rudivirus_1, Sulfolobus_islandicus_filamentous_virus, Sulfolobus_islandicus_rod-shaped_virus_1, Sulfolobus_islandicus_rod-shaped_virus_2, Sulfolobus_islandicus_rudivirus_3, Sulfolobus_spindle-shaped_virus_1, Sulfolobus_spindle-shaped_virus_2, Sulfolobus_spindle-shaped_virus_4, Sulfolobus_spindle-shaped_virus_6, Sulfolobus_spindle-shaped_virus_7, Sulfolobus_virus_Ragged_Hills, Sulfolobus_virus_STSV1, Sulfolobus_virus_STSV2, Synechococcus_phage_ACG-2014b, Synechococcus_phage_ACG-2014c, Synechococcus_phage_ACG-2014d, Synechococcus_phage_ACG-2014e, Synechococcus_phage_ACG-2014f, Synechococcus_phage_ACG-2014g, Synechococcus_phage_ACG-2014h, Synechococcus_phage_ACG-2014i, Synechococcus_phage_ACG-2014j, Synechococcus_phage_metaG-MbCM 1, Synechococcus_phage_P60, Synechococcus_phage_S-CAM1, Synechococcus_phage_S-CAM8, Synechococcus_phage_S-CBP1, Synechococcus_phage_S-CBP4, Synechococcus_phage_S-CBP42, Synechococcus_phage_S-CBS2, Synechococcus_phage_S-CBS4, Synechococcus_phage_S-CRM01, Synechococcus_phage_S-IOM 18, Synechococcus_phage_S-MbCM 100, Synechococcus_phage_S-PM2, Synechococcus_phage_S-RIM2, Synechococcus_phage_S-RIM8, Synechococcus_phage_S-RIP2, Synechococcus_phage_S-RSM4, Synechococcus_phage_S-ShM2, Synechococcus_phage_S-SKS1, Synechococcus_phage_S-SM1, Synechococcus_phage_S-SM2, Synechococcus_phage_S-SSM4, Synechococcus_phage_S-SSM5, Synechococcus_phage_S-SSM7, Synechococcus_phage_S-WAM1, Synechococcus_phage_S-WAM2, Synechococcus_phage_Syn9, Synechococcus_phage_Syn5, Synechococcus_phage_syn9, Temperate_phage_phiNIH1.1, Thalassomonas_phage_BA3, Thermoanaerobacterium_phage_THSA-485A, Thermoproteus_tenax_spherical_virus_1, Thermoproteus_tenax_virus_1, Thermus_phage_P7426, Thermus_phage_phiYS40, Thermus_phage_TMA, Tsukamurella_phage_TIN2, Tsukamurella_phage_TIN3, Tsukamurella_phage_TPA2, Tsukamurella_phage_TPA4, Uncultured_phage_WW-nAnB_ strain_3, Vibrio phage ICP3_2007_A, Vibrio phage ICP3_2008_A, Vibrio_phage_l, Vibrio_phage_CHOED, Vibrio_phage_CJY, Vibrio_phage_CP-T1, Vibrio_ phage_fs2, Vibrio_phage_H1, Vibrio_phage_H2, Vibrio_ phage_H3, Vibrio_phage_ICP2, Vibrio_phage_ ICP2_2013_A_Haiti, Vibrio_phage_ICP3, Vibrio_ phage_J2, Vibrio_phage_JA-1, Vibrio_phage_KVP40, Vibrio_phage_N4, Vibrio_phage_nt-1, Vibrio_phage_phi_l, Vibrio_phage_phi_3, Vibrio_phage_PVA1, Vibrio_ phage_pVp-1, Vibrio_phage_pYD21-A, Vibrio_phage_pYD38-A, Vibrio_phage_pYD38-B, Vibrio_phage_QH, Vibrio_phage_SIO-2, Vibrio_phage_vB_VchM-138, Vibrio_phage_VBP32, Vibrio_phage_VBP47, Vibrio_phage_VCY-phi, Vibrio_phage_Vf12, Vibrio_phage_VFJ, Vibrio_phage_VfO3K6, Vibrio_phage_VfO4K68, Vibrio_phage_VH7D, Vibrio_phage_VpKK5, Vibrio_phage_VpV262, Vibrio_phage_VvAW1, Vibrio_phage_X29, Vibrio_virus_MAR, Vibrio_virus_MAR10, Vibrio_virus_ValKK3, Vibrio_virus_VC8, Vibrio_virus_VHML, Vibrio_virus_VP2, Vibrio_virus_VP5, Vibrio_virus_VP585, Vibriophage_VP4, Weissella_phage_phiYS61, Weissella_phage_WCP30, Xanthomonas phage XacF 1, Xanthomonas_citri_phage_CP2, Xanthomonas_phage_Cf1c, Xanthomonas_phage_CP1, Xanthomonas_phage_OP2, Xanthomonas_phage_vB_XveM_DIBBI, Xanthomonas_phage_Xp15, Xylella_phage_Paz, Xylella_phage_Prado, Xylella_phage_Salvo, Xylella_phage_Xfas53, Yersinia_phage_phiR1-37, Yersinia_phage_phiR201, Yersinia_phage_phiR8-01, Yersinia_phage_PY54, Yersinia_phage_vB_YenP_AP10, Yersinia_virus_D1, Yersinia_virus_PST, and Yersinia_virus_R1RT, Yersinia_virus_TG1.

In some embodiments is provided an antibody specific to one or more of the above-listed bacteriophages.

In some embodiments, bacteriophages comprising PrDs comprise glutamine/asparagine (Q/N) enriched PrDs. In some embodiments, PrDs are determined using protein analysis (e.g., Western blot, ELISA) and/or algorithms (e.g., PLAAC algorithm or PrionW). Non-limiting examples of bacteriophage proteins comprising PrDs include, e.g., proteins involved in interactions between bacteriophages and host cells such as, e.g., proteins associated with attachment and/or penetration (e.g., Tail protein, Baseplate wedge protein, Putative tail lysin, Collagen triple helix repeat protein, Tape measure protein, Central tail fiber, PblA-like tail protein, Gp36, Gp17, Gp22, Gp7, Gp25, Gp54, Gp4, TmpC) and proteins associated with release (e.g., D-ala-D-ala carboxypeptidase, Putative endolysin, Hydrolase, Amidase). Additional non-limiting examples of such proteins are provided in Examples 14-16 and the accompanying tables and figures. In some embodiments, PrD contained in the bacteriophage compositions of the invention are inactivated (e.g., using PrD-specific antibodies).

Further details on bacteriophage compositions of the present invention and their administration can be found, e.g., in U.S. Pat. No. 6,699,701, which is incorporated herein by reference in its entirety. In another aspect, the invention provides a method for preventing or treating a disease of gastrointestinal (GI) microbiota or consequences thereof in a mammal in need thereof, wherein said disease of GI microbiota is secondary to, associated with, or caused by, entry of a bacteriophage and/or component(s) thereof (e.g., bacteriophage protein(s) and/or nucleic acid(s)) into GI microbiota of the mammal, said method comprising administering to the mammal an effective amount of a probiotic or a prebiotic composition or a combination thereof, wherein said composition(s) stimulates growth and/or activity in the GI microbiota of the mammal of one or more strains of bacteria which strain(s) decreased in abundance as a direct or indirect result of bacteriophage entry into GI microbiota of the mammal. In one embodiment, the bacterial strain is from *Actinomycetalis, Bacillales, Bacteroidales, Bifidobacteriales, Burkholderiales, Campylobacteriales, Clostridiales, Enterobacteriales, Flavobacteriales, Fusobacteriales, Lactobacillales, Neiserriales, Pasteuralles, Pseudomonadales, Phodobacteriales, Rhodospirillales, Spirochaetalles, Verrucomicrobiales, Synergistales, Halanaerobiales, Mycoplasmatales, Xanthomonadales, Sphingobacteriales, Caulobacterales, Desulfobacterales, Legionellales, Oceanospirillales, Deinococcales, Methanobacteriales, Myxococcales, Anaerolineales, Methylophilales, Chromatiales, Thermales, Bdellovibrionales, Desulfuromonadales, Solirubrobacterales, Methanomicrobiales, Planctomycetales, Methylococcales, Anaeroplasmatales, Coriobacteriales, Desulfovibrionales, Rhizobiales, Rhodocyclales, Sphingomonadales,* or *Victivallales.*

In one embodiment, such strain(s) is from one or more of Streptococcaceae, Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said composition comprises one or more strains of bacteria from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said strain(s) is from one or more of *Clostridium, Eubacterium, Staphylococcus, Coprococcus, Lactobacillus, Faecalibacterium, Catenibacterium, Collinsella, Blautia, Bifidobacterium, Dorea,* and *Prevotella* genera. In one embodiment, said composition comprises one or more strains of bacteria from one or more of *Clostridium, Eubacterium, Staphylococcus, Coprococcus, Lactobacillus, Faecalibacterium, Catenibacterium, Collinsella, Blautia, Bifidobacterium, Dorea,* and *Prevotella* genera.

In a related aspect, the invention provides a method for preventing or treating an increase in intestinal permeability in a mammal in need thereof, wherein said increase in intestinal permeability is secondary to, associated with, or caused by entry of a bacteriophage and/or component(s) thereof (e.g., bacteriophage protein(s) and/or nucleic acid(s)) into the gastrointestinal (GI) microbiota of the mammal, said method comprising administering to the mammal an effective amount of a probiotic or a prebiotic composition or a combination thereof, wherein said composition(s) stimulates growth and/or activity in the GI microbiota of the mammal of one or more strains of bacteria which strain(s) decreased in abundance as a direct or indirect result of bacteriophage entry into GI microbiota of the mammal. Non-limiting examples of the families in which said strain(s) are associated include, but are not limited to, Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said composition comprises one or more strains of bacteria from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said strain(s) is from one or more of *Clostridium, Eubacterium, Staphylococcus, Coprococcus, Lactobacillus, Faecalibacterium, Catenibacterium, Collinsella, Blautia, Bifidobacterium, Dorea,* and *Prevotella* genera. In one embodiment, said composition comprises one or more strains of bacteria from one or more of *Clostridium, Eubacterium, Staphylococcus, Coprococcus, Lactobacillus, Faecalibacterium, Catenibacterium, Collinsella, Blautia, Bifidobacterium, Dorea,* and *Prevotella* genera.

In one embodiment of any of the above methods involving administering probiotic and/or prebiotic compositions, said composition(s) is administered by a route selected from the group consisting of oral, rectal, sublingual, and via naso/oro-gastric gavage.

In one embodiment of any of the above methods involving administering probiotic and/or prebiotic compositions, the GI microbiota is selected from the group consisting of cecal, ileal, colonic, and fecal microbiota. In one specific embodiment, the GI microbiota is fecal microbiota.

In another aspect, the invention provides a method for preventing or treating a disease of skin microbiota or consequences thereof in a mammal in need thereof, wherein said disease of skin microbiota is secondary to, associated with, or caused by, entry of a bacteriophage into skin microbiota of the mammal, said method comprising administering to the mammal an effective amount of a probiotic or a prebiotic composition or a combination thereof, wherein said composition(s) stimulates growth and/or activity in the skin microbiota of the mammal of one or more strains of bacteria which strain(s) decreased in abundance as a direct or indirect result of bacteriophage entry into skin microbiota of the mammal. Non-limiting examples of the families in which said strain(s) are associated include, but are not limited to, Streptococcaceae, Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said composition comprises one or more strains of bacteria from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, such strain(s) is from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera. In one embodiment, said composition comprises one or more strains of bacteria from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera.

In one embodiment of any of the above methods related to diseases of skin microbiota, said composition is administered by a route selected from the group consisting of topical, ocular, otic, intradermal and transdermal.

In another aspect, the invention provides, a method for preventing or treating a disease of mucosal microbiota or consequences thereof in a mammal in need thereof, wherein said disease of mucosal microbiota is secondary to, associated with, or caused by, entry of a bacteriophage and/or component(s) thereof (e.g., bacteriophage protein(s) and/or nucleic acid(s)) into mucosal microbiota of the mammal, said method comprising administering to the mammal an effective amount of a probiotic or a prebiotic composition or a combination thereof, wherein said composition(s) stimulates growth and/or activity in the mucosal microbiota of the mammal of one or more strains of bacteria which strain(s) decreased in abundance as a direct or indirect result of bacteriophage entry into mucosal microbiota of the mammal. In one embodiment, such strain(s) is from one or more of Streptococcaceae, Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said composition comprises one or more strains of bacteria from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families.

In one embodiment, said strain(s) of bacteria is from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera. In one embodiment, said composition comprises one or more strains of bacteria from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera.

In one embodiment of any of the above methods related to diseases of mucosal microbiota, said composition is administered by a route selected from the group consisting of mucosal, vaginal, by inhalation, intranasal, oral, sublingual, rectal, ocular, and otic.

In another aspect, the invention provides a method for increasing longevity and/or decreasing aging in a mammal in need thereof, wherein said aging is secondary to, associated with, or caused by, entry of a bacteriophage and/or component(s) thereof (e.g., bacteriophage protein(s) and/or nucleic acid(s)) into a microbiota of the mammal, said method comprising administering to the mammal an effective amount of a probiotic or a prebiotic composition or a combination thereof, wherein said composition(s) stimulates growth and/or activity in the microbiota of the mammal of one or more strains of bacteria which strain(s) decreased in abundance as a direct or indirect result of bacteriophage entry into the microbiota of the mammal. In one embodiment, such strain(s) is from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families. In one embodiment, said composition comprises one or more strains of bacteria from one or more of Staphylococcaceae, Prevotellaceae, Lactobacillaceae, Lachnospiraceae, Erysipelotrichaceae, Coriobacteriaceae, Clostridiaceae, Bacillaceae, and Bifidobacteriaceae families.

In one embodiment, such strain(s) is from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera. In one embodiment, said composition comprises one or more strains of bacteria from one or more of *Clostridium, Eubacterium, Staphylococcus, Coprococcus, Lactobacillus, Faecalibacterium, Catenibacterium, Collinsella, Blautia, Bifidobacterium, Dorea*, and *Prevotella* genera.

In one embodiment of the above methods related to increasing longevity and/or decreasing aging, the aging is skin aging.

In one embodiment of the above methods related to increasing longevity and/or decreasing aging, the microbiota is selected from the group consisting of gastrointestinal (GI) microbiota (e.g., cecal, ileal, colonic, or fecal microbiota), mucosal microbiota, skin microbiota, microbiota of respiratory system, microbiota of otorhinolaryngology, and microbiota of urinary tract.

In one embodiment of the above methods related to increasing longevity and/or decreasing aging, the probiotic and/or prebiotic composition(s) is administered by a route selected from the group consisting of oral, rectal, sublingual, via naso/oro-gastric gavage, topical, ocular, otic, intradermal, transdermal, mucosal, vaginal, by inhalation, intranasal, oral, sublingual, rectal, ocular, and otic.

In one embodiment of any of the above methods related to administering a probiotic composition, said probiotic composition comprises one or more components selected from the group consisting of live bacterial cells, spores, conditionally lethal bacterial cells, inactivated bacterial cells, killed bacterial cells, recombinant carrier strains, cell extract, and bacterially-derived products. In various embodiments, the probiotic composition does not comprise any bacteriophages.

In one embodiment of any of the above methods related to administering a probiotic and/or prebiotic compositions, administering such probiotic and/or prebiotic compositions can be combined with any one or more of the above-specified methods for (i) inhibiting entry of bacteriophages into microbiota of the mammal and/or (ii) inactivating or modifying bacteriophages present in microbiota of the mammal and/or (iii) inactivating or modifying bacteriophages in one or more of food, drinking water, water for washing, water for air humidification, air, or habitat object of the mammal.

In one embodiment of any of the above methods, the mammal is human.

In another aspect, the invention provides a method for identifying a mammalian population that is sensitive to bacteriophage entry into the body comprising evaluating one or more of alterations to the human genome, expression of a particular protein, alteration of the microbiota composition in a qualitative and/or quantitative manner, an alteration of the KEGG pathway.

In one embodiment of the above methods relating to identifying a mammalian population, the mammalian population has reduced number of bacteria associated with a gene-ontology (GO) term of a KEGG pathway as compared to a corresponding healthy human or animal population.

In one embodiment of the above methods relating to identifying a mammalian population, the mammalian population has a reduced number of lytic and temperate bacteriophages as compared to a corresponding healthy human or animal population.

In one embodiment of the above methods relating to identifying a mammalian population, the mammalian population has a known genetic predisposition to a disease In one embodiment of the above methods relating to identifying a mammalian population, the bacteriophage enters the body through the gut or a biological fluid.

In one embodiment of the above methods relating to identifying a mammalian population, bacteriophage entry into the body is associated with the triggering of a disease or the progression of a disease. Non-limiting examples of diseases include, but are not limited to, bacteriophage entry into the body is associated with triggering or progression of endotoxemia, oncological diseases, obesity, age-related skin changes, vaginosis, irritable bowel syndrome, non-specific ulcerative colitis, celiac disease, diabetes, rheumatoid arthritis, multiple sclerosis, Amyotrophic Lateral Sclerosis, CADASIL Syndrome, Huntington's disease, stroke, psoriasis, Sudden arrhythmic death syndrome, depressive disorder, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia), Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, Crohn's disease, atopic dermatitis, ankylosing spondylitis, neurodegenerative diseases, bipolar disorder, schizophrenia, psoriasis, systemic lupus erythematosus (SLE), scleroderma, liver failure, cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, autism and autism spectrum disorder, primary biliary cirrhosis, primary sclerosing cholangitis, and asthma.

In another aspect, the invention provides a method for inhibiting entry of bacteriophages or components thereof into a body fluid during blood transfusion to a mammal, comprising treating said blood prior to its administration to the mammal to inactivate or modify bacteriophages and/or component(s) thereof contained in the body fluid.

In one embodiment of the above methods relating to inhibiting entry of bacteriophages or components thereof into a body fluid during blood transfusion to a mammal, the bacteriophage inactivation comprises treating said blood with filtration or an agent selected from the group consisting of polyhexamethylene guanidine derivatives, ozone, a peroxide, a metal, an antibody, an antibacteriophagal agent, free radicals, halogen-containing compounds, cationic compounds, glycolytic enzymes, nisin, anti-bacteriophage antibodies and one or more components of a bacterial or fungal biofilm matrix.

In one embodiment of the above methods relating to inhibiting entry of bacteriophages or components thereof into a body fluid during blood transfusion to a mammal, the agent or the component of the biofilm matrix is in a form selected from the group consisting of a liquid, a tablet, a capsule, drops, a lozenge, a gel, an ointment, a suppository, a chewing gum, and a candy.

In one embodiment of the above methods relating to inhibiting entry of bacteriophages or components thereof into a body fluid during blood transfusion to a mammal, the agent or the component of the biofilm matrix is administered in combination with at least one other compound that increases the activity of said agent or component.

In one embodiment of the above methods relating to inhibiting entry of bacteriophages or components thereof into a body fluid during blood transfusion to a mammal, the agent or the component of the biofilm matrix is contained in a composition further comprising a carrier or excipient.

In one embodiment of the above methods relating to inhibiting entry of bacteriophages or components thereof into a body fluid during blood transfusion to a mammal, the bacteriophage or the component thereof comprises a polypeptide with a prion-like domain.

In one embodiment of the above methods relating to inhibiting entry of bacteriophages or components thereof into a body fluid during blood transfusion to a mammal, the method further comprises detecting the presence of a bacteriophage or a component thereof in the blood, plasma, or serum of a donor and/or a recipient before, during or after the blood transfusion.

In one embodiment of the above methods relating to inhibiting entry of bacteriophages or components thereof into a body fluid during blood transfusion to a mammal, the method further comprises detecting the presence of a mammalian host protein or a bacterial host protein in the blood, plasma, or serum of a donor and/or a recipient before, during or after the blood transfusion, wherein the mammalian host protein or the bacterial host protein appears as a result of the presence of a bacteriophage in the blood, the plasma, or the serum of the donor and/or the recipient during the blood transfusion.

In another aspect, the invention provides a method for detecting a bacteriophage polypeptide comprising a prion-like domain comprising performing an assay selected from the group consisting of protein misfolding cyclic amplification and staining.

In one embodiment of the above methods relating to detecting a bacteriophage polypeptide comprising a prion-like domain, the staining comprises applying Congo red or thioflavin.

In another aspect, the invention provides a method for detecting a misfolded protein aggregate in a mammalian biological fluid comprising performing an assay selected from the group consisting of protein misfolding cyclic amplification and staining, wherein the misfolded protein aggregate formed after a bacteriophage polypeptide comprising a prion-like domain entered the mammal.

In one embodiment of the above methods relating to detecting a misfolded protein aggregate in a mammalian biological fluid, the misfolded protein aggregate comprises a bacteriophage protein comprising a prion-like domain.

In one embodiment of the above methods relating to detecting a misfolded protein aggregate in a mammalian biological fluid, the staining comprises applying Congo red or thioflavin.

In one embodiment of the above methods relating to detecting a bacteriophage polypeptide or a misfolded protein aggregate, the method is performed in connection with an endpoint in a clinical trial.

In another aspect, the invention provides a method for detecting an alteration in a bacteriophage protein comprising a prion-like domain, wherein the method comprises performing one or more of a protein misfolding cyclic amplification assay.

In another aspect, the invention provides a method of selecting a patient for a clinical trial comprising detecting the presence of a bacteriophage or a component thereof in the blood, plasma, or serum of the patient.

In one embodiment of the above methods relating to selecting a patient for a clinical trial, the method further comprises selecting the patient for the clinical trial if the bacteriophage or the component thereof is not present in the blood, plasma, or serum of the patient.

In one embodiment of the above methods relating to selecting a patient for a clinical trial, the method further comprises selecting the patient for the clinical trial if the bacteriophage or the component thereof is present in the blood, plasma, or serum of the patient.

In another aspect, the invention provides a composition comprising a probiotic, wherein the composition does not comprise a bacteriophage.

In one embodiment of the above aspect relating to a composition comprising a probiotic, the bacteriophage is a temperate bacteriophage. In one embodiment of the above aspect relating to a composition comprising a probiotic, the bacteriophage is a lytic bacteriophage. In one embodiment of the above aspect relating to a composition comprising a probiotic, the bacteriophage comprises a polypeptide with a prion-like domain. In one embodiment of the above aspect relating to a composition comprising a probiotic, the composition may be used to prevent a disease. Non-limiting examples of diseases include, but are not limited to, bacteriophage entry into the body is associated with triggering or progression of endotoxemia, oncological diseases, obesity, age-related skin changes, vaginosis, irritable bowel syndrome, non-specific ulcerative colitis, celiac disease, diabetes, rheumatoid arthritis, multiple sclerosis, Amyotrophic Lateral Sclerosis, CADASIL Syndrome, Huntington's disease, stroke, psoriasis, Sudden arrhythmic death syndrome, depressive disorder, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia), Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, Crohn's disease, atopic dermatitis, ankylosing spondylitis, neurodegenerative diseases, bipolar disorder, schizophrenia, psoriasis, systemic lupus erythematosus (SLE), scleroderma, liver failure, cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, autism and autism spectrum disorder, primary biliary cirrhosis, primary sclerosing cholangitis, and asthma.

In another aspect, the invention provides a method of vaccinating a mammal (e.g., a human) against a bacteriophage. In a related aspect, the invention provides a method of vaccinating a mammal against a bacteriophage comprising administering a composition to the mammal comprising a polypeptide or epitope of the bacteriophage.

In one embodiment of the above aspect relating to a method of vaccinating a mammal, the bacteriophage is a temperate bacteriophage. In one embodiment of the above aspect relating to a method of vaccinating a mammal, the bacteriophage is a lytic bacteriophage. In one embodiment of the above aspect relating to a method of vaccinating a mammal, the bacteriophage comprises a polypeptide with a prion-like domain.

In another aspect, the invention provides a humanized microbiota composition for use in an animal model, where the composition comprises a microbiota from a human and bacteriophages. In one embodiment, the bacteriophages are temperate bacteriophages. In one embodiment, the bacteriophages are lytic bacteriophages. In one embodiment, the bacteriophages comprise a polypeptide with a prion-like domain. In one embodiment, the bacteriophages do not comprise a polypeptide with a prion-like domain.

In another aspect, the invention provides a method for diagnosing the safety of the deposition of microbiota into a mammal, where the method comprises identifying whether a disease-promoting bacteriophage is present in the microbiota. In one embodiment, the disease-promoting bacteriophage is a lytic bacteriophage. In one embodiment, the disease-promoting bacteriophage comprises a polypeptide with a prion-like domain.

In another aspect, the invention provides a method for inactivating bacteriophages in a microbiota for deposition in a mammal, where the method comprises treating the microbiota to inactivate or modify bacteriophages contained in the microbiota for deposition. In one embodiment, the microbiota are treated prior to deposition in the mammal. In one embodiment, the microbiota are treated during deposition in the mammal. In one embodiment, the microbiota are treated after deposition in the mammal. In various embodiments, the mammal is a human.

In various embodiments of the above aspects, the mammal is a human, the mammalian population is a human population, or the patient is a human.

In another aspect, the invention provides an antibody specific to a bacteriophage listed in Table 18 or Table 19.

In another aspect, the invention provides an antibody specific to a PrD in a bacteriophage. In some embodiments, the bacteriophage is listed in Table 18 or Table 19.

In another aspect, the invention provides an antibody specific to a bacteriophage receptor on a bacterium or a eukaryotic cell, where the bacteriophage receptor is capable of binding to a bacteriophage listed in Table 18 or Table 19.

In another aspect, the invention provides a method of preventing bacteriophage entry into a bacterium. The method comprises contacting the bacterium with a gene editing nuclease configured to introduce a mutation into the genome of the bacterium, where the mutation is effective to reduce the expression or the function of a gene, and in which the gene encodes a protein whose function is required for a bacteriophage to enter the bacterium or to replicate within the bacterium. In some embodiments, the gene editing nuclease is CRISPR, Cas9, CasX, or CasY. In some embodiments, the gene editing nuclease introduces a palindromic repeat sequence into the genome.

In another aspect, the invention provides a use of lactic acid bacteria in food processing, where the lactic acid bacteria do not comprise a bacteriophage that causes a disease or a bacteriophage that causes increased intestinal permeability. In some embodiments, the disease is endotoxemia, an oncological disease, obesity, irritable bowel syndrome (IBS), non-specific ulcerative colitis, celiac disease, diabetes, rheumatoid arthritis, multiple sclerosis, CADASIL Syndrome, stroke, psoriasis, age-related changes of skin, vaginosis, Sudden arrhythmic death syndrome, Crohn's disease, atopic dermatitis, ankylosing spondylitis, systemic lupus erythematosus (SLE), scleroderma, liver failure, liver cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, primary biliary cirrhosis, primary sclerosing cholangitis, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia), Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, asthma, bipolar disorder, schizophrenia, depressive disorder, autism, autism spectrum disorders, Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD), Amyotrophic Lateral Sclerosis (ALS), Huntington's disease, a disease associated with the formation of a misfolded protein, Alzheimer's disease, Parkinson's disease, Spinal muscular atrophy, other neurodegenerative diseases, vaginitis, skin diseases, intestinal disorders, ulcerative colitis, inflammatory bowel diseases crohn's disease, Psoriasis, atopic dermatitis, asthma, cystic fibrosis, chronic obstructive pulmonary disease, and pathologies of the oral cavity. In some embodiments, the oncological disease is a cancer. In some embodiments, the oncological disease is a malignancy. In some embodiments, the disease is an amyloidosis.

In another aspect, the invention provides a method for processing a food product, the method comprising adding a bacteriophage not comprising a PrD, or a protein comprising a PrD, to the food product. In some embodiments, no PrD-containing proteins are encoded by, or otherwise present in, the bacteriophage. In some embodiments, the method comprises adding a bacteriophage not comprising a PrD, or a protein comprising a PrD, on the surface of the bacteriophage to the food product. In some embodiments, the bacteriophage does not comprise a PrD on a structure on the surface of the bacteriophage.

In another aspect, the invention provides a method for treating water, the method comprising adding a bacteriophage not comprising a PrD, or a protein comprising a PrD, to the water. In some embodiments, no PrD-containing proteins are encoded by, or otherwise present in, the bacteriophage. In some embodiments, the method comprises adding a bacteriophage not comprising a PrD, or a protein comprising a PrD, on the surface of the bacteriophage to the water. In some embodiments, the bacteriophage does not comprise a PrD, or a protein comprising a PrD, on a structure on the surface of the bacteriophage.

These and other aspects of the present invention will be apparent to those of ordinary skill in the art in the following description, claims and drawings.

BRIEF DESCRIPTION OF THE DRAWINGS

FIG. 1A shows changes in lactulose:mannitol ratio before and after treatment with the bacteriophage cocktail. FIG. 1B shows serum concentrations of CIC before and after treatment with the bacteriophage cocktail. In both FIGS. 1A and 1B, data are expressed as the mean±SE. *$P<0.05$ (Wilcoxon signed-rank test).

In FIG. 2A, intestinal permeability is expressed as the lactulose/mannitol ratio. Treatment with bacteriophages resulted in a significant alteration of intestinal permeability ($p<0.05$). FIG. 2B shows parameters of endotoxemia. Administration of bacteriophages increased the serum LPS levels ($p<0.05$). FIGS. 2C-2E show serum levels of inflammation-related cytokines: (FIG. 2C) TNF-$\alpha$, (FIG. 2D) IL-1$\beta$, and (FIG. 2E) IL-6. Data are expressed as the means±standard error of the mean (SEM). The nonparametric paired Wilcoxon signed-rank test was applied to the analysis of pre- and post-challenge differences.

FIG. 3A shows bacterial richness across the samples was calculated using Chao 1 and ACE. FIG. 3B shows bacterial diversity was evaluated using the Shannon, Simpson, and inverse Simpson parameters. $p<0.05$ using t-test analysis.

(FIG. 8A) Graphical representation of the highest LLR value in this group of proteins identified in the *Listeria* phage LMSP-25. (FIG. 8B) Graphical representation of the lowest LLR value in this group of proteins in the *Streptococcus* phage 5093.

FIG. 11 shows a statistical analysis of the bacteriophage families having more than five PrDs.

Figure 12F:
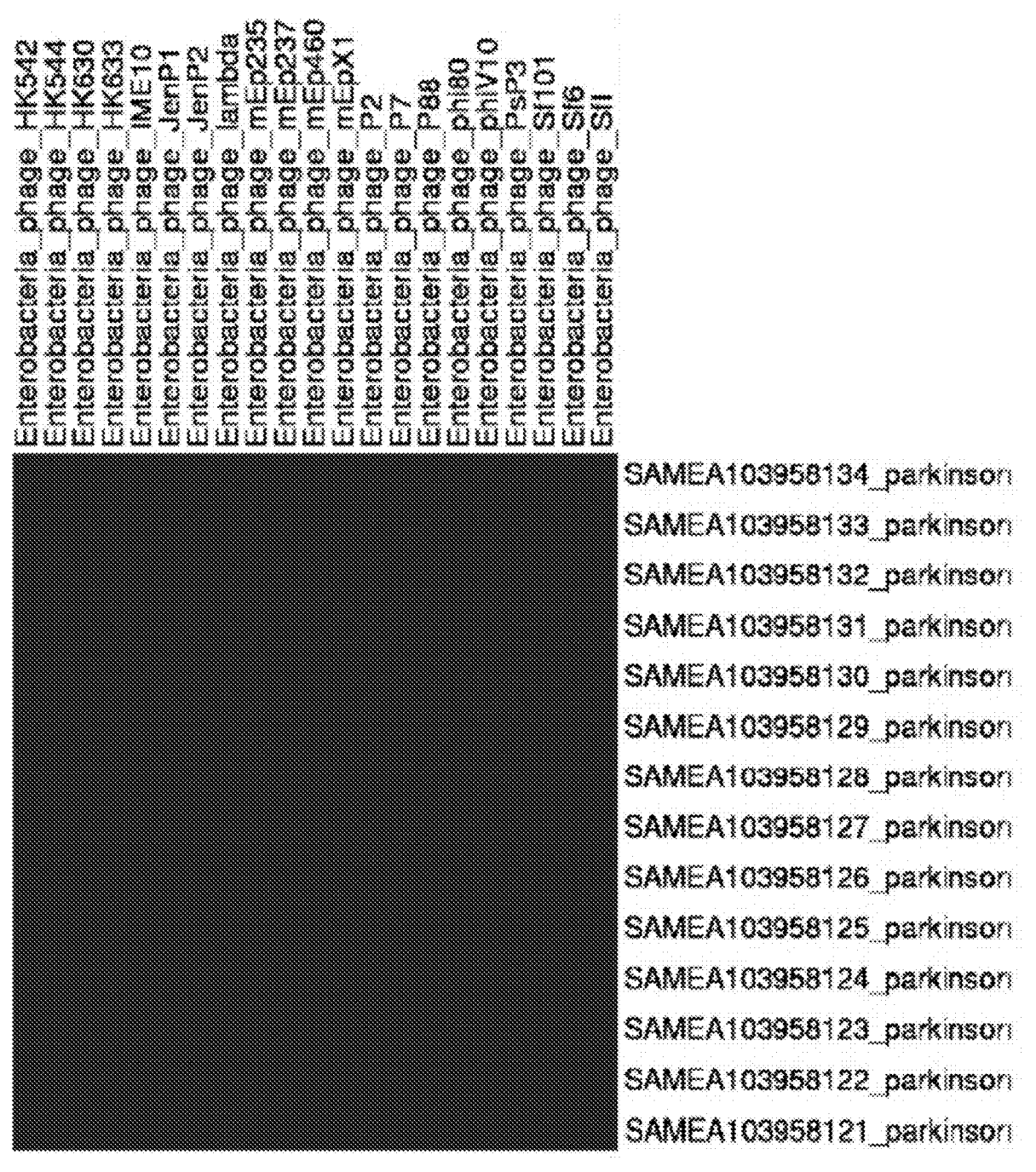
Figure 12F:
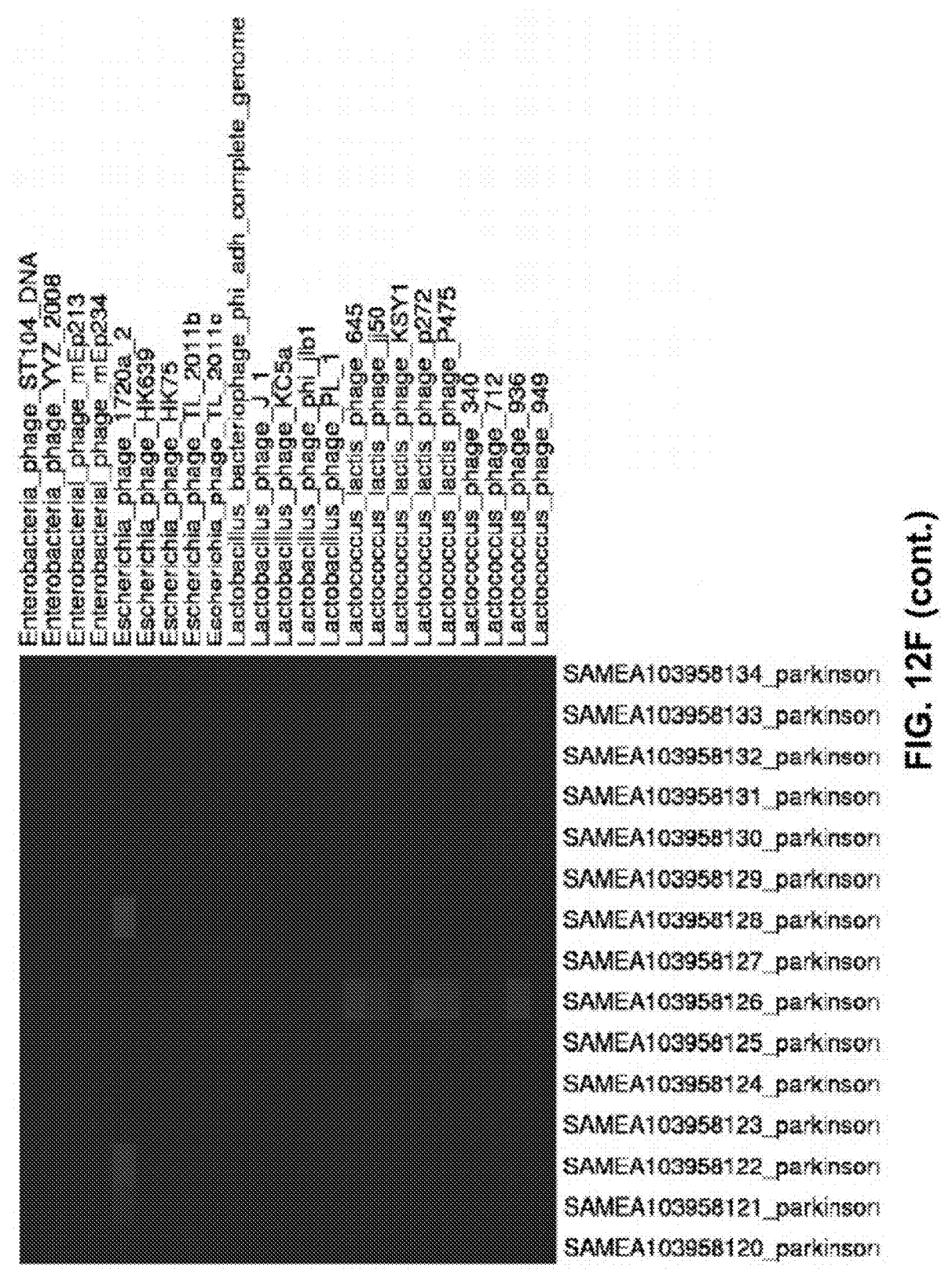
Figure 12F:
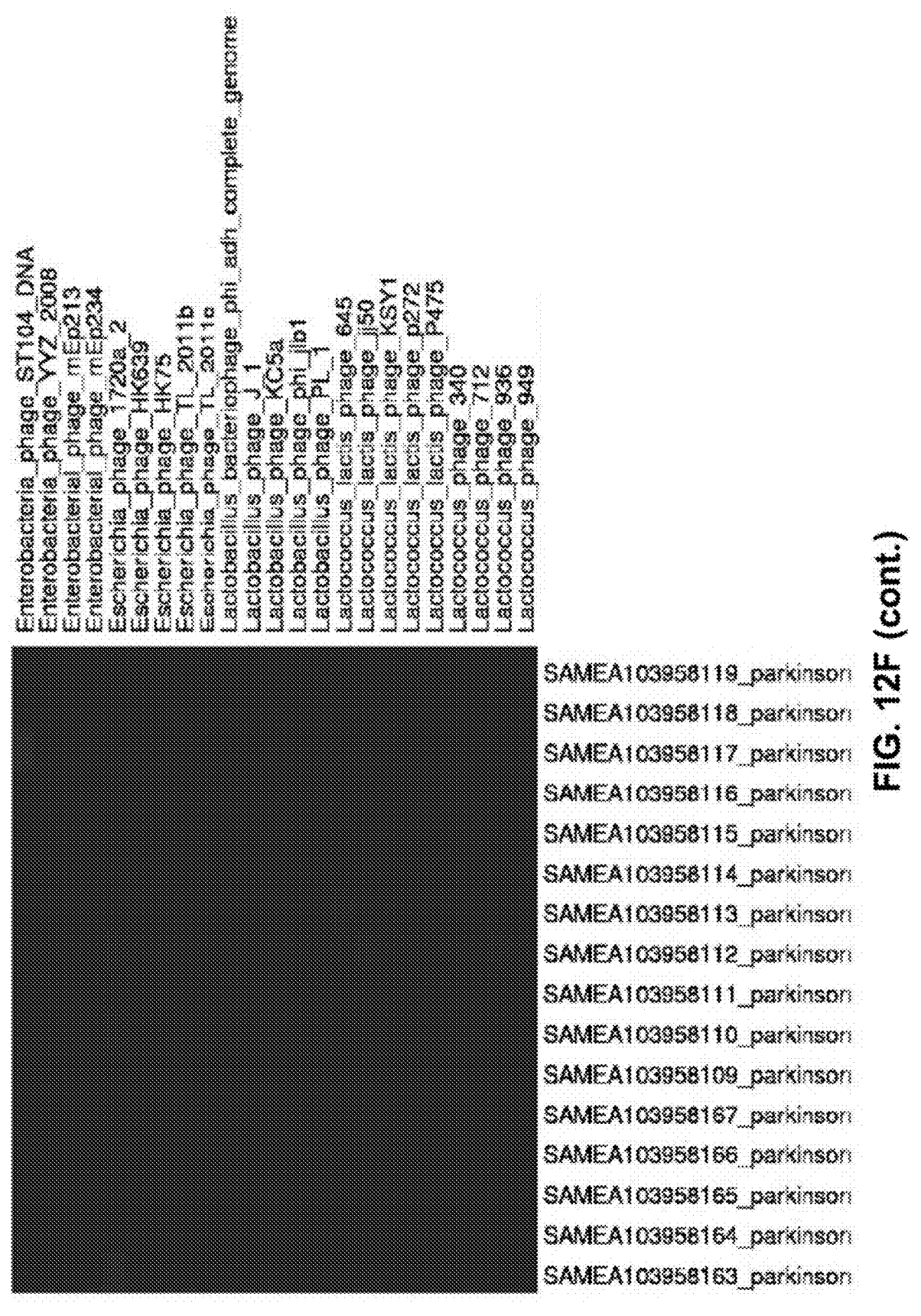

FIGS. 12A-12J are diagrams showing the quantification of phages in the human gut. The abundance of each bacteriophage taxon was used to determine its rank. Each row represents a bacteriophage taxon and each column represents one of the gut metagenomic samples. The cell shading indicates phage abundance in each sample, with the scale for FIGS. 12A-12H shown in FIG. 12I. FIG. 12J shows the PrD distribution in bacteriophages. The correlation between LLR score of the identified PrDs, their distribution across bacteriophage families, host bacteria, and their function in the bacteriophage-bacterial interaction are presented in FIG. 12J. The likelihood that an identified PrD is a prion is represented by a shading scale in FIG. 12J.

DETAILED DESCRIPTION OF THE INVENTION

Figure 1A:
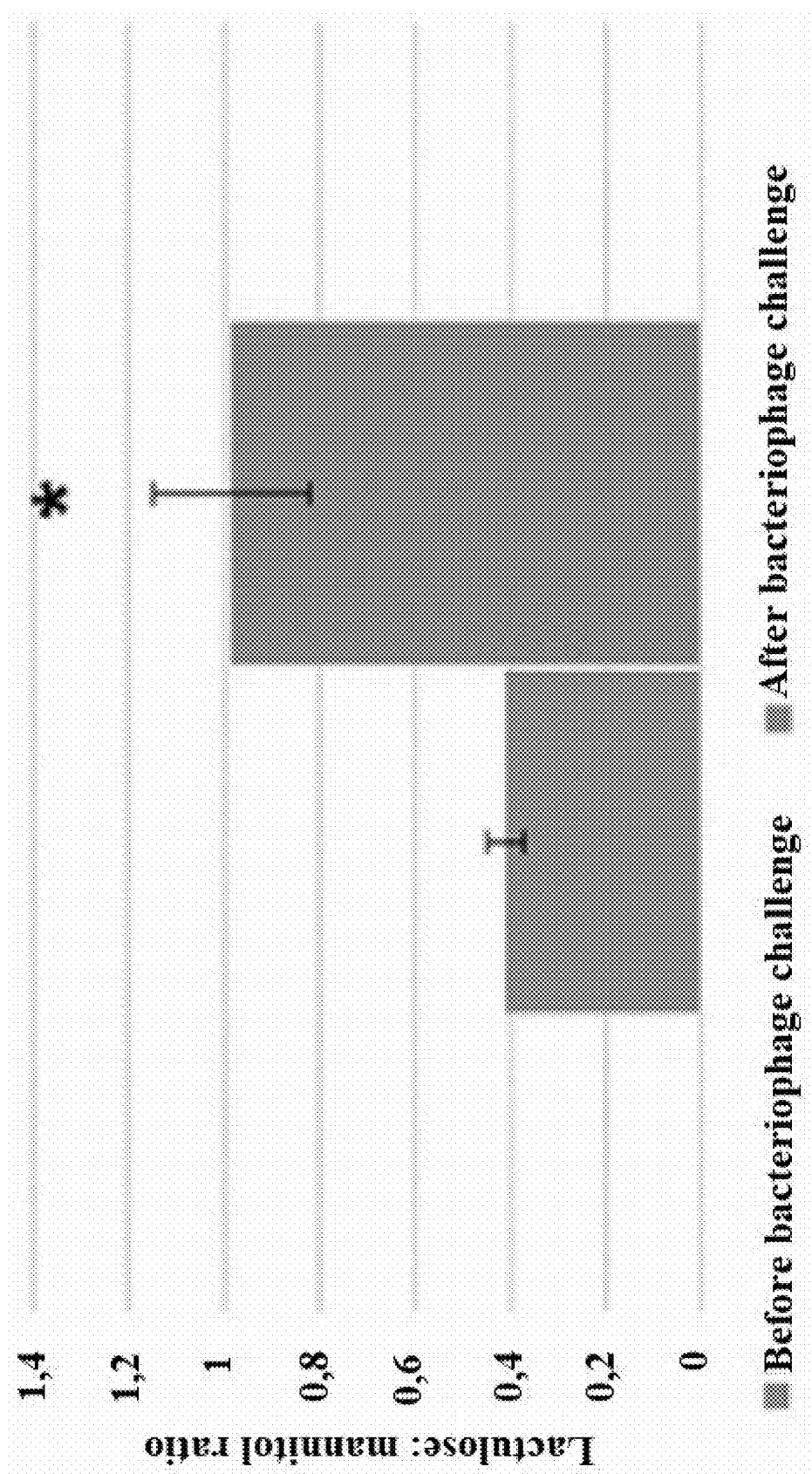
FIGS. 1A-1B show disruption of intestinal barrier integrity in rats treated with bacteriophage cocktail.

Bacteriophages can selectively target individual bacterial species and not affect eukaryotic cells (Tetz, G., and Tetz, V., 2016; Fischetti, V., 2005) If microbiota alterations have a role in the development of increased intestinal permeability, bacteriophages as important regulators of the microbiota diversity may be implicated in mucosal impairment and thus can indirectly be pathogenic to mammals. The overall stability and diversity of the microbiota can be maintained by not allowing bacteriophages to get into the human body where they can selectively target individual members of the microbiota population.

The present inventors have found that preventing bacteriophages from getting into the human body, or entering the human body, can preserve the stability and diversity of microbiota throughout the human body and in turn prevent diseases, particularly those of unknown etiology. Without wishing to be bound by theory, entry into the body of a particular bacteriophage can change the balance of various types of bacteria in the microbiota by either selectively killing certain bacteria or facilitating the transfer of genetic material among bacteria in the microbiota, which in turn can selectively kill some of the bacteria.

Using a rat model, the present inventors examined the effects of exposure to a bacteriophage cocktail on intestinal permeability and relative abundance of taxonomic units in the gut bacterial community. There was an increase in markers of impaired gut permeability, such as the lactulose/mannitol ratio, plasma endotoxin concentrations, and serum levels of inflammation-related cytokines, following the bacteriophage challenge. The present inventors observed significant differences in the alpha diversity of faecal bacterial species and found that richness and diversity index values increased following the bacteriophage challenge. There was a reduction in the abundance of Blautia, Catenibacterium, *Lactobacillus*, and *Faecalibacterium* species and an increase in *Butyrivibrio, Oscillospira* and *Ruminococcus* after bacteriophage administration. These findings provide novel insights into the role of bacteriophages as potentially pathogenic for mammals and their possible implication in the development of diseases caused by increased intestinal permeability.

Also disclosed herein are various ways of targeting and inactivating bacteriophages. Bacteriophages in food sources, drinking water, water for washing, materials for transplant (e.g., organ transplant, fecal transplant, and non-fecal transplant) can be inactivated. Also, bacteriophages can be inactivated on the skin and in the environment, e.g. in air conditioning systems, furniture, a room, dishes, a bath, a sink, a toilet bowl, a container for packaging and storage of food products and/or water. Bacteriophages may also be inactivated in the hospital environment. Without wishing to be bound by theory, free bacteriophages and temperate bacteriophages in the hospital environment may have a particularly high mutation rate. Mutations in such bacteriophages may allow them to overcome bacterial protective systems (e.g., against bacteriophages).

Inactivation can occur by various means, including chemical treatment (e.g., with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043), ozone, gamma irradiation, heat treatment, electron flow treatment, gamma irradiation, capsid-targeted viral inactivation, microwave radiation, pascalization and filtration.

Described herein, for the first time, is a detailed comparative metagenomic analysis of intestinal phagobiota in PD patients and non-parkinsonian individuals. A dataset of short sequence reads generated in the original study of Bedarf et al. was obtained from NCBI Sequence Read Archive (SRA) (www.ncbi.nlm.nih.gov/bioproject/382085) and analysed for bacterial and bacteriophage diversity using MetaPhlAn and HPviewer databases (Bedarf, J. et al., 2017, Reyes, A. et al., 2012 and Segata, N. et al., 2012). The obtained results reveal changes in the bacteriophage profile of PD patients, which may implicate bacteriophages in the pathogenesis of PD.

Definitions

Unless defined otherwise, technical and scientific terms used herein have the same meaning as commonly understood by one of ordinary skill in the art to which this invention belongs.

As used herein, the term "bacteria" encompasses both prokaryotic organisms and archaea present in mammalian microbiota.

The term "microbiota" is used herein to refer to microorganisms (e.g., bacteria, archaea, fungi, protozoa) and viruses (e.g., phages and eukaryotic viruses) present in a host animal or human (e.g., in the gastrointestinal tract, skin, oral cavity, vagina, etc.). Microbiota exerts a significant influence on health and well-being of the host. Viruses present in microbiota are separately described as "virobiota". The term "microbiome" refers to the collective genes of all organisms comprising the microbiota.

Specific changes in microbiota discussed herein can be detected using various methods, including without limitation quantitative PCR (qPCR) or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703.

As used herein, the terms "a microbiota disease" and "disease of a microbiota" refer to a change in the composition of a microbiota, including without limitation very small changes in a relative abundance of one or more organisms within the microbiota as compared to a healthy control. Microbiota diseases can result from, e.g., infections with pathogens including viruses, bacteria and eukaryotic parasites, antibiotic exposure as well as other causes. The present invention is focused on microbiota diseases secondary to, associated with, or caused by a bacteriophage entry into or interactions with microbiota. The term "consequences of a microbiota disease" refers to various disorders associated with microbiota diseases. For example, microbiota diseases in the GI tract have been reported to be associated with a wide variety of illnesses, such as, e.g., irritable bowel syndrome (IBS), inflammatory bowel disease (IBD), chronic fatigue syndrome, obesity, rheumatoid arthritis, ankylosing spondylitis, colitis, small intestinal cancer, colorectal cancer, metabolic syndrome, cardiovascular disease, Crohn's disease, gastroenteritis, food allergy, Celiac disease, gastrointestinal graft versus host disease, pouchitis, intestinal failure, short bowel syndrome, diarrhea, etc.

The terms "prion-like domain (PrD)" or "prionogenic domain" are used herein to refer to parts of a protein that can become a Prion protein (PrP). PrPs are characterized by self-propagation, undergoing a conformational switch from one conformational state to another, which leads to the creation of new prions (Bolton et al., 1982; Telling et al., 1995). Pathologically, prions are characterized by a process in which the infectious form of prion (PrPSc) interacts with the endogenous PrPs, catalyzing the transformation of the endogenous molecule into misfolded PrPSc aggregates (Ma and Lindquist, 2002).

Non-limiting examples of proteins comprising PrDs across bacteriophages are listed as follows (with accession numbers of exemplary proteins provided in parentheses): protein 15 (Q5YA95), protein 16 (Q76H13, Q8H9G1), protein 20 (Q76H14, Q8H9G2), protein 36 (Q6UGD1), 1,4-beta-N-acetylmuramidase (A0A1B1SDX1), 16.5 kDa protein (Q859Q1), 16.5 kDa protein (J9SG26), 2-keto-3-deoxy-D-arabino-heptulosonate-7-phosphate synthase I alpha (A0A193H326), 20G-Fe(II) oxygenase (E3SPC4), 20G-Fe(II) oxygenase (R9TLF0), 36 protein (Q38144), 3D domain-containing protein (G9J212), 770RF001 (Q6R868), AB1gp03 (E2GLU1), AB1gp76 (E2GM14), ADP ribosyltransferase (A0A1B3B085), ADP ribosyltransferase (A0A1B3B0Z8), Adsorption protein P2 (P27378), Amidase (A1BTX6), Amidase (I6T7N8), Antireceptor (A6XAE0, E7DNB8, A0A191KBB9, A0A191KBG1, A0A191KC24), Assembly protein (C0M2I8, C0M2L0, C0M336, C0M328, C0M332, C0M2J2, C0M2E2, C0M2J6), C0M3R9), Attachment protein G3P (P69169, P03661, 080297, P69168, G1K451, G1K453, G1K452, G1K452, P25129), Autolysin (S5MB56), Bacterial type single-stranded DNA-binding protein (B1GS51), Bacteriolytic protein (U6C860), Base plate (Q06ED5), Base plate [Enterobacteria phage RB32] (A0A0M9JDK4), Base plate wedge component (A0A0C5AMU7, E3SLQ3, Q58LT8, E3SP10, E3SQP7, A0A0E3EXE9, A0A0E3HTW3, A0A0E3F6D4, A0A0E3ELM1, A0A0E3FV56, A0A0E3ERY0, A0A0E3HVC5, A0A0E3F0H7, A0A0E3EMX4, A0A0E3HG14, A0A0E310V7, A0A0E3FY96, A0A0E3FCZ7, A0A0E3ERA4, A0A0E31188, A0A0E3FWH8, A0A0E3HNA6, A0A0E3FAX6, A0A0E3EVS7, A0A0E3HV45, A0A0E3EMJ7, A0A0E3G7U6, A0A0E3ET90, A0A0E3EL06, A0A0E3HKM9, A0A0E311K9, E3SJQ7, E3SK51), Base plate wedge component (E3SPX8), Base plate-tail tube initiator (A0A097J541, A0A097J5X2, A0A097J1B0, Q06ED4, A0A097J6M6, A0A097J208, A0A097J8Z5, A0A097J2Q8, A0A097J3K9, A0A097J4B0, A0A097J717, A0A097J870), Base plate-tail tube initiator [Enterobacteria phage RB32] (A0A0M7QB85), Baseplate assembly protein (A0A0M3LPA3), Baseplate hub+tail lysozyme (E3SSM5, E3SP22, A0A0E3F6M3, A0A0E31869, A0A0E310D3, A0A0E3EXF7, H8ZMC0, V5UU56, A0A0E3HD31, A0A1D8KMX3, E3SKT4), Baseplate hub subunit and tail length determinator (A0A192Y9J4, A0A0G2SSX5), Baseplate hub subunit and tail lysozyme (R9TF38), Baseplate hub subunit tail length determinator (A0A0A0Q0M0), Baseplate hub tail lysozyme (A0A127KL49), Baseplate J-like protein (A0A0S4KZ29), Baseplate protein (A0A0A0RSJ3, A0A0D5BHJ5, I7B737), Baseplate subunit (A0A097J916, A0A097J5V5, A0A097J179, A0A097J543, A0A097J6N1, A0A097J230, A0A097J2S8, A0A097J3F9, A0A097J4B2, D91EN1, D91EN0, A0A097J7F0, A0A097J876, D5JFD7), Baseplate tail tube (A0A0C5PQK2), Baseplate tail tube cap (A0A0K0QS45, K4FBE5, M9V150, A0A173GAH5, A0A160CBE5, G0X5W4, D4Z9Z4, K4FEU9, A0A023ZVK1, K7NRS1, E3SLQ4, K7Z9S9, A0A193H2B3, A0A193GZR4, A0A193H0B1, V5UU48, E3SK52, S5MRE6), Baseplate tail tube cap protein (H8ZMA9, A0A0E3F6W0), Baseplate tail tube initiator (A0A173GAJ7, G0X5W5, D4Z9Z5, K4FC27, A0A023ZV29, A0A193H1Y1, A0A193H039, S5M7E6), Baseplate tail-tube junction protein gp48 (P13339), Baseplate tail-tube junction protein gp54 (P13341), Baseplate wedge (M1HLR4, E3SLZ5, E3SQX8, K412A2, Q5GQX0), Baseplate wedge component (V5USJ8, R9TQE9, V5UU15), Baseplate wedge component gp53 (H6T4P7), Baseplate wedge initiator (A0A127KLS5, E3SMR8, E3SST6, Q58MP3, Q58LL8, A0A0E3FKH6, A0A0E3I3H6, A0A0E3I878, A0A0E3I2R1, A0A0E3FNH5, A0A0E3FN98, A0A0E3FQJ3, A0A0E3I7U4, A0A0E3I509, A0A0E3I1AQ5, A0A0E3FQC5, A0A0E3FQZ7, A0A0E3HM96, A0A0E3HLU9, A0A0E3I8V5, A0A0E3F7X0, A0A0E3HPW2, A0A0E3G2Z3, A0A0E3F3U2, A0A0E3ERA3, A0A0E3G1G6, A0A0E3HP68, A0A0E3FLP3, A0A0E3FNT4, A0A0E3HIM3, A0A0E3FHZ6, A0A0E3HLR9, A0A0E3IAB1, A0A0E3HAU2, A0A0E3FBK6, A0A0E3HL99, A0A0E3HX41, A0A0E3HGD2, A0A0E3G354, A0A0E3HPF9, A0A0E3HM37, A0A0E3FQU4, A0A0E3G0Z8, A0A0E3HL3, A0A0E3FSU5, A0A0E3F7K4, A0A0E3FLW8, A0A0E3HXD1, A0A0E3I8F8, A0A0E3G2U1, A0A0E3F0F4, A0A0E3FM34, A0A0E3IAG1, A0A0E3F877, A0A0E3HFH6, A0A0E3F482, A0A0E3IAK8, A0A0E3HQD3, A0A0E3FQD8, A0A0E3HNX3, A0A0E3I107, A0A0E3I8H1, A0A0E3HYP8, A0A0E3HQ83, A0A1D8KMY0, F5B3M5, E3SJZ5, E3SIZ1, E3SL19), Baseplate wedge protein (A0A067XQF5), Baseplate wedge protein gp10 (A0A0K1Y4V3, A0A159B7M1, A0A1B1P913), Baseplate wedge protein gp6 (E5E4E3, E5EPU7, G0YKD9, I6XLZ5), Baseplate wedge protein gp7 (C3V1L5, C3V2E2, A0A097J8W3, A0A159B6V5, G0X5S7, D4Z9V5, A0A0K1Y4W1, A0A159B7N3, A0A1B1P912, A0A193H0A4, A0A193H1M8, A0A097BX10, I7KRS9), Baseplate wedge subunit (A0A0C5AMW4, S6CGH1, M4PQ23, H6B114), Baseplate wedge subunit and tail pin (E1A295, H6B114, A0A0RQ64, A0A0C5AIR4, A0A0A7HEM7, G8EXP9), Baseplate wedge tail fiber connector (E1A294, A0A127KLF6, Q58LL7, E3SLZ3, E3SNK9, A0A0B4LAC3, M1EB86, A0A0E3FTG1, A0A0E3ICQ5, A0A0E3FDJ0, A0A1D8KMY7, A0A0E3F8U9, A0A0E3FID7, E3SIB0, E3SKD5, E3SQ54), Bbp22 (Q775C2), Bbp9 (Q775D5), BcepGomrgp16 (A5A3Q5), Bifunctional autolysin Atl/N-acetylmuramoyl-L-alanine amidase/endo-beta-N-acetylglucosaminidase (A0A141VTP3), Botulinum neurotoxin type C1 nontoxic-nonhemagglutinin component (Q332E1), CAMP-dependent protein kinase catalytic subunit (Q5DMM0), Capsid and scaffold protein (X4YGN8, A0A0F6WDA2), Capsid and scaffold protein (H6WTX7), Capsid maturation protease (A0A142K874, A0A160DE79, A0A160DDQ1, A0A160DDJ1), Carbamoyl-phosphate synthase large subunit (D2XPZ4, Carbamoyl-phosphate synthase large subunit (B5LPS3), Carboxypeptidase (A0A0A0RV50), Cell wall hydrolase Ply187 (O56785), Cell wall-associated hydrolase (C1KFL4), Central tail fiber (K7P796, K7P7R3, K7P7D9, K7PH86, K7PHJ8, K7PKR4, K7PMC2, K7PKM0), Central tail fiber J (K7P868, K7PJL6, K7PHL5), Coat protein (K9MCE9), Collagen triple helix repeat (E7DUN2), Collagen triple helix repeat domain protein (F5B3P3), Collagen triple helix repeat protein (Q2Q460, Q3HKT0, Q2LIE5, F5B3P0), Collagen-like protein (A0A088FWD5, A0A023W7M0), Collar/head-to-tail joining protein (A0A0F71JV8), Conserved hypothetical phage protein (B4XY75, B4XMY6, C6ZR17), Conserved phage protein (Q3HKS9), C-type lectin (A0A0M4RE14), Cupin domain protein (Q2Q459), D-ala-D-ala carboxypeptidase (S5M869, V5R9Q0, S5YNZ7, S5Y768, R4TQH2, A0A0H4THV1, A0A088FA76, S5Z9H1, V5RA48, V5R9U1, R4TET8, V5R7Y7, A0A0H4TKG8, V5R8J0, R4TLC2, R4J151, A0A088FTM4, A0A097EVC9, A0A059VGY0), Distal long tail fiber assembly catalyst (K4F9Z5, A0A0B6VSW1, G0X598, E3SQT4, A0A023W608), Distal tail protein (A0A0A7DMK4, A0A1B0Y2Q2), DNA delivery (Q3T528, Q3T4W6, F71TP7, Q3T4Z7), DNA delivery protein (Q6EDW2), DNA endonuclease V (A0A0E3HP84), DNA endonuclease V (A0A0E3IAM0), DNA injection protein (C8CLJ1), DNA pilot protein VP2 (A0A0G2UG08, A0A0G2UEA3, A0A0G2UK54, A0A0G2UFZ7, A0A0G2UMC9, A0A0G2UK20, A0A0G2UK25, A0A0G2UK30, A0A0G2UE95, A0A0G2UEB4, A0A0G2UEB8, A0A0G2UMH8, A0A0G2UED2, A0A0G2UMJ1, A0A0G2UEE7), DNA polymerase (U5PS02, A0A185AMW4, W5R9D5), DNA polymerase I (A0A0U1ZUE1), DNA primase-helicase subunit (L7TJL6), DNA replication protein (D2XQ16, B5LPL9, A0A191KBT0), DNA single-strand binding protein (H9A0R6, H9A0L6), DNA transfer protein (G5DA80, A0A088CPR8, A0A192Y6J3, A0A192Y6H9, A0A160CAX4, A0A160CAW0, C6ZR16, A0A0M5M1J8, A0A0M4RTU3, A0A0E3X992, A0A0E3T632), DNA transfer protein 1 (I1TEJ4), DNA transfer protein 2 (I1TEJ5), DNA transfer protein 3 (I1TEJ6), DNA transfer protein gp20 (Q01076), DNA transfer protein gp7 (Q9AYZ1, Q8HAD9, Q01074), DnaD (A0A0H3U4Y0), DnaD (A0A0D4DCE1), DnaD/DnaB repication protein (U5PVJ6, A0A0C5AN80, A0A0A0RVF7, A0A0A0RQ10), DNMP kinase (A0A0D5BHK7), DUF859 domain protein (A0A141DZH9), EcoT381 methyltransferase (Q83VT0), Ejection protein (B9UDL0), Ejection protein (B9UDK9), Endo-beta-N-acetylglucosamidase (U5PXM7), Endolysin (K41D66, E9LUR8, A0A024B3A4, Q0GXT8, C7T1V7, A0A0D3MSS4, Q7Y4H8), Endopeptidase (U5PRL8), Endopeptidase-endolysin (B6CXF5), ERF domain protein (A0A141DZL6, A0A141DZG7), Erf protein (C9WB98), ERF superfamily protein (K4LRR0, M1IEW6), Extracellular transglycosylase (A0A0A7DN24), Fat protein (A0A1D8KMT1), Fiber (M4QG90, E3SML2, E3SSN4, E3SLS7, E3SKU6), Fiber Ig/hemolysin (C7F4B4), Fiber protein (C7F4B9, M4PM98, M4PL12, M4PLR0), Fibritin (W6ASX6), A0A023ZUE5), Fibritin neck whisker protein (E5DIH5), Fibritin neck whiskers (A0A0K1LNU5, A0A0A0YVK5), Fibritin neck whiskers protein (A0A097J5T7), Formin protein (A0A097BYK4), G064 protein (G4KK03), G081 protein (G4KK20), G089 protein (G4KK28), G192 protein (G4KKD1), Gene 11 protein (Q716G4), Gene 27 protein (Q716E8), Gene 3 protein (Q716H2), Gene 32 protein (Q05241), Glutamine amidotransferase (K413T9, B0FIP5, A0A0B4N1Y5), Glutamine transaminase (K4F9T6), Glycine rich protein (K4JT54), Glycosyltransferase family 11 (A0A0E3FR08, A0A0E3HLH4, A0A0E3G2K3, A0A0E3HGX6, A0A0E31659, A0A0E3FS63, A0A0E3FRM6, A0A0E3HKQ9, A0A0E3EQX2), Gp10B (H6BFI3), Gp36-37.2 (Q858B5), Gp013 (G0YPJ5), Gp030 (G0YPL2), Gp036 (G0YQC8), Gp036 (A6MAA0), Gp038 (A6MAA2), Gp049 (A6MAB3), Gp05H (Q61WQ6), Gp050 (G0YQE2), Gp056 (A6MAC1), Gp065 (D4P7T3), Gp067 (D4P7H8), Gp080 (G0YQH2), Gp081 (G0YQH3), Gp10 baseplate wedge subunit and tail pin (E5DQD1, Gp10 baseplate wedge subunit and tail pin (Q76YM7), Gp100 (G8I DT8, Gp100 (G8I A66, Gp100 (G3M4V2), Gp101 (G8I A67), Gp103 (G1JW50, Gp103 (H9NBY0), Gp104 (G1JW51), Gp11 (H6BHX6, Gp11 (H6T4Q0, Gp11 (H6B117), Gp114 (B5LJB8), Gp12 (B3VD69), Gp120 (C9DAU5), Gp125 (G1BKM2, Gp125 (C9DBN1), Gp126 (C9DAV1), Gp127 (B5LM63), Gp127 (B5LJP3), Gp128 (E0YPQ2), Gp128 (Q19XD9, Gp128 (B5LJD2), Gp128 (B5LLA5), Gp129 (Q853F2), Gp13 head completion protein (Q19CM6), Gp130 (G1JXM2), Gp131 (G1BKM8, Gp131 (C9DBN7, Gp131 (B5LKN6, Gp131 (G8I CK8), Gp132 (G8I D89, B5LJD6, G1FIM2), Gp133 (G3MBJ5, I3WV00, B5LM69, B5LJP9), Gp134 (Q19XD3, G8I DX2, B5LLB1), Gp135 (Q853E6, G3M4Y7), Gp136 (G8I AA2), Gp137 (G1JW84, B5LKP2), G8I CL4), Gp138 (G8I D95), Gp139 (13WV06), Gp14 (G3MB84, D4N7F9, Q855J6, G81543, G1D1A8, J7KDM1, G8J7L6, B5U4L3, G1JTG0, G1D2W0, Q1A003, G1DUA2, B5U560, Q19YN9, G819N0, G1DTZ5, G1DUK8, H6WSB6, I7B1U2), Gp14 neck protein (H8ZN8I), Gp14 T (Q4L1H3), Gp140 (A8ASX4), Gp140 (G8I DX8), Gp141 (G3M4Z3), Gp142 (G8I AA8), Gp143 (G1JW90), Gp149 (D9J0U6), Gp15 (B5A6M2, Q854Y3, G1JZ32, G1D4C9, B5U5G2, E7EJN2, B7T0A5), Gp15 tail sheath stabilizer and completion protein (H6SUI7), Gp159 (G3MBM5), Gp16 (G816P9, G1JX31, E0YPE9, E0YQ16, B5U384, F6M811, G3MDZ6, B8K117, E7C9U6), Gp165 (E3SMF1, E3SNC8, Q58MB5, G8EY53), Gp17 (B8R882, D7RWK0, Q61WV2, A4JX12, Q8W6T4, I3WWQ3, Q855U6, B3VM44, B3FYL6), Gp170 (G9B1S1), Gp18 (A8ATB1, D7NW87), Gp183 (G3MBP9), Gp19 (D7RWK2, Q856F3), G1DU00), Gp193 (G3MBQ9), Gp2 (G1D0Z9), G1EBM7, G8I BZ2, B7T093, E0Y3N5), Gp2.52 (B6V2M5), Gp20 (G1JX35), Gp20 portal vertex protein of head (E5DRS2), Gp20 protein (D4HTV9), Gp21 (064335, Q6UAW1, G1D5N6), Gp22 (G816Q5, G1D0M2, Q857Y9, G1JWP2, G8I R12, B5A6Y4, B5A5Y4, G1DHV8, G1D274), Gp23 (G1JST1, G1DIE6, C9EHB3, Gp23; (224) (E4WL41), Gp239 (B5LJK9), Gp24 (Q9MCU0, Q1A147, D4N7G9, G81553, G1D1B8, J7KM26, G8J7M6, F6M819, B5U4M3, G1JTH0, G1D2X0, G1JS01, Q19ZZ3, B5U570, Q19YM9, C9DCJ0, G3ME04, G819P0, G1DUL8, I7B1V1), Gp25 (13WWR1, B5A6N2, Q85515, Q855T8, G1JZ42, A8WA13, G1DA74, G1D4D9, B5U5H2, H6WSC7, Q9ZX52, E7EJP2), Gp257 (H9NCD4), Gp259 (B5LJM9), Gp26 (F8UBT6, B5A6D5, G1D5P1), Gp266 (H9NCE3), Gp267 (H9NCE4), Gp27 (D9J0H4, E0YPT2, G3MCH7, G1D0M7, Q857Y4, E0YQI9, G814N4, G814D7, G1JWP7, A8WA15, G1FF78, B5A6Y9, B3VLV6, B5A5Y9, Q19Z59, G819E8, G1DHW3, G1D279), Gp28 (I6X329, G1EDW4, G817Z4, G1EDH5, G1JST6, G8I BR5, B3VLV7, B9W1F0, G1DIF1, G819E9, H9NCU2), Gp29 (G817F7, Q1A142, Q1A087, G814N6, B5U3Q7, G813G7, G1JS06, I6XHR9, C9DCJ5, Q857A5, G1D639, A4K496), Gp29 baseplate hub subunit (E5EYW9), Gp29 baseplate hub subunit tail length determinator (A7XFE5), Gp3 (K0G815, E0YQ79), Gp30 (B5U3H2, Q1A086, B5U3Q8, G8I AN9, Q19ZD7, B5A6D9, G1D640, G1FG95, B5U3Z6), Gp31 (Q8HAM8, Q6UKB9, G8I8G4, B2ZNS8, G1CZY9, B5U3H3, G8I AP0, G1FFV0, Q19ZD6, Q19YB8, B5U3Z7), Gp32 (B2ZNS9, G817Z8, C9DAB0, G81589, D2XRX8, G1DIQ3, G1D1Y5, G1D2M7, G812W4, G8I BR9, G1D3R7, G3MC61, G3MBW3, G1DAH1, Q19ZN5, G1DJ04, B9W1F4, Q19YB7, C9DCA1, D2XS80, G81953, G1D9N6, C9DCZ1, G1BP43, G1D6M3), Gp32 single-strand DNA binding protein (E1XT76), Gp32 single-stranded DNA binding protein (G3M0Z0), Gp32 T4-like ssDNA binding protein (C8XUH0), Gp33 (Q6UIZ8, F8UBU3, G817Q2, G3M492, G81756, G8I BJ6, Q856D9, Q9B088, B5U5T8, C9DAB1, D2XRX9, G813R3, G813H1, G812W5, G1D1Y6, G1D2M8, Q19ZN4, G1DJ05, Q19YX2, C9DCA2, Q857A1, D2XS81, G1DIQ4, C9DCZ2, G81954, G1BP44, G1D6M4), Gp33 putative acylhydrolase (B5AX52), Gp34 (F8UBU4, G81675, G815Y2, Q1A013, G1D1N0, G1D310, Q854N0, B5U5T9, B3VM61, G1D596, Q5J5S0, G3MEL9), Gp34 long tail fiber proximal subunit (D91CW7, Gp34 long tail fiber proximal subunit (D7RMP5), Gp35 (G9B1D6, G1EV87, G1D6X9, K0G8U5, G1DTS4, G1JTT5, B5LLN8, G1FGA0), Gp35 hinge long tail fiber proximal connector (E5DRN4), Gp36 (Q56EE3, G1D9Y9, G81613, B3VH18, G3MDR0, B3VGS4, B3VG07, G8I B74, B3VG96, G1D6D6, Q0QZJ2), Gp36 hinge connector of long tail fiber distal connector (E5DRZ3), Gp36 protein (Q2WC38), Gp36 putative tail-fiber protein (B5AX55), Gp36 small distal tail fiber subunit (Q19CF5), Gp36+37 fusion long tail fiber distal subunit (R9TFT8), Gp37 (A0A0B4U9C5, A0A0B4U8H4, Q856D5, G81594, G1D4Q9, G3LWZ6), Gp37 large distal tail fiber subunit (C3V1V7, Q56BB8, C3V2N4), E5FJ29), Gp37, tail fiber (Q38155), Gp37, tail fiber of bacteriophage Yer2 (Q38185), Gp37, tail fiber protein (Q76PK3), Gp37, tip of tail fiber (Q38191, Q38189, Q38190, Q38187, Q38188), Gp37, tip of tail fiber protein (Q38186), Gp373 (080182), Gp38 (C3V1V8, Q06E82, D2XRN2, Q19Y22, Q0QZJ0), Gp38 distal long tail fiber adhesin (A7XF30, Gp38 distal long tail fiber adhesin (D7RMP9), Gp38 distal long tail fiber assembly catalyst (E5DHZ0, Q5QC48, C4MZY7), Gp38 putative tail-fiber protein (B5AX57), Gp39 (G3MBA9, Q3V5F6, Q0QZI9), Gp4 (K0G9R6, F1BCI7, E0YQ80, I3WWE9, K0G171, G1DA54, I3WUE0, G8I AV1, G1FN43, C9DBY8, K0GA24, F6MDN2, G1JZT9, H9NCI3, B7T0F5), Gp41 (F8UBV1, D4P816), Gp42 (G1D000), Gp425 (G3MAG6), Gp427 (G3MAG8), Gp43 (Q6UKA7, G1DAI2), Gp44 (Q8HAL7, Q854M0), Gp45 (D7RWM8, D7RWG9, Q6UIY6, G1D3T0), Gp46 protein (D4HTY5), Gp48 (Q5G8U1), Gp48 base plate (C3V1Q3, C3V2H9), Gp48 baseplate tail tube cap (E5DQC0, Q76YN8, D91CF7), Gp5 (I6X309, G1EDU2, I6RTV2, G1EDF3, Q5J5L8, I3WWF0, I3WUE1, G8I AV2, G1FN44, C9DBY9, J7KDL4, K0GFM6, G8I R89, F6MDN3, G1DB24, G1JZU0, G1FN92, H6BHY5, H6T4Q9), Gp5 baseplate hub+tail lysozyme (H8ZMZ8), Gp51 (Q6UIY0), Gp52 (D7RWN5, Q1A0G5), Gp53 (Q5G8T6, G1D1P9), Gp53 base plate wedge component (H8ZMA8), Gp53 protein (A9J726), Gp54 (B7T0E4), Gp54 base plate-tail tube initiator (C3V1Q4, C3V210), Gp55 (G81437), Gp57 (Q856N7), Gp6 (Q9G0H9), Gp68 (Q61WR5), Gp681 (G3MB61), Gp7 (G81651, G1D104, G1EBN2, G1D1K6, B3VGP5, G1D356, G8I BZ7, D3JZ70, G1DB26, B8K115, E7C9U4, H6B142, H6T4W7, Q6WHG2), Gp70 (Q5DN35), Gp71 (Q30L74, G8J7S3), Gp72 (G1D318), Gp79 (Q855Z3, C9DAQ4), Gp7a baseplate wedge initiator (E5DRT7), Gp8 (G81652, G1D105, G1EBN3, G1D1K7, G8I BZ8, D3JZ71, G1JV60), Gp8 baseplate wedge protein (H8ZMI5), Gp83 (G1BKI0), Gp84 (C9DBJ0), Gp85 (G0YQ34, B5LM21, C9DAR0), Gp86 (G0YQ35, C9DAR1), Gp89 (G1BKI6), Gp9 (H6B143, H6BIQ4, H6T4W8), Gp9 baseplate wedge tail fiber connector (E5DQD0, Gp9 baseplate wedge tail fiber connector (Q76YM8), Gp90 (G1BKI7), Gp91 (C9DBJ7, G8I D48), Gp92 (C9DBJ8, B5LM28), Gp93 (B5LM29, Q19XH4, B5LK79, B5LL70), Gp94 (Q85316, Q19XH3, B5LK80, B5LL71), Gp95 (Q85315, G8I CH2), Gp96 (G1JXI8, B5LJA0, B5LKK1, G8I CH3), Gp97 (13WUW5, G1JXI9, G8I D54, B5LJA1, B5LKK2), Gp98 (13WUW6, G8I D55, G1FII8), Gp99 (G8I DT7, G3M4V1, G1FII9), Gp9plus10 baseplate wedge tail fiber connector and baseplate wedge subunit and tail pin (E5DRT4), GpH (Q2LL32, Q2LL53, Q2LL42, C6K2G9, Q2LMB3, Q2LMA3, Q2LM22, Q2LM93), GpORF098 (D3G7K8), GpORF123 (D3G7N3), Gram positive anchor (A0A0N9STB7), Haloacid dehalogenase-like hydrolase domain-containing protein (A0A0A0PUQ6), Head completion protein (J7KLN1), Head completion-like protein (E1A1H0), Head to tail connecting protein (A0A0F6TJD8), Head to tail joining protein (U5PZG8), Head vertex (A0A0E3G2N7), Head-tail connector protein (E3SN85, M1UH58, M1PL87), Head-to-tail joining protein (A0A0H4TG99, U5PVW2, A0A0C5ACD2, A0A0A0RPT2, U5PW66, A0A0A0RPX6, U5PWA5), Hef60 (F4YA83), Hemagglutinin domain-containing protein (M4PQY5), Hemagglutinin protein (J9ST38), Hinge connector of long tail fiber distal connector (I6X7P4, Q6U981, A0A0A0PZQ7), Hk97 family portal protein (A0A0A7DMV2), HNH endonuclease (W5R8M2), HNH homing endonuclease (A0A172J194, A0A0A7TYH1), Homing endonuclease (A0A193H244), Host specificity protein (Q5YA57, K7PKJ2, G8C7R4), Host specificity protein J (E4WL39, A0A0K2FI38), Hydrolase (A1BU73), Hydrolase-like protein (F2VHX8), Hyphothetical protein (V5KST6), Hypothetical cyanophage protein (F5B3T1, C7BV07, C7BVB2), Hypothetical membrane associated protein (G8C7K3), Hypothetical phage membrane protein (D5GVH7, D5GW25), Hypothetical phage protein (D5GV96, D5GVD4, D5GVC2, D5GVF2, D5GVR7, D5GVX1, C8XUD8), Hypothetical phage structural protein (D9ZNF0), Hypothetical tape measure protein (A7KUS0), Hypothetical-Protein/belonging to T4-LIKE GC: 726 (Q5GQD0), Hypothetical-Protein/belonging to T4-LIKE GC: 727 (Q5GQC9), Hypothetical-Protein/belonging to T4-LIKE GC: 734 (Q5GQB9), Hypothetical-Protein/belonging to T4-LIKE GC: 739 (Q5GQB4), Hypothetical-Protein/belonging to T4-LIKE GC: 826 (Q5GQT9), Hypothetical-Protein/belonging to T4-LIKE GC: 830 (Q5GQW5), Hypothetical-Protein/belonging to T4-LIKE GC: 858 (Q5GQH6), III (A7BJW8, D0U181, D0U161, D0U171), III protein (G4WZQ3, G4WZN3, G4WZP3), Immunodominant antigen a (K7QMG8), ImpA domain protein (A0A0H3YJ87), Infectivity protein P11 (P27382), Injection gp7 (B6SCW3), Injection protein (M1E2E4, M1E2W9, I6S1K1, A8CGD5, A8CGD4), Internal core protein (U5PVL2, A0A096VKF8, M1NXS5), Internal protein (A0A059PY91, U5PRG6), Internal virion protein (U3PFQ3, A0A0A6Z5B9, A0A0F6NYC8, A0A0F6NYE3, A0A0A6ZK91, A0A0G2SS10, L0CNX8, A0A096VKT1, A0A096VKV6, G8EYE3, A4ZRC4, V5Q7N1, V5Q8R5), Internal virion protein B (Q859E4, A0A059VF23), Internal virion protein C (A0A0S2MVP3, F1D0N0, F1D013, F1D087, F1D041, D0Q1C2, Q4TVW4, H9YAJ0), IV (A7BJX1, D0U164, D0U184, D0U174), IV protein (G4WZN6), JK_2P (Q45Q14), JK_75P (Q45PU1), JK_77P (Q45PT9), Kelch repeat-containing protein (E3SSN5), L-alanoyl-D-glutamate peptidase (A0A140HM05), Large distal tail fiber subunit (A0A076YIH3), Large subunit ribonucleotide reductase (Q8SCB8), Late control gene D protein (A0A0E3ICA9, A0A0E3FHJ6), Lipoprotein (A0A0K1LKD6), Long distal tail fiber subunit (I3WVZ0), Long tail fiber adhesin (A0A0A7HFM9, A0A1B0VVI5), Long tail fiber distal hinge connector (A0A0A0YR63), Long tail fiber distal subunit (W6ATP7, A0A097J7K1, A0A097J8C7, A0A097J974, D91ET6, A0A0U2DA62, A0A067ZHJ2, A0A060BN58, A0A0A7HBH2, A0A0A0Q211, E3SF66, A0A0D4DBD6, S5M9K9, A0A0B5A311), Long tail fiber distal subunit adhesine (A0A0A7HH19), Long tail fiber distal subunit receptor recognizing protein (A0A0A7HDR5), Long tail fiber protein (A0A0A7HG91, A0A0A7HEX1, A0A0A7HH41, A0A0A7HFL1, A0A0D4DA56), Long tail fiber protein p37 (Q38394), Long tail fiber protein proximal subunit (A0A0A7HDA3), Long tail fiber proximal subunit (I6X7W1, A0A0M5M1E1, K4F7E7, K4F9K4, A0A0A0Q3M7, A0A193H087, E3SF63), Long tail fiber, distal subunit (A0A0B6VP17), Long-tail fiber protein p37 (P03744), Lower collar protein (G9J314, Q859K7, Q85915, A0A173G9L6), L-shaped tail fiber protein (D5JFT2, K7NS29, A0A0K1LQV0, A0A162E4E0), L-shaped tail fiber protein pb1 (P13390), LukF-PV (O80067, Q783R0, O80066, Q783R1), Lyase (A0A0A8JA06), Lysin (K411Y4, A0A0A7NU10, A0A0A7NNW9, A0A1B11M89, Q09WT3, M118E3, A0A096XV24, H9ED82, H9EDE0, H9EDJ7, H9EDQ4, H9EDW2, H9EE17, H9EEA6, H9EED3, H9EE17, H9EEV1, H9EF09, H9EF67, H9EFC6, H9EFI5, H9EFP3, H9EFV2, H9EG08, H9EG65, H9EGC4, H9EGH8, H9EGN4, H9EGU2, H9EH00, H9EH58, H9EHB5, H9EHH0, H9EEP4, Q37969, Q38614, A5GYG5), Lysin A (A0A142KA99), LysM (A0A068CDR8), LysM domain protein (C9E2L5, R4TCT0, T2FIZ0, A0A0K2FMQ8, T2FIC3, R4TT50), LysM-like domain protein (R4TDK2), LysM-like endolysin (A0A1C9EH90), Lysozyme (E5E4E0, G0YKD6, K4FB41, H6X3N5, A0A0A8J8N9, Q6SE63, A0A0A0PZJ1), Lysozyme murein (E3SLR0), Lysozyme_like superfamily protein (A0A0S2SXL7), Lysozyme-like domain vision structural protein (A0A097PAR3), Lytic tail fiber (U5PZS4), Lytic tail protein (A0A0A0RVE6), Lytic transglycosylase (A0A0D3MVA9), Main hemagglutinin component HA-33 (Q332E2), Major capsid protein (A0A067XQK5, E3SN77, Q3T4U4, Q3T537, Q3T506, Q6EDX0, Q08659, F7IWD2, A0A088C3C1, A0A096VKG0), Major capsid protein P3 (P22535), Major capsid protein VP1 (A0A0G2UMC2), Major head protein (D9HP05, D9HP08, D9HP12), Major tail protein (A0A1B1PAF7, W6E8C3), Major tail subunit (A0A0A7HD42, Q6R6B2), Mannose-6-phosphate isomerase (Q218C5), Maturation/adhesion protein (B1GS50, E1XTI0), MbpF (I6XE08, D3G7H1, I6WAP7, I6X3U5), Member of DUF669 phage protein family (H6WU21, A0A060RJ47), Membrane protein (K7QN33), Membrane protein (A0A075BE89), Metallopeptidase domain protein (R9R4W0, R9R4B3), Metallopeptidase domain protein (A0A0B5H2M5), Minor capsid protein (G1C4Z6, B8R660, S6CUB9, G8I RU9), Minor CP2 (A0A186YBP6), Minor head protein (H9A0U7), Minor protein (A0A0D4DCQ3), Minor spike protein (P03650, P03649), Minor spike protein H (P11336), Minor structural protein (A0A097BY65, S5MX51, A0A0N7CEN8, H2D0F3, C9W9J1, E7DNB9), Minor structural protein 2 (A0A076GDI1), Minor structural protein gp58 (Q38355), Minor structural protein/putative tail fiber (J9PM59), Minor tail protein (A0A0K2D0N8, X2JIS0, A0A192Y8W4, A0A143FKE0, A0A1B1PB79, A0A024B0X2, A0A0K2FLK0, A0A0K2FM48, A0A024B299, A0A024B219, A0A1B1SGH3, A0A024B261, A0A143FNY7, A0A143FHG2, A0A143FP1, A0A143FJN3, A0A143FMM9, A0A173GBE1, A0A0K2D0A9, A0A0K2D043, A0A143FMF3, A0A075LYL9, S5Y0M7, A0A142KCK3, A0A1B3B0J8, A0A166Y273, K41476, A0A0H4J317, A0A0H41UC7, R4TC19, A0A0M4QU14, R4TCW6, X2KST1, G81367, X2KR16, A0A0K1LR24, A0A142F2F7, T2FHV8, R4TQ68, A0A0K1Y794, A0A0K1Y749, A0A0K1Y6J7, M4W6V4, A0A0S1S501, A0A0F6YRV7, A0A0B4ZYT9, W0LIX4, W0LIT7, A0A068F596, A0A068F4Y2, A0A068F250, A0A0F6WE18, A0A0A7RX87, A0A0A7S1Q8, A0A068F1M8, A0A068F8L3, A0A1B1SEW9, A0A023ZYE1, A0A023ZX34, R4TS61, X2KZC4, G81366, S5Z3Z0, A0A0A7RX22, V5UPQ5, V5UNJ7, G8I BJ5, A0A0K1LKZ8, A0A023ZWX2, V5UR19, A0A088FNM2, A0A088FRM3, A0A0B5H807, A0A059VAL9, A0A059VFP1, A0A0A1ENH1, W0LP30, W0LNQ8, A0A0A7RWR1, A0A0F6SJZ1, A0A076YS08, G3MC62, A0A023ZXL4, A0A059VL91, G1FFV1, W8FXJ2, W8FTY5, A0A142K7F6, A0A0F6YQH8, S5YDN6, G1BNU5, G1BNU4, A0A0B4ZY55, A0A0B5A0J0, A0A0K1LSH3, S5WL39, W6AT58, R4JHI9, R4JNT8, A0A023ZXD2, A0A0F6YRL9, A0A0B5A459, X2KNF0, X2KRQ6, T2FHV5, A0A0A7RWX4, A0A0S1S178, V5UPB7, X4YTN7, X4YDF3, G1D9N7, G8I8V0, G8I8V1, G3MBW4, A0A0F6YRP5, A0A0F6SJ18, G8I8J9, G8I8K0, A0A088FUE0, A0A068CD43, R4JHV3, G8FV34), Minor tail protein gp26-like (L0P7B8), Minor tail protein L (A0A0M3LQ48, Minor tail protein L (A0A0M3LNT0), Minor tail subunit (W8EAQ1, A0A0F6YQN5, W8FPC1, W8EB49, S5Z625, A0A0A0RU71, A0A088FV95, M4WNY9, M4W8R6, A0A088FPV2, A0A088FRL7), N4 gp52-like protein (C4NT64), N4 gp57-like protein (C4NT69), N-acetylmuramoyl-L-alanine amidase (A0A172JHR8, A0A060AHF9, A0A0M4S679), N-acetylmuramoyl-L-alanine amidase-like protein (A0A142F1B8), N-acetylmuramyl-L-alanine amidase (U5PXS5), Neck passage structure protein (A0A096XV14), Neck passage structure protein (A0A0B5A5V2), Neck protein (I6ZI76, E3SM00, A0A141VTN8, V5USJ6, Neck protein (M4QFE2, Neck protein (E3SKE2), NTNH (Q9ZX77), Nuclease (A0T2N5), ORF 1 (Q9QTH9), ORF 305 (Q6UG69), ORF 310 (Q6UG83), Orf 498 (080261), ORF 809 (Q6UG67), ORF B812 (Q6TRT2), ORF. 16 (Q8H9T0), ORF. 20 (Q8H9T4), ORF001 (Q4ZD05, Q4ZCL0, Q4Z915, Q4ZA08), ORF002 (Q4ZE13, Q4ZD63, Q4Z9E1), ORF003 (Q4ZCD0, Q4Z9Z8), ORF005 (Q4ZAV1, ORF005 (Q4ZBH7), ORF008 (Q4ZE60), ORF012 (Q4ZAM2), ORF013 (Q4ZCS7, Q4Z9Z0), ORF016 (Q4ZBL7), ORF017 (Q4ZAD0), ORF018 (Q4ZDQ6, Q4ZAK4), ORF019 (Q4ZDH7, Q4ZBF5), ORF020 (Q4ZD23, Q4ZB75, Q4Z9W5), ORF021 (Q4ZCR6), ORF022 (Q4ZCY3, Q4Z994), ORF023 (Q4ZA30), ORF025 (Q4ZB84, ORF025 (Q4ZBW2), ORF026 (Q4ZAT7), ORF029 (Q4Z9G6), ORF030 (Q4ZDI1), ORF032 (Q4ZCX0), ORF033 (Q4ZD98), ORF034 (Q4ZC22), ORF035 (Q4ZAK9), ORF041 (Q4Z9D4), ORF051 (Q4Z8Z7), ORF073 (Q5DMM1), Orf108 (Q5ULK6), ORF114 (Q6Y7K5), Orf121 (Q5ULJ3), Orf130 (Q5ULI4), Orf144 (Q9B0H6), Orf19 (B0YL69), ORF22 (Q9G023), Orf256 (Q9B0F9), ORF36 (Q9ZXE7, Q9MCJ7), ORF38 (Q6Y7S9), ORF39 (Q9MCJ5), ORF40 (034071), ORF46 (034077), Orf5 (Q9AZU7), Orf515 gp (064294, 064283), Orf52 (Q9AZL3), Orf53 (Q9AZR9), ORF55 (Q6Y7R2), ORF63 (Q6Y7Q4), ORF7 (Q9MCM3), ORF70 (Q6Y7P7), Orf88 (Q5ULM6), ORF9 (Q8H9Q6), ORF92 (Q6Y7M7), Orf94 (Q5ULMO), Orf97 (Q5ULL7), Orf98 (Q5ULL6), p08 (Q6PVL5), p11 (Q6PVK6), p2 gpV-like protein (A0A088C368, A0A088C445), p23 (Q6PVL9), p24 (Q6PVL2), p38.4 (Q9FZR0), p54 (Q94MR5), PA0724 (Q56VP1), Panton-Valentine leukocidin chain F (R4WAV6, A0A068A251, A0ZS60), Panton-Valentine leukocidin chain S (M1SVD4, G4KNR7, G4KNV8, G4KNR6, G4KNV9, R4WAN8, A0A068A2D7, A0ZS59), Panton-Valentine leukocidin subunit F (M1SNX0), Pas28 (Q6J803), Pas29 (Q6J802), Pas57 (Q6J7X4), PblA-like tail protein (D21YX6, D21Z39, D21ZB1, D21ZH4, D21ZN5, D21ZV0, D2J016), PE_PGRS family protein (F4YCN4), Pectate lyase (A0A0A8J9B0), PE-PGRS family protein (A0A1D8KSK1), Peptidase (H8ZNC7), Peptidase M23 (A0A0E3F0D8, A0A0E3HGM4, A0A0E3FPV4, A0A0E3HHG9, A0A0E3HKU4, A0A0E3EZS2, A0A0E3G4M9, A0A0E3G3Y1, A0A0E3ESF2, A0A0E3HKM5, A0A0E3F5B9, A0A0E3HJT2, A0A0E3G2N2, A0A0E3HPL2), Peptidase_S74 domain protein (A0A141DZA5), Peptidoglycan hydrolase (I6SMM4, H9A0W8), Peptidoglycan hydrolase gp181 (Q8SCY1), Peptidoglycan-binding protein LysM (A0A0A7NNK8), PfWMP3_26 (A5HL40), PfWMP3_27 (A5HL41), PfWMP3_28 (A5HL22), PfWMP3_38 (A5HL32), PfWMP4_33 (Q0GBT3), PfWMP4_34 (Q0GBT2), PfWMP4_35 (Q0GBT1), PfWMP4_42 (Q0GBS4), Phage assembly protein (J7HXF0), Phage baseplate hub (I6X2V3), Phage baseplate protein (G1FHB5), Phage baseplate tail tube cap (T4-like gp48) (17J474), Phage baseplate tail tube initiator (G1FHB6), Phage baseplate wedge initiator (I6XHE6), Phage host specificity protein (G8C7K1), Phage long tail fiber proximal subunit (G1FHG6), Phage long tail fiber proximal subunit (17LF50), Phage minor structural protein (D2XPZ6, K4LNZ9, B5LPS5, A0A0X8WPG8, S6CQC4), Phage particle protein (I2FLS3, W0XAG1, K0IP54), Phage portal protein (Q6V7P2, C51HN8, Q5ZGG1), Phage regulatory protein (I1W658), Phage replication protein (A6XMI0, Q0H278, A0ZS24, M9NS94), Phage structural protein (E1AC27, K0IK57), Phage tail assembly (17LHK7), Phage tail collar domain protein (F1BUP1, A0A0M7QEX0, B2ZY49), Phage tail collar protein (F6LQE6), Phage tail fiber (I6XHA6), Phage tail fiber adhesin Gp38 (A0A0M7QEC5), Phage tail fiber protein (Q6V7M8, Q6V7M9, I1TQP1, G4WAS8, I7K2R4), Phage tail fiber-like protein (Q58M60, Q58MX6, Q58MY1, H8ZN14, E3SIS8, E3SLD5, I7LHB5), Phage tail fibers (17KRW6), Phage tail protein (R9ZY24, R9ZYI7, S0A1H0), Phage tail tape measure protein (14DSJ9, E9LUJ2, A0A059PAI3, A0EX03), Phage tail tape measure protein like (A7TWK1), Phage tail tape measure protein, TP901 family, core region domain protein (D6R3Z8), Phage virion structural protein (J7KHQ4), Phi ETA orf 22-like protein (Q8SDM1), Phi92_gp147 (17HPG8), Phi92_gp180 (171032), PHIKZ067 (Q8SD95), PHIKZ069 (Q8SD93), PHIKZ070 (Q8SD92), PHIKZ124 (Q8SD38), Polysaccharidase protein (V9QL08), Pore-forming tail tip protein (H6WXP4), Portal protein (U5PVY8, A0A1B1PB52, A0A0K2FM31, A0A0A0RMP6, A0A024B3S8, A0A0A0RSG3, A0A143FQP7, A0A143FH18, A0A143FN30, A0A143FM60, A0A076G925, B6SCV6, I6XGE4, I6NV36, K4FBA4, U5PVC4, Q6XQB2, K41D36, A0A182BQ97, A5HL28, Q5QF74, M9MUA1, Q9AYZ9, W5RVB1, A0A060AFC9, W8FP98, W8EHI6), Portal vertex protein of head (K4F9K9), Possible phage tail protein (Q52PL2), Possible phage tail sheath completion protein (D5GVG6, D5GW14), PPE family protein (A0A0A7H9G8), Pre neck appendage protein (I6T7F4, I6SN53), Predicted hydrolase (F8UBD1, F8UBN2, F8UBI3), Predicted phage capsid scaffolding protein (D2EBT3), Predicted phage DNA Endonuclease (D2EBT0), Predicted phage virion protein (D2EBT7), Predicted protein (E3SND2, E3SND3, E3SP36, E3SP39, C7F4D3, Q58N23), Predicted tail fiber protein (E1XUC0), Pre-neck appendage protein (M4WNJ8, Q37893), Primosomal protein 1 (A0A0F6R7Q3), Pro- and Ala-rich protein (Q7Y2D4), Probable tail fiber protein (B0FIH7), Probable tape measure protein (064046, P51731), Probably distal tail fiber protein (E5DQP5), Prohead protease (H6WYH0), Protein 37 (Q99362), Protein C (W5S777), Protein Gp5 (Q6WHG9), Protein IV (A7BJY1), Protein ORF1940 (Q3V4U6), Protein P2 (055320), Protein P8 (Q9XJR5), Proximal tail fiber subunit (M9UVN2), Putative antireceptor (F8J176, A0A075KJA6, F7V9B9, U3PFX4), Putative ATP-dependent DNA helicase (Q331U3), Putative bacteriophage-related transmembrane protein (E3SIQ8), Putative base plate protein (Q71AV4), Putative baseplate component (V5KSI5, A0A0S1RUU1), Putative baseplate hub subunit (A0A0C5AE30), Putative baseplate lysozyme (A0A1D8KFU0), Putative baseplate protein (W6B200, 080120), Putative baseplate tail tube cap (A0A0A0PXI3, A0A159B6Z1, F2VXP9, Q0QZL4), Putative baseplate tail tube initiator (A0A0A0PU76, A0A159B707), Putative baseplate wedge (A0A0K0KWE1), Putative baseplate wedge initiator (A0A0K0KVS8), Putative baseplate-tail tube initiator (F2VXQ0), Putative capsid and scaffold protein (A0A0A1IWL8), Putative capsid protein (U6C6F9), Putative chromosome segregation protein (I6P4A8), Putative collagen-like protein (A0A077K9W7), Putative distal long tail fiber assembly catalyst (A0A0B7MRA5), Putative distal long tail fiber assembly catalyst (A0A162E321), Putative DNA binding protein (S5MUL0, S5MCI7, A0A0K2CNU3), Putative DNA condensation protein (A0A097EXJ8, A0A097EXF9, A0A097EXK7, A0A097EXE9), Putative DNA injection protein (K4F9S4, K4ICF0, B0FII6, A0A0B4N0C3, G0X4V3), Putative DNA methylase N-4/N-6 domain protein (A0A0A8WIQ4), Putative DNA polymerase (F1D0Q9, F1D105), Putative DNA polymerase I (M4QDT1), Putative DNA polymerase III subunits gamma and tau (A0A0E3D9M8), Putative DNA replication protein (A1BTZ6, B2ZYV7), Putative DNA transfer protein (U6C6A1, U6C6G7), Putative DNA transfer protein p32 (Q9T1R6), Putative DNA-binding protein (V6F820, A0A1L7QXH4, X2CXH0, H2E188, A0A1L7QV24), Putative end-filament protein (D1GF47), Putative endolysin (A0A1B1IMU2, R9R270, R9QM37, C7T209, C7T264, C7T2B6, C7T2G7, R9R1X0, B5SP49, V9VHX3, A5GYL4, I1TQ57, S5VZH2), Putative Erf protein (Q94M69), Putative gpH domain protein (K7QJH9), Putative head-binding domain of phage tailspike protein (E1XTI1), Putative head-tail connecting protein (A0A193GYI4, Putative head-tail connector protein (A0A075DXM3, E1Y3U5), Putative head-to-tail-joining protein (Q287B1), Putative Hef-like homing endonuclease (S5VLF9, S5VLN0, G8GJ26, G8GIS0), Putative helicase (B2BTL9), Putative host specificity protein (A8YQK1), Putative internal virion protein (K4FE74, A0A088FSC5, E1Y3V2, E1Y3V1, U3TIZ3, A0A068Q6Z2, A0A077KTK6), Putative internal virion protein 2 (17FWK5), Putative internal virion protein B (V9QKM0, D1L2Z1, A0A0C5Q3Z5, A0A1B1PEE3, A0A1B1PEK5, K4NYZ0), Putative L-alanoyl-D-glutamate peptidase (A0A0E3D983, A0A0E3DFB5), Putative large distal tail fiber subunit 2 (A0A060AMH2), Putative lectin-like domain protein (K4JS82, K4JQM9, K4JPR1, J3U9S0, K4JQK2, K4K730), Putative lipoprotein (K4JSL9, A0A0K1LNM4, A0A0A0YP81, A0A0S1S3A5, A0A059T7N4, R4WCT8, A0EWV3, U3PDY7, W5R929), A0ZS07, I1W5Z7), Putative long tail fiber proximal subunit (F2VXI0), Putative lower collar protein (A0A067XGU9, A0A185AMX1, W6E811, G9M971, G9M950), Putative L-shaped tail fiber protein (A0A1B1P9A5), Putative lysin (Q8LTP4, I6P8D3, M41776, A0A059PAE0, M41786, A0A059PAI9, A0A059PAE2, A1EAB6), Putative lysozyme (P21270), Putative lytic transglycosylase (Q858G0), Putative lyzozyme M1 (D6PSS2), Putative major tail protein (G9M967), Putative mannose 6-phosphate isomerase (Q2LIE4), Putative membrane protein (A0A0E3D918, M4HNS4, M4HNG2, W0TVV5), Putative membrane protein MbpF (I6W961, I6X5B8), 16WA64), Putative minor coat protein (E5F072), Putative minor structural protein (J9PS01, W5QUX5, J9PTW2, A0A0E3DEZ0, M1F224, 080185, L0P527), Putative minor structural protein 1 (G9J200), Putative minor structural protein 2 (G9J201, A0A0A0PQM7, L0L8X6, A0A0A0PIV5), Putative minor structural protein 1 (A0A0E3D9V0), Putative minor tail protein (A0A0E3DEV4, K4FCD0, Q333E6, Q6J1X5, X2CYG3, A7YGW7, Q0R566, 080179, F8HGU0), Putative neck protein (A0A060AH10), Putative neck protein (A0A0K0KVG1), Putative peptidoglycan hydrolase (X2CY74, V6F993, X2CXZ5, H2EIC0, X2CYK8, X2CYA8, H2E162), X2CYQ6), Putative phage cell wall hydrolase (A0A0A8WIF2), A0A0A8WJ93), Putative phage host specificity protein (S4USV0), Putative phage injection protein (A5VW66), Putative phage pre-neck appendage protein (A1BTX1, A1BU68), Putative phage protein (I6ZRN2, J7KDD6, A0A0A8WEY5), Putative phage replication protein (R4I FK6), Putative phage structural protein (C9E2K6), Putative phage tail fiber (S0A280, R9ZYR2, S0A4M9), Putative phage tail fiber protein (K7QKD5, B5BTX4, F1D0V5), Putative phage tail tape measure protein (Q2LIB9, Q2LIH2, A0A0A8WJN8, E2ELJ5, B6SBU0, M4I6A1, A0A059PAT4, M4I6C0, A0A059PAG9), Putative phage tape measure protein (V5JXQ9), Putative phage-related lysozyme domain (Q2Z0P8), Putative phage-related tail fiber protein (A0A068Q5X6), Putative phage-related tail tape measure protein (A3F654), Putative phage-tail protein (Tape measure) (B1GS57), Putative phospholipase (I7JC11), Putative portal protein (A0A0A0PLP0, L0L894, A0A0A0PUG5, A0A0R6CMJ0, I0J317, H2DE37, C1KFL6, B2BTH3, S4S2T1), Putative primosomal protein (Q286X4), Putative proximal tail fiber protein (A0A1D8KFZ3, A0A1D8KFC6, A0A1D8KI81), Putative Ras interacting protein RIPA (A0A0E3DF05), Putative receptor binding protein (R9R0R5, Q71AW0, Q71AV2, Q71AV6, R9R1T9, A0A1B11N44, R9R227), Putative receptor recognition protein (A0A0A0PZN5, A0A173GAQ2), Putative receptor-recognising phage tail fiber adhesin (J9Q7Y6), Putative receptor-recognizing protein (F2VXI4), Putative recombination related exonuclease (A0A0A0PJ70, A0A0A0PL30), Putative regulator of chromosome condenstation family protein (A0A0K2CN33), Putative regulatory protein (S4V6D4, S4SVD4, S4SVH7), Putative Rep protein (I6PC17, A0A076YSL7, W0TXR9), Putative replication initiation protein (A0A0K2CNJ1, A0A0C5ANB2), Putative repressor (B2BTL4), Putative scaffold protein (A0A0H4TEV6, Putative scaffolding protein (L7TME1, E5KJP7, A0A162HLG8, A0A0S1S0S6, A0A0S1RZV5, Q0E632, C0MQF8), Putative SGNH hydrolase (D0U203), Putative short tail fiber (A0A0E3FXT1, A0A0E3FE01, A0A0E3HHE7, A0A0E3F9K7, A0A0E318J6, A0A0E3G315, A0A0E3HIJ7, A0A0E3FLB8, A0A0E3G4N1, A0A0E3HKP8, A0A0E3FHA1, A0A0E3G3Y3, A0A0E3HTV3, A0A0E3HIK0, A0A0E3G2N6, A0A0E318H5, A0A0E3G187, A0A0E3EZS9, A0A0E3F0E5, A0A0E3IA69, A0A0E3HPP5, A0A0E3FMV3, A0A0E3F5C7, A0A0E31792, A0A0E314B7, A0A0E31130, A0A0E319X1, A0A0E3HK6, A0A0E3HFY5, A0A0E3FCN1, A0A0E3FJ26, A0A0E3HFQ9, A0A1D8KSQ3), C7BVH9), Putative side tail fiber protein (G1CCF5), Putative single strand binding protein (Q8SDG9), Putative single stranded DNA binding protein (B2ZYV4), Putative single-stand DNA binding protein (V5YTC4), Putative single-strand binding protein (M1PL31, M1NSA3, K4JXN0, M1R68, M1IRC1), Putative single-strand DNA binding protein (H9C0R6, Putative single-strand DNA binding protein (D5LH30, A0A0N7CGA6, A0EWX3, W5R941), Putative single-stranded DNA binding protein (H2A0F6, C51HK5, K4FBT7, M4QBP6, Q333D5, A0A162E3M3, S4S600, F8J185, A0A075KQE5, A0A075KL11, A0A075KL94, F7V9C8, U3PBI4, Putative single-stranded DNA binding protein Ssb (K7PHI1), Putative single-stranded DNA-binding protein (W6B0T9, A0A193GYD7, A9Q1R8, A0A059T676, X2CT42, A0A097PAQ3), Putative single-stranded DNA-binding protein 2 (R4IG44), Putative soluble lytic murein transglycosylase (A0A0K2QQH3), Putative SSB protein (F6LQB4, Q94M67), Putative ssDNA binding domain protein (A0A0E3DEM6), Putative ssDNA binding protein (G9I1D0), Putative ssDNA binding protein gp32 (I0J2S5), Putative ssDNA-binding protein (A0A192Y8G1, Q0R5A2), Putative structural lysozyme (G919K9), Putative structural protein (A0A0C5AAW8, K413R7, H6X4Y7, H6X4Z1, H6X4Z0, H6X4Y9, H6X4Y8, A0A0S2MYF5, A0A191ZCT8, A0A191ZCT7, A0A067Y192, A0A067ZJM1, M9PKX9, G0XNV2, B0FII0, G3LWQ1, I3WU69, R4JHS9, A0A0B4N235, Q2Z0W4, B5M9U3, B5MA34, A0A0N9ER92, T1S9Y0, T1SBJ1, V5XWK7, V5XVY7, K7REY2, A0A097PAT0), Putative T4-like proximal tail fiber (Q58M57), Putative tail assembly protein (A0A0B4SK05), Putative tail collar protein (X2CXQ4, H2EIC2, A0A1L7QNW5, X2CXI8, X2CXF4, X2CY07, H2E164, A0A1L7R005, X2CY41, V6F932, X2CYB9, A0A1L7R0B8), Putative tail component protein (Q9XJB0), Putative tail constituent protein (A0A0B5A6J3), Putative tail fiber (A9Q1W5, L7TMF5, L7TQV3, G3M190, I7B6A7, M4QBF1, K7PL69, K7PML6, X2CRN9), Putative tail fiber 1 (J9PRE8), Putative tail fiber assembly protein (A0A1421DL9), Putative tail fiber component (H8ZLV3), Putative tail fiber protein (A0A0D4DBQ5, A0A068CGF5, C51HQ3, C51HQ4, R4I G47, K4FB45, K4FCD2, A0A192Y7S7, B8QTW7, A0A1B21CX1, A0A1B21EA9, A0A0H3UDV7, S5MQT2, S5MDX5, G911M1, A0A0N7GFN8, A0A1B1PD96, C5H7L3, A0A023ZTR7, A0A023ZTU4, A0A023M125, H6W7W2, S4UT47, M4QBD9, B3RGI0, Q7Y5S2, A0A0A8J9X4, A0A0A8J9A5, A0A0A8JBR2, A0A0A8J9W2, A0A159B7L0, A0A076YL75, A0A0K0KVR6, F2W605, F2W6J0, E5E3G8, A0A0A1IWV7, V5JX11, S4S2F0, U3TM45, M9MUR4, F2VX00, D2K044, I6P9L3, I3PGW1), Putative tail fiber protein [Enterobacteria phage vB_EcoM-FV3] (A0A0M7QBC7), Putative tail fiber protein GP37 (Q6KGF6), Putative tail fibre protein (E5E4L4, C1KFN2, E0WQA9, E0WQB1, E0WQ98), Putative tail length regulator (A0A0B7MSY3), Putative tail length tape measure protein (I0J2Q1, L7TMG0, A0A023ZTS8, A0A0E3JQ03, Q7Y5T2, S6CLQ0, K7YY57, A0A0A1IWU9, A0A0A1IU71, A0A0D4DAK9), Putative tail lysin (W5QUF9, A0A0E3DFB4, S5MM68, A0A0C5K6Q6, C1KFN1, C1KFN0, I6P9R4), Putative tail lysin 1 (G9J205, J9PS02, J9PUY3, J9PQW6), Putative tail lysin 2 (J9PRF0, G9J206, A0A0A0PJ85, J9PUJ9, L0LA71, A0A0A0PL45), Putative tail protein (A0A068EP79, A0A068EMN7, F1C5E9, W0LHS3, W0LM75, D2XJU5, D2XJ94, D2XJE3, D2XJJ5, D2XJP6, B2BTI3, B2BTI2, E0YJ14, A0A075BU56, J7ME90, B7VFI9, K7RVF4, I6P8H4), Putative tail sheat stabilizer and completion protein (T4 gp15-like) (17JC41), Putative tail sheath monomer (A0A0K0KVG8), Putative tail spike protein (A0A0Y0AE86), Putative tail tape measure protein (W6AQY0, Q3HL06, K4JWVV0, K4JNJ2, I6PCW3, A0A193GYN8, I7A9A7, E0YJ17, V9VF10, A0A060D1L4), Putative tail tubular protein A (A0A088FWY4), Putative tail tubular protein A (17FXT3), Putative tail-fiber/lysozyme protein (H9C1A7), Putative tailspike (M1F225), Putative tailspike, beta-helical glycoside (M1IEB8), Putative tailspike, beta-helical glycoside (M1IQJ6), Putative tape measure protein (A0A075DXX4, A0A126D170, D9ZNE6, A0A0N9RUX9, A0A0N9S105, A0A0H3V0Q1, A0A0K0NL45, A0A0K0N732, B5SP40, V5JW01, F2W5Z6, F2W611, A0A0M4R5P3, G7YZ66, L0P3P2, A0A0K0N5D9, A0A0K0N545, A0A159B6P7, Q6UAW7, R9R1Z1, R9R1A4, Q9T1A7, R4JHS5), Putative transglycosylase (A0A077KC92), Putative transglycosylase (U6C7Z7), Putative transmembrane protein ORF1334 (Q3V4P9), Putative transmembrane protein ORF346 (A4ZUD1), Putative transmembrane protein ORF710 (Q3V4Q5), Putative uncharacterized protein (A7WKQ9, A7WKR0, Q50144, Q50151, D1GF98, E5E3Y8, E5EPE1, E5DQC2, Q19CF3, Q6RHV1, E5DRT0, E1A186, G9J1Z6, G9J295, G9JIV8, F8WPS8, A1Z015, G0LWG3, G0LWT4, G8GIW9, H6SU79, H6SUL7, H6SUN0, H6SUI2, F4YAD8, D0U2I5, H6WFV8, H6WFY2, H6WFU6, E9NIH7, E9NIH6, E9N112, E5AFX3, H2DE55, H2DE54, E5AGC7, Q70BH4, Q70BH3, H6VUB6, H6VUB5, Q6QGL0, Q6QGK9, G0XNV3, B0FII7, B0FII5, Q6XQB3, Q5ZGD1, F8S0T3, F8S0T5, Q9T0W8, C1KFR2, D6PSZ1, E9LUL1, E9LUJ3, Q9T1E3, D2KRE3, E9LUU2, Q6SEG3, Q6SE68, D3W0G1, B2BTK7, Q0GXW0, B1ABI7, B1ABI9, B1ABI8, Q38318, C3U2N5, 080210, A0A7S7, A0A7H9, A0A7F5, A0A7L2, A0A715, H6U5E8, F4N9U7, F4N9U6, F4N9U2, Q1I0Y7, E3SML1, E3SMT0, E3SMS9, E3SMT5, E3SMK4, E3SML3, E3SSN3, E3SSV2, E3SSV6, E3SSU7, E3SLZ4, E3SLQ9, E3SM58, E3SLR1, E3SLT2, Q58MB4, Q58M51, Q58MM9, Q58MX7, Q58MW9, Q58M26, Q58M59, Q58MF1, Q58MX9, Q58MY0, Q58MX8, Q58M58, Q58MM8, Q58LS3, Q58LG0, Q58LR0, Q58LR8, E3SP13, E3SNZ4, E3SP16, E3SNG0, Q58N22, Q58N09, E3SPB7, E3SPU7, E3SPR4, E3SPI6, E3SPC2, E3SPC0, E3SR48, E3SQY1, E3SQQ5, E3SQS8, E3SQQ6, E3SQS7, B8QU64, B3FJE3, B3FK56, B3FIW8, B3FIY6, B3FIY9, B3FJ66, Q5ZQW4, Q5QF54, Q5QF51, H6V836, E5E3K0, G919U9, G919W2, G919W3, G919V9, G91A19, E7CU76, B2ZYI2, B2ZYI8, B2ZY90, B2ZY20, B2ZY43, B2ZY50, B2ZY51, B2ZY46, B2ZYI6, B2ZYI4, B2ZXU0, F4YXT7, G0X4V6, E9N418, E9N419, G5DEB5, F2VX05, F2VXQ7, C4NT46, A8RHK2, A8RHJ8, A7YGQ9, A7YGN0, A4ZF86, A1BTY4, A1BU81, A0EWI9, A0EWQ4, A0EWX4, A0EX35, E0Y3M3, E0Y3Q1, G2Z198, G2ZID6, G2ZIC8, G2ZIC0, G2ZIG0, Q9XJB2, Q708Q2, A7DYB8, Q94M33, Q0R5A5, Q1WDF3, C4NTC4, Q5TJ88, Q8V9M9, Q8V9N5, Q8V9N0, A8TKE9, D1GF77, Q684A1, Q684C0, Q684D3, Q684E0, Q684D7, A0MN76, G8EXX4, G8EY14, G8EXW9, G8EXQ0, G8EXW8, G8EXU9, G8EYE4, F4YCK5, F5B3N1, F5B481, H6B144, H6T4W9, H6BIQ5, H6BHX3, H6BIJ6, H6BHZ6, H6T4S1, H6BIK7, H6BHZ7, H6T4S2, H6BIK8, H6BHY0, H6T4Q4, H6BIJ1, H6BIQ3, C7BV99, E3SJK4, E3SJZ6, E3SJX8, E3SJT4, E3SJT5, E3SIH5, E3SIA9, E3SIB1, E3S127, E3S154, E3S156, E3SIS5, E3SJD4, E3SIQ5, E3SKK2, E3SK57, E3SKK1, E3SKD4, E3SK80, E3SL23, E3SLE9, E3SL38, E3SKV1, E3SPY4, E3SQ55, E3SQ53, E3SQ06, E3SQB6, E3SQ14, E3SQE1, E3SPY5, E3SQ07, Q0QZC5, A8HNV9, A8HNV7, A8HP35, A8HNW8, Q647E9, A7XXT5, A0MNG9, A0MNC5, F9V106, F9VHR4, F9VHW2, F1D0Y4, F1D0Y2, Q6W161, G8CT79, Q8LT82, Q6RCF4, Q38198), Putative uncharacterized protein 061 (F8SJU3), Putative uncharacterized protein 063 (F8SJU5), Putative uncharacterized protein 064 (F8SJU6), Putative uncharacterized protein 140 (F8SK13), Putative uncharacterized protein 141 (F8SK14), Putative uncharacterized protein 19 (G3BLN4), Putative uncharacterized protein 23 (F1D0V4), Putative uncharacterized protein 25 (F1D0V6), Putative uncharacterized protein 43 (B8QTU1), Putative uncharacterized protein 47 (B0VK47), Putative uncharacterized protein 48 (G3BLR3), Putative uncharacterized protein 60 (C9DG31), Putative uncharacterized protein 60 (B8QTV8), Putative uncharacterized protein 89 (C9DG60), Putative uncharacterized protein eiAUOrf13 (E7EKQ2), Putative uncharacterized protein gp54 (D21ZN7), Putative uncharacterized protein gp56 (D21YX8), Putative uncharacterized protein gp57 (D21ZH7), Putative uncharacterized protein gp58 (D21Z41), Putative uncharacterized protein gp67 (D21ZB3), Putative uncharacterized protein orf14 (Q8W6L3), Putative uncharacterized protein orf14 (Q7Y3E8), Putative uncharacterized protein orf19 (Q8W6K8), Putative uncharacterized protein orf22 (Q08J83), Putative uncharacterized protein orf32 (Q08J73), Putative uncharacterized protein orf48 (Q6TM54), Putative uncharacterized protein orf48 (A7Y8Q7), Putative uncharacterized protein ORF48 (B7SE07), Putative uncharacterized protein vs. 1 (E5E4C1), Putative virion stractural protein (A0A0K2QQJ5, J7KE01, A0A1B219Z8, A0A1B21AB3, A0A1B21B3, A0A1B21BX0, A0A1B21CR3, A0A1B21DA5, A0A1B21D12, A0A1B21D10, A0A1B21DA2, A0A1B21E04, A0A1B21GH6, G919Q2, G91A35, G919U8, A0A0S0NA39, A0A0S0MWN7), Putative virion structural protein 16 (G5DEP3), Putative virion structural protein 20 (G5DER0), Putative YD repeat protein (I1TLF2), Receptor binding (F71TY5, Q3T4Y5, Q3T516, Q3T4V4, Q3T547), Receptor binding protein (A0A0A7RT04, A0A0A7RZA8, Q6EDY2, A0A161BZY1), Receptor recognition protein (D4ZA55), Receptor-binding protein (Q4FAC3, A0A192Y8U6, E9N493, A0A0A0RTY5, C9W9J0, R9TE48), Receptor-binding tail protein (11TE58, I7LEH0), Receptor-recognition protein (A0A023ZV71, P08234, P07875, Q9G0B4), Receptor-recognizing protein 37 (Q99363), Recombination related exonuclease (A0A076G7G7), Regulator of chromosome condensation (L7TKK2), Regulator of chromosome condensation RCC1 (L7TKJ3), Regulatory protein (R9QSV5), Rep protein (G4KNP0, G4KNT2, A1KX04, A1KX72, A0A0D3MV72, A0A0D3MW50), Replicase (D0U1H0), Replicase protein (C0M347, C0M3K0, C0M3F2, C0M391, C0M355, C0M442, C0M359, C0M1V4, C0M1X0, C0M387, C0M1N6, C0M3B5, C0M1M8, C0M498, C0M351, C0M3U6, C0M206, C0M1T4, C0M3K4, C0M202, C0M1W2, C0M1S6, C0M1T8, C0M278, C0M1Q2, C0M1U6, C0M1Y2, C0M1R4, C0M298, C0M274, C0M3H6, C0M262, C0M3G8, C0M3D6, C0M486, C0M3A7, C0M1P8, C0M4A2, C0M482, C0M3G4, C0M3C7, C0M3H2), Replication initiation protein (A0A068A235), Replication protein (U5PVX0, F1C5C3, A0A0E3TAG7, A0A075M4D6, W5R8N2), Ribonuclease III (F4YXU6), Rorf224 protein (003912), S protein (Q71TD5), S protein (Q71TP5), Scaffold protein (U5PZN4, A0A059PY43, V5Q8R0), Scaffolding protein (A0A0N71R69, A0A088F6K0, A0A023W7A0, A0A0F6SJV3, A9J7B6, U51CG3, A0A0B4N518), Scaffolding-like protein (B5BTW7), Scaffold-like protein (H6VUB1), Secreted N-acetylmuramyl-L-alanine amidase (U5PWL4, A0A0E3JQ51), Sericin I-like protein (E3SSU8, Q58LR6, E3SQS9, A0A0E3HBV3, H8ZME1, A0A0E3F9T0, A0A0E3HDN7, E3SJT7, E3SQ08), SGNH hydrolase (R9ZZU9), Short tail fiber protein (A0A193H2Y8), V5UR46), Short tail fibers (A0A192YBC5), Similar to bacteriophage P22 gp7 in GenBank Accession Number AAF75053 (Q76H15), Single strand annealing protein (R9QLK8), Single strand DNA binding protein (R9QMU0, G4WAH9, A0A059T663, C8CGY9, Q9MBS1), Single stranded DNA binding protein (A0A0K0VL95, I6SN68, I6ZXD0, S6CLP6, A0A0N7CEV3, A0A193GYG3, K41339, W8JYN2), Single-strand binding protein (E9LUM5, Q938M7), Single-strand DNA binding protein (H9A0Y8, A0A0A0YVW8), Single-stranded binding protein (E1ABY7, C9WBA0, Single-stranded DNA binding protein (A0A140G764, G1CST7, C9DFZ1, U5U3W5, U5U726, U5PVP1, X4YDM0, A0A075LZJ1, C51U12), Single-stranded DNA binding protein Ssb (A0A067YVN3), A0A067YXJ4), A0A067YYE9), A0A067YXU9), Single-stranded DNA-binding protein (Q9XJG4, A0A0P0IJE0, A0A0P017P6, A0A060AKV1, A0A076G5X9, A0A068CFX2, A0A0H4A790, S5M9Z7, M4SRQ0, A0A192Y6L6, A0A1B1W281, U5PYJ2, A0A160CA86, A0A1B0VAF5, A0A0H3U4B5, A0A0D4DD48, R9QTP7, M9NUI4, I1W659, A0A191KBE1, A0A191KBG9, R9TPS8, I3PUY5, A0A059WRL7, I3PGW4), Single-stranded DNA-binding protein ssb (A0A0N9SKG8), Single-stranded DNA-binding protein SSB-P1 (G8EYH4), Sit (Q71TD0), Sit (Q71TP0), SLT domain protein (D21ZU8, D2J014), SLT domain-containing tail protein (A1Z006), SLT-domain containing protein (W5R9Q7), Small distal tail fiber subunit (E1A188), Ssb (Q1MVN2, Ssb (A5PJ12), Ssb (A4ZF83), SSB domain protein (A0A141DZL2, A0A141DZG3), SSB protein (W8EK97), SsDNA binding (A0A0C5PS70), SsDNA binding domain (S5Y0B3), SsDNA binding domain protein (A0A0K2D0S7, X2JIV5, A0A0K2CZS6, A0A076G8U7), SsDNA binding domain-like protein (A0A142F116), SsDNA binding protein (A0A143FJS4, G0YPW7, A0A1B3AYF2, A0A160DD76, A0A160DD37, G8GDI0, A0A1B0Z158, K7YY32, O80084, Q9B0G2, A0A0A7HE94, A0A0H4U1T3, A0A0E3T9H6, A0A0E3XC62, G4KNN8, G4KNT0, A1KX68), STEC autoagglutinating adhesin (A0A0A0YS13), Structural protein (C7BV06), Structural lytic transglycosylase (O48376), Structural protein (U5PZZ5, A0A075DXE6, X2CXP2, X2CXY2, V6F7P7, V6F7Z6, X2CXL0, X2CXG3, H2EIB8, H2EIB1, X2CXH6, X2CY95, X2CXS6, X2CY16, X2CY28, H2E160, X2CYJ1, H2E153, X2CYC9, A0A067XQM9, S0A0Y9, R9ZZX2, S0A1K7, S0A184, S0A107, R9ZXA4, M1PL16, S0A2J5, S0A1S1, R9ZZ95, S0A0G4, S0A466, S0A2C4, S0A2C3, S0A401, S0A2C8, R9ZZ34, S0A2D1, R9ZYZ5, R9ZYG9, R9ZWK3, S0A2V8, S0A1Z5, S0A0F8, S0A1X0, M4PNT0, R9ZWK2, R9ZWV1, R9ZZB2, R9ZWK8, S0A572, S0A3R0, S0A231, S0A582, R9ZXB1, M4SNC0, S0A2L7, M4QH50, M4PNT5, M4QR16, M4T2D5, A0A127KM46, A0A0A7CHI7, J710P3, A0A097EYG7, A0A097EYC9, A0A097EWY4, A0A0A7X6X6, X2KMJ7, C3U2S6, T2A957, T2A8M8, L7TJT2, L7TMY2, S5VNL1, A0A142K5A9, T2A908, T2A8H0, T2A965, T2A7W3, U5P088, L7TGW5, L7TMM5, L7TMB0, L7TGK5, A0A0A7RT74, T2A8W7, L7TGB5, L7TM30, A0A097BXM0, S5VLS8, L7TG30, L7TLT0, A0A0A7RT13, E3SLZ2, R9S7S8, M4QRA1, E3SNK8, E3SQX9, X51353, A0A0U1ZVN8, A0A0U1ZUH6, S4T919, S4T8T8, M410B3, M410P7, A0A0M5M7E2, K4PAJ6, K4NZA8, A0A1B3SN24, A0A0E314E9, A0A0E3G7L5, A0A0E3EZ05, A0A0E3HXS2, A0A0E3EZX6, A0A0E3G5P6, A0A0E3EWS0, A0A0E3EXT3, A0A0E31358, A0A0E3IAP9, A0A0E3FZD5, A0A0E3EW82, A0A0E3FY41, A0A0E3F8P2, A0A0E3F884, A0A0E3EL74, A0A0E3FDW9, A0A0E3F6Q1, A0A0E3ERG4, A0A0E3EYF4, A0A0E3HVE8, A0A0E3HWP8, A0A0E316U4, A0A0E3F0N7, A0A0E3FZJ2, A0A0E3ESY9, A0A0E311B5, A0A0E3FEF3, A0A0E3HVN8, A0A0E3G013, A0A0E3HG45, A0A0E3HPM2, A0A0E3FFF2, A0A0E3F2W8, A0A0E3FD05, A0A0E3EN12, A0A0E3F174, A0A0E3FWV3, A0A0E3HMX0, A0A0E3IAJ6, A0A0E3ERF5, A0A0E3EPQ7, A0A0E3ENK5, A0A0E3F506, A0A0E3FX40, A0A0E3EQW0, A0A0E3FVT6, A0A0E3EX61, A0A0E3ELD6, A0A0E316E4, A0A0E3FHZ0, A0A0E3HDW5, A0A0E3F1V5, A0A0E3IAF9, A0A0E3G7R6, A0A0E3FTL4, A0A0E3F643, A0A0E3EM94, A0A0E3FVG9, A0A0E311N7, A0A0E3FE28, A0A0E3FX28, A0A0E3HD08, A0A0E3HV51, A0A0E31226, A0A0E3HSH0, A0A0E3HUT4, A0A0E3EYG1, A0A0E3FG64, A0A0E3FUS0, A0A0E3HT80, A0A0E3F948, A0A0E3EPA4, A0A0E3G801, A0A0E3FAM2, A0A0E3HU18, A0A0E3FM45, A0A0E3G5E5, A0A0E3HJU1, A0A0E3ICC9, A0A0E3F5E6, V5USF6, A0A0E3FG94, A0A0E3HIH6, A0A0E3FAB5, A0A0E3FCR5, A0A0E3FKG8, R9TM25, A0A0E3FAJ6, A0A0E3ICE3, A0A0E3F9M0, A0A0E3FFD4, A0A0E3G5R0, A0A0E3EL4, A0A0E3EMN8, A0A0E3EN93, A0A0E3G0C4, A0A0E3ESJ9, A0A0E3ERA0, E3SJZ4, M1U9S8, M1U9F0, M1U2Y1, M1T238, M1U2H2, A0A1D8KSF1, A0A1D8KT15, Q0QZJ6), Structural protein ORF567 (Q3V4U7), Structural protein ORF800 (Q3V4R2), Structural protein putative tail fiber protein (D6RRI0), Structural protein VP2 (F8RW83), Structural protein/betalactamase (T2AAG5), Structure protein putative major tail protein (G9M946), Surface protein 26-residue repeat-containing protein (A0A0E3HS79, A0A0E31817, A0A0E3HHJ0, A0A0E3HK27, A0A0E3HKB1, A0A0E3IAG3, A0A0E318H4, A0A0E3IA61, A0A0E3F4A6, A0A0E3FRR6, A0A0E318G1), T4-like virus tail tube protein gp19 (A0A0M7QAJ3), A0A0M7QHP0), Tail assembly chaperone (S5YZ58), Tail assembly protein (A0A160CBC6, K4HZF4, A0A193H089, V5Q8W6), Tail collar domain protein (A0A0F6THT2, A0A0F6R610, A0A0E3G487, A0A0E3FQQ4, A0A0E3FPA3, A0A0E3HHB9, A0A0E3F501, A0A0E3FWZ7, A0A0E3HPS2), Tail collar domain-containing protein (W6EKG4), Tail component (A0A0P0IZA1, U5U3S00, B4XYQ4, U5U775), Tail component protein (C9WB80), Tail fiber (I6XGF3, K7P831, K7PHS0, G0YPM1, G0YQ25, A0A067YXR4, A0A097EYK2, A0A067YYP2, A0A067YYV7, Q9MCR7, A0A0H4TGH1, E9LUR4, A0A0F6WEJ9, M1IPS2, A0A0E3HGU7, A0A0E3HFW0, A0A0E3FQC6, A0A0E3HKR3, A0A0E3G1S9, A0A0E318S8, A0A0E317L1, A0A0E3G4T3, A0A0E3FQP2, A0A0E3HQM3, A0A0E3HMI6, L0CQ12, A0A096VKG4, G8EYC2, A4ZRC7), Tail fiber adhesin (A0A097J588, A0A097J615, G8E059, G8E063, G8E060, G8E061, G8E062, A0A097J4F3, G8E065, G8E058, G8E056, O80267, A0A0A7HBP8, S5MLA1), Tail fiber adhesin gp38 (O80255), Tail fiber J (K7P6Q8), Tail fiber PblB-like protein (A0A0A0YV37), Tail fiber protein (A0A190XCC0, V5R8R3, A0A143FL46, A0A1B1PB74, A0A024B142, A0A024B3U2, A0A143FQ79, A0A143FGC9, A0A143FQ65, A0A143FQ50, A0A1B1SGJ7, A0A143FM83, F8WQ07, A0A143FL69, A0A024AZC2, S5MSK9, S5MB62, S5M627, S5MAE6, A6N3D8, I6NW36, A0A0M3UKZ0, A0A0K1LNL9, A0A0E3JTQ3, A0A172JG79, A0A0A0YQL9, A0A0A8WET9, A0A0A8WJ53, F6K8M0, F1C569, A0A0F7DD40, A0A0C4UQV0, E5AG01, E5AGK3, I1TE35, C9DGQ8, J9SG77, A0A0E3T9Y3, A0A0E3TAY1, A0A0A0RSC6, A0A0A0RLH0, A0A067YVW7, A0A067YYE5, A0A067YY41, A0A067YY47, A0A067YWB8, Q859H9, A0A0D4DA86, A0A023ZTT3, A0A0E3GML4, A0A0A0RPB1, D1L2X0, K9L8R5, K410E3, A0A0P0ID17, A0A0P0IJR2, A0A0P017K0, M5A995, A0A0H3YI38, A0A1B1PEJ9, Q859E1, A0A0A0YX94, A0A059VJZ6, A0A059VFW9, A0A059VFW2, A0A0S2MVP8, A0A1B1PE12, A0A1B1PE19, K9K8F7, U5PYI9, A0A160CA87, X4YW11, S4TSZ8, A0A193H2R1, Q8SDP3, H2BCT9, A0A1D8KS45, A0A1D8KS49, V5Q7R9, A0A0P0LE96), Tail fiber protein S (Q9T1V0), Tail fiber protein, T7 family (E5AG90), Tail fiber protein-like protein (K4NXY8), Tail fiber repeat family protein (A0A1B0V7G4), Tail fiber-like protein (A21811, D7RMI2, A0A0E3HAV7, A0A0E3HN99, V5USY2, A0A0E3FG97, A0A0E3HLE4, A0A0E3HCU2, A0A1D8KTA4), Tail fibers (A0A0K0QTD1), Tail fibers protein (A0A0N9RZJ9, A0A0S2MY36, A0A0D3QHB7, A0A160CBG9, A0A0F6SJB0, A0A0F6YQ13, W5S7J3, A0A193H093, A0A193H153, A0A173G9L8), Tail internal virion protein B (G0YQ80), Tail knob protein gp9 (Q37890), Tail length regulator (C4MZ04), Tail length regulator (Q76XG8), Tail length tape measure protein (Q218F0, I1TLF1, K7P7Q2, K7P6S7, K7P6L9, K7P6X5, K7PM62, K7PKG1, K7PGX8, K7PH87, A0A0A0YSN4, G8C7J5, Q9MCU6, Q9MCS3, A0A0M3LSU5, A0A0M3LS54, A0A0D4DC81, C8CH30, M9QQM6, U5U762, R9TMK1), Tail length tape measure protein H (K7P7L6, Tail length tape measure protein H (K7PM96), Tail length tape-measure protein (A0A0K1LPA2, A0A060ANI0, A0A0M5M3L4, A0A0S2MXY3, A0A182BQ85, A0A0M3UL96, A0A0M4R2V3, A0A09714X9, A0A097P6S4), Tail length tape-measure protein 1 (A0A0E3GMH8, A0A0E3JPV7, A0A1V0E7M6), Tail lysin (A0A143FKE2, A0A120HUN9, A0A120HUN7, A0A1B1SGM9, A0A0A0RMV8, A0A0A0RS48, A0A0A0RNB0, A0A143FPM9, A0A143FH61, A0A143FNI1, A0A143FJL3, U5PRP6, A0A076G7X7, U5Q0P5, W5R8K4, A0A0D3MWD9, K7QMK7, A0A075BDS9), Tail lysin 1 (A0A0K2D106, A0A024B0Y1, A0A024B187, A0A143FLP3, A0A0K2CZX6, A0A075M4J8, S5Y744), Tail morphogenetic protein (W0TWE6), Tail morphogenetic protein, tape measure protein (W0TWD7), Tail protein (A6XAD6, A0A192Y8X8, A0A0K2FKZ5, A0A024B2B1, A0A024B3U8, M4W9Q4, A0A1B1SGT5, A0A143FMA6, Q9FZW6, S5MMQ8, I3PV23, I3PV49, I3PV78, U5PVN7, E5AGJ8, E5AG85, B1ABI4, Q9AZS0, V5R475, V5R580, R9RUK8, A0A088FW76, A0A088FW76, A0A097BXN8, A0A0B5A5U6, A0A0K1LJQ3, A0A097BXB1, V5R5S6, A0A0F6NYI7, A0A0U2NVB5, Q859L1, A0A185AMW7, Q859J0, A8D3S2, H9A0W4, H9A0P5, H9A0P8, Q56S88, C9WB82, C9W918, Q38005, A0A068YP78, A7J2A5, A0A0B4MZ94, A0A1D8KSS7, Q938K3, G3FFM3), Tail protein Pb4 (R9RG81, R4VV12, R9RGK0, R9RGW0), Tail sheath monomer (K4F6R7), Tail sheath stabilizer and completion protein (I6WC40), Tail spike (A0A024B3A9), Tail spike protein (A0A0A0RUQ7, A0A0A0RMU7, Q0PDK6, A6N3F8, E9N118, A0A0F7LC06, A0A0A8J8S8, Q858F5), Tail spike protein 1 (G8GDR2), A0A1B0Z1E3), Tail tape measure (A0A0G3EYJ4, I6NKY8, J9QEB7, K414C2, R9QN01, A0A0H3U4E2), Tail tape measure domain containing protein (V9QJ75, S5MLP4), Tail tape measure protein (A0A172JIA9, Q3HL62, A0A1B1P8E8, A0A067YVL5, A0A067YW42, A0A067YYN5, A0A067YWB5, M4QBM9, K7PHW5, C3U2R3, A0A0D3MT00, A0A059T7P2, A0A0S0N1V8, A0A0M4REK7, R9W108, A0A076G7H2, W5R812, A0A0K1LKC4, A0A0B5A2F0, A0A1B1SDY9, A0A0B5CU25, A0A0K2CXX8, A0A0K2CYL9, A0A0B5A0F2), Tail tubular A protein (A0A0G2SSE7), Tail tubular protein B (A0A059PYE2, A0A192Y7B5, H6VUB4), Tail:host specificity protein (C6ZCZ5), Tail-associated lysozyme (V9M052), A0A0D4DB99), Tailfiber like protein (C7BVB4), Tail-length tape measure protein (M1TB03), Tail-like protein (A21806), Tailspike (U5PSK6, U5PSF7, U5PWQ4, T1S9Y2, T1SBJ2, A0A0C5PS12, H2D0F8), Tail-tube assembly protein (A0A0M4S555, A0A0M7QAK3, A0A0M7QDH0, A0A0K1LQD5), Tap measure protein (A0A192YA25), Tape measure (A0A0P0IQK3, A0A0S1S333, G1FTV4, A0A0K2FNG4, A0A097BXR0, A0A0S1S1Q3), Tape measure domain protein (E5AFZ2), Tape measure protein (A0A0A0RSI6, A0A173GB82, U5Q080, A0A0E3M0Y3, U5Q1E0, A0A0E3T6B7, I6NL19, A6N3F2, A0A0A0RVQ8, X2KUA9, A0A1B3AY93, A0A142KC22, A0A166XZ24, A0A142KA90, A0A142K9T4, A0A160DDD3, L0AQN0, Q9T0X1, A0A0A7NNM6, A0A1B0Y2Q3, A0A096XUZ3, R9QMA6, A0A0M4S2S3, A0A142K618, S5Y943, S5YNZ2, S5YBF3, S5Z4B5, S5Y764, A0A0M4RSA7, S5YLV3, A0A0K2FMW4, A0A0M4RE20, A0A0K2FMW9, A0A0K2FPD5, A0A0M4QUU1, A0A143FPM7, T2FIW9, A0A0M4R1N6, A5YJY2, S5Y3W0, S5YA4, A0A0K2FNH3, H6WU09, A0A060RJ18, G8GWF6, A0A1B1W284, A0A088C3U4, A0A0M3N013, Q7Y400, S5Z9G6), Tapemeasure (A0A0K2D039, R4TT78, A0A088FTM1, R4TAA0, X2KSD1, V5RAH0, A0A142F2F1, T2FJ14, R4TBR1, V5R9P2, R9R594, A0A088FPQ9, A0A0A0RQ57, A0A097EYK3, A0A076YH23, A0A0B5A173, V5R9T7, A0A0K1Y732, W0LIX1, R4TQG9, A0A0H4THU6, S5M864, A0A088FA71, A0A088FWF2, R4TCC9, A0A0K1LRC3, A0A1B1SEL1, R4TQN4, A0A076YK66, X2KTH4, V5RA44, A0A076YLZ5, S5YL46, R9RWD9, R9RUM5, A0A0K1LLI9, A0A088FRK9, A0A0B5H802, A0A0A1ENG5, A0A076YNS5, A0A023ZY61, R4TET5, V5R7Y3, A0A0H4TKG5, A0A023W7N5, V5R8I3, A0A0K1Y6S9, R4TLB7, R4J148, A0A0K1LTT8, W6AT48, A0A0A7S290, R4JMF6, A0A076G771, A0A088F8S6, S5XW47, R4JGF5, A0A0A0RQH0), Tape-measure protein (S5M424, A0A143FK77, A0A097EVC4, S5WBP1, A0A0K1Y6J2, A0A076G5P4, W8G0N7, G3LWP6, A0A0F6SJZ0, A0A0H4U0C0, A0A0F6YR17, T2AAG2, S5VVV8, A0A068C904, A0A076G7R6, A0A059VG07, A0A0K0MWQ1), Tapemeaure (A0A0B5A360), ThyX (A0A097BYK6), Tip attachment protein J (P03749), TMP (Q9G097), Tmp (A8ASK6), A8ATH6), TMP protein (A0A0D3MUV0), TmpC (I6XJN0), 16X4X4), 16WJJ0), D3G7J1), 16XFJ9), A0A076YN89), 16X6F5), 16WJ35), TmpF (I6W9C0), 16XE35), D3G7K0), 16X5D9), 16XK40), 16WAR4), 16XDL9), Topoisomerase II large subunit (H6X3W4), Topoisomerase II large subunit (A0A0A8J9T9), Transcriptional regulator (W5RAQ9), Transglycosylase (A0A088CQ71), Transglycosylase SLT domain protein (A0A1B0VDM8), Triple helix repeat-containing collagen (F4YCN3, F5B3N3), Tubular tail protein B (M1UH51), UDP-3-O-[3-hydroxy-myristory] glucosamine N-acyltransferase (A0MN70), Uncharacterized 38.6 kDa protein (P19297), Uncharacterized protein (Q04391, Q04392, V9SHQ9, V9VEK4, V9VHQ0, V9S139, V9VHL9, V9SKR7, A0A0B5A516, A0A0G3F094, A0A0G3EVJ8, A0A0K2FIE8, A0A0K2FI31, A0A0K2FIC5, A0A0N9P969, A0A0N9PAW9, A0A0N9NWG4, A0A0N9PCU3, A0A0N9P9D9, A0A0N9P792, A0A125SJ71, A0A125SJ98, A0A125SJB6, I2GUE7, I2GUG1, L7TQP3, R41PS9, K4PB47, A0A190XCB0, U5PZZ8, A0A075DXW2, A0A126DI162, A0A126DI136, A0A0D4DCD0, A0A0A0RMP5, I3WVW2, A0A068C8K3, I6WBU6, E1A2L0, Q76YN6, J7FAQ4, R9RG68, A0A059PY42, A0ZYS9, A0A140G6V4, A0A140G6Y3, A0A172J153, A0A172J114, S5M427, S5M458, S5MS67, J9PUM1, X2JN84, J9PRK8, A0A0E3D9L0, J9PRE6, J9PRM6, A0A0S2SXP6, A0A0S2SXY5, A0A0S2SY94, A0A0S2SXX2, A0A0A0PJ49, A0A0A0PUQ7, W5QUS1, W5QUP4, J9PV63, A0A140HLZ6, A0A140HM01, A0A140HLZ2, A0A140HLU9, A0A1B1PB80, A0A0Y0AMI7, A0A0Y0AFT7, A0A0Y0C537, A0A0Y0ADW2, A0A024B062, A0A024B0J4, A0A024B136, A0A0K2FKZ0, A0A024B123, A0A024B2A5, A0A024B1S8, A0A024B2R3, A0A0E3DEY9, A0A1B1SH35, A0A1B1SGL5, A0A0A0RMV3, A0A0A0RMR9, A0A024B3U7, A0A0A0RSG7, A0A0A0RPJ2, A0A0A0RNB4, A0A143FNT3, A0A143F116, A0A143FNH7, A0A0H4U1M4, A0A0H4TKH9, A0A1P8CWQ1, A0A143FJM1, M5ABV5, M4ZQV9, A0A143FLE6, A0A173GBG5, A0A173GC72, A0A127AW92, A0A0K2D017, A0A0K2D0B2, U5J9M9, U5J9M2, M4HPF3, M4HNQ1, L0LBQ0, L0L815, M1F46, J9PW1, J9PRU5, J9PL92, J9PLT5, J9PM61, J9PLP4, U5PRQ1, U5PSH1, A0A076G703, A0A0A0PL07, A0A0A0PKW1, A0A024B031, A0A024AZ00, A0A024AZ79, M1HMI4, M1IQC7, U5PXN1, U5PU78, U5PTU7, S6ATL0, S6ATR7, U5PZ67, U5PVB6, A0A0C5AN76, A0A0A0RNF8, A0A0A0RNQ2, U5PWV3, U5PWF5, A0A0A0RNK3, A0A0A0RVH6, U5PZI2, U5PVM5, A0A075M0A7, U5PWR1, U5PXD8, A0A0E3JJ53, U5PY97, A0A0E3T5M1, A0A0K2CNS4, A0A0K2CNJ0, X2CYH5, V6F7J3, X2CY85, H2EIB9, A0A1L7QQ51, X2CXR5, X2CYM4, H2E161, A0A1L7R075, A0A1L7QQB0, X2CXU9, I6NP94, A0A0A115M8, A0A0A1I652, A0A0A1I626, A0A0A8KWM5, A0A0A8KXI1, A0A0A8KWU6, A0A0A8KWP4, A0A0A8KXM2, A0A0A8KWW9, U3PCK3, I6NRM9, I6NQ16, I6NRD4, J9SWI0, J9RWZ6, A0A1B0XW82, A0A1B0XVW9, I7JCA2, S5WAE2, A0A067XR00, A0A067XRJ1, A0A0M4RDH8, A0A0M4S4X7, K4JR33, S0A0L1, S0A124, R9ZYS3, S0A4N6, R9ZZW6, M4SLC3, S0A0Y4, M4T1V1, A0A0K0QS24, A0A0M5M3J0, A0A0K1LNE3, A0A076YPD5, A0A172JG26, A0A1B1 IXF0, X5JB43, J9QD15, M9Q2I5, I6S2U2, W8CQR0, R4I FF3, R41135, R4I FN6, R4I FA0, R41108, A0A0K8I WM3, F1C594, A0A0K1YB89, A0A0K1YAT3, K4F6T5, K4F7G7, K4F7V5, K4F6V8, K4F919, K4F604, K4F9R9, K4F7E5, K4FBA8, A0A096XUU3, A0A096XUU1, A0A096XUT9, K9S009, I1TRF3, I1TRN1, I1TR83, I1TR53, A0A060ALS9, A0A060ACJ9, A0A060AG28, K4F9B4, K4F718, M4QE99, M4QER6, M4Q144, M4QR96, M4QGU6, M1NXF9, U5PS36, M4QDJ8, M4QE30, M4QDR3, M4QHS9, M4QHN2, M4QQU4, M4QDR9, M4QG86, M4QHI8, M4QQL7, M4QGB0, M4QDN8, M4QQJ5, M4SKW9, M4SLN3, M4SQ94, M4T1X6, M4SQ89, M4SQ26, M4SLU2, M4T200, M4SNW6, M4T2D0, E3SQN9, E3SQP0, E3SQI9, A0A0C5AIV6, A0A0C5AE55, A0A0C5AIX3, A0A0C5AIQ2, A0A0C5AAS4, A0A0C5AMX8, A0A0C5AMV3, A0A0C5AE37, A0A0C5AAS8, A0A127KM73, A0A127KLZ9, A0A127KMK7, A0A127KLS9, A0A127KLS6, A0A127KLG9, A0A127KL32, A0A127KLI9, M1UAC7, M1TVT8, A0A097PAP1, A0A023NGT6, A0A023NGH3, A0A0A7CHI9, W0LLU2, W0L109, K4PYC9, K4PW82, K4PXG3, K4PWS4, L0MX80, A0A0C5ACS3, A0A193GYN3, A0A193GY13, A0A193GYJ4, A5LH71, A0A076YNZ2, K7P878, K7P6F6, K7P7N1, K7P856, K7P7C4, K7P7J1, K7P6J5, K7PHQ0, K7PJV8, K7PGX6, K7PLS8, K7PGR3, K41158, K4HZQ9, M9NZD9, L7TMG4, L7TLQ7, H6X3N8, H6X3P5, H6X3K1, H6X4Y2, H6X4U2, H6X3M8, H6X3Q5, H6X4C4, H6X3M5, H6X3T9, K7PKY0, K7PJX2, A0A096XSW4, A0A097BY29, A0A0C5KL48, A0A0E3T978, A8E2B5, W6ARR1, W6AT83, W6AR29, W6ARK6, W6B1Q2, W6B1R8, W6ATJ2, W6ARM4, W6B1M4, W6ASB8, W6B181, W6ARV8, W6ASC2, W6AR80, W6ARM3, F1BUU7, A0A0A0YRB3, W8CZE8, W8CZV6, W8D0J4, W8CZD2, W8CZC8, J7KE73, J7KCG7, A0A1B21AC9, A0A1B219V9, A0A1B219X5, A0A1B21BG5, A0A1B21CK8, A0A1B21C98, A0A1B21CE4, A0A1B21CD1, A0A1B21CZ3, A0A1B21DI8, A0A1B21EA8, A0A1B21DN3, A0A1B21DQ3, A0A1B21G09, A0A1B21GH1, A0A1B21G75, A0A1B21G55, A0A0F6R6B6, A0A0F6TKF1, A0A0F6TJV9, A0A0F6TI61, A0A0F6THQ7, A0A097EY78, A0A097EY82, A0A0D5BI44, A0A0D5BHL1, A0A0D5BHF7, A0A0D5BI16, A0A0D5BHK0, K4HYW7, J9RVT5, J9ST34, J9SML9, A0A0F6N5T9, A0A0F6N5M8, I7B2Q5, W6ARS2, W6ASL0, W6AS62, W6B203, W6ATS4, L7TM46, L7TL41, L7TIH0, L7TKJ8, L7TK00, L7T118, L7TQD9, L7TQA5, L7TKW0, K7QJW2, A0A0A0YPX7, A0A0A0YW97, A0A0M7Q827, A0A0M7QB26, A0A0M7QCC6, A0A0M7QC74, A0A0M7Q7Y1, A0A0M7QAP0, A0A0M7QA54, A0A0M7QCX6, A0A0M9JJ99, A0A0M7RFE8, A0A0M9JJC4, A0A0M7Q9P6, G9L6C2, A0A166LWA2, A0A023MHI8, A0A023MHN3, X2L015, K4NZE1, A0A067Y163, A0A067Y0D6, A0A067ZGY3, A0A067ZK07, A0A0A7X8G3, K4FKB3, A0A0D4D9P7, A0A0D4D9K3, D5LH13, A0A023ZVH3, J9RVQ5, I6ZYD5, I6ZYH9, A0A023M103, H6W8B6, K4MPY5, K4MN11, K4N0H5, A0A0E3JSV3, A0A0E3JQ19, A0A0E3GMI0, A0A0E3M2Q1, A0A0E3M390, A0A0E3JST0, S4USD3, K4NX13, M4QBM5, K7PMK4, A0A0A0RTJ6, B3RGZ8, A0A0A7HCF3, A0A0A0YQB4, A0A0A0YQ48, A0A0A0YUT5, A0A088C3C4, A0A142KC53, A0A142KBW3, A0A0K0N638, A0A0E3X9T9, A0A0E3T647, A0A0E3T611, A0A1B3B0N2, A0A160DH50, A0A142K914, I1VX60, I1VXJ4, I1VXJ5, I1VX80, I7HFW3, I7HFX8, A0A0A8J8P5, A0A0A8J9V8, A0A0A8J997, A0A0A8J9W4, A0A0A8JBL6, A0A0K0VLS5, A0A0P013T8, A0A0C5AFR8, A0A0C5ANA1, F8J1E9, A0A0A7NQR5, A0A0A7NQU3, A0A0A7NQU0, A0A0A7NNP9, A0A0A7NNN4, A0A0A7NQU6, A0A0A7NQS7, A0A0A7NQV6, A0A0A1EKZ5, X2CXX7, A0A1B0Y2R2, A0A024B2K8, Q38326, R9R1C0, X4YE16, X4YE34, X4YUH6, X4YWF2, X4YWJ6, X4Y7Z8, X4Y823, X4Y899, X4YWS4, X4YWT6, V9VFQ1, A0A0D3MST0, M4I684, A0A060AC85, A0A068C743, A0A068CG40, A0A068CA71, A0A059T608, M4H0F5, A0A059T783, A0A059T5N1, A0A059T8D2, S4U878, A0A076YNW7, W8NWJ5, A0A075BUR8, A0A075BV08, A0A075BU50, W8ECA9, W8EC76, A0A097EVU4, V5UQR9, V5UPR8, V5UPR1, A0A0A7HAJ7, S5YEI5, W8G0Y7, A0A0B5A4D1, S5WD38, A0A142K5B0, R4TBY4, V5R6D1, R4TK32, A0A127KPL4, X2KYE0, W0LI51, W0LM41, V5RBI6, S5WBP9, T2FHS6, R9R4A1, R9R485, M4W8L2, A0A088FPR6, R4JFH4, A0A0S1S132, A0A127KP29, A0A0K2CM86, A0A0K2CMX8, V5R3T3, V5R4Q4, S5YNL9, S5Z4C4, A0A0K1Y742, R4JKK9, R4JN21, W0LIC0, W0LNS7, A0A0A7RUT1, A0A097EW81, A0A088F712, A0A088FB80, R4TCD3, A0A0K1LRD1, A0A0A7RXG4, A0A0A7RVE0, A0A1C9EGR3, R4TKY2, A0A1B1SFG0, V5R3R7, A0A076YK74, A0A0A1ER04, A0A0A1EKQ3, S5YLW3, W8FPZ8, A0A0K2FMZ8, A0A076YM07, A0A0S2MV19, A0A0S2MUY6, R9RUP6, W8ECN8, A0A023W5Q8, A0A023W5Z1, S5YB78, X2KZV2, W0LNL7, A0A142K512, A0A0F6WDK8, A0A0F6YRL2, A0A1B1PC85, A0A1B1PCB4, A0A088FRR7, A0A0A7S2M4, S5Z731, S5Y6B7, W0LMH9, A0A142F1U0, A0A142F1Y1, A0A0F6WEP4, R4TAL4, R4TD88, A0A0K1LS92, W0LP43, W0LJF4, W0LPF4, W0LJG3, S5M9N2, A0A0H4TI96, A0A1B1PCX6, A0A0N9SIC8, R4JFT0, A0A023W6Y4, A0A0K1Y6T9, A0A0N9BDM1, A0A142K814, A0A059VA80, A0A076YM69, A0A0K1LSJ3, A0A0K1LTU8, A0A097BXP2, G3M5B5, S5Y555, W8EBN3, A0A097EWH6, A0A0K2FKS5, A0A0K2FKV4, S5ZGP4, S5YL79, X2KTV2, A0A0K2FPE5, A0A0M4RAP5, R4JFY2, T2FIU4, R4JMG1, A0A0H4TKU2, I1V1G2, A0A0K2CXI6, A0A0N9SKW3, A0A0K2CKV0, A0A0A7S2W5, A0A076YN47, A0A076YPM3, A0A1C9EHD2, A0A1 C9EH88, A0A0A7RWB8, A0A076YMA9, S5YAC9, A5YJZ3, A0A0K1 LJB2, A0A097BXA8, A0A097BXE6, A0A088FTB9, S5XW54, S5YDJ2, A0A068C8X8, R4JJD7, A0A142K7M2, A0A0K2FNI5, V5R5S1, V5R471, V5R576, V5R4D0, M4W8F7, A0A0B5A0B7, A0A0A0Q0G6, K9L501, M1ICP6, M1IP10, M1IP22, M1IPN7, M1HM90, M1ID80, I6S6V7, I6S6P8, A0A0B4N0V2, A0A0B4N238, R9S7P6, R9S7K9, M4QHR5, M4QJ45, M4QPW6, M4QQ24, M4QFN0, M4QD42, M4QD90, M4QD46, M4QDG1, M4QH38, M4QEF2, R9S924, R9S7Y9, R9S994, R9S7Q9, R9S8M9, R9S8F0, R9S8N9, R9S878, R9S7J4, R9S6B1, R9S8V4, R9S727, R9S7Y5, R9S7J8, R9S8D4, R9S7T1, R9S734, R9S7P7, R9S725, R9S847, M4QHZ7, R9S838, R9S6L3, R9S719, R9S8L6, R9S660, R9S6Q5, R9S891, M1UAS8, M1UH48, Q58N14, A0A0K0KW20, A0A0K0KVR0, A0A0K0KWC8, A0A0K0KVF3, A0A0K0KVR8, A0A0K0KWC9, A0A0K0KVF1, A0A0K0KWF8, K4HMX7, K4HP13, A0A0E3DJ54, A0A0F6NY87, A0A0H41NZ7, M4SNJ8, M4T423, M4SQM8, R4JE26, S5M9Y1, K8DWI5, B7VGA6, K4NYZ6, K4NWJ2, A0A1B1SE14, A0A1B1SE17, A0A1B1SEH5, H2ELX5, H2ELW9, A0A0F6WD13, Q2Z0X8, Q2Z100, Q2Z0P9, Q2Z146, L7TKU8, L7THA0, J9SVR7, L7P7X2, L7P7V8, A0A125RND6, L7P7Z4, X4Y6R9, J7M9C2, X51378, I1TQS9, I1TQP3, A0A1B0Z2K9, B7SDV6, A0A075CDX7, S4T009, K4RKP0, K8DWA1, K4RM72, H8ZM17, A0A172PZS6, A0A172PZV9, S5WKN9, A0A0S0MXG5, A0A0S0NAE1, A0A0S0N6E6, A0A0U4B013, Q9ZXK0, V5R4V5, W8E9T5, W8EBH7, W8EBD9, I2FLS2, A0A0K0L913, A0A0K0L9H0, A0A0A1IVA1, A0A172B638, A0A0A1IVY4, A0A0S4KWG1, D6RRH2, V5JW89, S4S2N1, S4S2E0, A0A097ZIF9, A0A0K2QRH8, A0A0K2QQQ3, A0A0K2QR05, A0A0K2QQN9, A0A0A8JB16, A0A14615K7, A0A0A8JB60, A0A0A8JBC4, A0A0A8J8P3, A0A0A8J917, A0A0A8J9B3, A0A0A8J9E6, A0A0A8JB70, A0JC13, B5UAS0, A0A077KA04, A0A0X8WPD0, A0A0X8WPP2, A0A0X8WQK8, L7TMS4, L7TK61, L7TMM1, W6EKH7, W6EC01, W6E8M7, A0A076YKL6, A0A076YQ75, A0A076YQ17, L7TRG4, M4SPQ3, A0A0K1LLL2, M9MUJ3, M9MUC7, G9FHH1, G9FHL3, A0A0E3JI98, A0A0E3GMA9, M4SRR7, F5A399, F5A398, H9D1G5, T1SA42, T1SA02, A0A192Y6R4, A0A192Y8K7, A0A192YAB3, A0A173GC5, A0A173GCJ6, A0A173GCA6, A0A0N7CE17, A0A140XFZ6, A0A140XG67, A0A097P4A8, M9NVD6, S4TNT1, S4TSV1, S4TT64, S4TNV3, A0A193GXU6, R9XPT5, A0A1B1W2D9, A0A1B1W274, A0A162E9B6, A0A162E9C2, K41GJ8, K41360, K4F378, H2D0F2, M1EZ62, A0A0A0RTU7, A0A0A0RPP7, K41174, K41EM0, W6EK94, A0A088C487, A0A088C3E1, A0A088C4N3, A0A088C3J2, A0A088C4L6, A0A088C3X6, A0A088CD67, M9QT57, M9QT50, M9QQI9, A0A0A7NV04, A0A0A7NV01, A0A097BX37, A0A097BX60, A0A097BX98, V5UP3, V5UR90, A0A0F6TH46, A0A0U1WFM0, A0A0U1WYP7, A0A0U1WFB7, A0A0U1WGD3, A0A0U1WF38, A0A0U1WIX4, A0A0U1 UYC2, A0A0U1X2G0, A0A0U1WF58, A0A0U1WHX0, A1YTQ6, A1YTQ9, A1YTQ4, A0A141VTQ1, I6TJR6, I6TJZ8, W5R9R0, W5R8T1, A0A0D3MVB4, A0A0D3MWH2, A0A0D3MUZ0, A0A0D3MV48, A0A0N6WMQ8, A9CR44, 080085, V5XWL2, V5XXB7, V5XWJ8, V5XXD3, G0XM71, G0XMA8, G0XMA0, G0XM92, G0XMD0, A0A0N9RTX0, A0A0U1ZYD8, A0A0U1ZW61, A0A0U2A0V1, A0A0U1ZYF5, A0A0U1ZVF3, M9NS30, W5R815, H9A0X8, A0A0N9SKG5, H9A0K2, I1W624, S4T994, S4T8U2, S4T9C0, S4T8Z0, M41010, M410P9, M410Q9, M410F1, I6WK25, I6W9E1, I6XIT3, I6XE61, I6W9S3, I6X5G2, A0A075BDV2, I6PCK6, I6PC40, I6P8K8, A0A0E3T4Z6, A0A0E3T5C4, A0A0E3XAU4, A0A0E3T509, A0A0E3T5D8, A0A0E3X9G4, A0A0E3X9Z2, K7QMQ2, K7QMP3, A0A076G3Y4, A0A076G4X8, A0A076G4Q4, A0A076G614, A0A076G4S7, K7R2A3, I6X5X8, I6XK67, A0A076YN95, A0A076YQY5, I6WLF5, I6WAT4, V5XVY0, V5XWL8, V5XVX8, V5XWN9, I7DA03, I7CMX5, I7CMY2, I7CCR2, I7DMU2, I7CCL8, I7CMV4, W0TXT1, K7RV03, I6XIB9, I6XDN9, A0A075BF41, A0A075BEA6, A0A0M3WLN6, A0A0M3MX75, J7HY71, 003974, K4K7M8, K4JXN5, A1EAC5, U6E979, U6E9F4, L0P392, L0P2N6, F8HGP5, A0A0K1Y8C1, A0A0S2MU32, A0A0E3JJG4, A0A0E3M143, B6EFD3, B6EFD4, M4PYG3, M1SVB8, K9ME48, K9MCF7, K9MCS6, K9ME37, K9ME32, A0A0E3FSN1, A0A0E3HU68, A0A0E3G5S0, A0A0E3FSZ6, A0A0E3EXK9, A0A0E3HZS4, A0A0E3EY15, A0A0E3EUZ6, A0A0E3G6G4, A0A0E3FTC8, A0A0E3EW34, A0A0E3I459, A0A0E3HXN4, A0A0E3G508, A0A0E3EWN2, A0A0E3F361, A0A0E3G710, A0A0E3EWJ8, A0A0E3I445, A0A0E3HXM3, A0A0E3I3I7, A0A0E3EW07, A0A0E3G501, A0A0E3F9T1, A0A0E3ELA0, H8ZMQ9, V5UTB3, H8ZMB1, V5URN1, H8ZMB5, A0A0E3FY13, A0A0E3HC2, A0A0E3F6W4, V5UU51, V5UTI4, A0A0E3ESH3, A0A0E3HDM3, A0A0E3FF07, A0A0E3I133, A0A0E3HX81, A0A0E3I0M5, A0A0E3F1Q4, A0A0E3I7L0, A0A0E3HB04, A0A0E3I0B7, A0A0E3EZ88, A0A0E3G6S2, A0A0E3EMI2, A0A0E3G789, A0A0E3FUT7, A0A0E3EX70, A0A0E3I097, A0A0E3HXR9, A0A0E3FXR8, A0A0E3FDL0, A0A0E3F119, A0A0E3EMX1, A0A0E3HDU6, A0A0E3I4U7, A0A0E3FFL1, A0A0E3G768, A0A0E3HVF3, A0A0E3FTX5, A0A0E3EV41, A0A0E3HD30, A0A0E3FXX6, A0A0E3FE66, A0A0E3I1F7, A0A0E3EMY2, A0A0E3HX68, A0A0E3EYS1, A0A0E3I943, A0A0E3F2I5, A0A0E3G658, A0A0E3G5E6, A0A0E3FM46, A0A0E3G2G1, A0A0E3FLQ5, A0A0E3I4Y7, A0A0E3G1T1, A0A0E3HS8, A0A0E3G4T4, A0A0E3EVE7, A0A0E3G4V2, A0A0E3HPA6, A0A0E3EVL2, A0A0E3FLG8, A0A0E3HL80, A0A0E3HLT8, A0A0E3HXY8, A0A0E3I3T3, A0A0E3HHN5, A0A0E3F479, A0A0E3HC42, A0A0E3I481, A0A0E3HMU9, A0A0E3HQ09, A0A0E3FBD6, A0A0E3ETD9, A0A0E3HHF7, A0A0E3HVK4, A0A0E3FRD6, A0A0E3FM30, A0A0E3F8D2, A0A0E3HIV5, A0A0E3F1L8, A0A0E3HFL1, A0A0E3G1A9, A0A0E3G1Z1, A0A0E3HMC6, A0A0E3FS39, A0A0E3I2M9, A0A0E3FNL7, A0A0E3HCK7, A0A0E3FDE4, A0A0E3FC04, V5UTB4, V5URI3, V5UT34, A0A0E3FGE6, A0A0E3FHE7, A0A0E3HGC9, A0A0E3FHT7, A0A0E3HEH7, A0A0E3FCS3, A0A0E3HCW5, A0A0E3HII1, A0A0E3FAC3, A0A0E3FCX4, A0A0E3FKH2, A0A0E3FJY9, A0A0E3FJC0, A0A0E3FC2, A0A0E3HCE7, A0A0E3HG06, H8ZNE6, H8ZMZ3, H8ZN15, H8ZMZ4, H8ZN25, H8ZN16, L0CQP2, M4QIP5, M4Q118, A0A1D8KFN3, M4QF76, M4QFF7, M4QEW5, M4QRV1, M4QIN9, A0A1D8KN60, R9TQR5, G8EXV0, G8EXV1, A0A1D8KMS1, A0A1D8KMQ3, R9TQR7, G8EXW3, R9TP00, A0A1D8KMR7, R9TQT3, A0A1D8KMT6, A0A1D8KN04, G8EXU8, A0A096VKG5, A0A096VKE6, M1NXU0, R9TH03, R9TJZ2, R9TLC6, R9TQ10, R9TPK1, R9TM36, R9TLP8, R9TL45, R9TL38, R9TND3, R9TMS4, A0A0E3HBZ8, A0A0E3HDC9, A0A0E3HQX6, A0A0E3ERX4, A0A0E3FBY1, V5UT96, A0A0E3ICD5, A0A0E3HV49, A0A0E3G096, A0A0E3FGY5, A0A0E3HGE3, V5UTP3, A0A0E3HDF2, A0A0E3EQ82, V5UTJ9, A0A0E3ETP0, A0A0E3EN64, A0A0E3FJH3, V5UUR6, A0A0E3G6P8, A0A0E3HZM7, A0A0E3I5K5, V5UTK4, A0A0E3FAG6, A0A0E3FFA7, A0A0E3ESG1, V5USC6, M4PM80, M4PQ21, M4PLP0, M4PY89, M4PX59, M4PXP2, M4PWX3, M4PPI3, M4PP01, M4PQJ6, M4PY60, M4PLI4, M4PM15, M4PM14, M4PL03, M4PLI2, M4PR49, M4PM11, M4PKZ4, M4PLH8, M4PMA2, M4PL15, M4PLR5, M4PPY2, M4PWT1, M4PPE0, M4PR09, M4PNW8, M4PQF8, M4SRL5, M4T4Y9, M4SP75, M4SR81, M4SSN6, M4SR66, M4T4L1, M4SSN9, M4ST26, M4NNS2, M4NJY8, M4NK34, M4SR96, M4SRP0, M4SRG4, M4T3M3, M4SMQ3, M4T3A0, M4SQ86, M4SMT4, M4T3B8, M4R1Z4, M4QRQ4, M4QP69, M4QRQ0, M4QTR3, M4QPH6, M4QPN3, M4QPP7, M1UG92, M1T271, M1TV46, M1U2G7, M1U2U9, M1TUM2, M1UGL8, M1T2B4, M1TV41, M1T2Q5, M1UG78, M1UGG6, M1T2G2, M4PQZ6, M4PNP5, M4PZ31, M4PNF3, M4PYT3, M4PS5, M4PZ36, A0A1D8KSF7, A0A1D8KS64, A0A1D8KS71, A0A1D8KSP5, A0A1D8KT82, A0A1D8KT05, A0A1D8KSU5, M4SJC7, M4SNK0, M4T115, M4SM15, M4SJE6, M4T0P3, M4SMG6, M4SK59, M4SKA7, M4SKC6, M4SJC2, M4T0X9, M4SKX5, M4SJY6, M4SKW0, M4T1E8, M4T188, M4SPF3, M4SJW5, I3VYW2, I3VYV2, I3VYW7, I3VYV3, A0A0K0N5M8, A0A0K0N5F3, F1B2R8, W8G0E8, W8FT81, W8FPS3, A0A0A7HA27, H9C0A9, A0A089YQU5, A0A0A7HB32, A0A0A7HE58, A0A0A7HAC4, A0A076GB71, A0A076G6F1, A0A076G4I6, A0A076GBD5, A0A076G6L5, A0A0A7HAR2, A0A0A7HDY0, I6X284, R9TEG1, A0A0B5H344, A0A0B5GYV3, M4QC33, R9TP18, H9C0Y6, M4SR30, M4SQL9, V9LZ57, A0A088FAR6, A0A088FAP5, I3PUW7, K7R2S4, K7RFJ5, A0A0D4DAX1, A0A1B1SDS2, A0A077JGB2, K7ZMK0, I7HBC6, Q2NPA3, Q2NPA4, I7K2J2, S5M9G3), Uncharacterized protein 510 (Q8QL30), Uncharacterized protein 56 (Q914H6), Uncharacterized protein 562 (Q8QL25), Uncharacterized protein 60 (Q914H2), Uncharacterized protein A-291 (P20197), Uncharacterized protein ORF133 (A4ZUE2), Uncharacterized protein ORF170 (A4ZUB2), Uncharacterized protein ORF180 (Q573D9), Uncharacterized protein ORF193 (Q3V4R8), Uncharacterized protein ORF338 (Q573D4), Uncharacterized protein ORF5 (Q88416), Uncharacterized protein ORF81 (A4ZU87), VHS1049 protein (H8YJ69), VIP2-like toxin (A0A142K5A4), Virion associated protein (I6WB45), Virion export protein (P03666), Virion export protein (P03665), Virion protein (A0A172J119, A0A172JHW6, A0A0F6NYD5, A0A0U5AQV0, H6WU10, A0A060RFL0, A0A1B3SN28), Virion RNA polymerase (M9PKF9), Virion RNA polymerase (S4TNI5, S4TRR6), Virion structural protein (A7KUS9, H6WFW0, H6WFV4, H6WFY5, H6WFW1, E3SPU8, E3SPU6, E3SPB9, B3FJ80, B3FJD7, B3FJU8, A0A076FWZ1, A0A0S0MWU0, F8SK27, V5UUA2, A0A0E3F952, A0A0E3FVH1, A0A0E3HD14, A0A0E3FM16, A0A0E3FLD9, A0A0E3FLA6, A0A0E3I8V3, A0A0E3FHP1, A0A0E3FHL0, A0A0E3HEJ8, A0A0E3FB51, A0A0E3FKE0, A0A0E3FJV1, A0A0E3F9Z7, A0A0E3FB07, A0A1D8KFV1, M4QHA6, A0A1D8KHZ1, A0A1D8KGK5, A0A1D8KHA5, A0A1D8KFV0, M4QF23, Q5GQG2, Q5GQB5, Q5GQW7, Q5GQW2, Q5GQW3), Virion-associated phage protein (A8YQQ7, C51HQ8), Viron-encapsulated RNA polymerase (R9R4M8, R9R4K1), Virulence-associated structural protein (A0A1D8KT17), Vpf491 (Q7DKP5, O88107), Vpf504 (Q783U1, Q9MBW8), VrlC protein (Q58LL4), VrlC protein (V5UR92), Wac (Q56EL5), Wac fibritin neck whisker (A0MNH0, F9VHI9, F9V107), Whisker fibers at base of head (Q6U9F4), WLM domain-containing protein (E3SP17), YadA domain protein (V5UTS3), YadA domain structural protein (H8ZN74), YadA domain-containing protein (J9QGS2), YadA domain-containing structural protein (A0A1D8KSC4), YapH protein (E3SMS8, E3SSU6), YomR (W8CZP9), and YomR-like protein (A0A142F1G1).

As used herein, the term "therapeutically effective amount" refers to the amount of a compound, composition, particle, organism (e.g., a probiotic or a microbiota transplant), etc. that, when administered to a subject for treating (e.g., preventing or ameliorating) a state, disorder or condition, is sufficient to effect such treatment. The "therapeutically effective amount" will vary depending, e.g., on the agent being administered as well as the disease severity, age, weight, and physical conditions and responsiveness of the subject to be treated.

As used herein, the phrase "pharmaceutically acceptable" refers to molecular entities and compositions that are generally regarded as physiologically tolerable.

The terms "patient", "individual", "subject", "mammal", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "inactivating" or "inactivate" as used herein in connection with bacteriophages refers to a treatment that prevents bacteriophage replication within bacterial cells of mammalian microbiota. Such treatment may or may not prevent an entry of bacteriophages into bacterial cells of mammalian microbiota. Preferably, an inactivated bacteriophage useful in the methods of the present invention does not inhibit growth or activity of mammalian microbiota.

The term "modifying" or "modify" as used herein in connection with bacteriophages refers to a treatment that alters bacteriophage activity within mammalian microbiota in a way that prevents the ability of bacteriophage to cause a microbiota disease and/or consequences thereof such as diseases recited therein. Preferably, a modified bacteriophage useful in the methods of the present invention does not inhibit growth or activity of mammalian microbiota.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

Non-limiting examples of diseases and conditions treatable by bacteriophage inhibition or inactivation according to the methods of the present invention include, without limitation, diseases caused by changes in properties of microbiota (e.g., skin, mucosal, or GI microbiota); endotoxemia;

oncological diseases; obesity; age-related changes of skin; vaginosis, neurodegenerative diseases (e.g., Alzheimer's disease, Parkinson's disease); Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD); diseases and conditions accompanied by increased intestinal permeability (e.g., irritable bowel syndrome [IBS], non-specific ulcerative colitis, celiac disease, diabetes, rheumatoid arthritis, multiple sclerosis, Amyotrophic Lateral Sclerosis [ALS], CADASIL Syndrome, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia) Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, Huntington's disease, a disease associated with the formation of a misfolded protein, stroke, psoriasis, Sudden arrhythmic death syndrome, diabetes, Crohn's disease, atopic dermatitis, ankylosing spondylitis, bipolar disorder, depressive disorder, schizophrenia, carcinogenesis, psoriasis, systemic lupus erythematosus [SLE], scleroderma, liver failure, liver cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, autism and autism spectrum disorder, primary biliary cirrhosis, primary sclerosing cholangitis, and asthma.

The term "about" or "approximately" means within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The terms "a," "an," and "the" do not denote a limitation of quantity, but rather denote the presence of "at least one" of the referenced item.

The practice of the present invention employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ. Additional techniques are explained, e.g., in U.S. Pat. No. 7,912,698 and U.S. Patent Appl. Pub. Nos. 2011/0202322 and 2011/0307437.

Methods of the Invention

The inventors have surprisingly found the possibility of preventing and changing pathological changes by inactivating bacteriophages originating from the external environment, microbiota or organ transplants.

Bacteriophages are the most numerous group of viruses widely spread in the biosphere. They actively enter into the human body from the external environment, e.g. with drinking and piped water, dairy products, fish and meat food, daily-life articles. Moreover, bacteriophages are ubiquitous and are widely used as preservatives in the food industry.

Bacteriophages are selective with respect to the bacteria type they can infect. Bacteriophage entry into the human body can destroy a specific population of microorganisms. According to the invention, as a means for the inactivation of phages in a body (e.g., in microbiota, bodily fluid(s) or tissue(s)), in utilized water and/or food and/or air and/or objects of the environment, filtration, metals, chemical action of "polyhexamethylene guanidine derivatives" (e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043), ozone, $H_2O_2$, halogen-containing compounds, physical action (temperature, high pressure, photocatalysis, microwave radiation, gamma radiation, an electron flow, ultraviolet radiation), plant extracts (e.g., persimmon extract), cationic compounds, cetyltrimethylammonium bromide (CTAB), chitosan, nisin, lysozyme-based methods of capsid-targeted viral inactivation and photocatalytic inactivation, blocking receptors on target cells by inactivated bacteriophages and/or their receptors and/or changing properties of target bacteria, biological drugs (e.g., antibodies against bacteriophages or receptors on bacteria that can be infected by bacteriophages), bacteria, bacteriophages-antagonists, and bacteria with altered structure, as well as a combination of physical, chemical and biological methods can be used.

In various embodiments, disease in a mammal is prevented or treated by preventing entry of bacteriophages into the body (e.g., into microbiota, bodily fluid(s) or tissue(s)) or by inactivating or modifying bacteriophages (e.g., in microbiota, bodily fluid(s) or tissue(s)). In some embodiments, bacteriophages are inactivated in the hospital environment.

In some embodiments of any of the above methods involving preventing entry or inactivation or modification of bacteriophages, the methods specifically target bacteriophages comprising prion-like domains (PrDs) (e.g., using antibodies targeting bacteriophage proteins comprising PrDs). In some embodiments, proteins comprising PrDs comprise glutamine/asparagine (Q/N) enriched PrDs. In some embodiments, PrDs are determined using protein analysis (e.g., Western blot, ELISA) and/or algorithms (e.g., PLAAC algorithm or PrionW).

In some embodiments of any of the above methods involving preventing entry or inactivation or modification of bacteriophages, the methods specifically target bacteriophages not comprising PrDs (e.g., using antibodies targeting bacteriophage proteins not comprising PrDs or antibodies targeting synthetic bacteriophages or genetically-modified bacteriophages).

In some embodiments, the bacteriophages are inactivated by persimmon extract cationic compounds. The persimmon extract cationic compounds may be part of persimmon extract itself, or used in any number of formulations. In some embodiments, persimmon extract cationic compounds, and persimmon extract itself, is used to inactivate bacteriophage MS2.

In various embodiments, disease is prevented and treated by preventing entry of bacteriophages into the body (e.g., into microbiota, bodily fluid(s) or tissue(s)) by modifying bacteriophages. For example, DNase, RNase, proteases, or amyloid-like proteins can be applied to the bacteriophage in an amount that affects the bacteriophage surface without inactivating the bacteriophage.

In some embodiments, changes in the normal microbiota and development of increased intestinal permeability are prevented by limiting entry of bacteriophages from the environment into the mammalian body (e.g., into microbiota, bodily fluid(s) or tissue(s)). In one embodiment, "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043 are used to prevent entry of the bacteriophages into the body. In one embodiment, filtration is used wherein to prevent entry of the bacteriophages into the body. In one embodiment, pascalization is used to prevent entry of the bacteriophages into the body. In one embodiment, to prevent entry of the bacteriophages into the body, heat treatment is used. In one embodiment, to prevent entry of the bacteriophages into the body, gamma radiation is used. In one embodiment, to prevent entry of the bacteriophages into the body, an electron flow is used. In one embodiment, to prevent entry of the bacteriophages into the body, microwave radiation is used. In one embodiment, to prevent entry of the bacteriophages into the body, the bacteriophages are inactivated in a food product by ozone. In one embodiment, to prevent entry of the bacteriophages into the body, capsid-targeted viral inactivation is used. In one embodiment, to prevent getting the phages into the body, photocatalytic inactivation is used.

In some embodiments, to prevent entry of the bacteriophages into the body (e.g., into microbiota, bodily fluid(s) or tissue(s)), the bacteriophages are inactivated in a food product. In one embodiment, "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043 are used to inactivate bacteriophages in a food product. In one embodiment, filtration is used to inactivate bacteriophages in a food product. In one embodiment, pascalization is used to inactivate bacteriophages in a food product. In one embodiment, heat treatment is used to inactivate bacteriophages in a food product. In one embodiment, gamma radiation is used to inactivate bacteriophages in a food product. In one embodiment, an electron flow is used to inactivate bacteriophages in a food product. In one embodiment, microwave radiation is used to inactivate bacteriophages in a food product. In one embodiment, capsid-targeted viral inactivation is used to inactivate bacteriophages in a food product. In one embodiment, photocatalytic inactivation is used to inactivate phages in a food product. In one embodiment, ozone is used to inactivate phages in a food product.

In one embodiment, the food product is treated with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043 to inactivate bacteriophages in the food product. In one embodiment, the food product is treated by filtration to inactivate bacteriophages in the food product. In one embodiment, the food product is treated by pascalization to inactivate bacteriophages in the food product. In one embodiment, the food product is heat treated to inactivate bacteriophages in the food product. In one embodiment, the food product is gamma irradiated to inactivate bacteriophages in the food product. In one embodiment, the food product is treated with electron flow to inactivate bacteriophages in the food product. In one embodiment, the food product is treated with microwave radiation to inactivate bacteriophages in the food product. In one embodiment, the food product is treated with capsid-targeted viral inactivation to inactivate bacteriophages in the food product. In one embodiment, the food product is treated with photocatalytic inactivation to inactivate phages in the food product. In one embodiment, the food product is treated with ozone to inactivate phages in the food product.

In some embodiments, to prevent entry of the bacteriophages into the body (e.g., into microbiota, bodily fluid(s) or tissue(s)), the bacteriophages are inactivated in drinking water. In one embodiment, the bacteriophages in drinking water are inactivated by "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043. In one embodiment, the bacteriophages in drinking water are inactivated by filtration. In one embodiment, the bacteriophages in drinking water are inactivated by photocatalysis. In one embodiment, the bacteriophages in drinking water are inactivated by ozone. In one embodiment, the bacteriophages in drinking water are inactivated by a peroxide (e.g., $H_2O_2$). In one embodiment, the bacteriophages in drinking water are inactivated by a metal. In one embodiment, pascalization is used to inactivate the bacteriophages in drinking water. In one embodiment, heat treatment is used to inactivate the bacteriophages in drinking water. In one embodiment, gamma radiation is used to inactivate the bacteriophages in drinking water. In one embodiment, an electron flow is used to inactivate the bacteriophages in drinking water. In one embodiment, microwave radiation is used to inactivate the bacteriophages in drinking water. In one embodiment, capsid-targeted viral inactivation is used to inactivate the bacteriophages in drinking water. In one embodiment, photocatalytic inactivation is used to inactivate the bacteriophages in drinking water. In one embodiment, an antibody is used to inactivate the bacteriophages in drinking water.

In one embodiment, the drinking water is treated with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043 to inactivate the bacteriophages in the drinking water. In one embodiment, the drinking water is treated with filtration to inactivate the bacteriophages in the drinking water. In one embodiment, the drinking water is treated with photocatalysis to inactivate the bacteriophages in the drinking water. In one embodiment, the drinking water is treated with ozone to inactivate the bacteriophages in the drinking water. In one embodiment, the drinking water is treated with a peroxide (e.g., $H_2O_2$), to inactivate the bacteriophages in the drinking water. In one embodiment, the drinking water is treated with a metal to inactivate the bacteriophages in the drinking water. In one embodiment, the drinking water is treated with pascalization to inactivate the bacteriophages in the drinking water. In one embodiment, the drinking water is treated with heat sufficient to inactivate the bacteriophages in the drinking water. In one embodiment, the drinking water is treated with gamma irradiation to inactivate the bacteriophages in the drinking water. In one embodiment, the drinking water is treated with electron flow to inactivate the bacteriophages in the drinking water. In one embodiment, the drinking water is treated with microwave radiation to inactivate the bacteriophages in the drinking water. In one embodiment, the bacteriophages in the drinking water are inactivated by capsid-targeted viral inactivation. In one embodiment, the bacteriophages in the drinking water are inactivated by photocatalytic inactivation. In one embodiment, the drinking water is treated with an antibody to inactivate the bacteriophages in the drinking water.

In some embodiments, to prevent entry of the bacteriophages into the body (e.g., into microbiota, bodily fluid(s) or tissue(s)), the bacteriophages are inactivated in air.

In some embodiments, to prevent entry of the bacteriophages into the body (e.g., into microbiota, bodily fluid(s) or tissue(s)) via fecal microbiota transplant, the bacteriophages are inactivated in the fecal microbiota transplant. In one embodiment, the bacteriophages are eliminated from fecal microbiota transplant by filtration. In one embodiment, the bacteriophages are eliminated from fecal microbiota transplant by centrifugation. In one embodiment, the bacteriophages are eliminated from fecal microbiota transplant by differential exposure. In one embodiment, the bacteriophages are eliminated from fecal microbiota transplant by antibacteriophagal agents.

In some embodiments, to prevent entry of the bacteriophages into the body (e.g., into microbiota, bodily fluid(s) or tissue(s)), the bacteriophages are inactivated in non-fecal microbiota transplant. In one embodiment, the bacteriophages are eliminated from non-fecal microbiota transplant by filtration. In one embodiment, the bacteriophages are eliminated from non-fecal microbiota transplant by centrifugation. In one embodiment, the bacteriophages are eliminated from non-fecal microbiota transplant by differential exposure. In one embodiment, the bacteriophages are eliminated from non-fecal microbiota transplant by antibacteriophagal agents. In some embodiments, the bacterioprophages are identified and eliminated from fecal and non-fecal microbiota transplant.

In some embodiments, to prevent entry of the bacteriophages into the body (e.g., into microbiota, bodily fluid(s) or tissue(s)), the bacteriophages are inactivated in organ transplant.

In some embodiments, to prevent entry of the bacteriophages into the body (e.g., into microbiota, bodily fluid(s) or tissue(s)), the bacteriophages are inactivated in water for washing. In one embodiment, the water for washing is treated by "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, to inactivate the bacteriophages. In one embodiment, the bacteriophages in the water for washing are inactivated by filtration. In one embodiment, the bacteriophages in the water for washing are inactivated by photocatalysis. In one embodiment, the bacteriophages in the water for washing are inactivated by ozone. In one embodiment, the bacteriophages in the water for washing are inactivated by a peroxide (e.g., $H_2O_2$). In one embodiment, the bacteriophages in the water for washing are inactivated by a metal. In one embodiment, pascalization is used to inactivate the bacteriophages in the water for washing. In one embodiment, heat treatment is used to inactivate the bacteriophages in the water for washing. In one embodiment, gamma radiation is used to inactivate the bacteriophages in the water for washing. In one embodiment, an electron flow is used to inactivate the bacteriophages in the water for washing. In one embodiment, microwave radiation is used to inactivate the bacteriophages in the water for washing. In one embodiment, capsid-targeted viral inactivation is used to inactivate the bacteriophages in the water for washing. In one embodiment, photocatalytic inactivation is used to inactivate the bacteriophages in the water for washing.

In some embodiments, to prevent entry of the bacteriophages into the body (e.g., into microbiota, bodily fluid(s) or tissue(s)), the bacteriophages are inactivated in water for washing. In one specific embodiment, the water for washing undergoes filtration sufficient to inactivate the bacteriophages. In one specific embodiment, the water for washing undergoes photocatalysis sufficient to inactivate the bacteriophages. In one specific embodiment, the water for washing is treated with sufficient ozone to inactivate the bacteriophages. In one specific embodiment, the water for washing is treated with sufficient peroxide (e.g., $H_2O_2$) to inactivate the bacteriophages. In one specific embodiment, the water for washing is treated with a sufficient amount of metal to inactivate the bacteriophages. In one specific embodiment, the water for washing is treated by pascalization sufficient to inactivate the bacteriophages. In one specific embodiment, the water for washing is treated with heat sufficient to inactivate the bacteriophages. In one specific embodiment, the water for washing is gamma irradiated to inactivate the bacteriophages. In one specific embodiment, the water for washing is treated with electron flow sufficient to inactivate the bacteriophages. In one specific embodiment, the water for washing is treated with microwave radiation sufficient to inactivate the bacteriophages. In one specific embodiment, the water for washing is treated by capsid-targeted viral inactivation sufficient to inactivate the bacteriophages. In one specific embodiment, the water for washing undergoes photocatalytic inactivation sufficient to inactivate the bacteriophages.

In some embodiments, to prevent entry of the bacteriophages into the body (e.g., into microbiota, bodily fluid(s) or tissue(s)), the bacteriophages are inactivated in the water for air humidification. In one specific embodiment, the water for air humidification is treated with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, to inactivate the bacteriophages. In one specific embodiment, the water for air humidification undergoes filtration sufficient to inactivate the bacteriophages. In one specific embodiment, the water for air humidification undergoes photocatalysis sufficient to inactivate the bacteriophages. In one specific embodiment, the water for air humidification is treated with sufficient ozone to inactivate the bacteriophages. In one specific embodiment, the water for air humidification is treated with sufficient peroxide (e.g., $H_2O_2$) to inactivate the bacteriophages. In one specific embodiment, the water for air humidification is treated with a sufficient amount of metal to inactivate the bacteriophages. In one specific embodiment, the water for air humidification is treated by pascalization sufficient to inactivate the bacteriophages. In one specific embodiment, the water for air humidification is treated with heat sufficient to inactivate the bacteriophages. In one specific embodiment, the water for air humidification is gamma irradiated to inactivate the bacteriophages. In one specific embodiment, the water for air humidification is treated with electron flow sufficient to inactivate the bacteriophages. In one specific embodiment, the water for air humidification is treated with microwave radiation sufficient to inactivate the bacteriophages. In one specific embodiment, the water for air humidification is treated by capsid-targeted viral inactivation sufficient to inactivate the bacteriophages. In one specific embodiment, the water for air humidification undergoes photocatalytic inactivation sufficient to inactivate the bacteriophages.

In some embodiments, to prevent entry of the bacteriophages into the body (e.g., into microbiota, bodily fluid(s) or tissue(s)), the bacteriophages are inactivated on a skin and mucosa surface.

In some embodiments, to prevent entry of the phages into the body (e.g., into microbiota, bodily fluid(s) or tissue(s)), the phages are inactivated in the environment. In one embodiment, the phages are inactivated in the environment by treating items of habitat (e.g., furniture, a room, dishes, a bath, a sink, a toilet bowl, a container for packaging and storage of food products or water) with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043. In one embodiment, the phages are inactivated in the environment by treating items of habitat (furniture, a room, dishes, a bath, a sink, a toilet bowl, a container for packaging and storage of food products or water) with heat treatment. In one embodiment, the phages are inactivated in the environment by treating items of habitat (e.g., furniture, a room, dishes, a bath, a sink, a toilet bowl, a container for packaging and storage of food products or water) with gamma radiation.

In one embodiment, the phages are inactivated in the environment by treating items of habitat (e.g., furniture, a room, dishes, a bath, a sink, a toilet bowl, a container for packaging and storage of food products or water) with an electron flow. In one embodiment, the phages are inactivated in the environment by treating items of habitat (e.g., furniture, a room, dishes, a bath, a sink, a toilet bowl, a container for packaging and storage of food products or water) with ultraviolet. In one embodiment, the phages are inactivated in the environment by treating items of habitat (e.g., furniture, a room, dishes, a bath, a sink, a toilet bowl, a container for packaging and storage of food products or water) with ozone.

In one embodiment, the phages are inactivated in the environment by treating items of habitat (e.g., furniture, a room, dishes, a bath, a sink, a toilet bowl, a container for packaging and storage of food products or water) with a peroxide (e.g., $H_2O_2$). In one embodiment, the phages are inactivated in the environment by treating items of habitat (e.g., furniture, a room, dishes, a bath, a sink, a toilet bowl, a container for packaging and storage of food products or water) with a method of capsid-targeted viral inactivation. In one embodiment, the phages are inactivated in the environment by treating items of habitat (e.g., furniture, a room, dishes, a bath, a sink, a toilet bowl, a container for packaging and storage of food products or water) with a method of photocatalytic inactivation.

In some embodiments, the invention provides a method to prevent entry of bacteriophages into the body (e.g., into microbiota, bodily fluid(s) or tissue(s)) comprising inactivating bacteriophages in the environment by preventing their distribution via an air conditioning and humidification system. In various embodiments, the bacteriophages are inactivated in an air conditioning and humidification system in a room, in a hospital environment, a motor vehicle, a train, an airplane, a surface vessel, a submarine vessel and a spacecraft. In one embodiment, the bacteriophages are inactivated in an air conditioning and humidification system by filtration of air and a liquid used for the humidification. In one embodiment, the bacteriophages are inactivated in an air conditioning and humidification system by ultraviolet treatment of air and a liquid used for the humidification. In one embodiment, the bacteriophages are inactivated in an air conditioning and humidification system by treating air and a liquid used for the humidification with "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043. In one embodiment, the bacteriophages are inactivated in an air conditioning and humidification system by capsid-targeted viral inactivation of air and a liquid used for the humidification. In one embodiment, the bacteriophages are inactivated in an air conditioning and humidification system by photocatalytic inactivation of air and a liquid used for the humidification. In one embodiment, the bacteriophages are inactivated in an air conditioning and humidification system by heat treatment of air and a liquid used for the humidification.

In some embodiments, bacteria having their bacteriophage receptors inactivated are transplanted to microbiota to interfere with an interaction between bacteriophages with the bacteria of microbiota. In one embodiment, the bacteriophage receptors are inactivated by a method of capsid-targeted viral inactivation. In one embodiment, to interfere with an interaction between bacteriophages with the bacteria of microbiota, for inactivation of receptors for bacteriophages on bacteria, antibodies are used, or administered to the mammal. In one embodiment, to interfere with an interaction between bacteriophages and the bacteria of microbiota, targeted bacteria are substituted with their variants lacking corresponding receptors to inactivate receptors for the bacteriophages on the bacteria of the microbiota. In one embodiment, the variants are administered to the mammal. In one embodiment, to interfere with an interaction between bacteriophages with the bacteria of microbiota, receptors on the bacteria are blocked by inactivated phages. In one embodiment, the inactivated phages are administered to the mammal.

In some embodiments, to interfere with an interaction between bacteriophages with the bacteria of microbiota, receptors on bacteria are blocked by modified bacteriophages not able to cause death of target bacteria.

In some embodiments, to interfere with an interaction between bacteriophages with the bacteria of microbiota, receptors on bacteria are blocked by phage receptors for attaching to bacteria not able to cause death of target bacteria. In one embodiment, the phage receptors are obtained as recombinant proteins.

In some embodiments of any of the above aspects and embodiments, the methods are used for increasing longevity and/or decreasing aging in a mammal. In one specific non-limiting embodiment, the aging is skin aging.

In some embodiments of any of the above aspects and embodiments, the methods are used for treating and preventing development of endotoxemia, oncological diseases, obesity, age-related skin changes, vaginosis, irritable bowel syndrome, non-specific ulcerative colitis, celiac disease, diabetes, rheumatoid arthritis, multiple sclerosis, Amyotrophic Lateral Sclerosis, CADASIL Syndrome, Huntington's disease, stroke, psoriasis, Sudden arrhythmic death syndrome, depressive disorder, Hashimoto's thyroiditis, Dentatorubro-pallido-Luysian atrophy, Kennedy disease, familial amyloidotic polyneuropathy, medullary carcinoma of the thyroid, Friedreich's ataxia, cerebellar ataxia, spinocerebellar ataxia, dementia (e.g., fronto-temporal dementia, familial Danish dementia, and familial British dementia) Lewy body diseases, an amyloidosis (e.g., hereditary cerebral haemorrhage with amyloidosis, primary systemic amyloidosis, secondary systemic amyloidosis, familial Mediterranean fever, serum amyloidosis, senile systemic amyloidosis, hemodialysis-related amyloidosis, Finnish hereditary systemic amyloidosis, Atrial amyloidosis, Lysozyme systemic amyloidosis, Insulin-related amyloidosis, and Fibrinogen a-chain amyloidosis), Spinal muscular atrophy, Crohn's disease, atopic dermatitis, ankylosing spondylitis, a disease associated with the formation of a misfolded protein, neurodegenerative diseases (e.g., Alzheimer's disease, Parkinson's disease), bipolar disorder, schizophrenia, psoriasis, systemic lupus erythematosus (SLE), scleroderma, liver failure, cirrhosis, aseptic inflammation, unstable angina, chronic heart failure, atherosclerosis, myocardial infarction, thrombosis, gout, cancer cachexia, acute respiratory distress syndrome, graft-versus-host reactions, rhythm and conduction disturbances, autism and autism spectrum disorder, primary biliary cirrhosis, primary sclerosing cholangitis, and asthma.

In another aspect is provided a method for preventing and treating a disease or increasing longevity and/or decreasing aging in a mammal, comprising, administering an anti-phage drug, wherein the anti-phage drug is in a form of a liquid for intake, a liquid for treating a surface of a human and/or a domestic animal body and/or a surface of an object or an equipment, tablets or capsules, drops and a rinser, troches, a gel, an ointment, rectal and vaginal suppositories, a chewing gum, or a candy.

In another aspect is provided a method for preventing and treating a disease or increasing longevity and/or decreasing aging in a mammal comprising adding anti-bacteriophage drugs to food products, water and other products for drinking, water for washing.

In an embodiment of any of the above aspects and embodiments, the method further comprises administering a compound in combination with at least one compound that potentiates activity of the compound. In some embodiments, the compound is used with pharmaceutically acceptable carrier or excipient. In some embodiments, the compound is used with other drugs for increasing the effect. In an embodiment of any of the above aspects and embodiments, the method is effective to prevent or treat an increase in intestinal permeability. In an embodiment of any of the above aspects and embodiments, the increase in intestinal permeability is caused by entry of a bacteriophage into gastrointestinal tract of the body.

In an embodiment of any of the above aspects and embodiments, the method further comprises preventing changes in the normal microbiota leading to the development of increased intestinal permeability, by limiting exposure to bacteriophages from the objects of the environment, including products of daily use.

In an embodiment of any of the above aspects and embodiments, the method further comprises prevention of changes in the normal microbiota leading to obesity, by exposure to bacteriophages from the environment.

In various embodiments, disease is prevented and treated by interfering with an interaction between bacteriophages with the bacteria of microbiota. One way to interfere with this interaction is to substitute targeted bacteria with their variants lacking corresponding receptors to inactivate receptors for the bacteriophages on the bacteria of the microbiota.

Another way to interfere with an interaction between bacteriophages with the bacteria of microbiota is to block receptors on bacteria by modified bacteriophages not able to cause death of target bacteria.

Another way to interfere with an interaction between bacteriophages with the bacteria of microbiota is to block receptors on bacteria by adding phage receptor proteins that attach to bacteria, but are not able to cause death of target bacteria.

In various embodiments, specific changes in microbiota discussed herein can be detected using various methods, including without limitation quantitative PCR or high-throughput sequencing methods which detect over- and under-represented genes in the total bacterial population (e.g., 454-sequencing for community analysis; screening of microbial 16S ribosomal RNAs (16S rRNA), etc.), or transcriptomic or proteomic studies that identify lost or gained microbial transcripts or proteins within total bacterial populations. See, e.g., U.S. Patent Publication No. 2010/0074872; Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281: 36269-36279; Mahowald et al., PNAS, 2009, 14:5859-5864; Wikoff et al., PNAS, 2009, 10:3698-3703.

In one embodiment of any of the above methods involving preventing entry or inactivation or modification of bacteriophages, the methods specifically target bacteriophages comprising prion-like domains (PrDs) (e.g., using antibodies targeting bacteriophage proteins comprising PrDs). In some embodiments, proteins comprising PrDs comprise glutamine/asparagine (Q/N) enriched PrDs. In some embodiments, PrDs are determined using protein analysis (e.g., Western blot, ELISA) and/or algorithms (e.g., PLAAC algorithm or PrionW).

In one embodiment of any of the above methods involving preventing entry or inactivation or modification of bacteriophages, the methods specifically target bacteriophages not comprising PrDs (e.g., using antibodies targeting bacteriophage proteins not comprising PrDs or antibodies targeting synthetic bacteriophages or genetically-modified bacteriophages).

A mammalian population that is sensitive to bacteriophage entry into the body may be identified by a method comprising evaluating one or more of alterations to the human genome, expression of a particular protein, alteration of the microbiota composition in a qualitative and/or quantitative manner, an alteration of the KEGG pathway. If the mammalian population has reduced number of bacteria associated with a gene-ontology (GO) term of a KEGG pathway as compared to a corresponding healthy human or animal population, then identification of bacteriophages that may infect other bacteria associated with the same GO term of the KEGG pathway is undertaken. Without wishing to be bound by theory, such identified bacteriophages may have an exaggerated effect on the GO term of the KEGG pathway in such patients because there is already a reduced number of bacteria associated with the same GO term.

In one embodiment of the above methods relating to identifying a mammalian population, the mammalian population has a reduced number of temperate bacteriophages as compared to a corresponding healthy human or animal population. As described herein, various conditions and diseases may be triggered or may progress when lytic bacteriophages become more abundant than temperate bacteriophages. For example, in Parkinson's Disease (PD), the present inventors describe a significant increase in the ratio of lytic lactococcal phages to temperature lactococcal phages. See Example 20. Without wishing to be bound by theory, the gain in number of lytic phages relative to temperate phages may substantially reduce the population of bacteria that play a role in maintaining homeostasis. Such reduction in bacteria could trigger or allow for progression of disease. For example, the increase in lytic lactococcal phages may deplete *Lactococcus* bacteria that serve as an important source of dopamine and other microbiota-derived neurochemicals.

In various embodiments of any of the above methods involving preventing entry or inactivation or modification of bacteriophages, bacteriophages whose levels are increased in patients with neurodegenerative diseases, e.g., Parkinson's Disease (PD), are targeted. The inventors have shown that the bacteriophage community (phagobiota) of PD patients significantly differs from that of healthy individuals. Phagobiota may be involved in the development and progression of PD. Preventing entry or inactivation or modification of bacteriophages associated with the development and progression of PD may be effective to prevent PD, treat PD or ameliorate the effects of PD.

Metagenome sequencing has greatly facilitated the investigation of the human microbiome; however, current understanding of the role of microbiota in health and disease mainly comes from the analysis of diversity and abundance of bacterial species, whereas little is known about those of bacteriophages (Hatfull, G. et al., 2015). Therefore, changes in bacteriophage composition are rarely associated with human diseases. Phages may be implicated in protein misfolding, altered intestinal permeability, and chronic inflammation in mammals. Phages may play a critical role in the development of neurodegenerative diseases, such as PD. Such multifactorial diseases may have increased intestinal permeability as a triggering or aggravating factor.

The disclosure and examples described herein indicate that bacteriophages are previously overlooked human pathogens. Shifts in the gut phagobiota in are identified PD patients, some of which can be considered to be associated with the disease and may be used in the development of novel diagnostic and therapeutic tools. The shifts in gut phagobiota in PD patients may be caused by bacteriophages. Based on the functional analysis of phagobiome alterations in PD, similar changes may also be found in other multifactorial neurodegenerative conditions, including Alzheimer's disease. Thus, bacteriophages may cause or promote the development of any number of other neurodegenerative conditions.

Also provided is a method of vaccinating a mammal (e.g., a human) against a bacteriophage comprising administering a composition to the mammal comprising a polypeptide or epitope of the bacteriophage. The bacteriophage may be a temperate bacteriophage. Alternatively, the bacteriophage may be a lytic bacteriophage. For neurodegernative diseases, such as PD, vaccination against lytic bacteriophages, particularly those that target *Lactobacillus* bacteria, may be beneficial to prevent the neurodegenerative disease, inhibit the triggering of the neurodegenerative disease or to reduce the progression of the neurodegenerative disease. Such course of treatment may help preserve the *Lactococcus* bacteria in the mammal, allowing for production of adequate amounts of dopamine and other neurotransmitters.

Another way of targeting bacteriophages is to administer an antibacteriophagal agent is effective to inhibit replication of bacteriophage. Various antibacteriophagal agents may be used, with non-limiting examples including but not limited to phlepmycin, glycopeptide antibiotics (e.g., vancomycin, teicoplanin, telavancin, ramoplanin, decaplanin, and bleomycin), esterified milk proteins, Rifampcin, polymerase inhibitors (e.g., ribavirin, ribamidil, favipiravir, azidothymidine, and umifenovirum), nucleases and proteases. The antibacteriophagal agent may be an antifungal agent. For neurodegenerative disease treatment, antibacteriophagal agents that are effective against lytic bacteriophages that target *Lactococcus* bacteria may be administered.

Yet another way of targeting bacteriophages is to administer a gene editing nuclease that is configured to edit the genome of bacteriophages that target *Lactococcus* bacteria, or any other bacteria of interest. An exemplary, but non-limiting, gene editing nuclease is CRISPR. The nuclease may be configured to specifically target a sequence in one bacteriophage, such as a lytic bacteriophage targeting a bacterium, while not being effective to target other temperate bacteriophages that target the same bacterium. In the context of neurodegenerative diseases such as PD, the gene editing nuclease can specifically target *Lactococcus* bacteria that are in group 936 and/or are c2-like.

Yet another way of targeting bacteriophages is to administer an antibody that is specific to an epitope on the bacteriophage targeting *Lactococcus* bacteria, or any other bacteria of interest. The epitope may be on a polypeptide in the virion required for entry of the bacteriophage into the *Lactococcus* bacteria. Also, antibodies known to be neutralizing antibodies against such bacteriophage may be used. In the context of neurodegenerative diseases such as PD, the gene editing nuclease can specifically target *Lactococcus* bacteria that are in group 936 and/or are c2-like. Yet another way of targeting bacteriophages is to administer genetically-modified bacteria that are specific to a bacteriophage of interest (such as the lytic bacteriophages targeting *Lactococcus*). Such bacteria may be genetically engineered so that the bacteriophages enter the bacteria but cannot take advantage of the bacterial replication machinery so as to lyse the bacteria. Such genetically-modified bacteria may be effective to divert lytic bacteriophages from targeting *Lactococcus*.

Yet another way to target bacteriophages is by contacting bacteriophages with gene editing nucleases (e.g., CRISPR) configured to introduce a beneficial mutation or gene into the bacteriophages. As used herein, a bacteriophage comprising a "beneficial mutation or gene" reduces the progression or symptoms of a disease when administered into a mammal. For example, a beneficial mutation or gene may reduce the ability of a bacteriophage to target bacteria in the microbiome, such as by reducing the ability of lytic bacteriophages to cause lysis. Alternatively, a beneficial mutation may be sufficient to convert a lytic beteriophage into a temperate bacteriophage.

In another embodiment, bacteriophages with a beneficial mutation or gene are administered to a mammal. The administration may be conducted as part of one or more methods for preventing or treating a microbiota disease or consequences thereof, preventing or treating an increase in a barrier permeability, preventing or treating an increase in intestinal permeability, preventing or treating a disease in a mammal in need thereof, increasing longevity and/or decreasing aging, decreasing negative side-effects of a microbiota transplant, preventing or treating a disease of gastrointestinal (GI) microbiota or consequences thereof, preventing or treating a disease of skin microbiota or consequences thereof, or preventing or treating a disease of mucosal microbiota or consequences thereof. The administered bacteriophages may be effective to prevent lytic bacteriophages or other bacteriophages from targeting bacteria in the microbiome, e.g., *Lactococcus* bacteria.

The various methods of treating or inactivating bacteriophages described herein may be adapted so as to avoid targeting beneficial bacteriophages. As used herein, a "beneficial bacteriophage" reduces the progression or symptoms of a disease when administered into a mammal.

To prevent development of neurodegenerative diseases, such as PD, the various methods of targeting bacteriophages described herein may be adapted to target lytic bacteriophages specific to bacteria that are beneficial for the production of neurotransmitters. For instance, lytic bacteriophages that target *Lactococcus* bacteria may be selectively eliminated from food, water, and blood for transfusions.

A diagnosis of a neurodegenerative disease, such as PD, may be undertaken by any of the methods described herein for detection and diagnosis. The methods may be adapted to detect lytic bacteriophages specific to bacteria that are beneficial for the production of neurotransmitters. For instance, lytic bacteriophages that target *Lactococcus* bacteria may be selectively detected. Detection may occur in the transcriptome. The detection may be qualitative or quantitative. Such detection may be particularly helpful in the context of neurodegenerative diseases that are latent because the patient may be amenable to the various treatments described herein before damage to neurons occurs and other obvious symptoms develop. Further, early detection of a latent neurodenerative disease can provide the patient an opportunity to pursue other treatments and reduce other risk factors implicated in the progression of such neurodegenerative disease. For example, if PD is detected early by any of the methods herein, lytic bacteriophages targeting *Lactococcus* bacteria may be cleared and/or drugs that bolster the levels of dopamine may be administered. Also provided is a method to diagnose a disease comprising detecting the presence of a mutation or gene in a bacteriophage. The gene or mutation may increase the ability of the bacteriophage to target a specific bacterium in a microbiome. The mutation may be a beneficial mutation, a mutation that reduces the ability of the bacteriophage to target a specific bacterium in a microbiome, or a mutation that increases the ability of the bacteriophage to target a specific bacteria in a microbiome. As a non-limiting example, the gene or mutation may allow the bacteriophage to overcome bacterial antiphage systems. A non-limiting example of a bacterial antiphage system is the Abortive infection (Abi) systems.

Also provided is a method to treat a disease comprising detecting the presence of a mutation or gene in a bacteriophage, and then targeting the bacteriophage. The gene or mutation may increase the ability of the bacteriophage to target a specific bacterium in a microbiome. As a non-limiting example, the gene or mutation may allow the bacteriophage to overcome bacterial antiphage systems. A non-limiting example of a bacterial antiphage system is the Abortive infection (Abi) systems. The bacteriophage with the detected mutation or gene may be inactivated by any of the methods described herein.

Also provided is a method for diagnosing the potential for a phage to cause a disease by detecting the presence of certain mutations in genes that or detecting the presence of genes within bacteriophages or a bacterium in the microbiota. The bacteriophages may be acquired by a mammalian patient in a hospital. The disease may be caused by a bacteriophage or a prophage present in a hospital. The detected genes or detected mutations within bacteriophages may be effective to increase the ability of bacteriophage to target bacteria in the microbiome that prevent or reduce the progression of the disease. The detected genes or detected mutations within the bacterium in the microbiota may increase the ability of the bacterium cause progression of the disease. For example, the gene or mutation in the bacteriophage may increase the ability of a bacteriophage to overcome bacterial antiphage systems. Similarly, the gene or mutation in the bacterium may increase the ability of a bacteriophage to overcome the bacterium's antiphage systems. A non-limiting example of a bacterial antiphage system is the Abortive infection (Abi) systems.

Also provided is a method for assaying for an elevated level of a pathogen-associated molecular pattern (PAMP) associated with bacteriophage infection. The method comprises determining the concentration of total cell free DNA in a sample from a patient and comparing the concentration of total cell free DNA in the sample with a concentration of total cell free DNA in a subject who does not have the bacteriophage infection. The PAMP may comprise one or more of bacterial DNA, extracellular DNA, biofilm-derived DNA, LPS, a component of bacteria, or a component of a bacterial biofilm.

In various embodiments of methods of treatment disclosed herein, the method is effective to prevent a pathogenic effect of a bacteriophage, wherein the pathogenic effect is correlated with elevated levels of PAMPs. The PAMP may comprise one or more of bacterial DNA, extracellular DNA, biofilm-derived DNA, LPS, a component of bacteria, or a component of a bacterial biofilm.

A summary of how bacteriophages may cause various infections or diseases is provided in Table 1 below:

TABLE 1

| Main factors that may cause bacteriophage infections | Comments |
|---|---|
| Infection by lytic phages | Primary infection by a bacteriophage in the environment |
| Infection by bacteria carrying prophages in their DNA | Primary infection by a bacterium in the environment that harbor prophages |
| Induction of prophages | Can be due to a variety of different internal and external triggers that lead to progeny release and an increase in the number of free phages |

TABLE 1-continued

| Main factors that may cause bacteriophage infections | Comments |
|---|---|
| Increased translocation of phages to biological fluids | Can be due to increased intestinal permeability or increased blood-brain barrier permeability |
| Alteration of the microbiota | Alteration can shift the number of, or relative amount of, prophages or lytic phages |
| Mutations in prophages leading to Abi-escape phage mutants | The mutated phages are able to overcome bacterial protective systems |
| Changes in macroorganism's sensitivity to bacteriophages | |

1. A use of a drug to prevent bacteriophage entry into a microbiota of a mammal, wherein the antibiotic is tacrolimus, pentosan polysulfate, quinacrine, a macrolide, a fluoroquinolone, a teracyclin, an aminoglycoside, an ansamycin, carbacephem, cephalosporins, a glycopeptide, a lincosamide, a monobactam, an oxazolidinone, penicillins, or a sulfonamide.

2. A use of a drug to prevent entry of bacteriophage into a microbiota of a mammal, wherein the drug is tacrolimus, pentosane polysulfate or quinacrine, and wherein the bacteriophage comprises a PrD.

3. A method of analysing the abundance of temperate and lytic bacteriophages in a microbiota, the method comprising determining the amount of temperate bacteriophages, determining the amount of lytic bacteripahges, and determining the amount of bacteria in the microbiota.

4. The method of embodiment 3, wherein the bacteria host the temperate bacteriophages.

5. The method of embodiment 3, wherein the bacteria host the lytic bacteriophages.

6. A method of analysing the abundance of a bacteriophage in a microbiota, wherein the genome of the bacteriophage comprises a mutation or a gene that increases the virulence of the bacteriophage against bacteria, the method comprising determining the amount of the bacteriophages and determining the amount of bacteria in the microbiota.

7. A method of analysing the abundance of a bacteriophage in a microbiota, wherein the genome of the bacteriophage comprises a mutation or a gene that increases the virulence of the bacteriophage against bacteria, the method comprising detecting the presence of the mutation or the gene.

8. The method of embodiment 7, wherein the detecting comprises performing a polymerase chain reaction on a sample comprising the bacteriophage.

9. A method for detecting bacteriophage that may cause a disease in a human comprising performing the methods of any one of embodiments 6-8, wherein the mutation reduces the function of the Abortive infection (Abi) system.

10. A method of treating a disease in a human comprising detecting bacteriophage that may cause a disease in a human comprising performing the methods of any one of embodiments 6-8, wherein the mutation reduces the function of the Abortive infection (Abi) system, and inactivating the detected bacteriophage.

11. A method of vaccinating a mammal against a bacteriophage.

12. A method of vaccinating a mammal against a bacteriophage listed in Tables 18 or 19, wherein the method comprises administering an epitope of the bacteriophage to the mammal.

13. The method of embodiment 11, wherein the mammal is human.

14. A use of a bacteriophage not comprising a PrD for processing food.

15. A use of a bacteriophage not comprising a PrD for treating water.

16. A use of a bacteriophage not comprising a PrD on the surface of the bacteriophage for processing food.

17. A use of a bacteriophage not comprising a PrD on the surface of the bacteriophage for treating water.

18. A method for preventing or treating a disease in a mammal in need thereof, said method comprising one or more of (i) inhibiting adhesion of bacteriophage to bacterial cells, (ii) inhibiting entry of bacteriophage into bacterial cells, (iii) inhibiting bacteriophage nucleic acid synthesis, (iv) inhibiting bacteriophage replication, (v) inhibiting bacteriophage assembly, or (vi) inhibiting bacteriophage release.

19. A method for preventing or treating a disease in a mammal in need thereof, said method comprising inhibiting attachment, adhesion or adsorption of a bacteriophage to a microbial biofilm or to a component of the microbial biofilm.

20. A method for preventing or treating a disease in a mammal in need thereof, said method comprising inhibiting the interaction between a bacteriophage and a eukaryotic cell.

21. A method for preventing or treating a disease in a mammal in need thereof, said method comprising administering a drug to the mammal, wherein the drug is effective to inhibit a bacteriophage from encoding a protein or wherein the drug is effective to inhibit the activity of a protein encoded by a bacteriophage.

22. A method for preventing or treating a disease in a mammal in need thereof, said method comprising administering a drug to the mammal, wherein the drug is effective to prevent transcytosis of bacteriophages.

23. The method of embodiment 20-22, wherein the drug is administered systemically to a tissue or body fluid comprising bacteriophage.

24. The method of embodiment 23, wherein the body fluid is blood, saliva, or CSF.

25. The use of embodiment 23, wherein the drug is administered systemically to a tissue or body fluid comprising bacteriophage.

26. The use of embodiment 25, wherein the body fluid is blood, saliva, or CSF.

27. A method for preventing or treating a disease in a mammal in need thereof, comprising preventing prophage induction.

28. A method for preventing or treating a disease in a mammal in need thereof, comprising administering bacteria with an altered protective antibacteriophage system to the mammal.

29. The method of embodiment 28, wherein the protective antibacteriophage system is the Abi system.

30. The method of embodiment 28 or 29, wherein the bacteria are resistant to bacteriophages comprising mutations that confer ability to overcome a bacterial protective system.

31. A use of a bacteriophage comprising a PrD against another bacteriophage.

32. A use of a PrD from a bacteriophage against another bacteriophage.

33. A use of a bacteriophage comprising a PrD against bacteria.

34. A use of a PrD from a bacteriophage against bacteria.

35. The use of embodiments 33-34, wherein an interaction between the bacteria and the bacteriophage is inhibited by the PrD.

36. A use of a synthetic bacteriophage comprising a PrD against another bacteriophage.

37. A use of a synthetic bacteriophage comprising a PrD against bacteria.

38. A use of a synthetic bacteriophage comprising a PrD against a eukaryotic cell.

39. A use of a synthetic bacteriophage comprising a PrD against a malignant cell.

40. A use of a synthetic bacteriophage comprising a PrD to treat an oncological disease.

41. The use of embodiments 36-40, wherein the PrD is synthesized or modified in a synthetic manner.

42. A method comprising screening bacteriophages to find a bacteriophage expressing a PrD that can inhibit the ability of another bacteriophage to enter bacteria.

43. A method comprising screening bacteriophages to find a bacteriophage expressing a PrD that can inhibit the ability of another bacteriophage to enter a eukaryotic cell.

44. A method comprising screening bacteriophages to find a bacteriophage expressing a PrD that can inhibit the ability of another bacteriophage to enter a malignant cell.

45. A method comprising screening bacteriophages to find a bacteriophage expressing a PrD, wherein the bacteriophage or the PrD is effective to treat an oncological disease.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Bacteriophages Introduced to Rats Increase Intestinal Permeability

A group of five, healthy adult, male, albino Wistar rats from Rappolovo, St. Petersburg, Russia was used, with all experiments performed in accordance with the guide for the care and use of laboratory animals. Ethical approval was granted by the Human Microbiology Institute Ethics Committee (T-Ph2015). Alterations of urinary mannitol and lactulose excretion, and changes in the lactulose:mannitol ratio were measured and compared as follows.

Two commercial bacteriophage cocktails were used: (i) Salmonella bacteriophage cocktail (Microgen, Russia) containing phages infecting Salmonella enterica serotypes: Paratyphi, Typhimurium, Heidelberg, Newport, Choleraesuis, Oranienburg, Infans, Dublin, Enteritidis, Anatum, and Newlands, and (ii) Pyobacteriophage Polyvalent, another commercial phage cocktail (Microgen, Russia) containing phages infecting Staphylococcus aureus, Streptococcus pyogenes, Proteus mirabilis and P. vulgaris, Pseudomonas aeruginosa, Klebsiella pneumoniae, and Escherichia coli. A mixture of these commercial bacteriophage cocktails (1.5 ml [$1\times10^6$ plaque-forming units/ml] of each phage according to the manufacturer's instruction) was given daily to animals (n=5) for 10 days. Parameters of each animal before bacteriophage challenge were used as controls.

A lactulose-mannitol permeability test was performed to determine whether bacteriophages may cause microbiota diseases resulting in alterations in the host organism in the form of increased intestinal permeability. The lactulose:mannitol ratio was measured as a marker of intestinal permeability 2 days before and 10 days after phage challenge as described by Meddings et al. (Meddings, J. B. et al., 2000). Lactulose (L7877, Sigma-Aldrich) and mannitol (M8429, Sigma-Aldrich) were utilized for all arms of the study. For permeability testing of both probes simultaneously, animals were fasted for 4 h and then gavaged with 120 mg lactulose and 80 mg mannitol in 2 ml of water. Animals were placed in metabolic cages, and the urine passed over 24 hours after the gavage was collected and assayed for the concentration of each probe by gas chromatography as described previously (Keshavarzian A. et al., 1994). Thus, alterations of urinary mannitol and lactulose excretion and changes in the lactulose:mannitol ratio were compared at 2 days before and on the 10th day after daily challenge with the bacteriophage cocktail.

The excretion of mannitol was slightly but not significantly reduced after the bacteriophage challenge, as compared to the level of excretion before the bacteriophage challenge. At the same time, rats exhibited a significant increase ($P<0.05$) in lactulose excretion after bacteriophage treatment as compared to before the treatment. The animals displayed a significantly elevated lactulose:mannitol ratio ($P<0.05$), which was considered to reflect increased intestinal permeability. See Table 2. The increase was at least 2.4-fold in all animals. All animals had a leaky gut with a benchmark lactulose/mannitol ratio >0.46 (Keshavarzian A. et al., 1994). (All results are reported as the mean±standard error (SE). Non-parametric paired Wilcoxon signed rank test was applied to analyze pre- and post-challenge differences. $P<0.05$ was considered significant.)

TABLE 2

Changes in lactulose and mannitol excretions after bacteriophage challenge

| Experimental animals | Lactulose (pmol) | | Mannitol (pmol) | |
| --- | --- | --- | --- | --- |
| | Before bacteriophage challenge | After bacteriophage challenge | Before bacteriophage challenge | After bacteriophage challenge |
| 1 | 56 | 145 | 145 | 158 |
| 2 | 62 | 183 | 156 | 175 |
| 3 | 59 | 189 | 128 | 152 |
| 4 | 48 | 166 | 108 | 180 |
| 5 | 43 | 133 | 117 | 164 |
| Mean | 53.6 ± 7.9 | 163.2 ± 24.0 | 130.9 ± 19.7 | 165.8 ± 11.6 |

This study demonstrated that increased intestinal permeability may be induced by bacteriophages that affect the microbiota. Ten days of administration of a bacteriophage cocktail active against Staphylococcus spp., Streptococcus spp., Proteus spp., Pseudomonas spp., E. coli, K. pneumonia, and Salmonella spp. did not lead to apparent clinical changes in the gastrointestinal tract or abnormal stool in rats. At the same time, all animals showed weight loss, messy hair, and decreased activity starting from the fifth day of the bacteriophage treatment, which are considered to be related to the translocation of endotoxins across leaky mucosa.

Next, the serum concentrations of CIC were measured to determine whether alterations caused by bacteriophages induced a systemic inflammatory reaction in the rats. The presence of CIC is an element of the normal immune response, and elevated levels of CIC are associated with different pathological conditions including intoxication (Schietroma M. et al., 2013). Heparinized blood samples were collected at day 0 and day 10 from the tail vein of rats under sterile conditions. CIC were evaluated by sedimentation with a 4.0% polyethylene glycol solution followed by spectrophotometry as described by Ramos et al. (Ramos, G. S. et al., 1987). The CIC concentration was evaluated as the difference between the values of the probes before and after bacteriophage challenge.

Figure 1B:
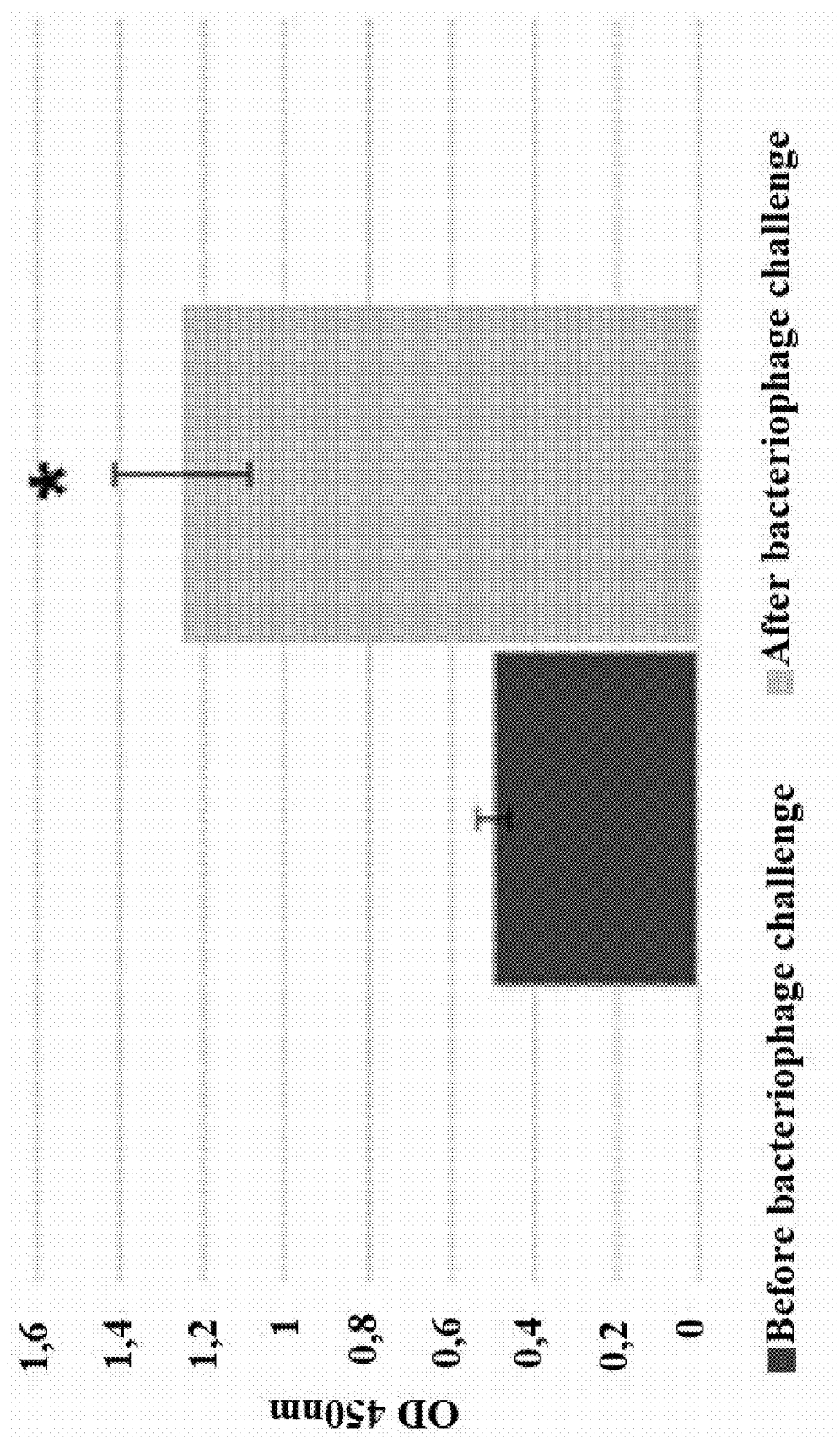

As shown in FIGS. 1A and 1B, at the 10th day of treatment, the mean level of CIC was 2.5 times higher than before treatment (P<0.05), indicating endogenous intoxication, most likely caused by increased intestinal permeability and ongoing leaky gut. (All results are reported as the mean±standard error (SE). Non-parametric paired Wilcoxon signed rank test was applied to analyze pre- and post-challenge differences. P<0.05 was considered significant.) Untreated negative control animals that were kept under the same conditions as the treated animals did not show any changes over the study period.

The data presented herein indicate that experimental bacteriophage infection may be harmful for macroorganisms (Sarker, S. A. et al., 2012; Yilmaz, C. et al., 2013). The pathological effect was revealed as increased intestinal permeability, and was associated with the phages' selective effect on the microbiota, without any direct effect on the host eukaryotic cells (Dabrowska, K. et al., 2005). The data indicate that bacteriophages can promote microbiota-associated diseases and thus indirectly cause pathological conditions of mammals that are associated with leaky gut. It can be assumed that the incidence and distribution of such pathological conditions may be caused by bacteriophages originating from the outer environment, because bacteriophages are widely spread and humans are constantly exposed to them (Tetz., G. and Tetz, V., 2016; De Paepe M. et al., 2014).

Example 2: Comparison of Intestinal Microbiota and Endotoxemia Before and after Bacteriophage Challenge An investigation on how microbial composition of the gut microbiota changes with bacteriophage challenge and whether microbial composition correlates with the increased intestinal permeability and endotoxemia was conducted. Illumina sequencing of the V3-V4 region of the 16S ribosomal RNA (rRNA) gene was carried out to compare the microbiota composition before and after a bacteriophage challenge and to uncover its role in the increased intestinal permeability and endotoxemia in rats (Claesson, M. et al., 2010).

To investigate whether bacteriophages can cause a shift in microbiota leading to increased gut permeability, a rat model was used to measure markers of intestinal permeability and endotoxemia. To understand the nature of impaired gut permeability in response to bacteriophage exposure, faecal material was collected from the same animals before and after the phage challenge. Daily phage challenge involved administering a bacteriophage cocktail comprised of commercially available and characterised phages active against the Enterobacteriaceae, Staphylococcaceae, Streptococcaceae, and Pseudomonadaceae families. One cocktail included a Salmonella bacteriophage cocktail from Microgen (Moscow, Russia; product batch number H20), containing bacteriophages against Salmonella enterica serotypes: S. Paratyphi, S. Typhimurium, S. Heidelberg, S. Newport, S. Choleraesuis, S. Oranienburg, S. Infans, S. Dublin, S. Enteritidis, S. Anatum, and S. Newlands. Pyobacteriophage, another polyvalent commercial phage cocktail from Microgen (product batch number 4), contained phages against seven bacterial species, Staphylococcus aureus, Streptococcus pyogenes, Proteus mirabilis, Proteus vulgaris, Pseudomonas aeruginosa, Klebsiella pneumoniae, and Escherichia coli. The cocktails were mixed. Phages (1.5 mL, $1 \times 10^6$ plaque-forming units/mL of each phage cocktail) were added to drinking water according to the manufacturer's instruction and administered orally for 10 days. Each animal was used as its own control before the bacteriophage challenge.

Gut permeability function was examined in animals before (at baseline) and 10 days after the daily challenge with a bacteriophage cocktail using each animal as its own control. Without wishing to be bound by theory, because bacteriophages are known to selectively interact with bacteria and not affect eukaryotic cells, any impaired gut permeability can only be a consequence of altered microbiota.

Healthy adult male Wistar rats (n=5; 12-week-old, 240-280 g) were maintained in individual metabolic cages in a P3 room under a 12-h light/dark cycle, at a temperature of 22 to 25° C. and 60±5% atmospheric humidity. All animals had free access to food and water according to the Guide for the Care and Use of Laboratory Animals (Albus, U. Guide for the Care and Use of Laboratory Animals (8th Ed.) by the National Research Council of the National Academies Washington, DC: National Academies Press, 2011. *Lab. Anim.* 46, 267-268 (2012)). An ethical approval was granted by the Human Microbiology Institute Ethics Committee (B12/2016). The animals were monitored daily for any changes of their activity, behavior, and general health status, including the weight loss, ruffled coat, wheezing or abnormal respiration, and the presence of unformed faeces. Body weights of all animals were measured using a digital balance (Mettler-Toledo, Inc., Columbus, OH, USA). Urine was collected for 24 h.

All animals survived the entire duration of the experiment, with no clinical changes in the gastrointestinal tract or stool alteration. No statistically significant differences in the total weight at baseline and after bacteriophage treatment were detected; however, a trend towards weight loss was registered. After bacteriophage administration, the average weight of each rat was 231±45 compared with 269±28 g in the pre-treatment period. At the same time, all animals showed unkempt hair coats and decreased activity starting from the 5th day of bacteriophage administration, which the present inventors believe was due to the induction of endotoxemia and impaired intestinal permeability.

Figure 2A:
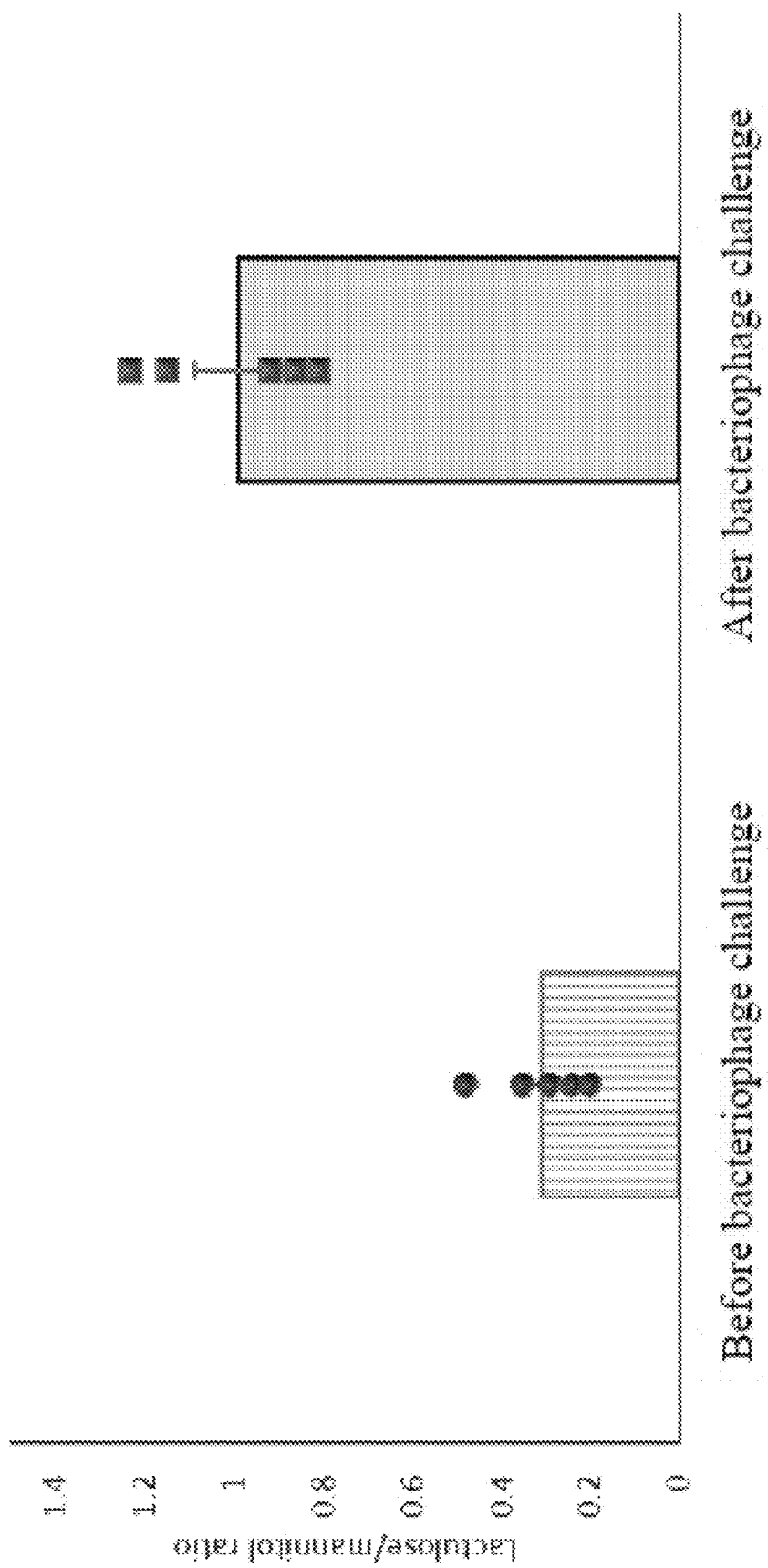
FIGS. 2A-2E show the effects of bacteriophages on intestinal permeability and endotoxemia. Albino Wistar male rats (n=5) were challenged with a bacteriophage cocktail for 10 days. Each animal was used as its own baseline control. Blood and urine samples were collected from all rats at the same time and subjected to various analytical tests described in Example 2.

To assess the damage to the gastrointestinal tract, intestinal permeability was measured using a clinical test based on saccharide permeability, which measures the ratio of lactulose to mannitol after oral ingestion of the sugars. The lactulose/mannitol ratio was measured using gas chromatography as described previously. The animals showed higher gut permeability following the bacteriophage challenge, with an average post-treatment lactulose/mannitol ratio of 0.99±0.08 compared with that of 0.31±0.05 pre-bacteriophage treatment (p<0.05) (FIG. 2A). An increased lactulose/mannitol ratio was found compared with that at baseline, which was determined prior to administration of the bacteriophages, indicating increased intestinal permeability following oral administration of bacteriophages.

The results also showed significantly elevated levels of blood serum endotoxin, TNF-α, IL-1β, and IL-6 compared to those in the pre-treatment period. Levels of TNF-α, IL-6, and IL-1β were measured in the serum using respective commercial rat-specific enzyme-linked immunosorbent assay (ELISA) kits (BioLegend, San Diego, CA, USA) according to the manufacturer's instructions. LPS was measured using a Pyrochrome Limulus Amebocyte lysate kit (Associates of Cape Cod, Inc., East Falmouth, MA, USA) according to the manufacturer's instructions. In brief, collected blood specimens were stored in LPS-free vials (Eppendorf, Germany) on ice. Plasma was centrifuged, transferred to a glass tube, and stored at −20° C. until analysis. Optical densities were measured by ELISA and read at 405 nm.

Figure 2B:
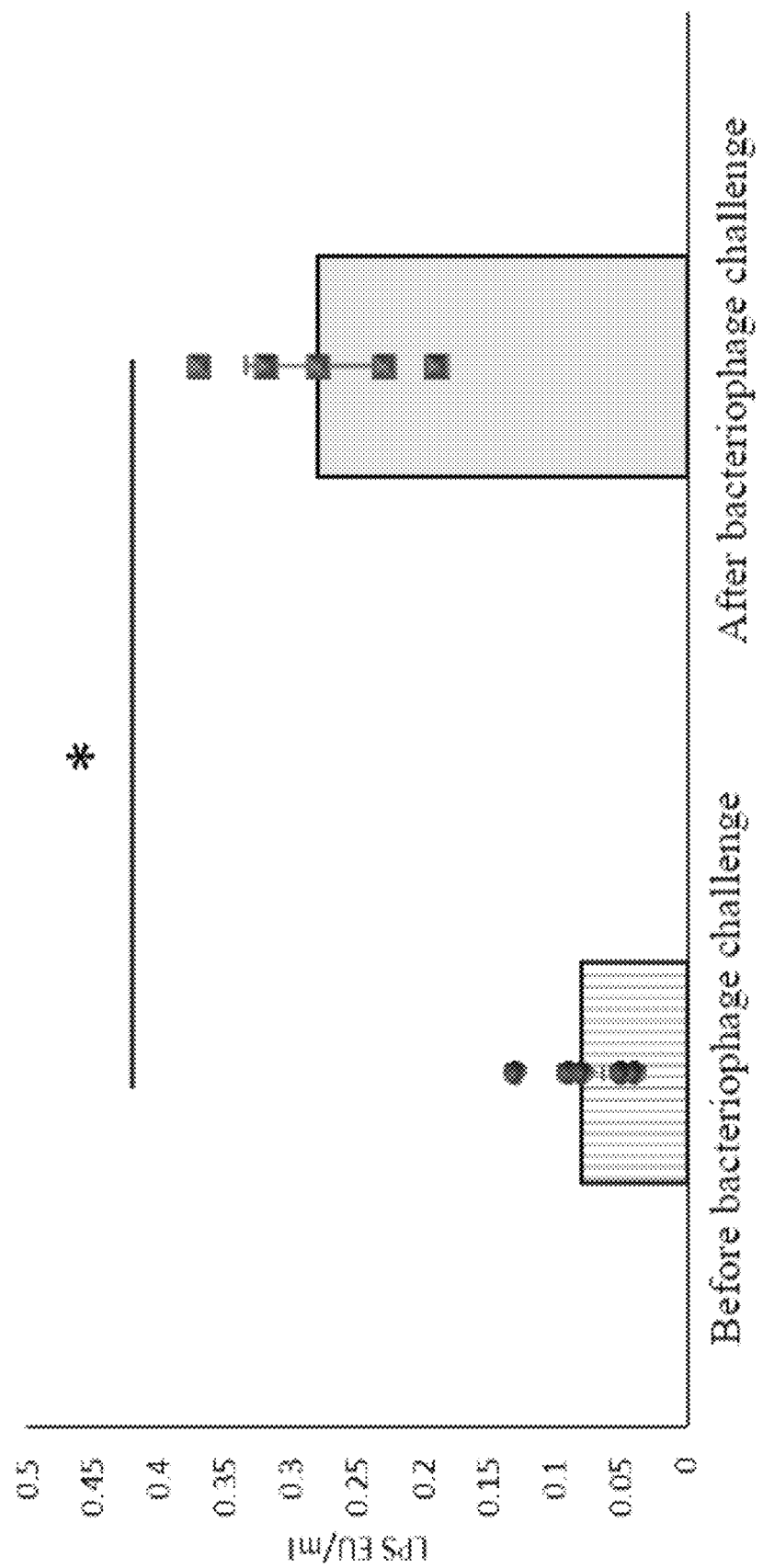
Figure 2C:
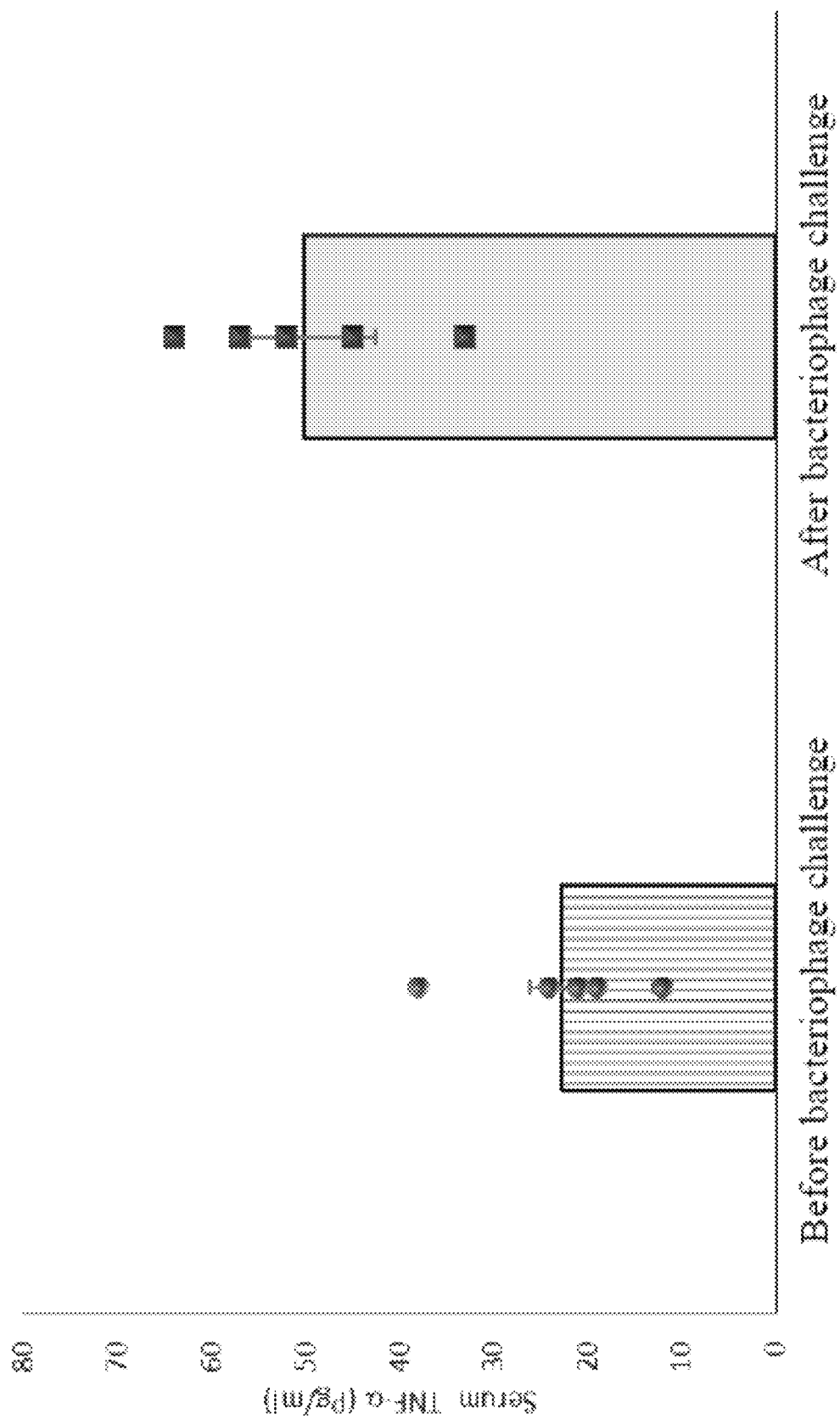
Figure 2D:
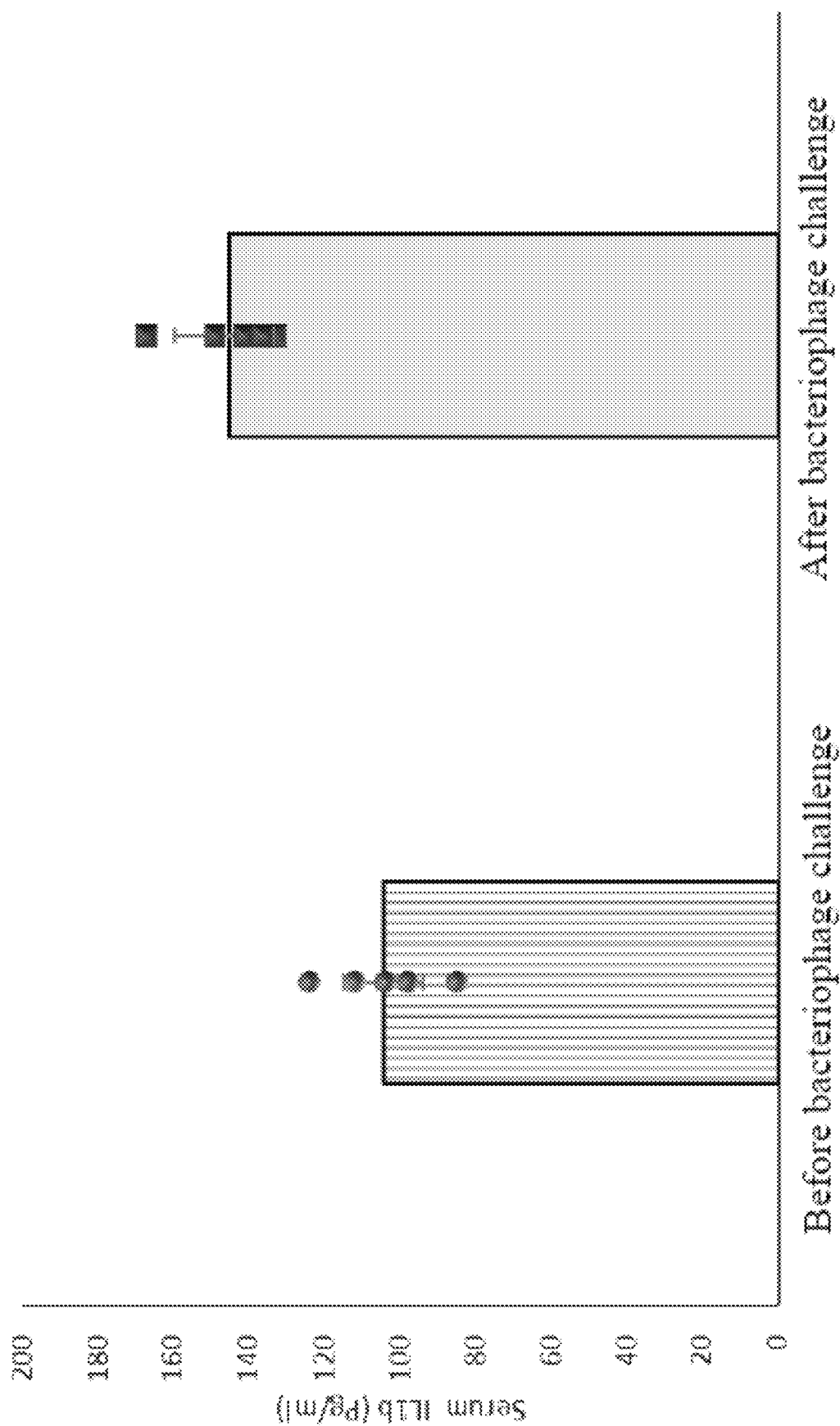
Figure 2E:
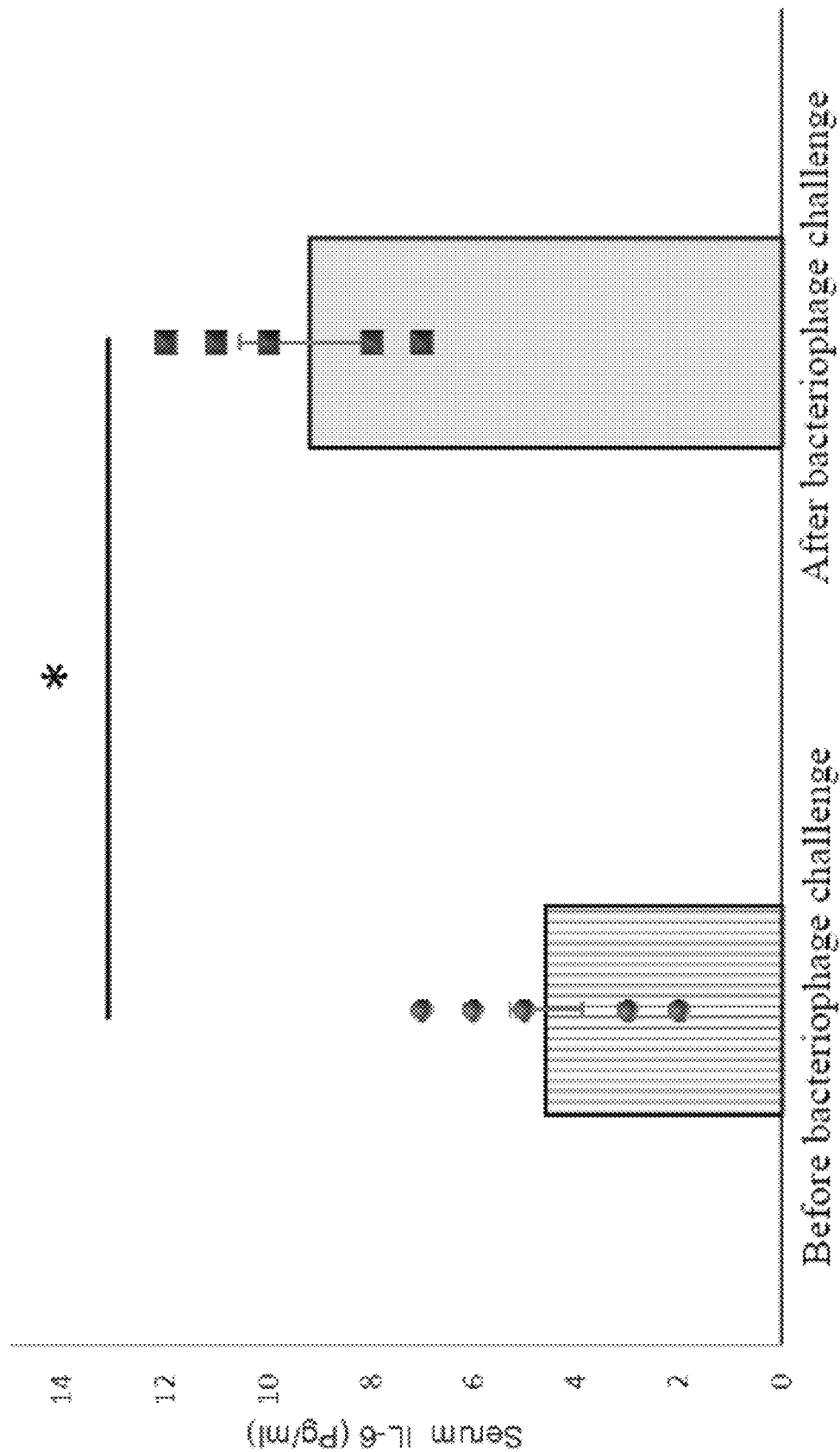

Rats were assayed to determine whether bacteriophage treatment and altered intestinal permeability could cause endotoxemia. As shown in FIGS. 2A-2E, the rats exhibited dramatically elevated serum levels of endotoxemia markers after the phage challenge, as compared to the pre-treatment baseline data. The inventors found that the animals had higher levels of plasma lipopolysaccharide (LPS) after the bacteriophage challenge, with an average of 0.28±0.07 endotoxin units (EU)/mL as compared with an average of 0.08±0.02 EU/mL (p<0.05) before the treatment (FIG. 2B). Accordingly, the levels of serum inflammatory cytokines were also elevated after the bacteriophage challenge. Treatment with phages resulted in a significant increase in the serum concentrations of tumour necrosis factor-alpha (TNF-α), interleukin (IL)-1β, and IL-6 (p<0.05 compared with the baseline pre-treatment data; FIG. 2C-E).

The present inventors showed herein that bacteriophages could induce inflammation, most likely through an increase in the circulating endotoxin level, which is likely to be a result of an altered intestinal microbiota and increased intestinal permeability. Without wishing to be bound by theory, there are different ways by which a disrupted gut barrier can lead to immune modulation; the most well described is stimulation of inflammatory responses by the intestinal-derived endotoxin (increased serum LPS levels), which subsequently results in elevated levels of inflammatory mediators.

Example 3: Analysis of Gut Microbiota Composition Before and after Bacteriophage Challenge To determine the effects of bacteriophages on the intestinal microbiota, gut microbiota composition was analyzed in the rats before and after the bacteriophage challenge using Illumina-based 16s rRNA sequencing.

Faecal samples were collected at baseline and after 10 days of the bacteriophage challenge into a sterile container and immediately stored at −80° C. until further processing. Bacterial DNA extraction was performed using a QIAamp stool DNA mini kit according to the manufacturer's instructions (Qiagen, Germany). Sequencing libraries of the V3-V4 region were prepared according to the Illumina MiSeq system instructions (available at res.illumina.com/documents/products/appnotes/16s-metagenomic-library-prep-guide.pdf). In brief, the V3 and V4 regions of the 16S bacterial rRNA gene were amplified using a two-step polymerase chain reaction (PCR) protocol with V3 and V4 region primers (forward: 5'-TCGTCGGCAGCGTCA-GATGTGTATAAGAGACAGCCTACGGGNGGCWG-CAG-3' (SEQ ID NO: 1); reverse: 5'-GTCTCGTGGGC-TCGGAGATGTGTATAAGAGACAGGACTACHVGG-GTATCTAATCC-3') (SEQ ID NO: 2) for the first PCR and Nextera XT index primers for the second PCR. Amplicons were cleaned using AMPure XP magnetic beads, and then, Illumina sequencing adapters and dual-index barcodes were added to each amplicon. Libraries were assessed with the Qubit dsDNA HS assay kit (Thermo Fisher Scientific) and TapeStation high sensitivity D1000 ScreenTape (Agilent) and normalised and sequenced on an Illumina MiSeq instrument using a MiSeq reagent kit v2 (500 cycles). Data was analysed with the MiSeq Reporter software Metagenomics workflow v2.5.1.3 (Illumina). After quality control filtering, the inventors obtained an average of 147,191 reads of the V3-V4 region of 16S rRNA genes per sample.

Overall, the faecal microbiota of animals exhibited distinct alterations in the bacterial composition following the treatment with bacteriophages.

FASTQ files generated by Illumina sequencing were qualitatively evaluated using FASTQC. Adaptor contamination and low-quality reads were detected with Trimmomatic. Raw data were quality-filtered to remove sequences with <200 nucleotides or containing ambiguous bases, uncorrectable barcodes, and homopolymer runs of more than six bases. Sequences were grouped into OTUs with a 97% threshold of pairwise identity. Operational taxonomic units (OTUs) were defined as a set of sequence reads with the similarity cutoff of 97%. For clarity and visualisation purposes, the most abundant sequences with a relative abundance of ≥0.5% within each taxa were designated as 'representative sequences'. OTUs that had a mean relative abundance of >0.001% were designated as 'total sequences' and were analysed separately. Representative and total sequences were assigned at different taxonomic levels (from phylum to genus) to bacterial SILVA datasets.

Figure 3A:
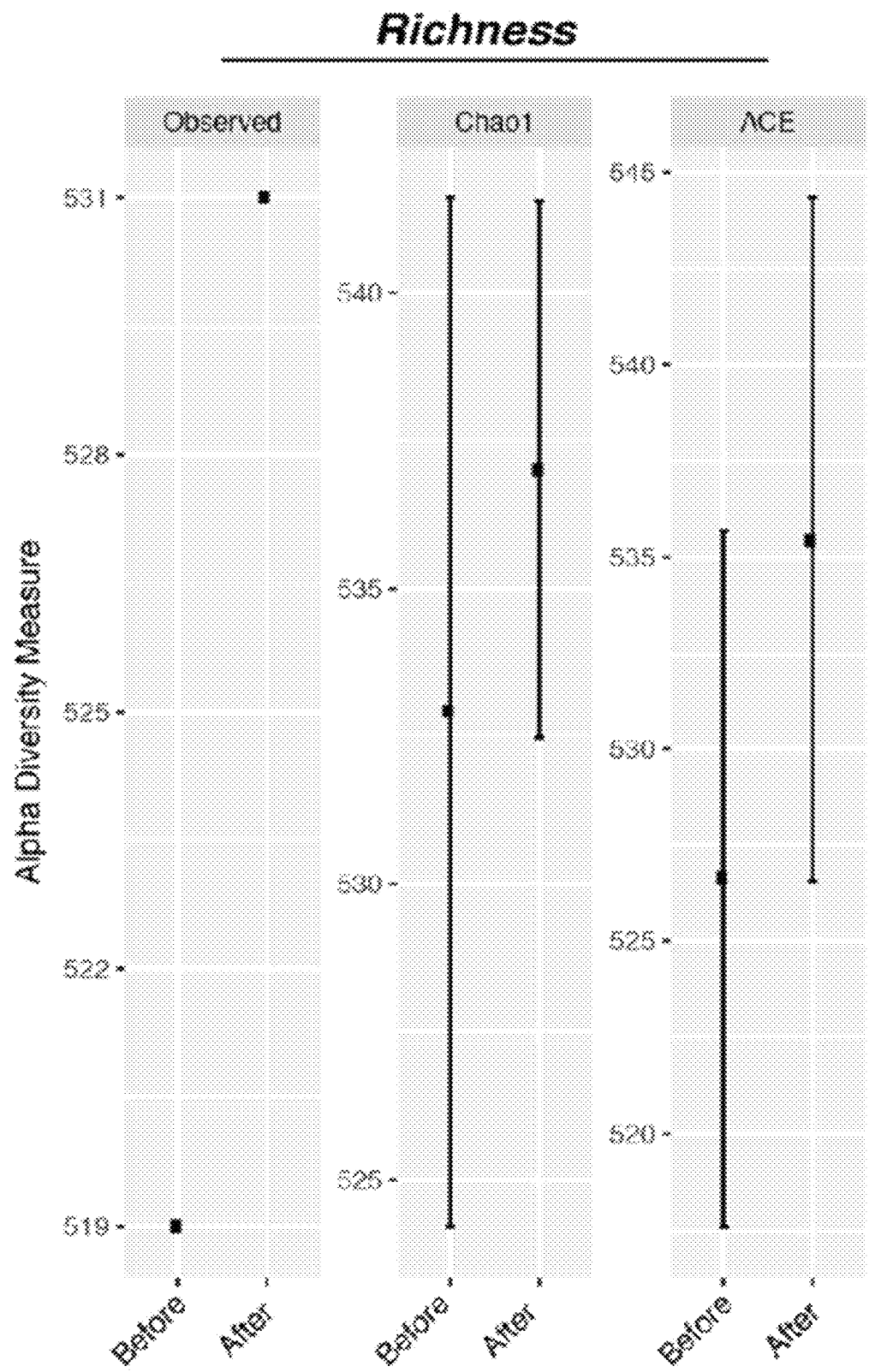
FIGS. 3A-3B show alpha diversity before and after bacteriophage challenge as calculated by multiple diversity measures. Comparisons of the alpha diversity indexes revealed alterations after the bacteriophage challenge.
Figure 3B:
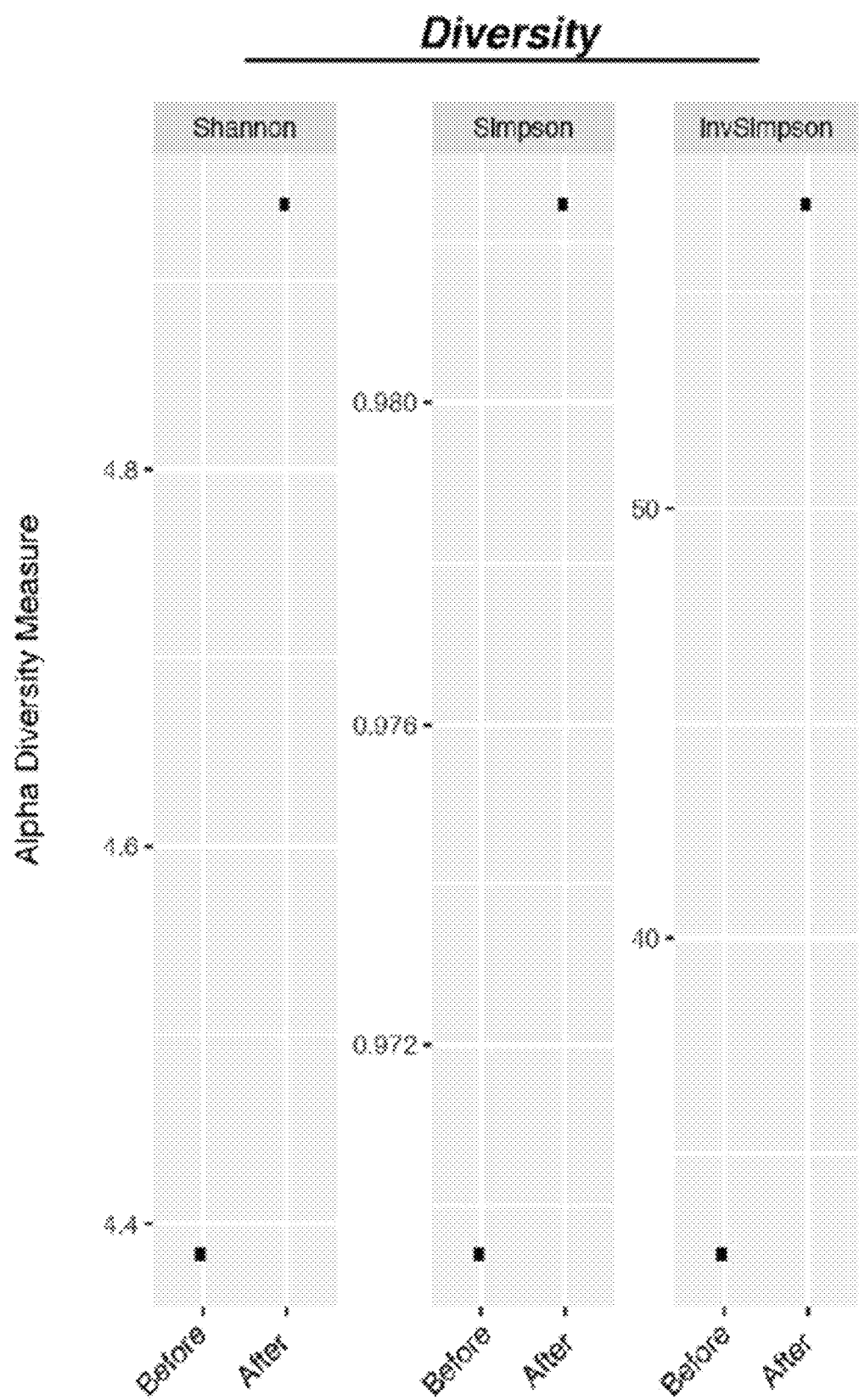

The sequence reads were then used to investigate whether there was an overall gain or loss of diversity by examining the alpha diversity, which represented a difference in the microbiome composition between groups at baseline and after administration of bacteriophages. The QIIME pipeline was used for quality filtering of DNA sequences, chimera removal (using the USEARCH software), taxonomic assignment, and calculation of the alpha diversity as previously described. Downstream data analysis and calculation of diversity metrics was completed in R3.3.2 using ggplot2 and phyloseq libraries and DESeq2 for calculating the log fold change. The abundance-based coverage estimator (ACE), Chao 1 richness estimator, Shannon, Simpson, and inverse Simpson diversity indices were calculated using the phyloseq R library (McMurdie, P. J., & Holmes, S. phyloseq: An R Package for Reproducible Interactive Analysis And Graphics Of Microbiome Census Data. *PloS* one, 8, e61217 (2013)). Species diversity (Shannon, Simpson, and inverse Simpson indices) and richness estimators (Chao 1 and ACE) were calculated pre- and post-phage challenge. An increase in the alpha diversity was found on day 10 of phage administration. The bacterial richness also differed, and the Chao 1 and ACE values, as well as the Shannon, Simpson and inverse Simpson indexes, increased following the phage challenge (FIG. 3). These data demonstrated that the faecal microbiota exhibited a rapid and marked increase in the overall microbial diversity after bacteriophage infection.

All statistical analyses were performed using the statistics package Statistica for Windows (version 5.0). Results are reported as the mean±SEM for each group. The non-parametric paired Wilcoxon signed-rank test was applied to the analysis of pre- and post-challenge differences. A value of p<0.05 was considered significant.

Figure 4A:
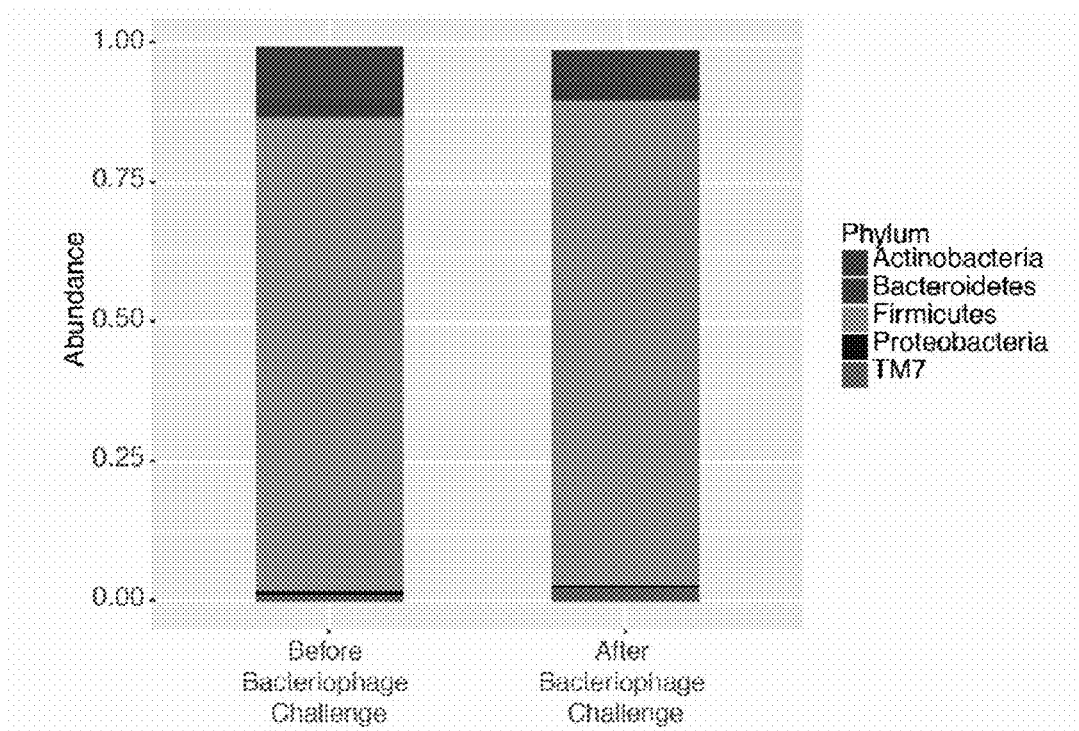
FIG. 4A-4C show comparison of relative abundance of predominant genera. Faecal bacterial communities were analysed by high-throughput sequencing of the 16S rRNA gene. Relative abundances of bacterial (FIG. 4A) phyla, (FIG. 4B) families, and (FIG. 4C) genera before and after the bacteriophage challenge at a level of ≥0.5% relative abundance. The term 'other' refers to the genera with the minimum abundance of <0.5%.
Figure 5A:
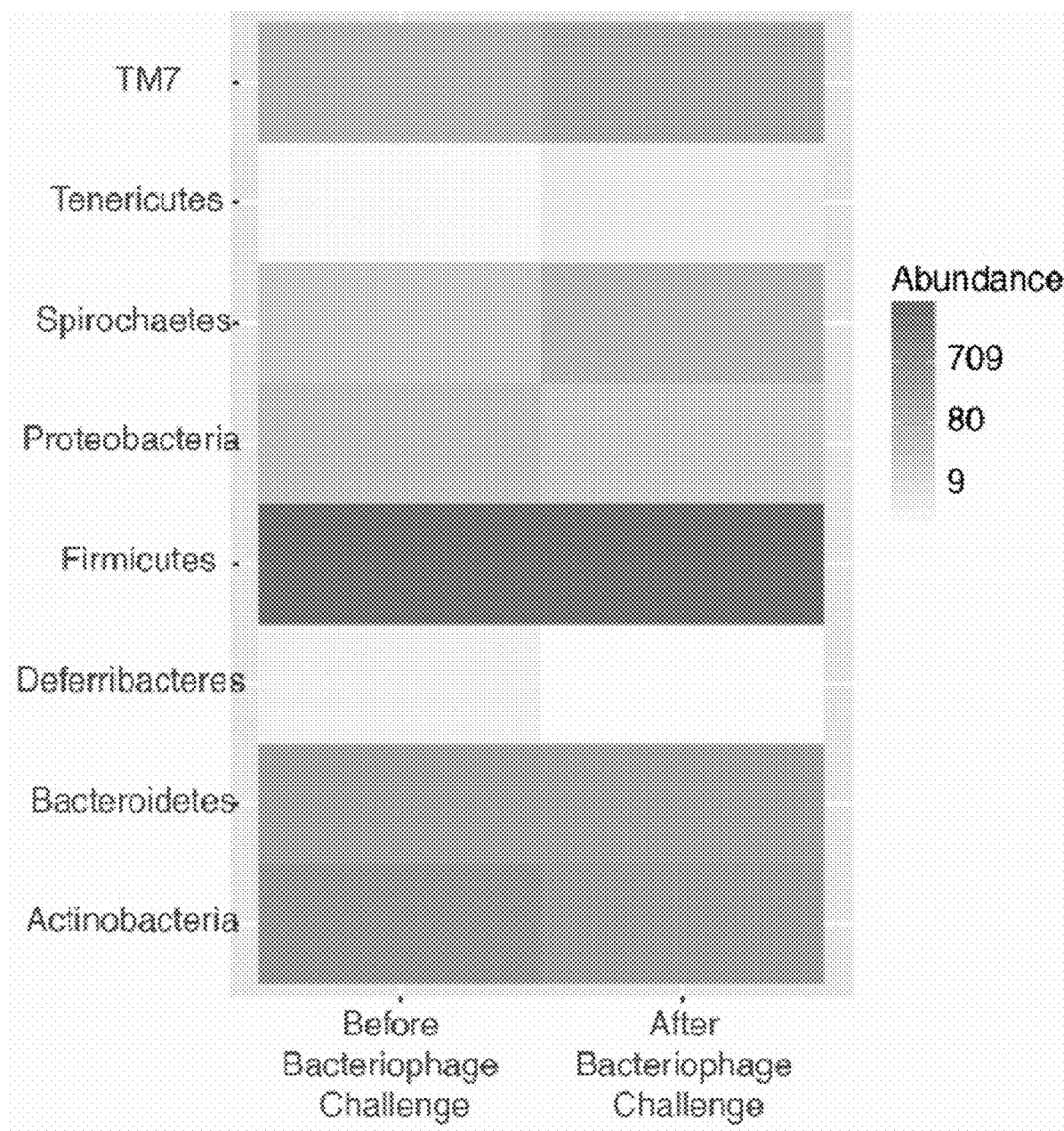
FIGS. 5A-5E show bacteriophage challenge affects the gut bacterial community. Bacterial OTUs occurring at an abundance of >0.001% before and after bacteriophage challenge. Heatmap of the relative abundances of bacterial (FIG. 5A) phyla, (FIG. 5B) families, and (FIG. 5D) genera. Population scores of enriched taxa of bacterial (FIG. 5C) families and (FIG. 5E) genera that differed by at least two-fold (i.e. $\log_2=1$) between pre- and post-treatment samples. A positive $\log_2$-fold change value indicates that OTU is significantly enriched in samples, and a negative $\log_2$-fold change indicates that OTU is significantly depleted in post-treatment samples.

The taxonomic identity of the reads was analysed using available annotation source databases. With OTUs at a relative abundance of ≥0.5% at the phylum level (representative sequences), *Firmicutes* was the predominant phylum in the untreated and bacteriophage-treated animals (FIG. 4A). At the phylum level, there were no significant changes in the untreated and bacteriophage-treated animals (FIG. 4A). However, analysis of all phylum level (OTUs >0.001%) abundance data revealed a decreased abundance of *Actinobacteria, Deferribacteres*, and *Proteobacteria* after the bacteriophage challenge. Notably, three phyla, *Spirochaetes, Tenericutes*, and candidate division TM7, increased following bacteriophage treatment (FIG. 5A).

Figure 4B:
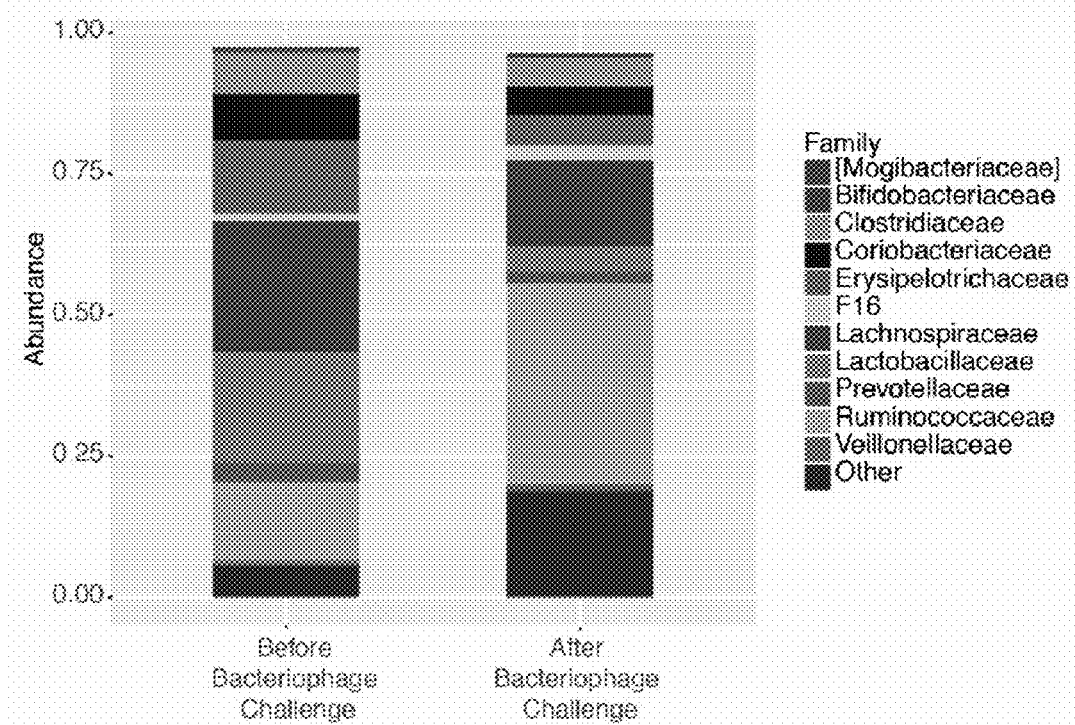
Figure 4C:
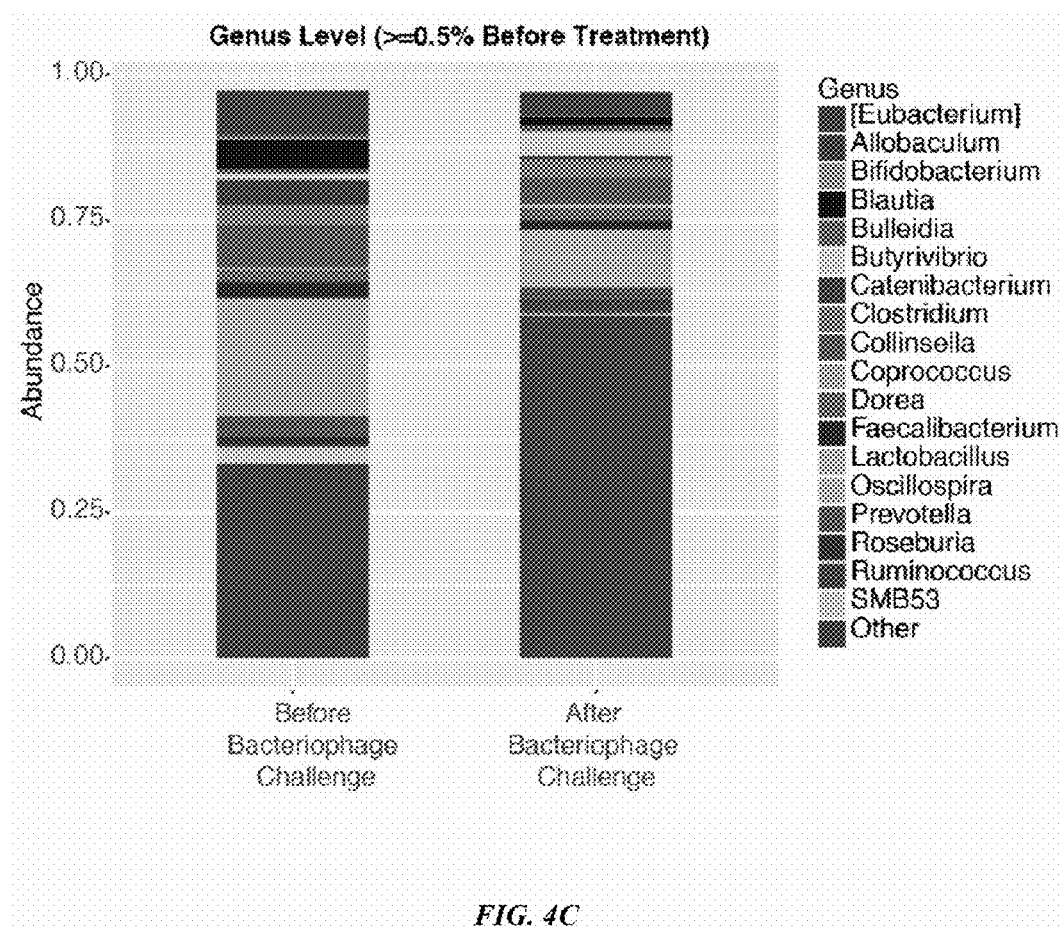
Figure 5B:
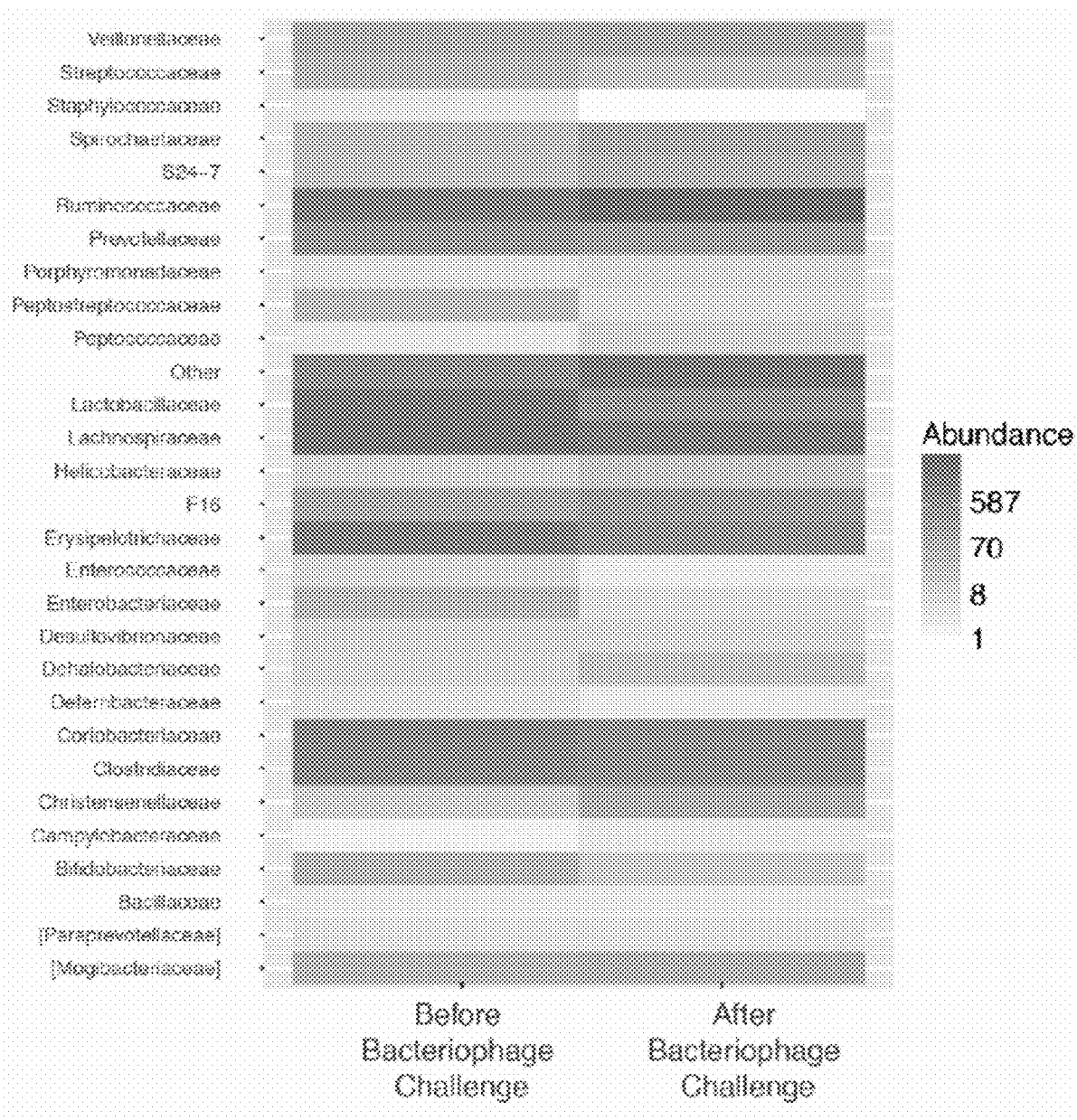
Figure 5C:
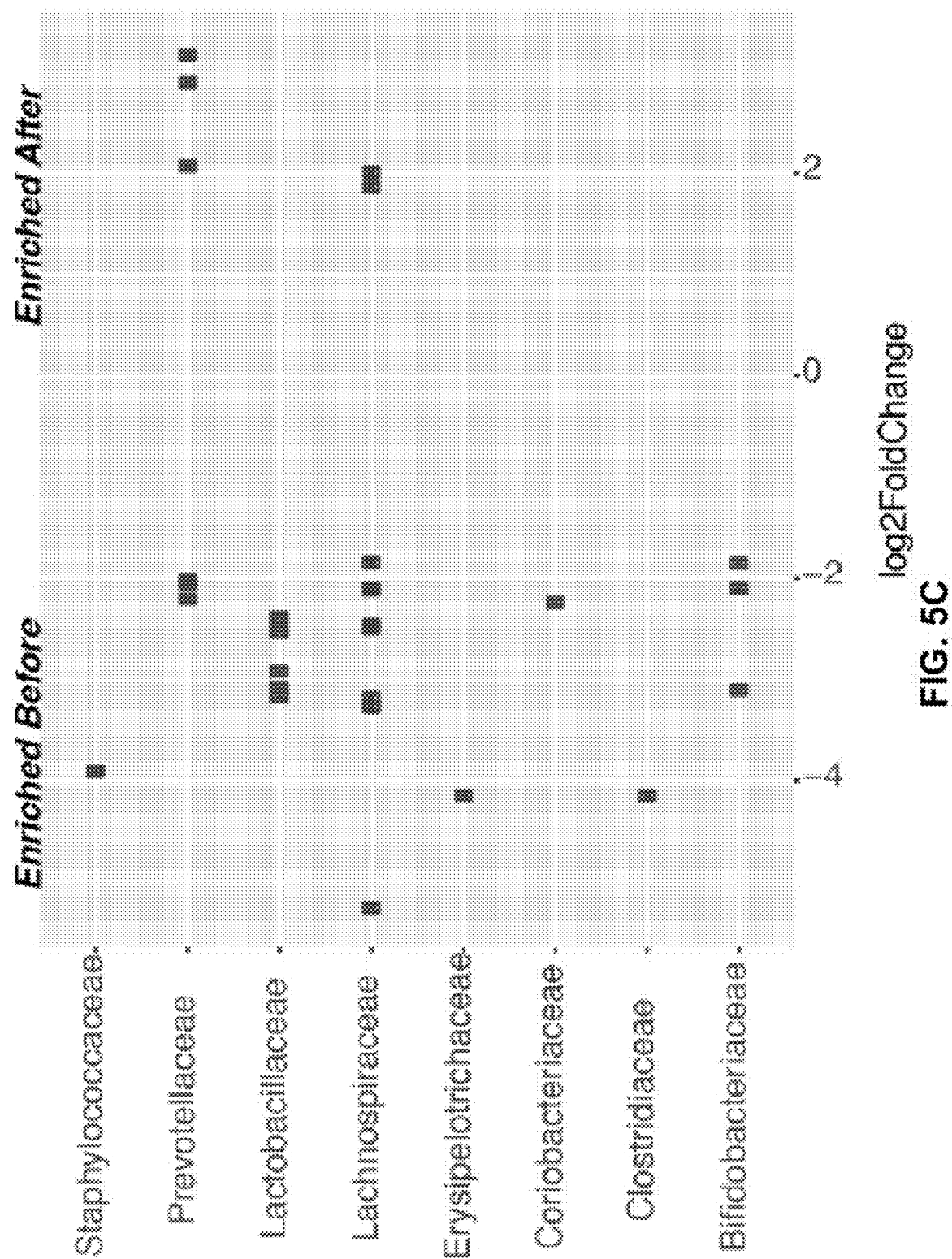

The compositional changes at the family level were next examined, with taxa detectable at ≥0.5% (FIG. 4B). Consequently, a decrease in the abundance of Bifidobacteriaceae, Clostridiaceae, Erysipelotrichaceae, Lachnospiraceae, Lactobacillaceae, and Prevotellaceae was detected. However, post-bacteriophage samples revealed an increase of Veillonellaceae, Ruminococcaceae, and unclassified organisms after bacteriophage treatment. More detailed data were generated by the analysis of OTUs detectable at relative abundances of >0.001% (FIG. 5B). The inventors evaluated the families differing by at least two-fold (i.e. $\log_2=1$) between pre- and post-treatment samples (FIG. 5C). The key two-fold alterations following the bacteriophage challenge included a decrease in Staphylococcaceae, Prevotellaceae, Lactobacillaceae, Lachnospiraceae, Erysipelotrichaceae, Coriobacteriaceae, and Bifidobacteriaceae and an increase in certain members of Prevotellaceae and Lachnospiraceae.

At the genus level, the treatment with phages resulted in substantial *Blautia, Catenibacterium, Lactobacillus*, and *Faecalibacterium* depletion and a simultaneous increase in *Butyrivibrio, Oscillospira, Ruminococcus* at a relative abundance of >0.5% (FIG. 4B). Notably, the number of unclassified bacteria significantly increased at the genus level.

Figure 5D:
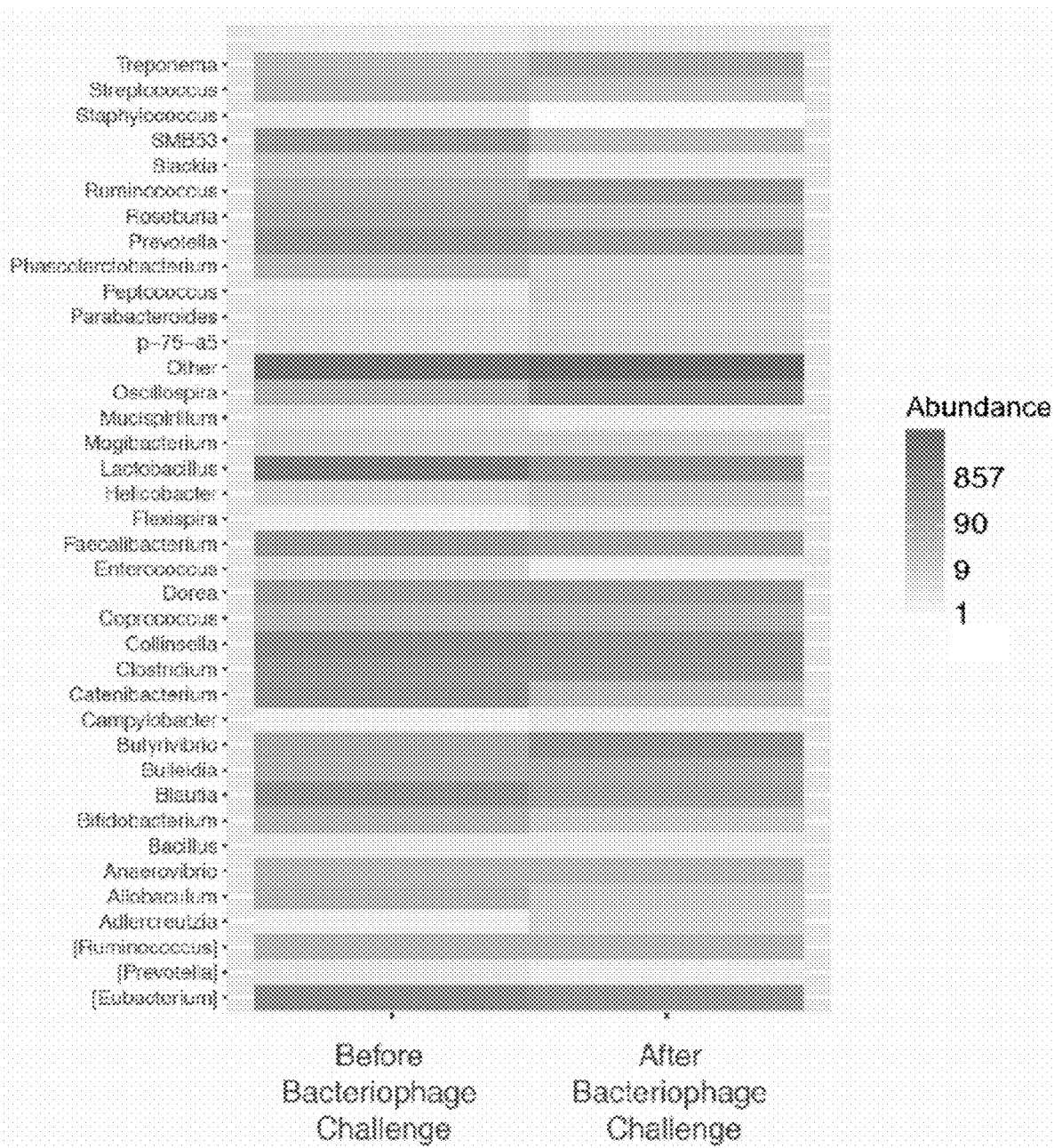
Figure 5E:
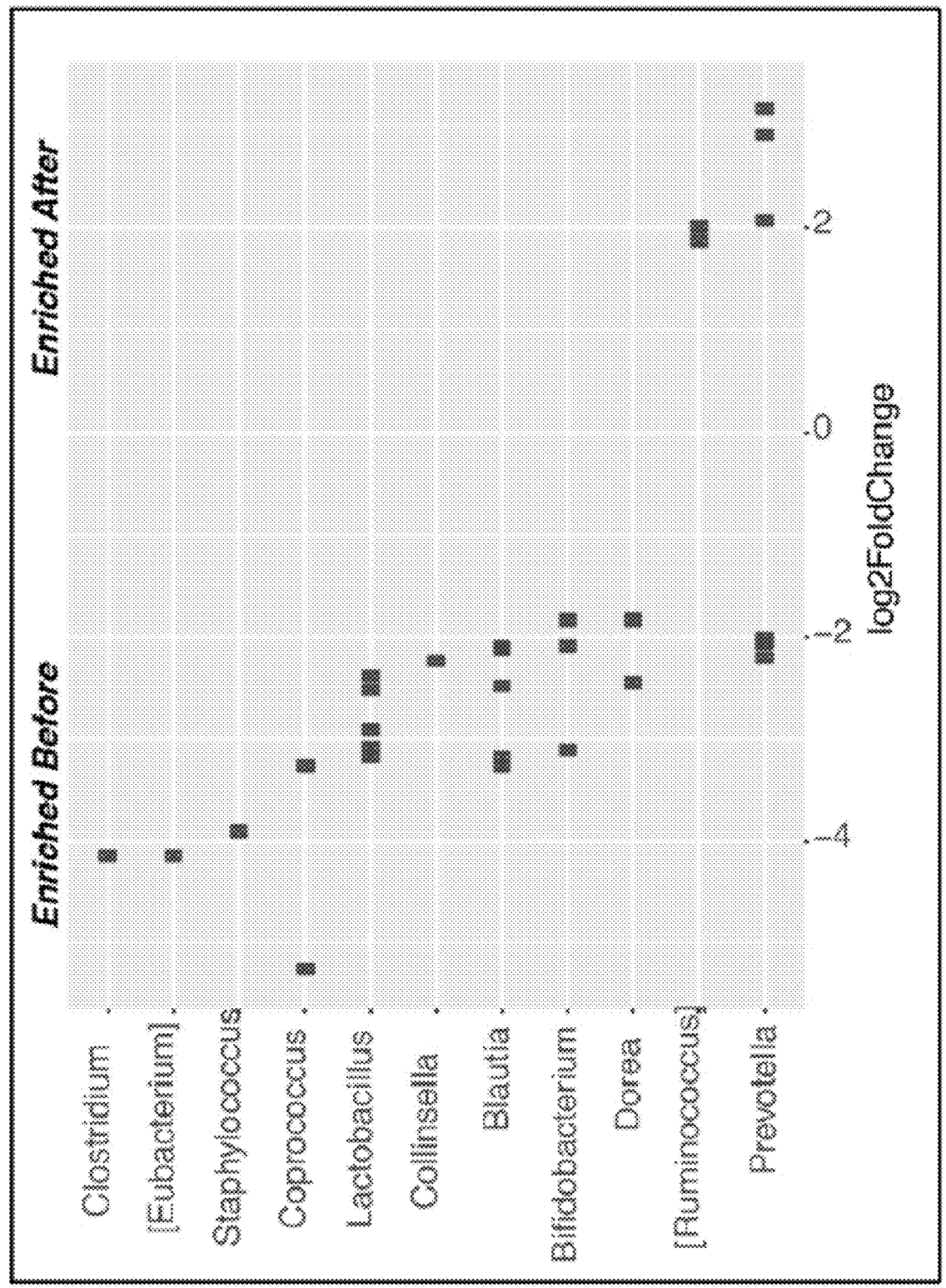
Figure 6A:
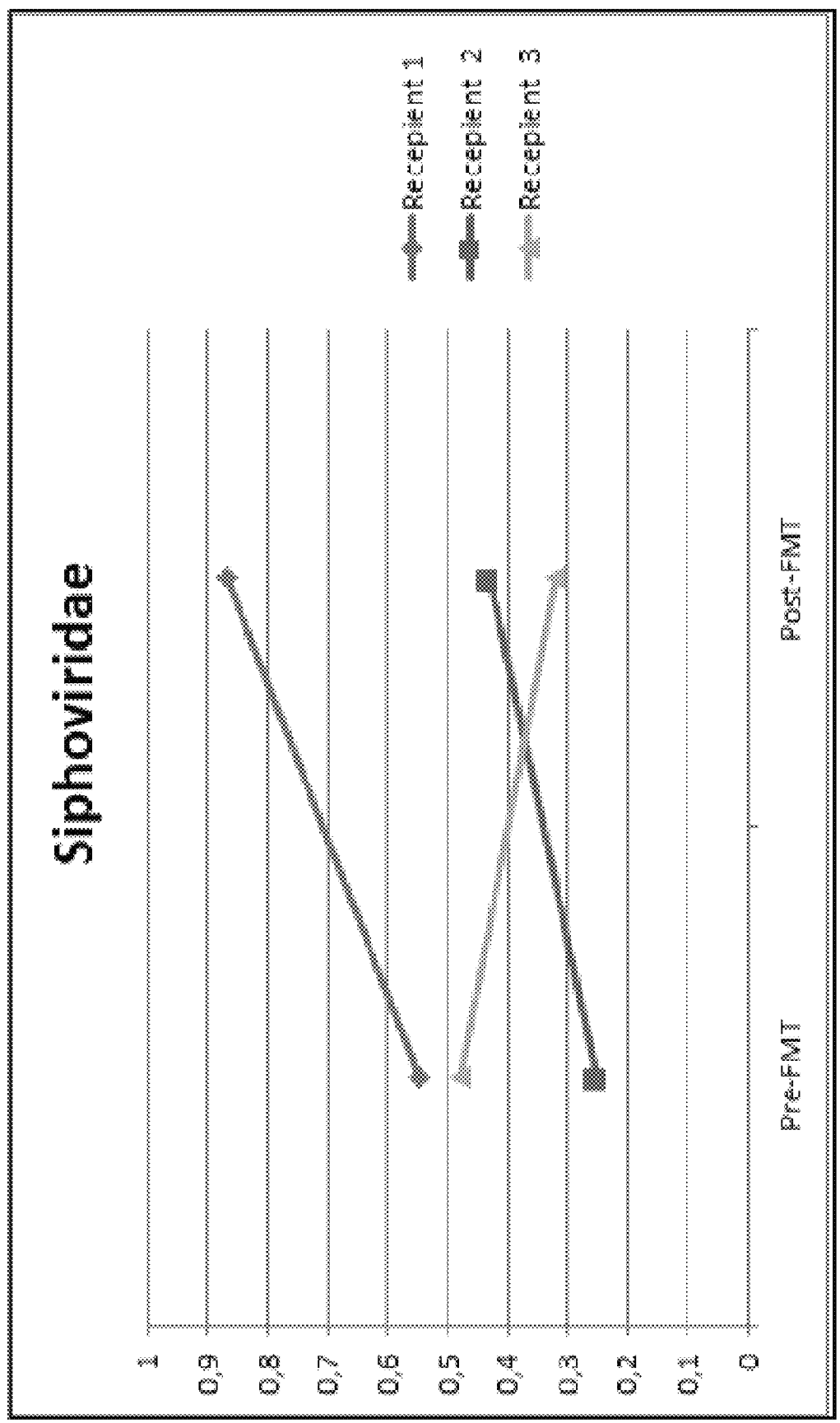
FIGS. 6A-6E show alterations in the gut virome of recipients after faecal microbiota transplantation (FMT).
Figure 6B:
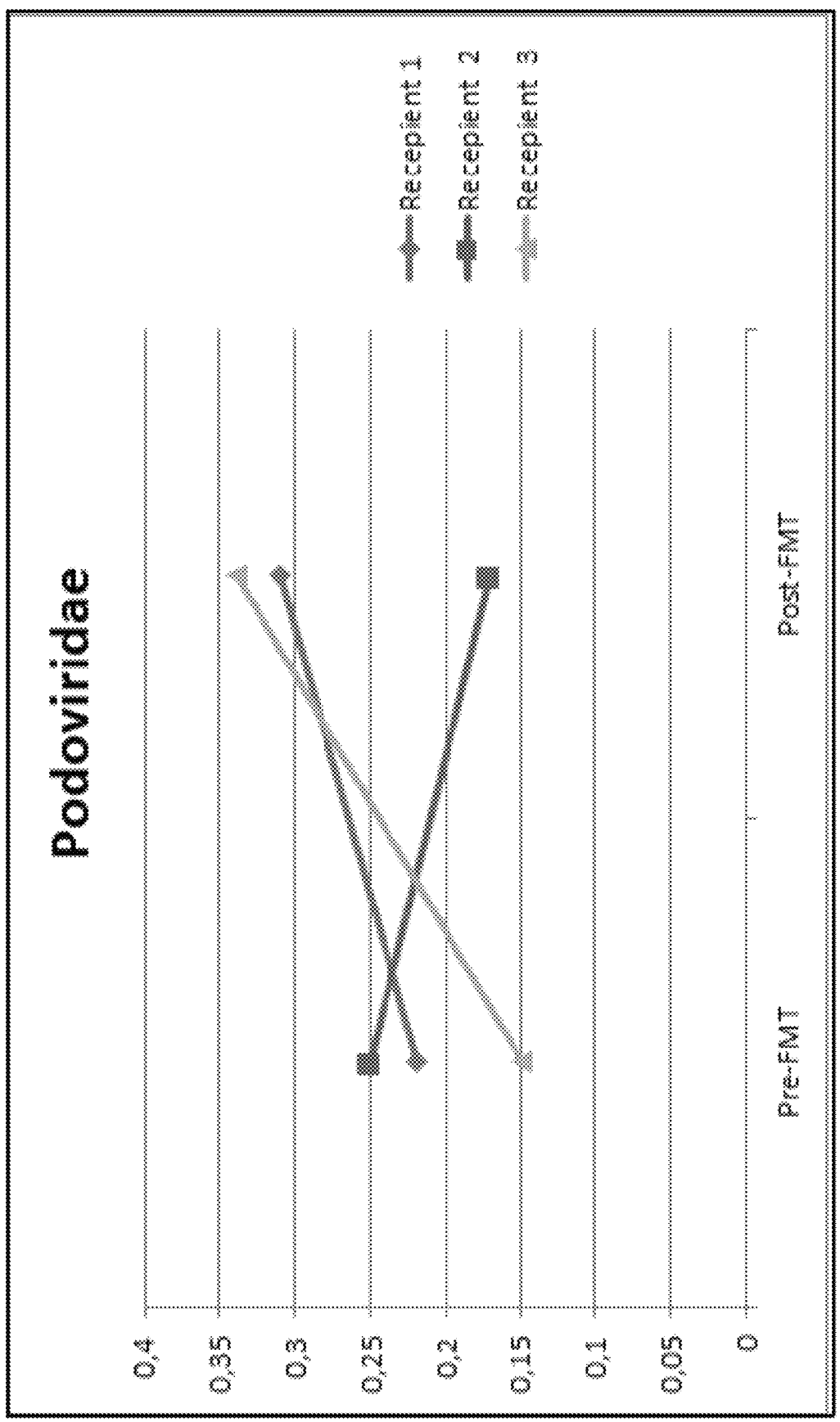
Figure 6C:
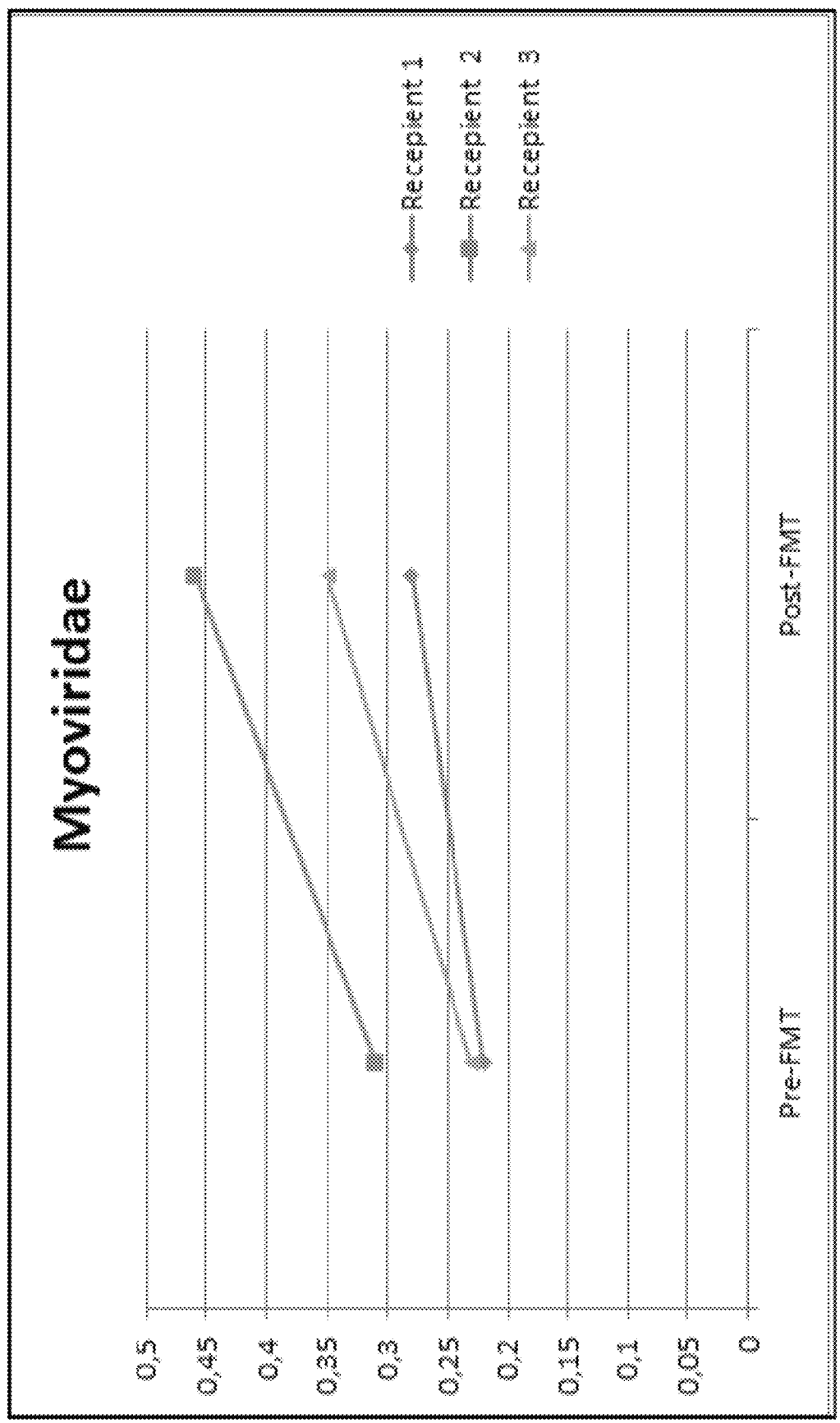
Figure 6D:
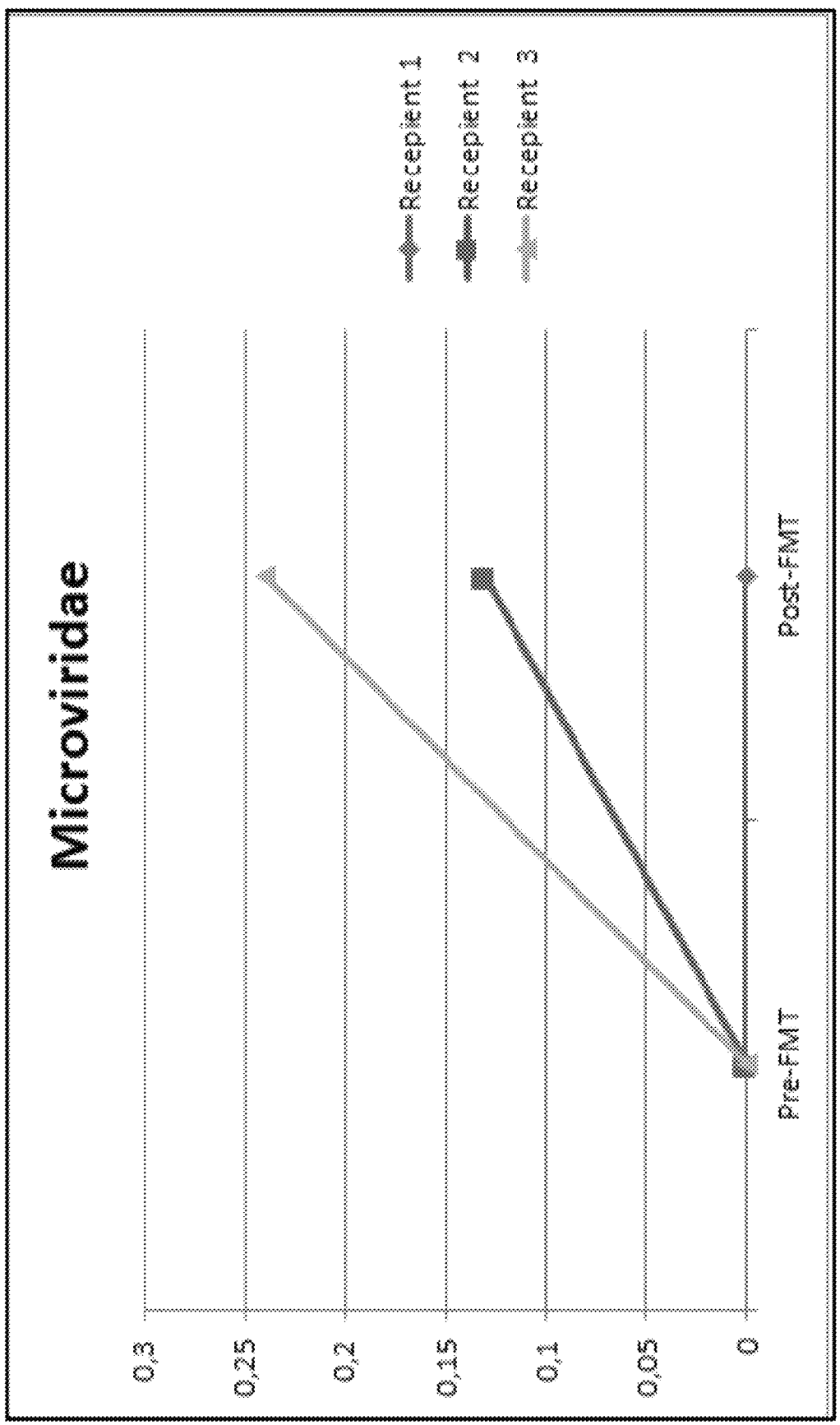
Figure 6E:
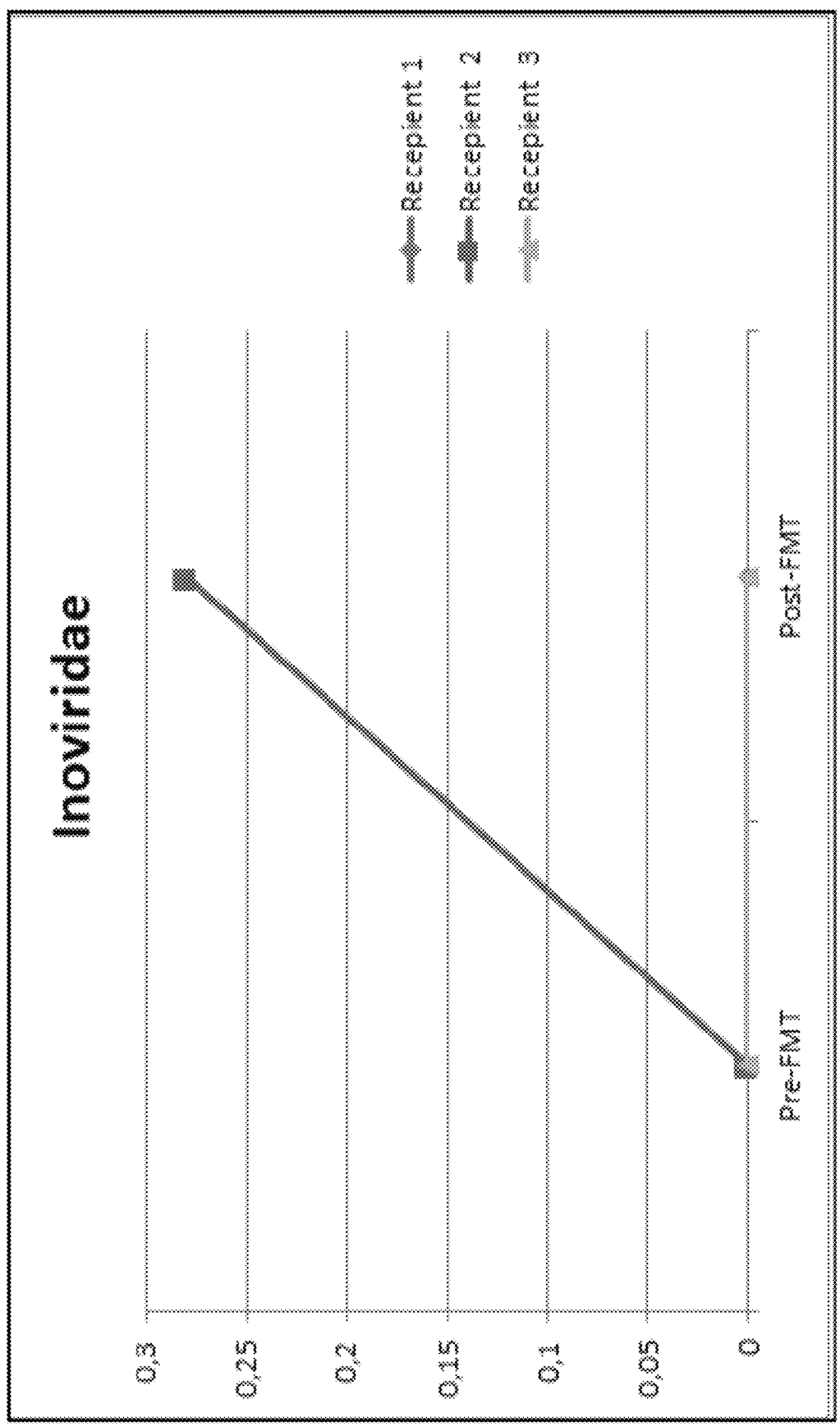

In addition, the 16s rRNA data were analyzed at the species level with OTUs detected at the level of abundance of >0.001% (FIG. 5D). The highest depletion at the genus level, >two-fold (i.e. $\log_2=1$), was registered post-bacteriophage treatment for the genera *Clostridium, Eubacterium, Staphylococcus, Coprococcus, Lactobacillus, Collinsella, Blautia, Bifidobacterium, Dorea*, and *Prevotella*. Simultaneously, certain members of the genera *Ruminococcus* and *Prevotella* were significantly enriched (FIG. 5E).

In this study, the present inventors found that the bacteriophage challenge affected the microbial alpha diversity. Overall, an increase in the richness and diversity of faecal microbiota was detected, indicating that the total number of bacterial species increased after phage treatment compared to the baseline pre-treatment data. The increased richness of intestinal microbiota is considered one of the signatures of a leaky gut and a feature of intestinal inflammation. Similar patterns have been described in other diseases associated with increased intestinal permeability (Costello, M. et al. Brief Report: Intestinal Dysbiosis in Ankylosing Spondylitis. *Arthritis Rheum* 67, 686-691 (2015); McLean, M., Dieguez, D., Miller, L. & Young, H., Does the microbiota play a role in the pathogenesis of autoimmune diseases? *Gut* 64, 332-341 (2014)). This study identified bacteria whose abundance changed following the bacteriophage challenge, and this alteration resulted in increased intestinal permeability, since phages selectively target bacteria with no effect on mammalian cells.

At the genus level, samples collected after the treatment with bacteriophages showed increases in *Oscillospira* and *Butyrivibrio* and decreases in *Lactobacillus* and *Faecalibacterium*; however, only *Lactobacillus* showed a two-fold change. The decreases in *Lactobacillus* and *Faecalibacterium* represent an important pattern that may reflect a signature of impaired gut permeability and inflammation. Both bacterial genera are known to be beneficial for mammals, and studies have shown that their depletion is associated with barrier abnormalities. In a number of studies, both bacterial genera, which are considered effective anti-inflammatory microorganisms, were shown to restore the function of the intestinal barrier. Thus, *Lactobacillus rhamnosus* CNCM I-3690 and the commensal bacterium *Faecalibacterium prausnitzii* A2-165 exhibited similar protective effects against induced barrier hyperpermeability in mice.

There was an increase in relative abundance of the butyrate-producing bacteria *Butyrivibrio*, known to lead to decreased expression of proinflammatory cytokines and suppression of proinflammatory responses. *Butyrivibrio* are known to reduce bacterial translocation by potentiation of mucin synthesis, are beneficial for tight junctions, and are suggested to suppress intestinal hyperpermeability (Burger-van Paassen, N. et al. The regulation of intestinal mucin MUC2 expression by short-chain fatty acids: implications for epithelial protection. Biochem. J. 420, 211-219 (2009)).

Of note, the bacteriophages used in this study had a direct impact on the genera *Lactobacillus, Faecalibacterium*, and others, which were significantly altered. This is consistent with previous studies, which have shown that microbiota is characterised by temporal stability and a dynamic equilibrium and its alterations result in complex and poorly predicted responses and consequences. See Blaser, M. & Kirschner, D. The equilibria that allow bacterial persistence in human hosts. Nature 449, 843-849 (2007).

Example 4: Reducing Intestinal Permeability by Limiting Bacteriophage Entry into the Gut As a source for the isolation of bacteriophages, waste water from canalization was used. The phages were isolated by Gratia's method (Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76). Test material (waste water) was filtered through 0.45 μm Millipore membrane filters. The resulting filtrate was incubated at 60° C. for 60 minutes to inactivate bacteria and was added to water or products (e.g., milk, yogurt, curd, cheese, minced meat, minced chicken, fish, fruit mix, vegetable mixture) in 100 μL volume. The resulting food products enriched with phages were included in the mice diet. The following groups were formed (each included 5 Wistar rats of both sexes at the age of 3.5-4 months):

Positive control groups: food products without the addition of bacteriophages.

Negative control groups: food products with the addition of bacteriophages.

Group "PHG": products with the addition of bacteriophages and with addition of a 0.1% (1000 mg/L) polyhexamethylene guanidine derivative preparation. The polyhexamethylene guanidine preparation used in this treatment was prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043.

Group "Filtration 0.45": water with the addition of bacteriophages, filtered through 0.45 μm Millipore membrane filters.

Group "Filtration 0.22": water with the addition of bacteriophages, filtered through 0.22 μm Millipore membrane filters.

Group "Pascalization": water with the addition of bacteriophages, treated with high pressure (340 MPa).

Group "Temperature": water with the addition of bacteriophages, treated with 90° C. temperature for 20 minutes.

Group "Autoclaving": products with the addition of bacteriophages, treated in an autoclave.

Group "Gamma radiation": products with the addition of bacteriophages, treated with gamma radiation.

Group "Electron": products with the addition of bacteriophages, treated with an electron flow.

Group "Microwave radiation": products with the addition of bacteriophages, treated in the microwave oven.

Group "Prototype": products with the addition of bacteriophages, treated with potassium nitrate.

Fourteen days after including any product enriched with bacteriophage mixture into the mice diet, the mice blood was aseptically taken and bacterial DNA content in the bloodstream was evaluated. Increased DNA content in blood indicates an increase of intestinal permeability reflecting increased translocation of microorganisms from the gastrointestinal tract into the systemic circulation. (See Deitch E. A., et al. Effect of hemorrhagic shock on bacterial translocation, intestinal morphology, and intestinal permeability in conventional and antibiotic-decontaminated rats. Critical care medicine 18.5 (1990), 529-536). DNA was isolated with a kit for the isolation of nucleic acids DNAQamp Qiagen. Quantitative determination of DNA was carried out by RT-PCR using universal bacterial primers for 16S rRNA (upb2 with a universal FAM-probe for bacteria: (5'FAM) aat acg ttc ccg ggt ctt gta cac acc gcc cgt cac act att (3'RTQ1) and DG74 5'aac tgg agg aag gtg ggg at 3') on Bio-Rad CFX96 amplifier. Reaction conditions: 95° C.-5 min. 45 cycles 95° C.-15 sec, 60° C.-30 sec, fluorescence reading. The results are shown in Table 3 below.

TABLE 3

Assay results

| Group | Product, to which bacteriophages were added | Number of cycles during which bacterial DNA appears (Cq)* |
|---|---|---|
| Positive control | milk | 33.70 |
| Negative control | milk | 16.59 |
| | minced meat | 16.62 |
| | water | 17.77 |
| PHG | water | 31.73 |
| Filtration 0.45 | water | 19.51 |
| Filtration 0.22 | water | 30.42 |
| Pascalization | milk | 30.87 |
| | yogurt | 28.11 |
| Temperature | minced meat | 29.61 |
| Autoclaving | minced chicken | 32.46 |
| Gamma radiation | fruit mix | 27.59 |
| Electron | fish | 29.73 |
| | curd | 32.06 |
| | vegetable mix | 31.23 |
| | cheese | 30.38 |
| Microwave radiation | minced meat | 28.02 |
| Prototype | water | 17.28 |
| | cheese | 19.79 |

*The average of the results of 3 independent experiments

These data demonstrate that in animals that received products enriched with a mixture of bacteriophages, there is an increase of intestinal permeability associated with microorganisms from GI microbiota entering systemic circulation. The chemical and physical methods used allow inactivating bacteriophages coming from the external environment and can be used for the treatment and prevention of pathologies associated with an increased intestinal permeability.

Example 5: Inactivating Bacteriophages in External Environment Prevents Increase in Intestinal Permeability Bacteriophages were obtained from the swabs from hands and masks of medical staff and work surfaces in surgical clinics. The hands, masks and surfaces were subjected to various kinds of treatments in order to reduce the amount of phages on them. After the treatment, phages were isolated by the Gratia's method (Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76). Test material (swabs) was filtered through 0.45 μm Millipore membrane filters. The resulting filtrate was incubated at 60° C. for 60 minutes to inactivate bacteria and was added to 100 μL of water. The resulting solutions were given to animals with water, and the development of an increased intestinal permeability was evaluated as described in Example 4, above. The animals were divided into the following treatment groups:

Positive control groups: water without the addition of bacteriophages.

Negative control groups: water with the addition of bacteriophages obtained from untreated objects and surfaces.

Group "PHG": water with the addition of bacteriophages obtained from objects and surfaces treated with a 0.1% (1000 mg/L) polyhexamethylene guanidine derivative preparation. The polyhexamethylene guanidine preparation used in this treatment was prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043.

Group "Photocatalyst": water with the addition of bacteriophages obtained from objects and surfaces treated with $TiO_2$ and activated by ultraviolet radiation.

Group "Ozone": water with the addition of phages obtained from objects and surfaces treated with ozone.

Group "Peroxide": water with the addition of phages obtained from objects and surfaces treated with $H_2O_2$.

Group "Metals": water with the addition of phages obtained from objects and surfaces treated with $Cu^{2+}$.

Group "Prototype": water with the addition of phages obtained from objects and surfaces treated with potassium nitrate.

The results are shown in Table 4 below.

TABLE 4

Assay results

| Group | Number of cycles during which bacterial DNA appears (Cq)* |
|---|---|
| Positive control | 34.85 |
| Negative control | 15.62 |

TABLE 4-continued

Assay results

| Group | Number of cycles during which bacterial DNA appears (Cq)* |
|---|---|
| PHG | 32.12 |
| Photocatalyst | 28.19 |
| Ozone | 27.74 |
| Peroxide | 31.65 |
| Metals | 29.51 |
| Prototype | 17.92 |

*The average of the results of 3 independent experiments

These data demonstrate that in animals that received water enriched with a mixture of phages from non-treated surfaces and objects, there is an increase of intestinal permeability associated with microbiota microorganisms entering into the systemic circulation. The use of the chemical and physical methods allows inactivating bacteriophages coming from the external environment, and such methods can be used to prevent the development of pathologies associated with an increased intestinal permeability.

Example 6: Limiting Bacteriophage Entry from the Environment Prevents Obesity Group #1 was formed with 6 females and 6 males of C57BL/6 mice (12 weeks old). The mice were fed the high-fat diet (HFD) to form obesity (Cani et al. Changes in gut microbiota control metabolic endotoxemia-induced inflammation in high-fat diet-induced obesity and diabetes in mice. Diabetes 2008, 57:1470-1481). Additionally, water for animals was daily supplemented by bacteriophages isolated by the above procedure described in Example 5 from the feces of 10 people suffering from obesity (BMI>38). After 21 weeks, the average body weight of animals in the group was 64 grams, whereas the weight of the control animals was 21 grams.

To assess a possibility of preventing changes in the GI microbiota leading to obesity by limiting bacteriophage entry from the environment, bacteriophages were isolated from the feces of Group #1 mice in which obesity was modeled. The obtained phages were added to drinking water of mice (age 12 weeks) from Group #2 for 21 weeks. The diet of the animals remained standard, i.e., not a high fat diet. The mice in Group #2 were divided into the following treatment groups:

Positive control group: water without the addition of bacteriophages.
Negative control group: water with the addition of bacteriophages.
Group "Filtration": water with the addition of bacteriophages, filtered through 0.45 μm Millipore membrane filters.
Group "Pascalization": water with the addition of bacteriophages, treated with high pressure (340 MPa).
Group "Prototype": water with the addition of bacteriophages, treated with potassium nitrate.
The results are shown in Table 5 below.

TABLE 5

Animal body weight after 21 weeks

| Group | Body weight |
|---|---|
| Positive control | 21 |
| Negative control | 48 |
| Filtration | 23 |
| Pascalization | 21 |
| Prototype | 46 |

The data demonstrate that limiting bacteriophage entry from the environment allows preventing development of obesity.

Example 7: Slowing Skin Aging by Limiting Bacteriophage Entry from the Environment In the experiment, hairless mice, 5 males and 5 females, (C57BL/6 albino/hairless, The Jackson Laboratories) of both sexes were used. Starting from 4 weeks of age, animals were daily treated with tap water or mineral water from artesian source, the water applied on the right half of the back. After 36 weeks, skin condition parameters were evaluated (SoftPlusCPU (Callegaris.p.a.)) in the application area, compared with the untreated left part of the back. Animals were divided into the following treatment groups:

Positive control group: water without external influences.
Group "Filtration": water filtered through 0.22 μm Millipore membrane filters.
Group "Electron": water treated with an electron flow.
Group "Prototype": water treated with potassium nitrate.
The results are shown in Table 6 below.

TABLE 6

Assay results

| Group | Water | Change in parameter of general skin elasticity (%) |
|---|---|---|
| Positive control | Tap | −38.2 |
|  | Well | −32.4 |
| Filtration | Tap | +8.7 |
|  | Well | +10.3 |
| Electron | Tap | +9.1 |
|  | Well | +11.1 |
| Prototype | Tap | −42.9 |
|  | Well | −41.4 |

The data demonstrate that limiting bacteriophage entry from the environment prevents development of age-related skin changes.

Example 8: Inactivation of Bacteriophages in an Air Conditioning and Humidification Systems Bacteriophages targeting *E. coli* were added to water for humidifying indoor air (Ultrasonic Air Humidifier B-742). After 1 hour of the humidifier work swabs were taken from the surface of the furniture and the floor. It was found that all samples contained bacteriophages causing infection in test microbes that can be detected by titration according to the Gratia's method (Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76).

After the inactivation of air conditioning and humidification systems, by using 0.005% solution of "polyhexamethylene guanidine derivatives", e.g., those prepared by condensation polymerization of hexamethylenediamine with guanidine salt and hydrazine hydrate, as described in U.S. Provisional Pat. Appl. No. 62/510,446, U.S. Pat. No. 8,993,712, U.S. Pat. Appl. Pub. No. 2017/0013838 and Int. Pat. Appl. Pub. No. WO2016/118043, only few bacteriophages' induced lesions were registered after taking swabs were taken from the surface of the furniture and the floor. The results are shown in Table 7 below.

TABLE 7

| Number of bacteriophage lesions | Number of phage lesions from 1 sq/cm of furniture | Number of phage lesions from 1 sq/cm of floor |
|---|---|---|
| Before treatment | 29 +/− 8 | 26 +/− 7 |
| After treatment | 4 +/− 1 | 6 +/− 2 |

Example 9: Prevention of Bacteriophage Action by Capsid-Targeted Viral Inactivation Antibodies to bacteriophages against *P. aeruginosa* were obtained after hyperimmunization of a rabbit by the method according to "The guidelines for the production of antibodies in laboratory animals" See acuc.berkeley.edu/guidelines/antibodies.pdf. After treating bacteriophages with these antibodies, the bacteriophages lost the ability to cause infection in those microbes as detected by titration according to the Gratia's method (Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76).

Example 10: Blocking Bacteriophage Receptors of Bacteria by Inactivated Bacteriophages Bacteriophages of *E. coli* (titer $10^7$) were inactivated by irradiation with UV light for 30 min. The protective effect of inactivated bacteriophages is shown in Table 8, which demonstrates that UV treatment of bacteriophages reduces the titer to undetectable levels (as determined by Gratia's method, see Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76). As a control, when the original phage is added back, the titer increases. The results are shown in Table 8 below.

TABLE 8

| Assay results | |
|---|---|
| Sample | Phage titer (by Gratia's method) |
| *E. coli* and original phage | $3 \times 10^7$ |
| *E. coli* and UV-treated phage | 0.00 |
| *E. coli* and UV-treated phage, original phage* | $5 \times 10^2$ |

*The original phage was added after 1 hour exposure.

Example 11: Slowing Down the Aging Process by Limiting the Bacteriophages Entering the Organism from the Environment For the experiment, *Drosophila melanogaster* flies were used. The flies were kept on Harvey Peterson medium. The flies were divided in 2 groups: 1) Control group—intact flies and 2) Test group, wherein a nutrient medium was supplemented with a mixture of bacteriophages of Gram-positive and Gram-negative bacteria. A mixture of two commercial bacteriophage cocktails was used (1.5 ml [$1 \times 10^6$ plaque-forming units/ml] of each phage according to the manufacturer's instruction): (i) *Salmonella* bacteriophage cocktail (Microgen, Russia) containing phages infecting *Salmonella enterica* serotypes: Paratyphi, Typhimurium, Heidelberg, Newport, Choleraesuis, Oranienburg, Infans, Dublin, Enteritidis, Anatum, and Newlands, and (ii) Pyobacteriophage Polyvalent, another commercial phage cocktail (Microgen, Russia) containing phages infecting *Staphylococcus aureus*, *Streptococcus pyogenes*, *Proteus mirabilis* and *P. vulgaris*, *Pseudomonas aeruginosa*, *Klebsiella pneumoniae*, and *Escherichia coli*. The insects on the nutrient medium comprising bacteriophages lived 10.6% less compared to the control. The bacteriophages caused a statistically significant decrease in the median lifespan in both females and males (Table 9).

TABLE 9

The effect of bacteriophages on the lifespan of Drosophila melanogaster D-32.

| Group | N | ALS ± SE | MLS | Significance | M90 | M90-K |
|---|---|---|---|---|---|---|
| Females | | | | | | |
| Control | 466 | 45.1 ± 0.8 | 48.0 | P <0.01 | 58 | +9.4* |
| Test | 435 | 37.6 ± 0.9 | 39.0 | — | 53 | |
| Males | | | | | | |
| Control | 446 | 31.9 ± 0.8 | 32.0 | — | 48 | +11.6* |
| Test | 480 | 32.7 ± 0.6 | 33.0 | | 43 | |

N is sample size, ALS±SE is average lifespan±standard error of mean (days); MLS is median lifespan (days); Significance is statistical significance when comparing survival curves of a certain group versus corresponding control group using the log-rank test, M90 is survival time of 90% population—max lifespan (days); M90-K is max lifespan difference from control percentage. The * symbol indicates a significant difference from control (Wang-Allison test).

These results indicate that the presence of phages reduces the lifespan of the insects.

Example 12: Analysis of Entry of Bacteriophages into Microbiota of the Mammals

The entry of bacteriophages into gut microbiota and gut microbiota composition were analyzed in five rats (Rappolovo, Russia) before and after bacteriophage challenge using shotgun sequence technology (Illumina). As a source of bacteriophages milk (365 Organic) artificially enriched with *Enterobacteria* and *Staphylococcus* phages was used.

Fecal samples were collected at baseline, after 2 days and after 30 days of the bacteriophage challenge into a sterile container and immediately stored at −80° C. until further processing. DNA extraction was performed from faecal samples and control sample of the milk enriched with phages using a QIAamp stool DNA mini kit (Qiagen, Germany) according to the manufacturer's instructions. Shotgun whole genome sequencing was performed according to the Illumina system instructions. Data were analyzed with the software Metagenomics workflow (Illumina). The taxonomic identity of the reads was analysed using available annotation source databases (NCBI database). Data of the shotgun sequencing are shown in Table 10.

TABLE 10

Bacteriophage composition analysis.

| | | Identified phages in animals | | | | | | | | | | | | | | |
|---|---|---|---|---|---|---|---|---|---|---|---|---|---|---|---|---|
| | Milk artificially enriched with | Baseline metagenomic faecal probes | | | | | Day 2 after bacteriophage challenge | | | | | Day 30 after bacteriophage challenge | | | | |
| Phage description | phages | 1 | 2 | 3 | 4 | 5 | 1 | 2 | 3 | 4 | 5 | 1 | 2 | 3 | 4 | 5 |
| Enterobacteria phages (including, among others, *Caudovirales; Myoviridae; Tevenvirinae*) | + | – | – | – | – | – | + | + | + | + | – | + | + | + | + | – |
| Staphylococcus phages (*Caudovirales; Siphoviridae*) | + | – | – | – | – | – | + | + | + | + | + | – | + | + | + | + |
| Lactobacillus phages (*Caudovirales; Siphoviridae*) | + | – | – | – | – | – | + | + | + | + | + | + | – | + | + | + |
| Other phages present in mammalian gut flora (including, among others, *Caudovirales, Ligamenvirales, Ampullaviridae Bicaudaviridae Clavaviridae Corticoviridae Cystoviridae Fuselloviridae Globuloviridae Guttaviridae Inoviridae Leviviridae Microviridae Plasmaviridae Tectiviridae*) | – | + | + | + | + | + | + | + | + | + | + | + | + | + | + | + |

There was an appearance and presence of certain phages present in the food and their presence and persistence in gut microbiota of animals.

Example 13: Analysis of Bacteriophage Composition of Donor Fecal Transplant and of Recipient Microbiota Following Fecal Transplant A composition of bacteriophage virome in gut microbiota of three subjects with Clostridium difficile infection was analyzed before and after faecal transplant using shotgun sequencing technology (Illumina) and computational predisposition method.

Fecal samples of the donor were analyzed from the same lot as was used for the fecal microbiota transplant (FMT). Fecal samples of the FMT recipients were collected at baseline (pre-FMT) and after FMT (post-FMT). DNA extraction was performed using a QIAamp stool DNA mini kit (Qiagen, Germany) according to the manufacturer's instructions. Shotgun whole genome sequencing was performed according to the Illumina system instructions. Data was analyzed with the software Metagenomics workflow (Illumina). The taxonomic identity of the reads was analyzed using available annotation source databases. Results are shown in Table 11 (pre-FMT samples), Table 12 and FIG. 6 (pre- and post-FMT samples).

TABLE 11

Analysis of phage composition in the donor's FMT material and recipients' pre-FMT fecal samples

| | Identified phages | | | | | |
|---|---|---|---|---|---|---|
| Phage's families | Donor | | | Recipient Pre-FMT | | |
| | 1 | 2 | 3 | 1 | 2 | 3 |
| *Siphoviridae* | + | + | + | + | + | + |
| *Podoviridae* | + | + | + | + | + | + |
| *Myoviridae* | + | + | + | + | + | + |
| *Microviridae* | – | + | + | – | – | – |
| *Inoviridae* | – | + | – | – | – | – |

TABLE 12

Mathematical prediction of the presence of certain phages in the pre-FMT and post-FMT recipient fecal samples

| Phage description | Identified phages | | | | | | Mathematically predicted | | |
|---|---|---|---|---|---|---|---|---|---|
| | Donor | | | Pre-FMT | | | Post-FMT | | |
| | 1 | 2 | 3 | 1 | 2 | 3 | 1 | 2 | 3 |
| Siphoviridae | + | + | + | + | + | + | + | + | + |
| Podoviridae | + | + | + | + | + | + | + | + | + |
| Myoviridae | + | + | + | + | + | + | + | + | + |
| Microviridae | − | + | + | − | − | − | − | + | + |
| Inoviridae | − | + | − | − | − | − | − | + | − |

The data demonstrate qualitative alterations of the bacteriophage composition of the recipients' gut microbiota and transfer of the donor's bacteriophages to recipients (Microviridae and Inoviridae), confirmed by their appearance in recipients' post-FMT fecal samples. Experimental data obtained confirmed data obtained by the mathematical predication of virome alterations following FMT Example 14: Identification of Prionogenic Domains (PrD) in Bacteriophage Proteomes The inventors used a computational algorithm, prion-like amino acid composition (PLAAC), to detect prion-like domains in 370,617 publicly available bacteriophage protein sequences, which resulted in the identification of 5040 putative prions. A set of these prion-like proteins was analyzed, regularities in their distribution across different phage families, associated with their interactions with the bacterial host cells, was observed. The inventors found that prion-like domains could be found across all phages of various groups of bacteria and archeae.

The results obtained in this study indicate that bacteriophage prion-like proteins are predominantly involved in the interactions between bacteriophages and bacterial cell, such as those associated with the attachment and penetration of bacteriophage in the cell, and the release of the phage progeny. These data allow the identification of phage prion-like proteins as novel regulators of the interactions between bacteriophages and bacterial cells.

Here, the inventors studied in detail the putative prion like domains (PrDs) in bacteriophages. An HHM algorithm was employed for the analysis of bacteriophage proteomes, using the UniProtKB database to identify candidate PrD sequences among bacteriophages. Furthermore, the inventors analyzed the trends in the distribution of PrDs in different protein families and the correlations between bacteriophage families and the host bacterial host. The present predictive approach uncovers a large set of putative prionogenic proteins.

Attachment and penetration are known to represent crucial steps in the bacteriophage-bacterium interaction, since these processes allow the entry of the bacteriophage DNA inside the host. The inventors identified PrDs in the proteins forming different structural components of bacteriophages, including head, neck, sheath, baseplate and fibers, for tailed viruses, receptor-binding proteins for tailless Tectiviridae, and in the coat proteins III and IV of the filamentous Inoviridae (Hulo et al., 2017). This may indicate a role of the identified PrDs in the formation of surface structures and specific and non-specific attachments to bacterial cells (Spinelli et al., 2014). Moreover, a similar trend in the distribution of prion-like domains in proteins responsible for interactions and virulence was defined by Gene Ontology GO terms across bacteria (Iglesias et al., 2015). Notably, PrDs were common across different bacterial and bacteriophage families, indicating the universal regulatory role of these putative prion domains (Iglesias et al., 2015).

Furthermore, since the identification of PrDs in the interacting proteins in different bacteriophage families infecting a variety of bacterial hosts implies that these PrDs are conserved across species. However, the presence of PrD-containing proteins may be beneficial, but not obligatory since PrDs in the surface proteins were not identified in all analyzed bacteriophages, and in those where they were identified, PrDs were found in some, but not all surface proteins of the given phage. The attachment of bacteriophages is a complex process, accompanied by a number of bacteriophage-resistance responses initiated in a bacterial cell (Labrie et al., 2010). The inventors' findings may indicate that the proteins with the PrDs can alter their conformational states, adding further complexity and specificity in the phage-bacterial interactions, and this may serve as a mechanism to overcome some bacterial resistance mechanisms.

Without wishing to be bound by theory, PrDs in the interacting proteins may be involved not only in the interactions with host bacteria, but also in the interactions of bacteriophages with other components of microbial communities. Such is consistent with reports that oral administration of bacteriophages may induce an increase in the intestinal permeability and endotoxemia in mammals, significantly change the microbiota composition in a manner beyond the possible direct effect of bacteriophages.

The presence of PrDs in bacteriophages may be associated with a number of mammalian diseases in which the role of prions was demonstrated both in macroorganisms and in gut bacteria. *C. elegans* fed with the prion-producing *Escherichia coli* were shown to have an enhanced prion aggregation in brain (Chen et al., 2016). Without wishing to be bound by theory, it can be assumed that a similar process may be observed following the introduction of bacteriophages and that bacteriophages contribute to the observed processes.

Proteins that are involved in the bacterial cell wall interactions and the release of progeny phages from the host were shown to harbor PrDs as well. The release stage involves bacterial cell wall degradation from within the cells with bacteriophage-encoded peptidoglycan hydrolases synthesized at the end of the multiplication cycle. The majority of PrDs identified in phage-encoded endolysins was found in the Siphoviridae family, with only a few detected among the members of Podoviridae and Myoviridae.

In various embodiments, administration of PrDs or bacteriophages with PrDs can be "used against" other bacteriophages or to target bacteriophages. An exemplary, but non-limiting mechanism, could involve the PrD as a decoy that blocks an otherwise unwanted interaction between bacteria and the target bacteriophages.

Some of the proteins enriched in the PrDs are involved in the replication of bacteriophage DNA and protein synthesis. In eukaryotes, PrD-containing proteins were shown to play a role in the interactions and binding with the nucleic acids (King et al., 2012).

In bacteriophages, the presence of PrDs can also be associated with the single-strand binding proteins, known as essential components of bacteriophage DNA synthesis. Therefore, this indicates that these PrDs can be easily misfolded into PrPSc through the interactions with the DNA, which was shown to be an important component inducing this misfolding (Cordeiro et al., 2001). Without wishing to be bound by theory, this type of interaction with the host cell may represent an additional process through which the bacteriophages control bacterial intracellular functions (Wagner and Waldor, 2002; Davies and Davies, 2010).

Bacteriophages are important vehicles facilitating the genetic exchange between microorganisms, including the spreading of virulence factors and the antibiotic resistant genes (Lina et al., 1999). Here, the inventors identified a PrD in the LukS-PV protein of some Siphoviridae members and unclassified phages. This cytotoxin can be found among methicillin-resistant S. aureus and belongs to the group of 1-pore-forming toxins (Vandenesch et al., 2003). The presence of LukS-PV is known to be associated with the increased virulence of S. aureus, leading to abscess formation and severe necrotizing pneumonia. The detected PrDs located in LukS-PV indicates the role of these domains in the virulence potential of the cytotoxins and their role in the pathogenicity. The examples may indicate that the presence of PrDs in LukS-PV affects its interactions with the membranes of the targeted eukaryotic cells and induce the pore-forming potential.

The inventors have identified numerous putative PrD-containing proteins in bacteriophages and observed consistent patterns of the distribution of PrDs across different bacteriophage families. However, since the infectious agents of some bacteria were shown to lack PrDs, this may indicate on the HMM and trained using the known PrDs, by identifying the compositional bias towards N and Q residues. To identify the PrDs in bacteriophages using the PLAAC algorithm 2111 bacteriophage proteomes, comprising a total of 370,617 proteins retrieved from the UniProtKB database, were analyzed. By employing a cutoff of 0.003 LLR, 5040 PrDs were identified (i.e. 1.35% of the total bacteriophage protein dataset) (Lancaster et al., 2014).

The enrichment values obtained for the proteins detected in the bacteriophage family subsets were compared with the total number of analyzed proteins. In Table 13, the trends in the PrD distribution across different bacteriophage families are presented. PrD frequency ranged from 1.16% to 4.49% when analyzing bacteriophage families with at least 400 sequenced proteins. Due to the low representation of archaeal phages, it was not possible to compare them with the bacteriophage proteins with sufficient reliability. Therefore, the inventors focused on the analysis of the PrDs in bacteriophages.

Within *Caudovirales*, the most well-studied order of phages, the highest numbers of proteins containing the PrDs when analyzing bacteriophage families with more than 10,000 sequenced proteins were found among Podoviridae, with over 1.74% of the total Podoviridae proteins were shown to harbor PrDs ($p<0.001$), constituting 4.21% of the total detected PrDs among *Caudovirales* (Table 13).

TABLE 13

Summary of the prion predicted in different bacteriophage families.

| Phage Order | Phage Family | Host | # Proteins | # PrD predictions | % of the proteome |
|---|---|---|---|---|---|
| Undefined | Ampullaviridae | Archaeal | 173 | 6 | 3.46 |
| Undefined | Bicaudaviridae | Archaeal | 445 | 20 | 4.49 |
| Undefined | Fuselloviridae | Archaeal | 404 | 10 | 2.47 |
| Undefined | Globuloviridae | Archaeal | 87 | 1 | 1.14 |
| Ligamenvirales | Rudiviridae | Archaeal | 941 | 18 | 1.91 |
| Undefined | Lipothrixviridae | Bacterial | 599 | 7 | 1.16 |
| Undefined | Inoviridae | Bacterial | 1073 | 46 | 4.28 |
| Undefined | Leviviridae | Bacterial | 1082 | 52 | 4.8 |
| Undefined | Corticoviridae | Bacterial | 21 | 1 | 7.76 |
| Undefined | Microviridae | Bacterial | 2827 | 35 | 1.23 |
| Caudovirales | Myoviridae | Bacterial | 166120 | 2425 | 1.45 |
| Caudovirales | Podoviridae | Bacterial | 38922 | 678 | 1.74 |
| Caudovirales | Siphoviridae | Bacterial | 157433 | 1665 | 1.05 |
| Undefined | Tectiviridae | Archaeal/Bacterial | 490 | 20 | 4.08 |
| Undefined | Undefined | Bacterial | N/A | 19 | N/A | that the diversity of phagobiota and phogobiome is underestimated. Although bacteriophage genomes are significantly smaller than bacterial genomes, currently less than 2,500 phage genomes are deposited in the NCBI database, compared with almost 90,000 bacterial whole genome sequences.

The predictive approach employed and described herein revealed a large set of putative PrPs, and further experimental characterization of these proteins may contribute to the understanding of bacteriophage biology.

To identify the PrDs present in bacteriophage proteomes, protein sequences were obtained from the UniProt KnowledgeBase (Swiss-Prot and TrEMBL) (UniProt C., 2017).

The protein functions were manually curated using the information from the UniProt database, the National Center for Biotechnology Information (NCBI) protein sequence database (www.ncbi.nlm.nih.gov/), and the literature.

The presence of PrDs was analyzed in all bacteriophage proteins using the PLAAC prion prediction program based Here, PrDs were more frequently found among archaeal phages, and the analysis of the three best-known Caudovirales families showed that these domains are more abundant among Podoviridae than Myoviridae or Siphoviridae.

There is an interesting trend of representation of prionogenic domains among different bacteriophages families and host organisms. The inventors' analyses demonstrated that approximately 50% of all sequenced bacteriophages available in public databases contain at least one PrD. The majority of bacteriophages contain less than five PrDs per proteome. Surprisingly, the vast majority of bacteriophages with more than five PrDs per proteome were shown to belong to the Myoviridae family. Since the total numbers of PrDs found in Myoviridae (2425) and Siphoviridae (1665) are of the same order of magnitude, these further supports the enrichment of PrDs in the Myoviridae proteomes. However, Myoviridae members have larger proteomes than the members of Siphoviridae family, which may explain the observed differences in the PrD enrichment (Sandaa, R. A. (2009). Viruses, Environmental, 553-567). Further analyses indicated a direct correlation between the proteome size and the PrD enrichment, and therefore, the inventors further explored whether the proteome size of bacteriophages in the Myoviridae family is related to the PrD enrichment. However, the inventors have not observed a linear correlation between these parameters, suggesting that the PrD enrichment does not depend only on the size of a Myoviridae proteome.

The following were analyzed: regularities in the likelihood of the identified PrDs to be prions, their distribution among bacteriophage families, host bacteria, and protein functions. The obtained data were used to generate a heatmap with R-statistical computing (www.r-project.org), using the "levelplot" package. The key indicates a range between the lowest (white) and the highest (black) LLR values. Statistical analyses were performed using the statistics package Statistica for Windows (version 5.0). Data were compared between bacteriophage families by using a $X^2$ test or the Fisher's exact test. Significant differences were calculated using one-way analysis of variance (ANOVA) with multiple comparisons and a standard confidence interval of 95%. A value of $p<0.001$ was considered statistically significant in all tests. Correlations between the size of bacteriophage proteome and PrD enrichment were calculated using the Spearman's rank correlation coefficient test.

Figure 7A:
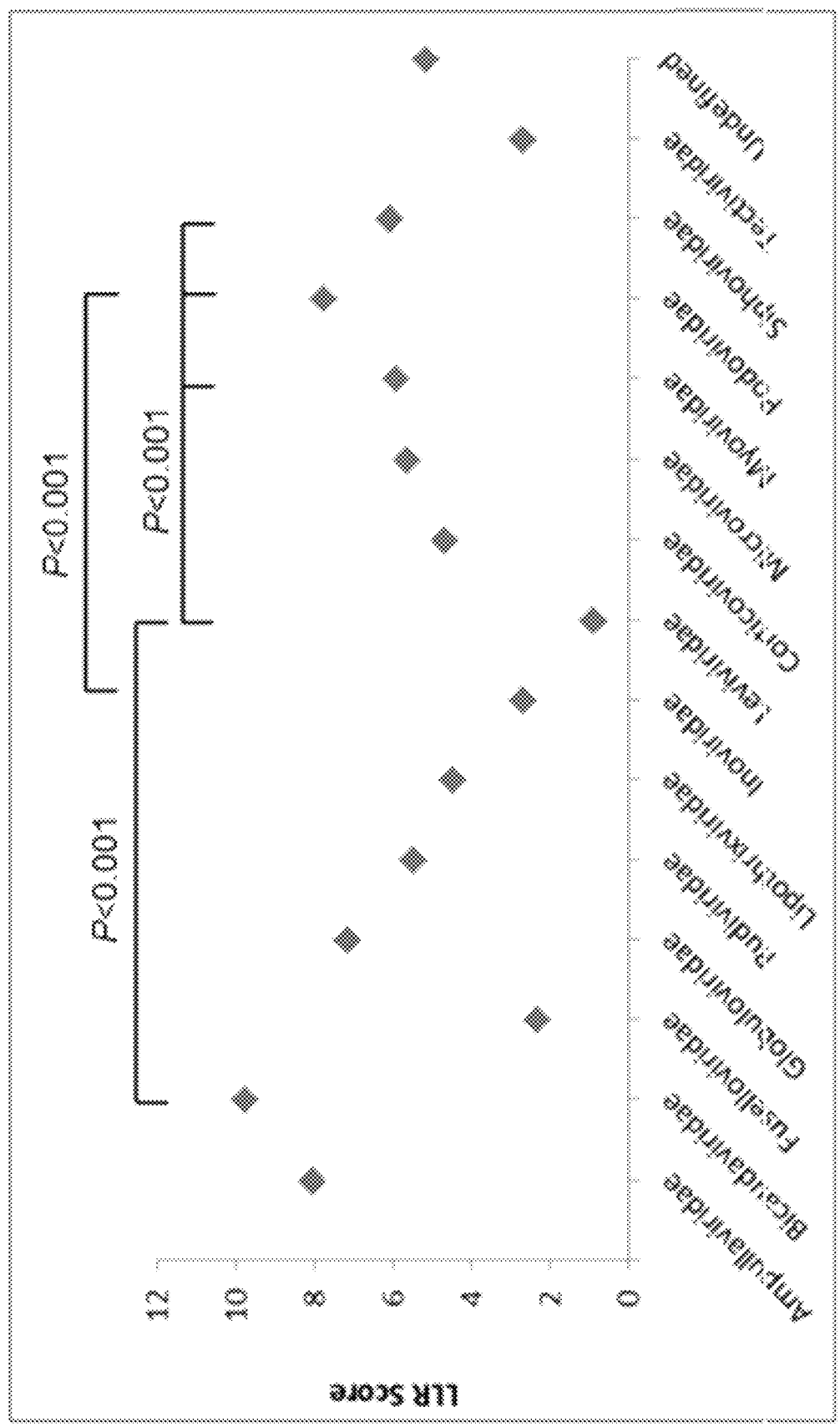
FIG. 7A illustrates an LLR score showing the predicted putative PrDs across bacteriophage families. Results were analyzed using one-way ANOVA.

Example 15: Determination of Correlation Between Bacteriophage Families and LLR Scores Next, the inventors determined the patterns of correlation between bacteriophage families and LLR scores (FIG. 7A; Table 14).

TABLE 14

Summary of the LLR score of prion predictions across different phage families

| Phage Order | Phage Family | Host | LLR Score |
|---|---|---|---|
| Undefined | Ampullaviridae | Archeal | 8.033500 |
| Undefined | Bicaudaviridae | Archeal | 9.782100 |
| Undefined | Fuselloviridae | Archeal | 2.333500 |
| Undefined | Globuloviridae | Archeal | 7.176000 |
| Ligamenvirales | Rudiviridae | Archeal | 5.505778 |
| Undefined | Lipothrixviridae | Bacterial | 4.488143 |
| Undefined | Inoviridae | Bacterial | 2.690261 |
| Undefined | Leviviridae | Bacterial | 0.863692 |
| Undefined | Corticoviridae | Bacterial | 4.680000 |
| Undefined | Microviridae | Bacterial | 5.643914 |
| Caudovirales | Myoviridae | Bacterial | 5.908475 |
| Caudovirales | Podoviridae | Bacterial | 7.780928 |
| Caudovirales | Siphoviridae | Bacterial | 6.080153 |
| Undefined | Tectiviridae | Archeal/Bacterial | 2.699050 |
| Undefined | Undefined | Bacterial | 5.177220 |

The inventors aimed to select bacteriophage proteins in bacteria that may have a greater prion-forming potential. To this end, the correlation between the LLR score of the PrD proteins and the host bacteria was analyzed. The average LLR score varied significantly between the bacteriophages of different bacterial species. The lowest mean LLR values were detected among *Cellulophaga* and *Escherichia* bacteriophages (3.49 and 3.98, respectively) and the highest LLR score was obtained for the *Bacillus* bacteriophages, with the average LLR of 8.96 ($p<0.001$).

The average numbers of LLRs between three most abundant bacteriophage families, Myoviridae, Podoviridae, and Siphoviridae, were similar, with the highest LLR scores obtained for Podoviridae family, with an average LLR of 7.78 ($p<0.001$) (Tables 15-17).

TABLE 15

| Source | DF | Type III SS | Mean Square | F Value | Pr > F |
|---|---|---|---|---|---|
| Family | 2 | 1920.410170 | 960.205085 | 16.84 | <.0001 |

TABLE 16

95% Confidence interval of bacteriophage families

| | Family | LLR Score LSMEAN | 95% Confidence Limits | |
|---|---|---|---|---|
| 1 | Myoviridae | 5.908475 | 5.608805 | 6.208146 |
| 2 | Podoviridae | 7.780928 | 7.212436 | 8.349420 |
| 3 | Siphoviridae | 6.080153 | 5.717382 | 6.442923 |

TABLE 17

Least squares means for effect of bacteriophage family on LLR score
Least Squares Means for effect Family
Pr > |t| for H0: LSMean(i) = LSMean(j)
Dependent Variable: LLR Score

| i/j | Myoviridae | Podoviridae | Siphoviridae |
|---|---|---|---|
| 1 | | <.0001 | 0.7545 |
| 2 | <.0001 | | <.0001 |
| 3 | 0.7545 | <.0001 | |

Figure 7B:
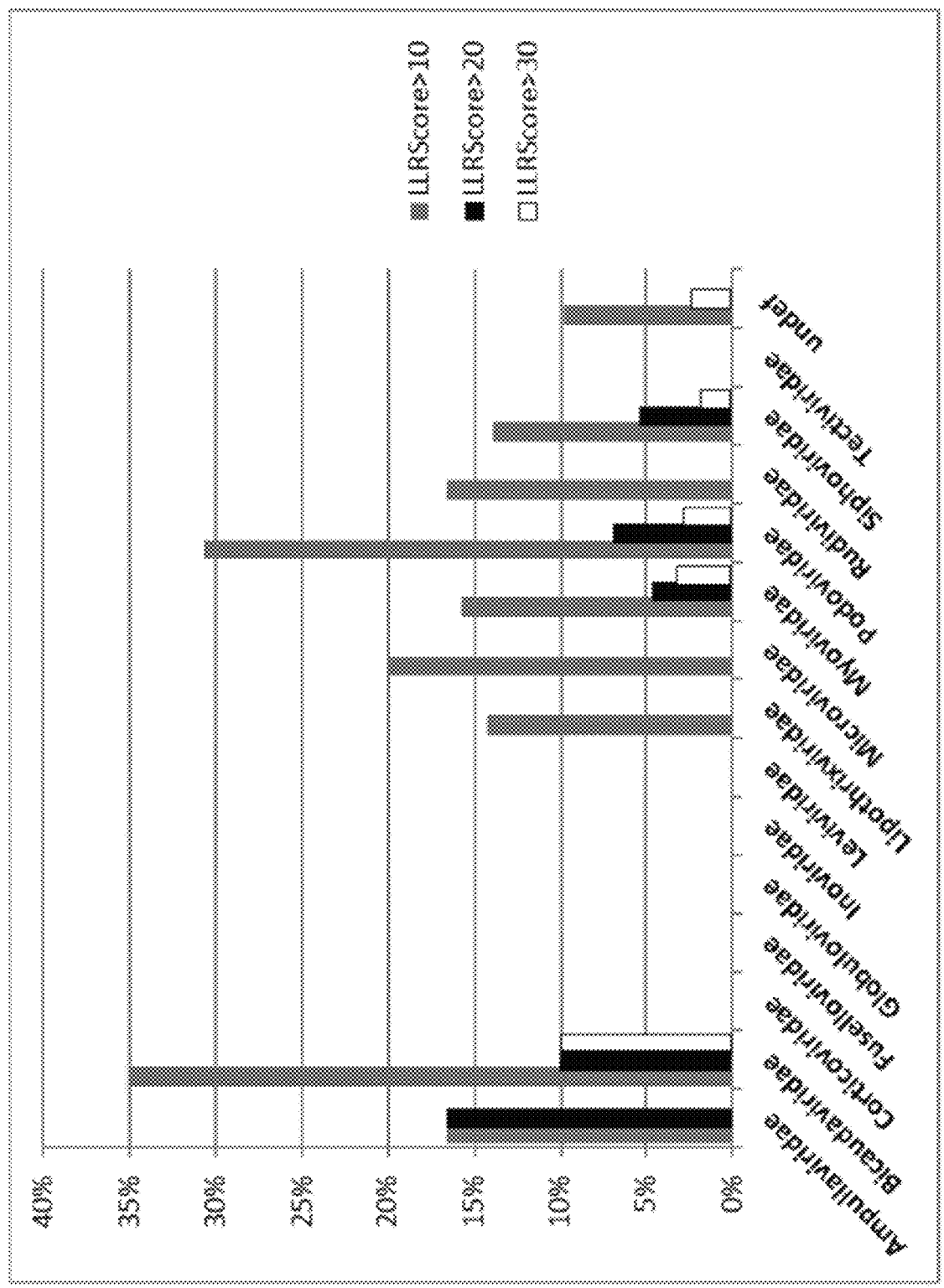
FIG. 7B illustrates the distribution of bacteriophage families with the LLR scores higher than 10, 20, and 30.

Under the same conditions, the LLRs were compared between the remaining bacteriophage families. Myoviridae were shown to have the highest number of PrDs, with the LLR score over 30.114 PrDs were identified with the medium LLR score over 20 within Myoviridae family, yielding 3.29% of the total number of PrDs identified in this bacteriophage family (FIG. 7B).

The same trend was observed when analyzing top 100 scoring PrDs. Over 60% of these 100 PrDs were derived from Myoviridae bacteriophages, with the medium LLR score of 40.55.

Figure 8A:
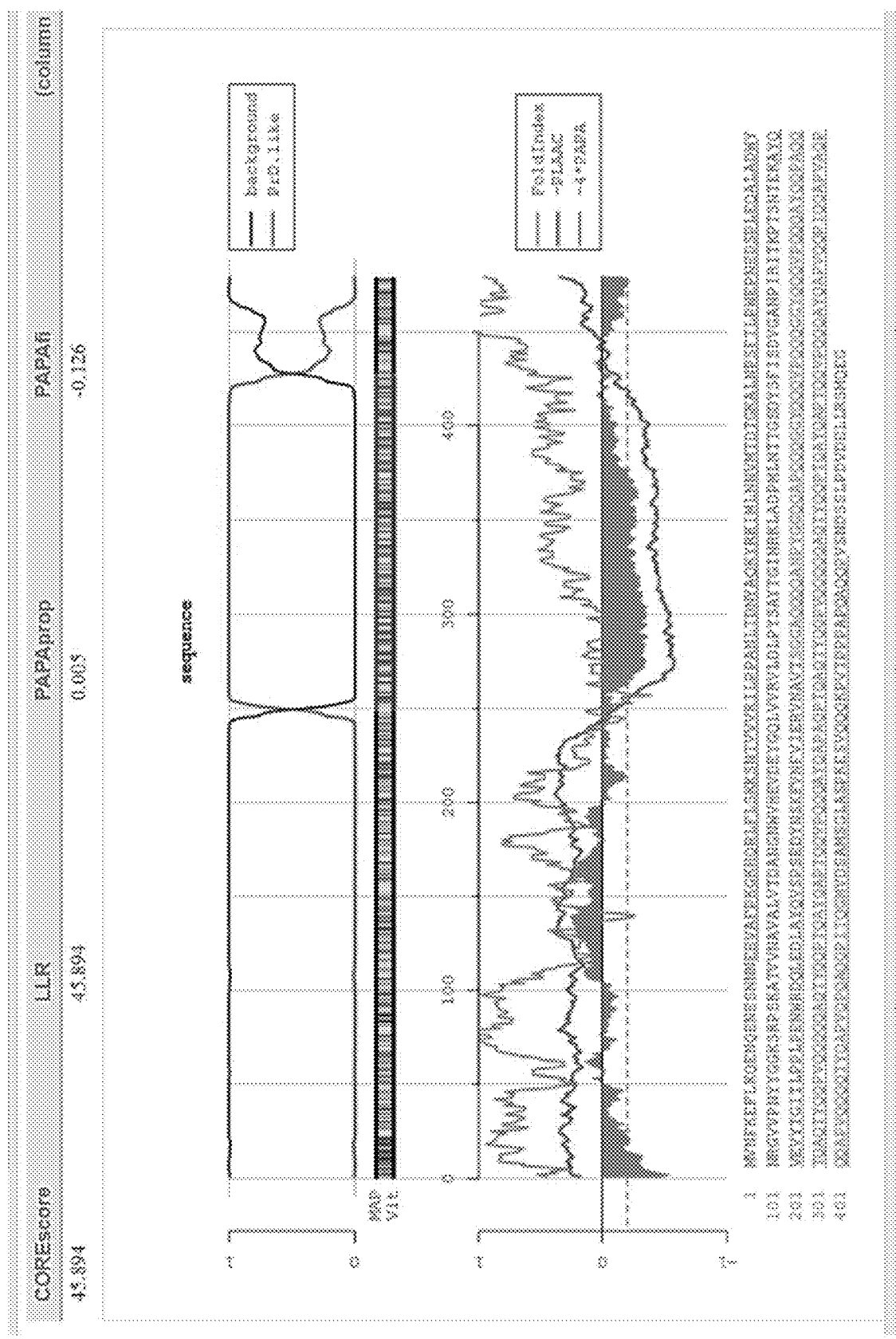
FIGS. 8A-8B show the characterization of the candidate bacteriophage PrDs in the single-stranded DNA binding proteins.
Figure 8B:
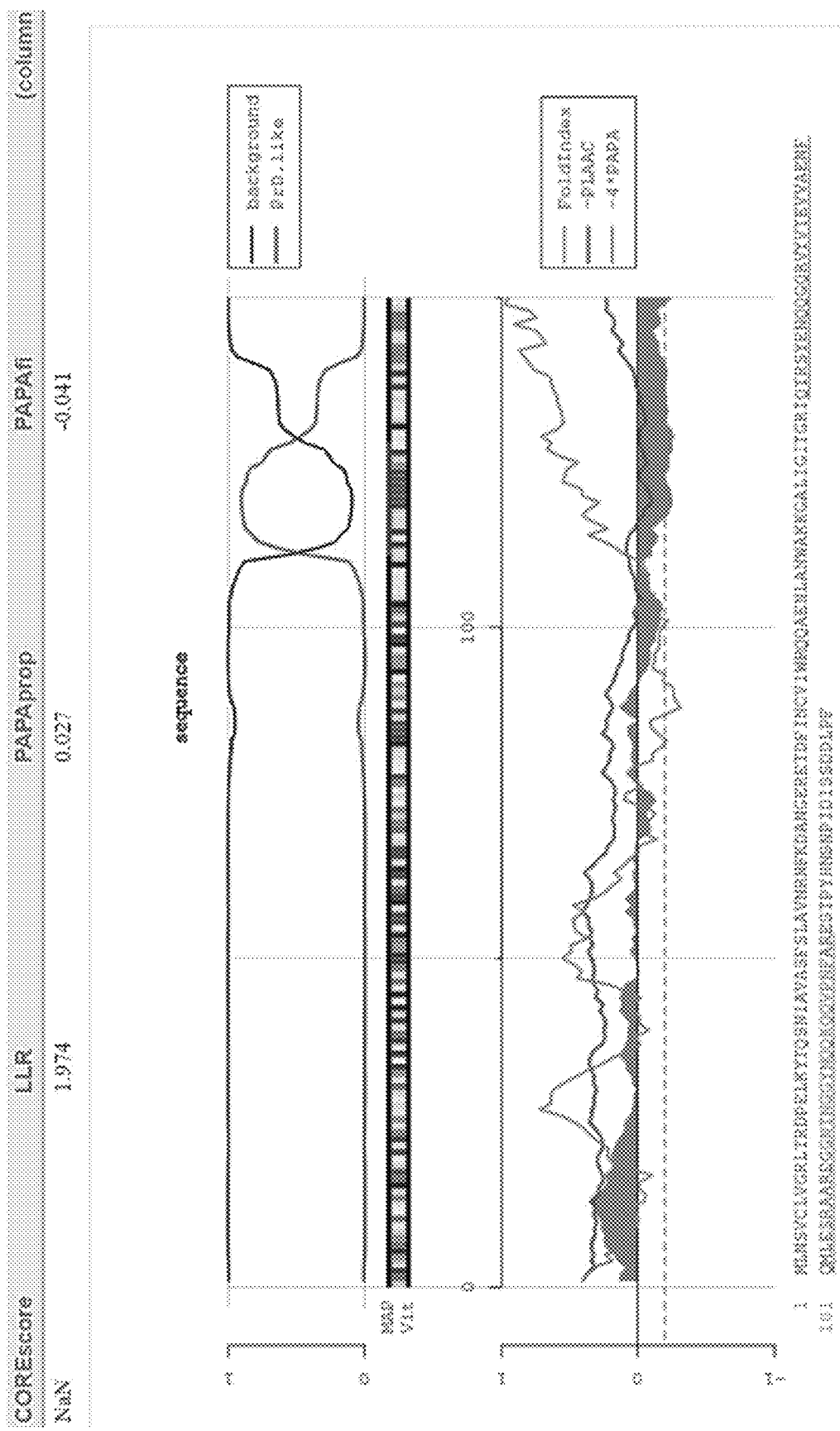
Figure 9A:
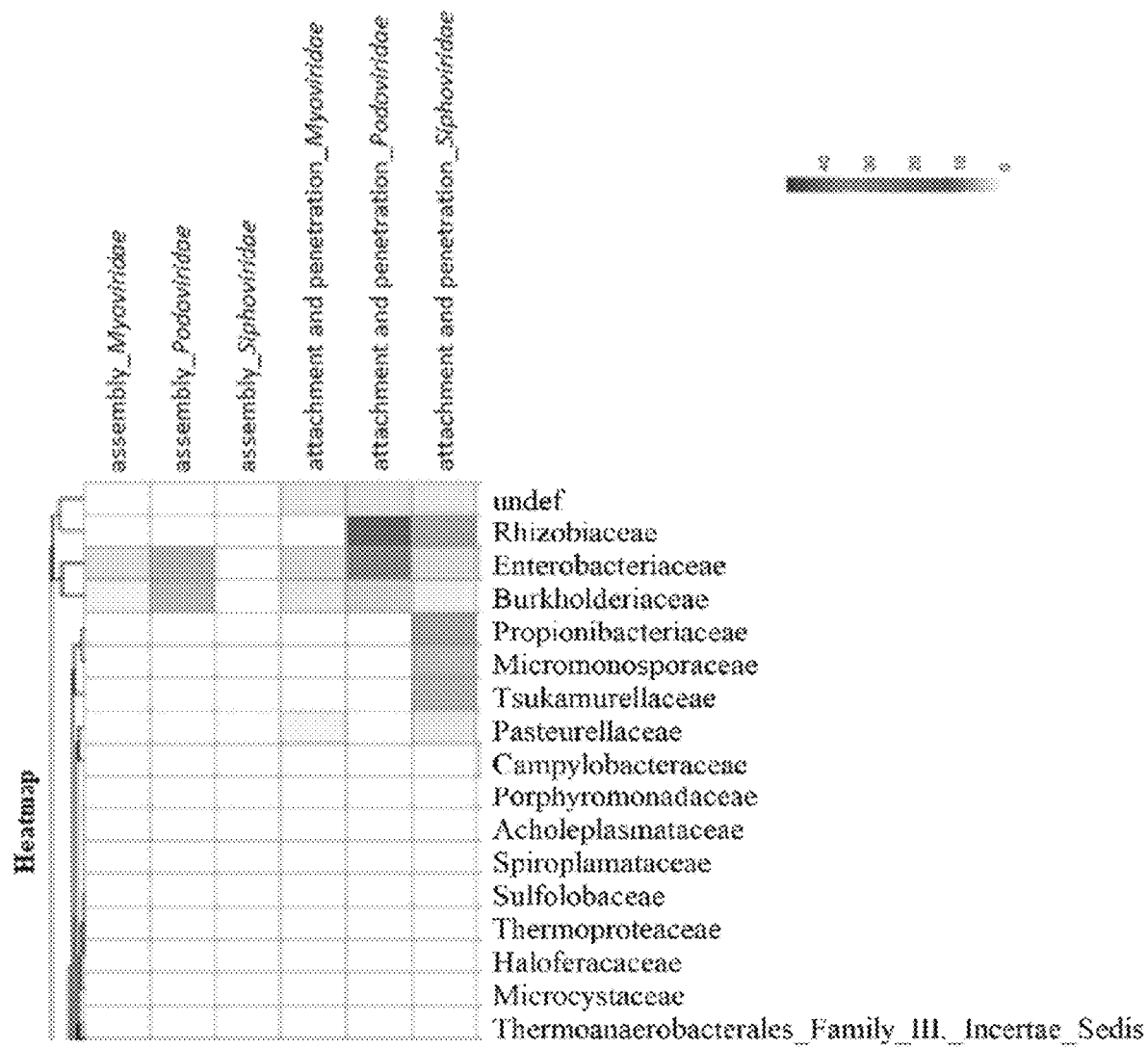
FIGS. 9A-9H are Heatmaps showing PrD distribution in bacteriophages. The correlation between LLR score of the identified PrDs, their distribution across bacteriophage families, host bacteria, and their function in the bacteriophage-bacterial interaction are presented. The likelihood that an identified PrD is a prion is represented by a scale.
Figure 9B:
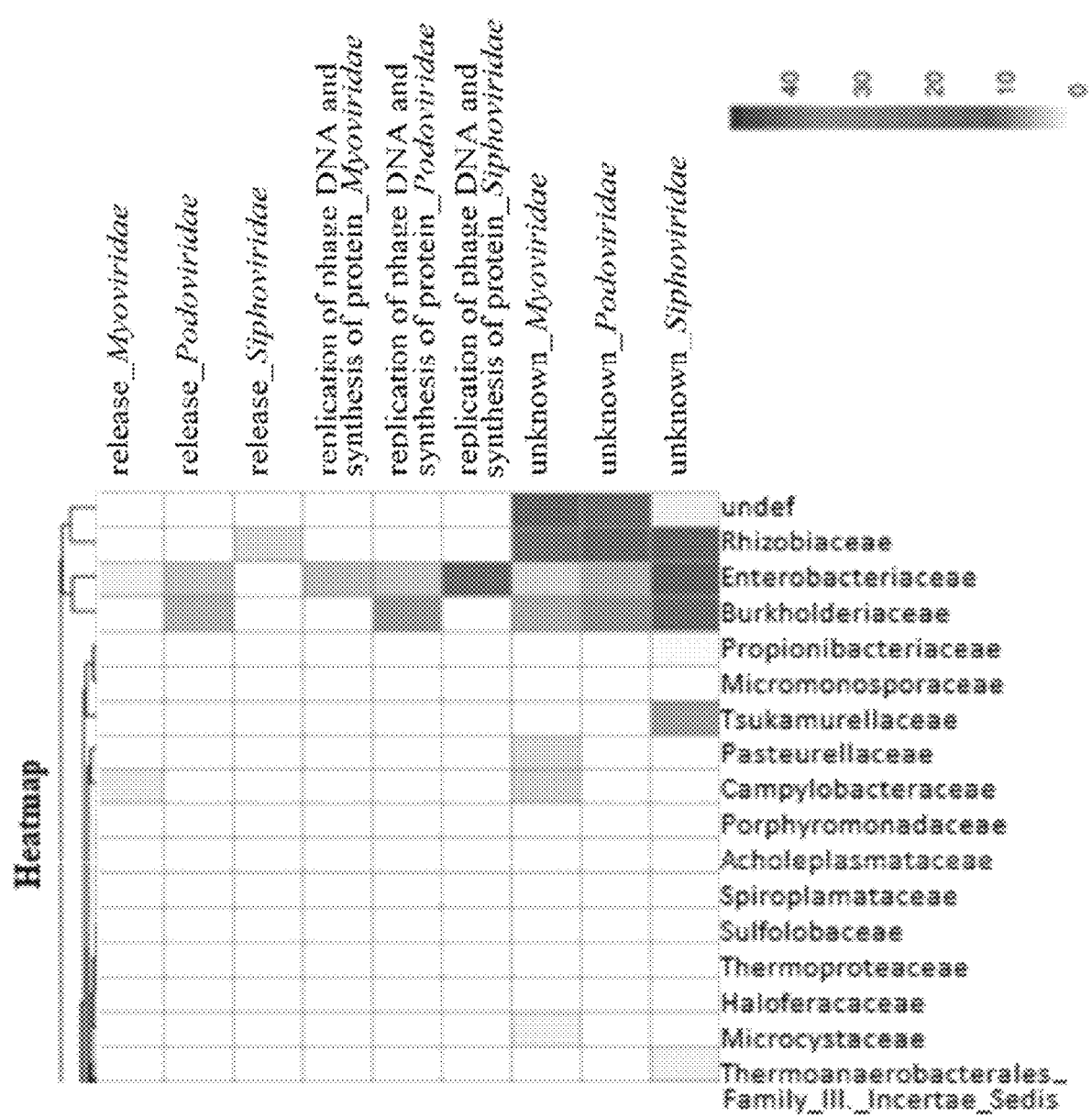
Figure 9C:
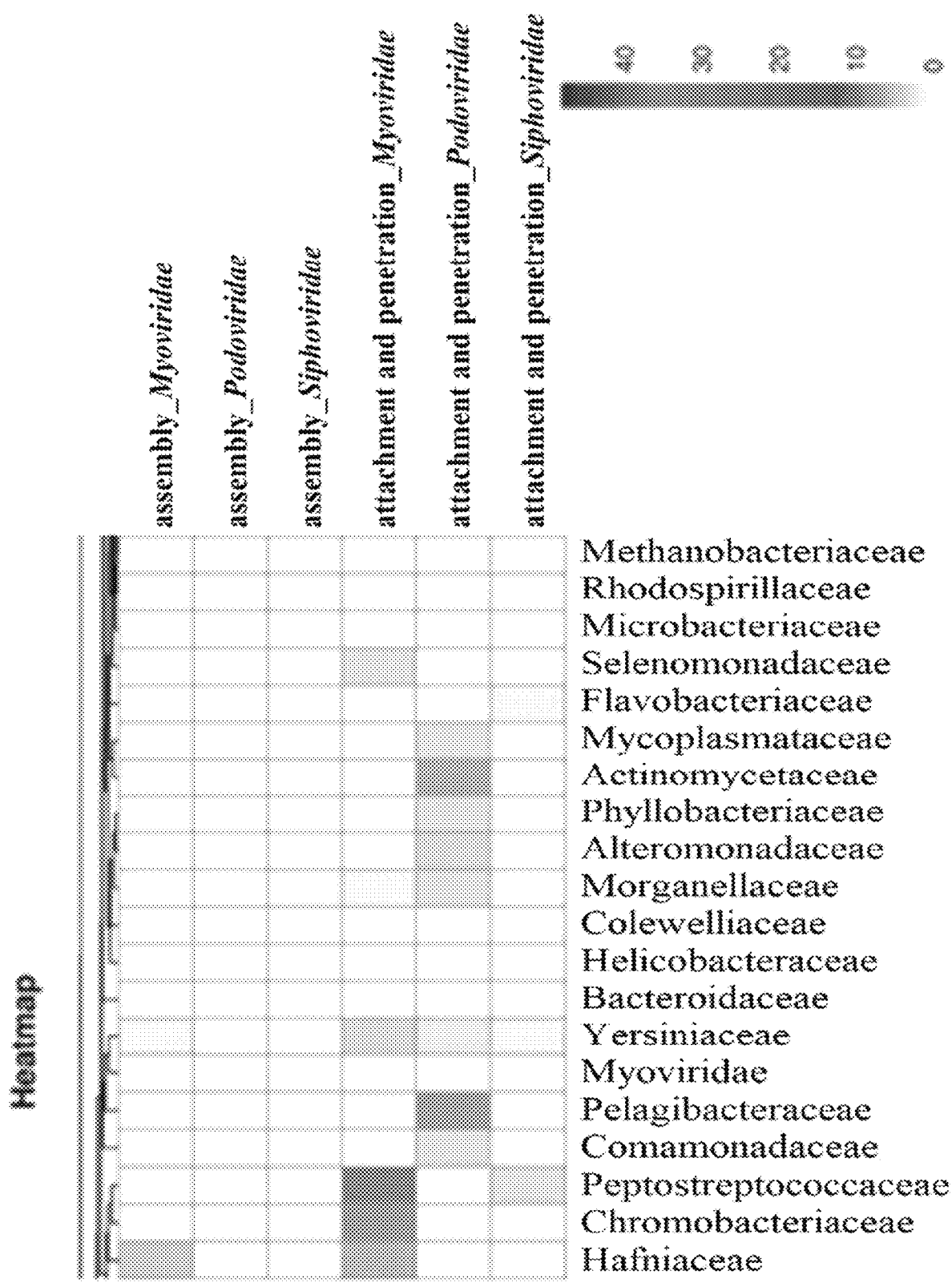
Figure 9D:
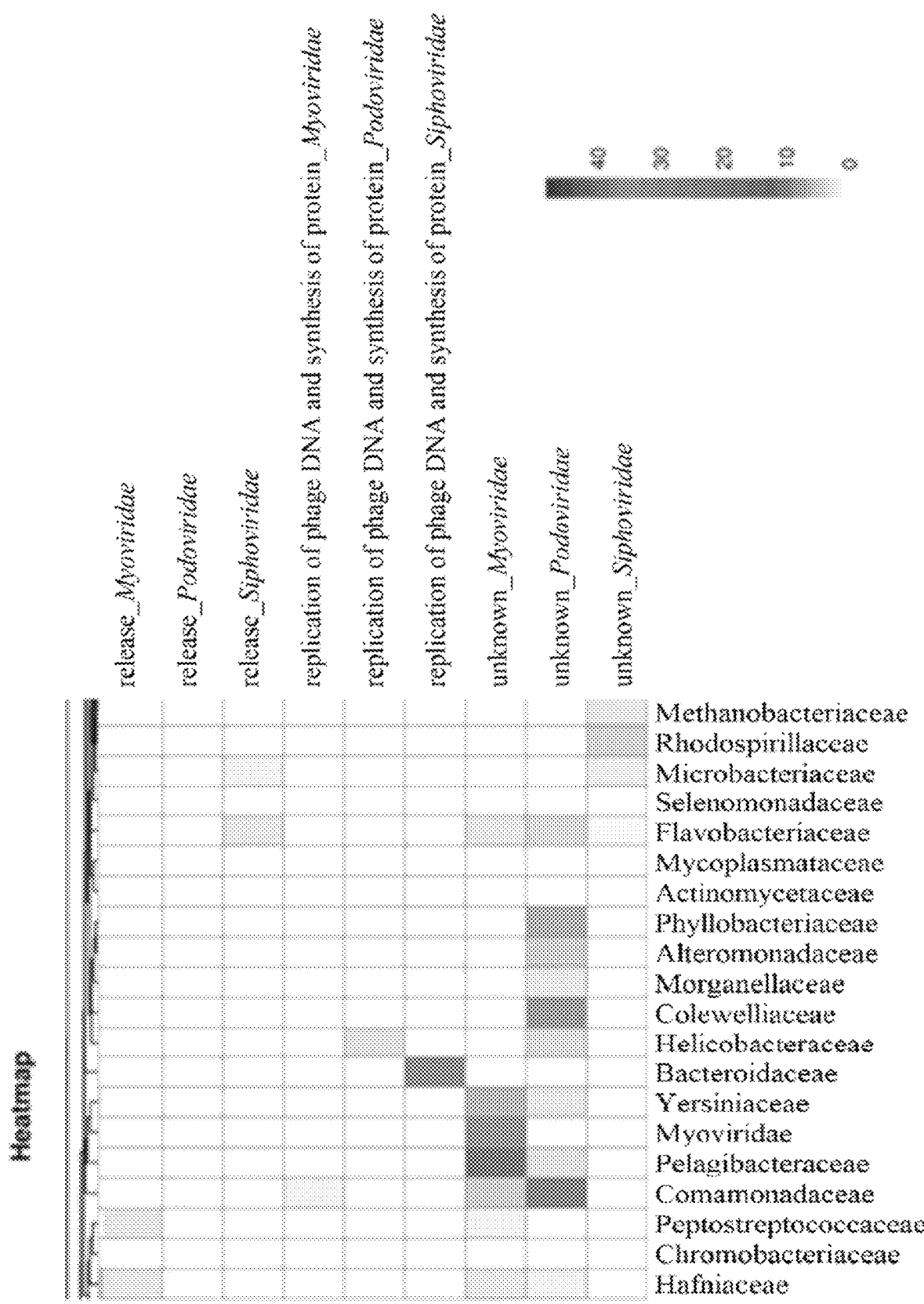
Figure 9E:
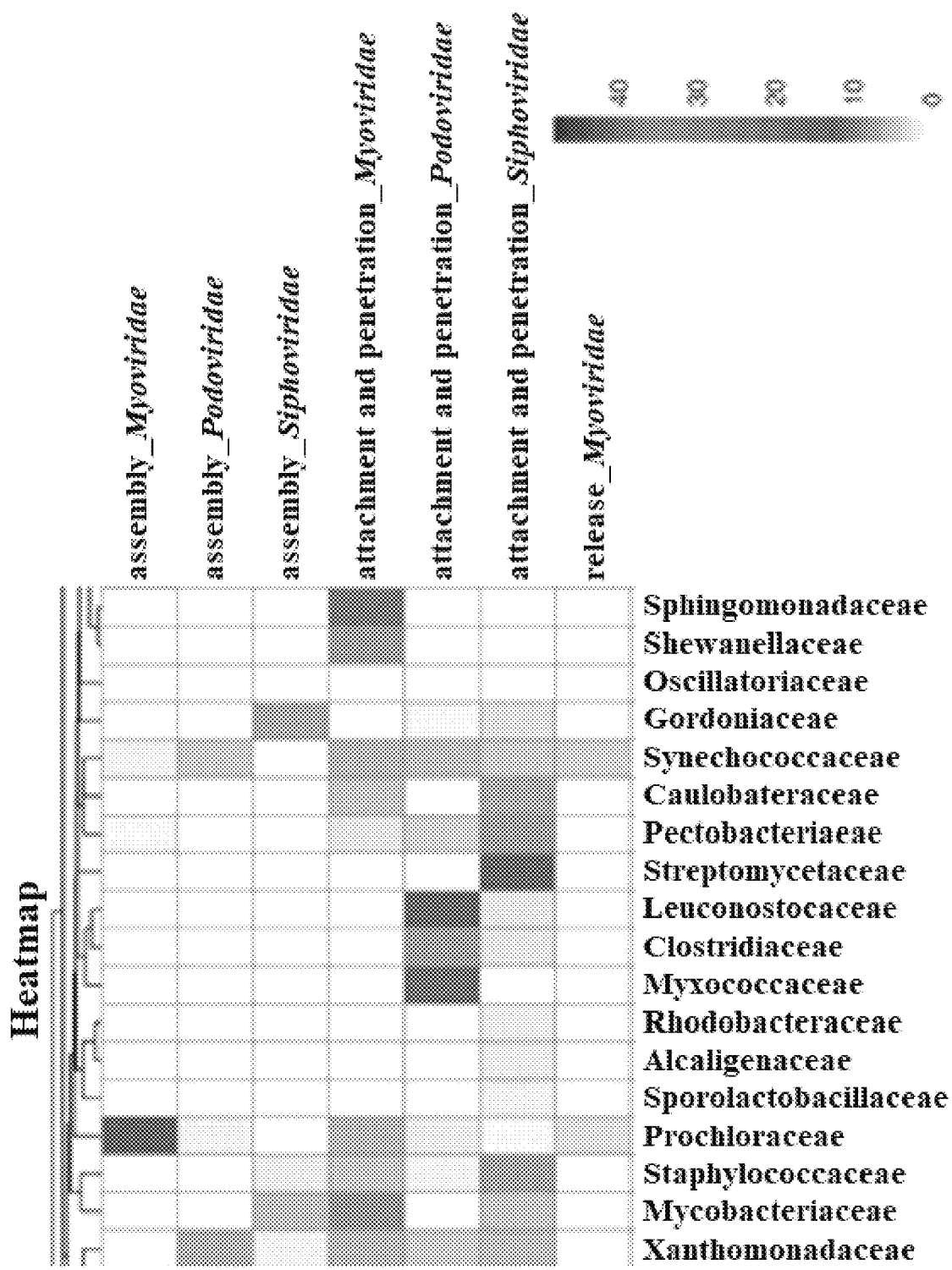
Figure 9F:
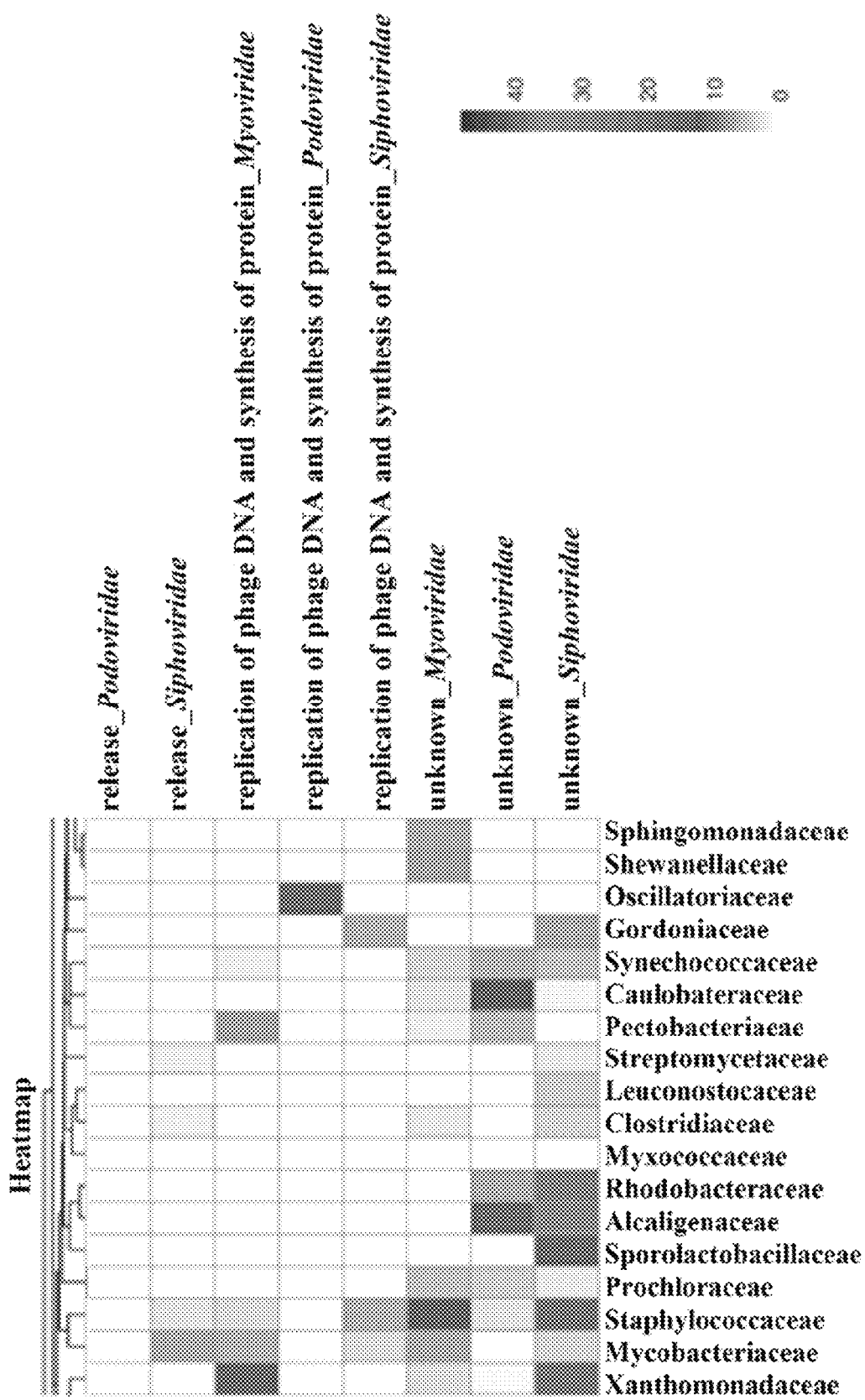
Figure 9G:
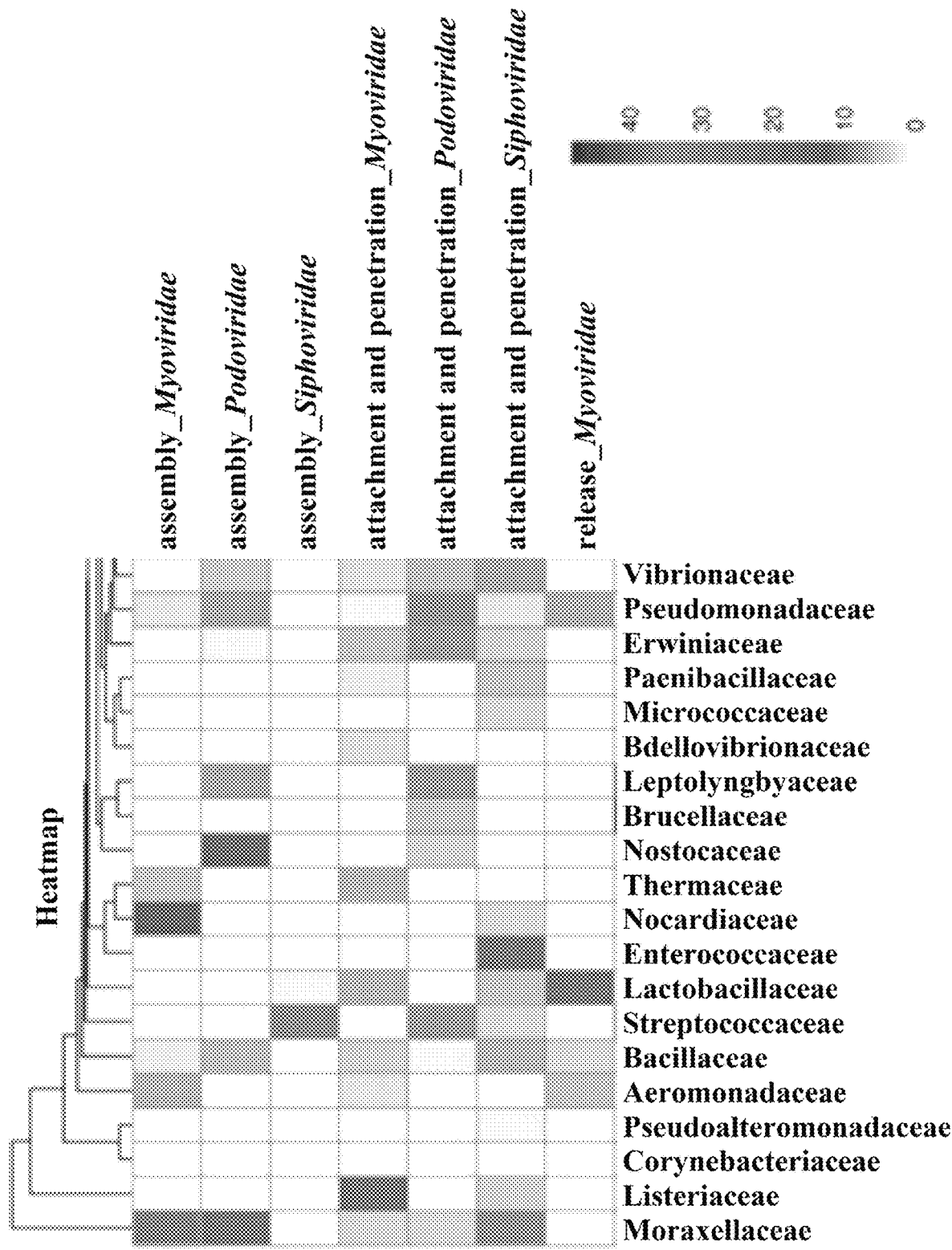
Figure 9H:
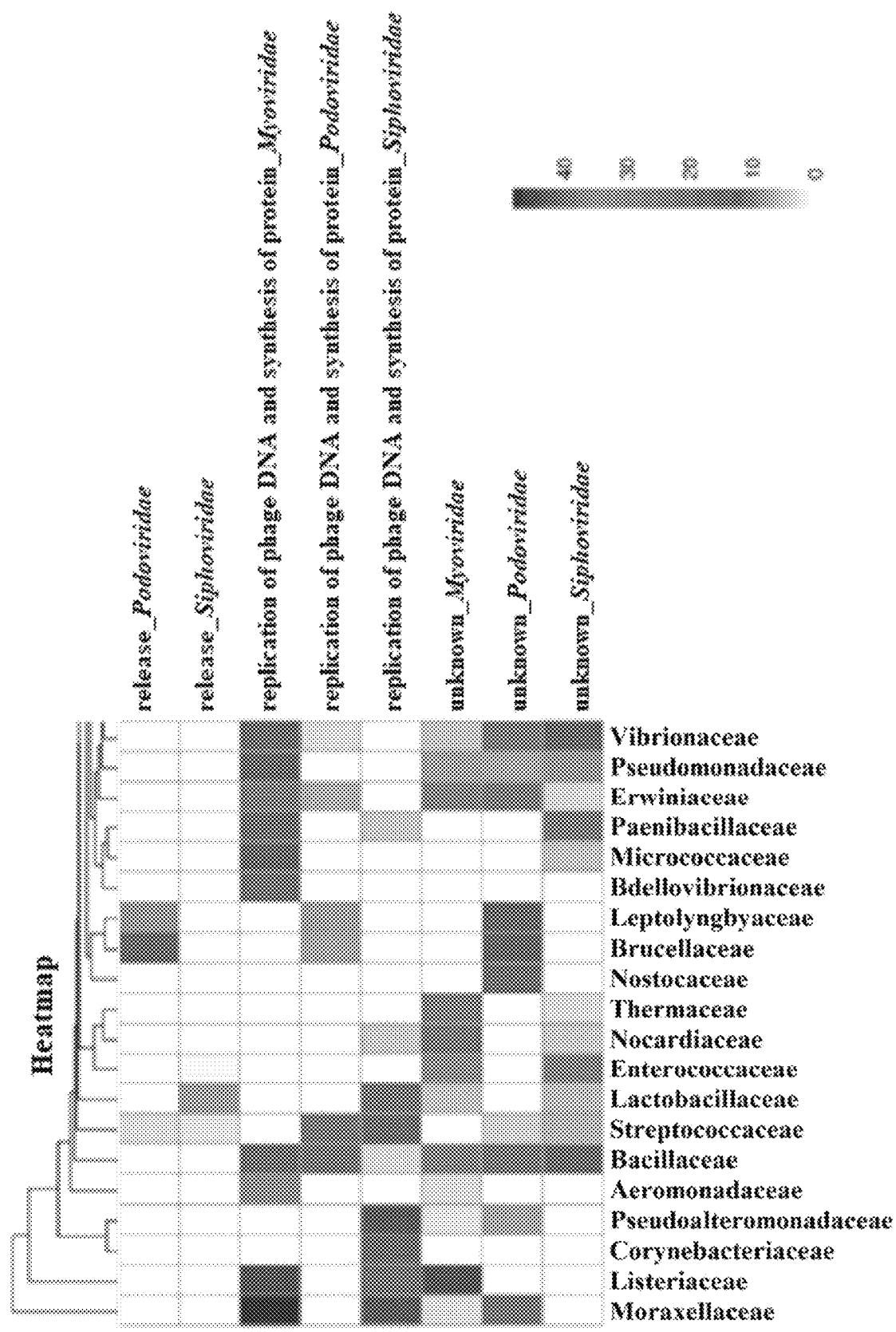
Figure 10A:
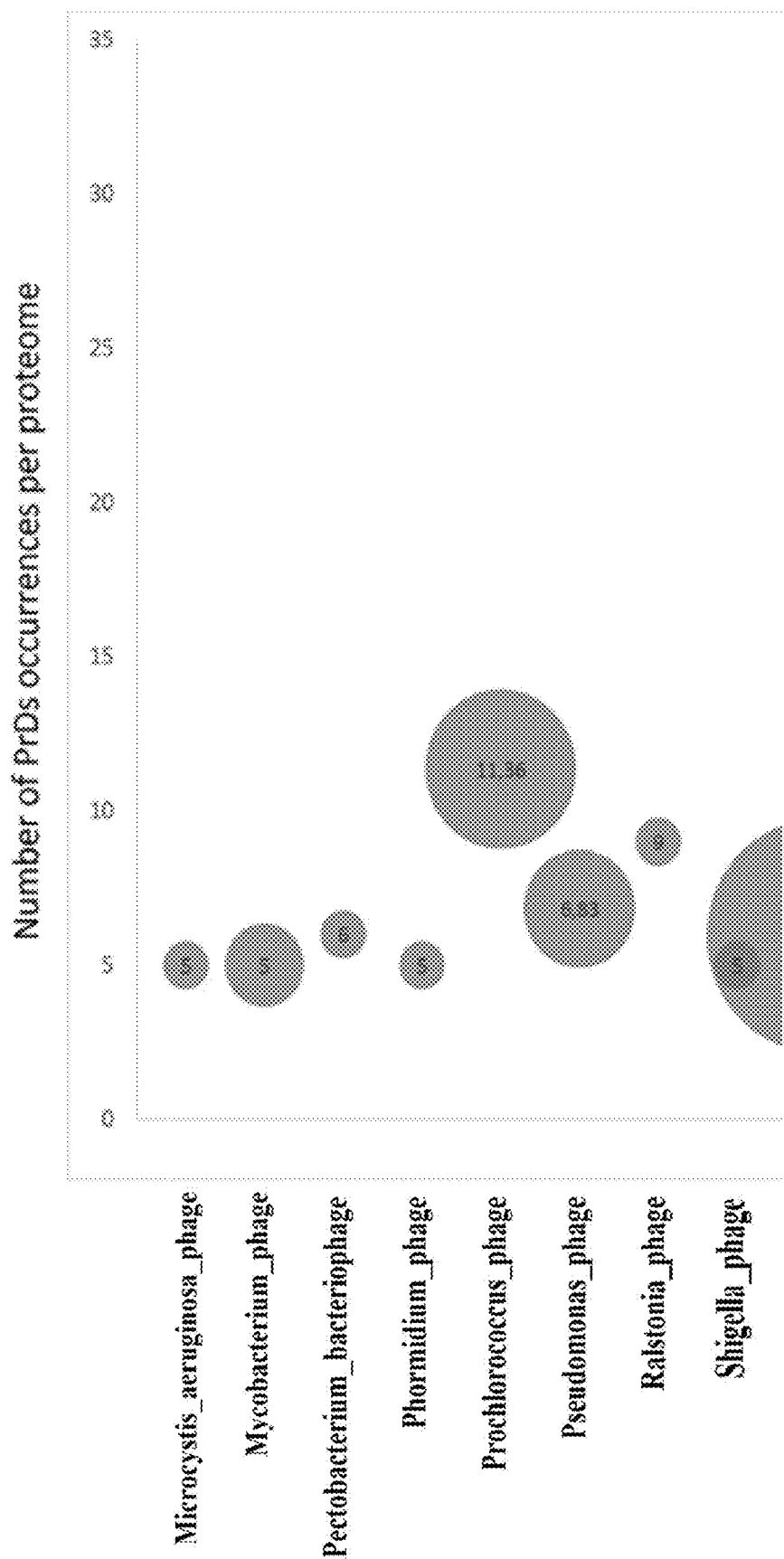
FIGS. 10A-10D show proteome enrichment for PrDs across bacteriophages. The bubble charts represent the medium enrichment rate with PrDs per bacteriophage proteome (phages with at least five PrDs per proteome have been considered) and the number of phages in which these PrDs were identified. The values in the bubbles are the median number of PrDs occurring per proteome in each bacteriophage group. Larger bubble size indicates a higher number of phages with at least five PrDs per proteome, and smaller size indicates a lower number of phages with at least five PrDs per proteome.
Figure 10B:
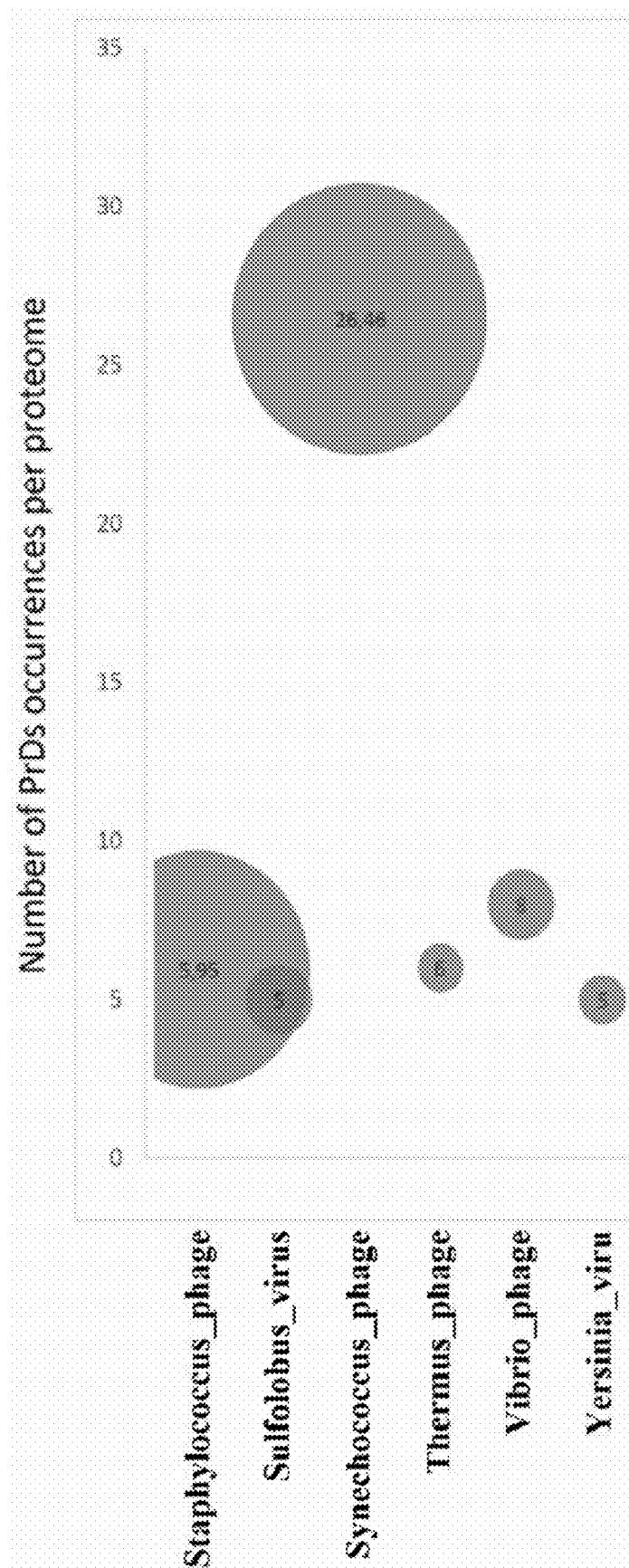
Figure 10C:
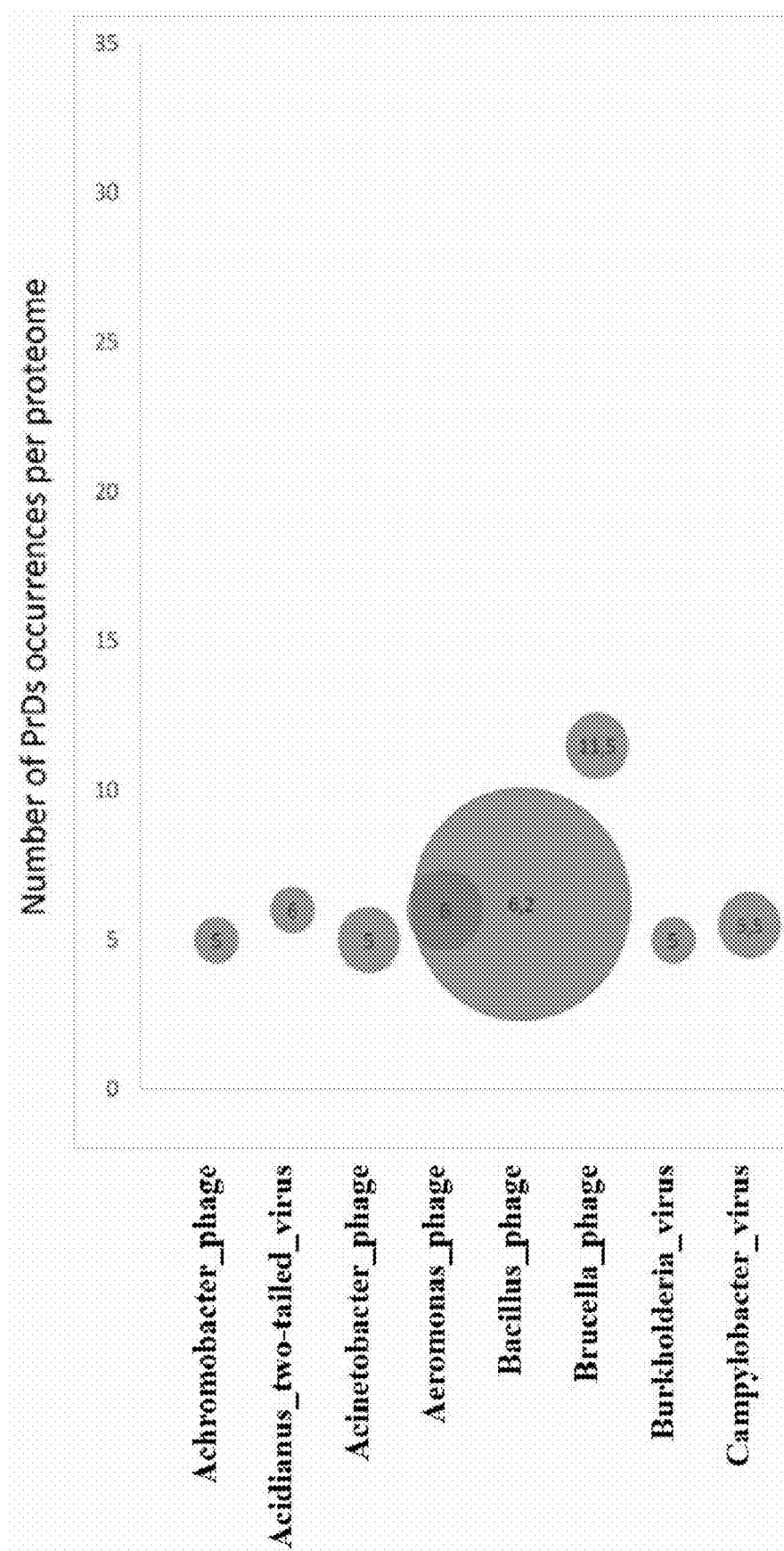
Figure 10D:
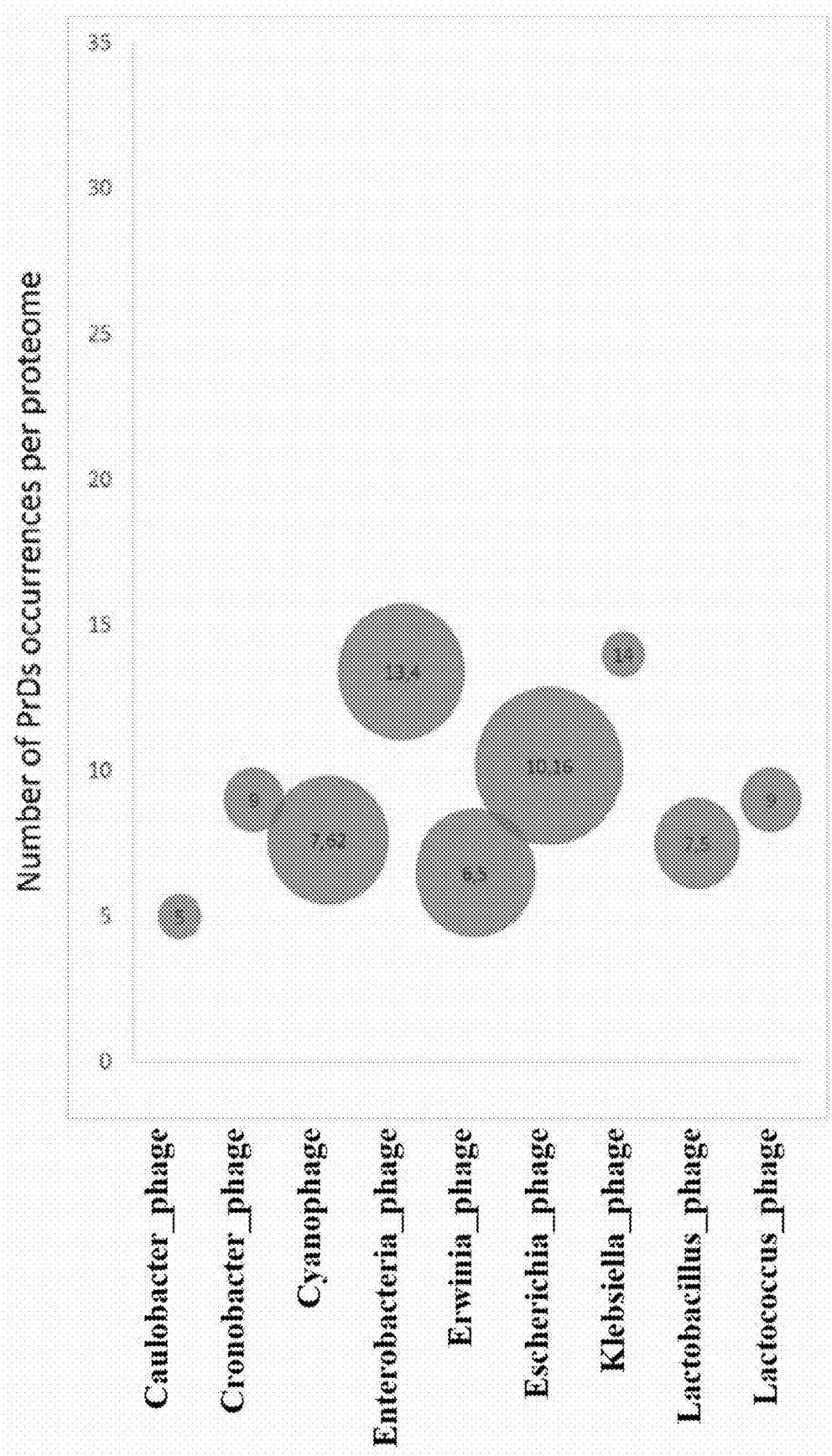
Figure 12A:
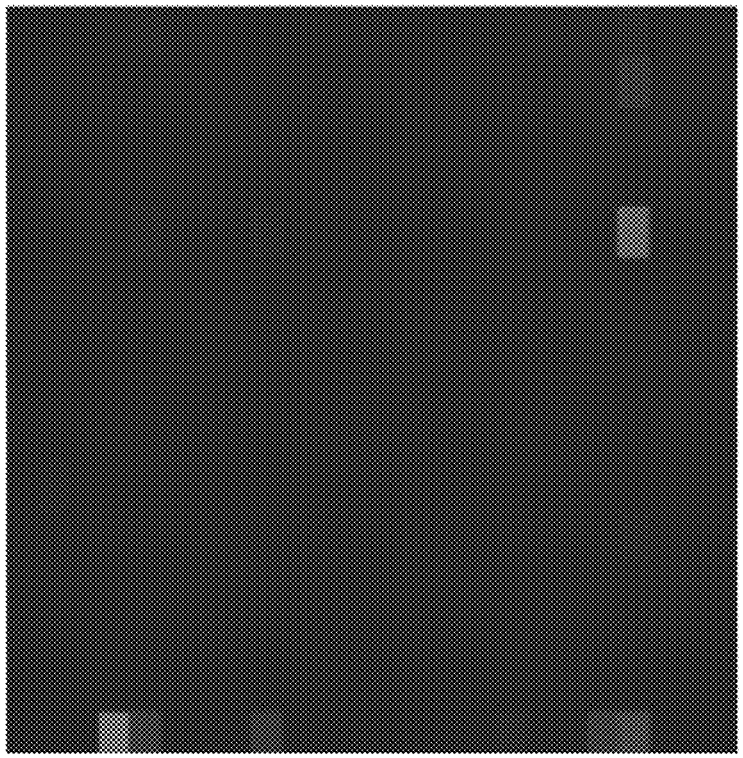
Figure 12A:
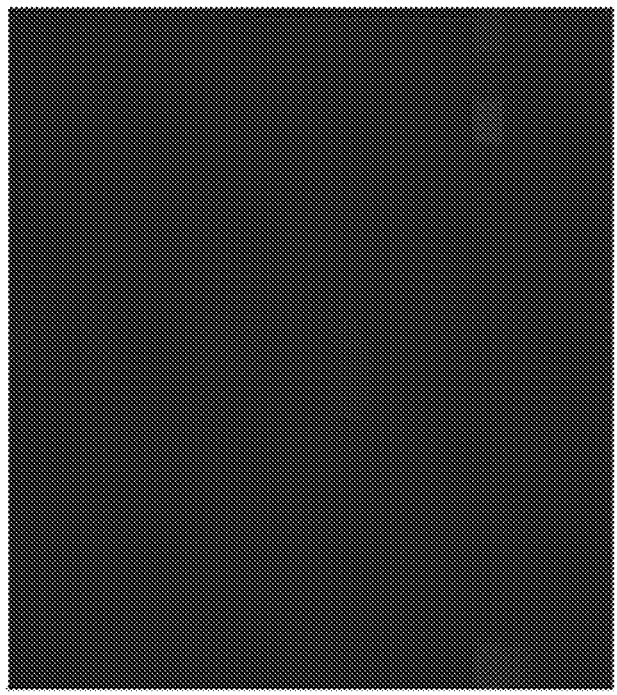
Figure 12A:
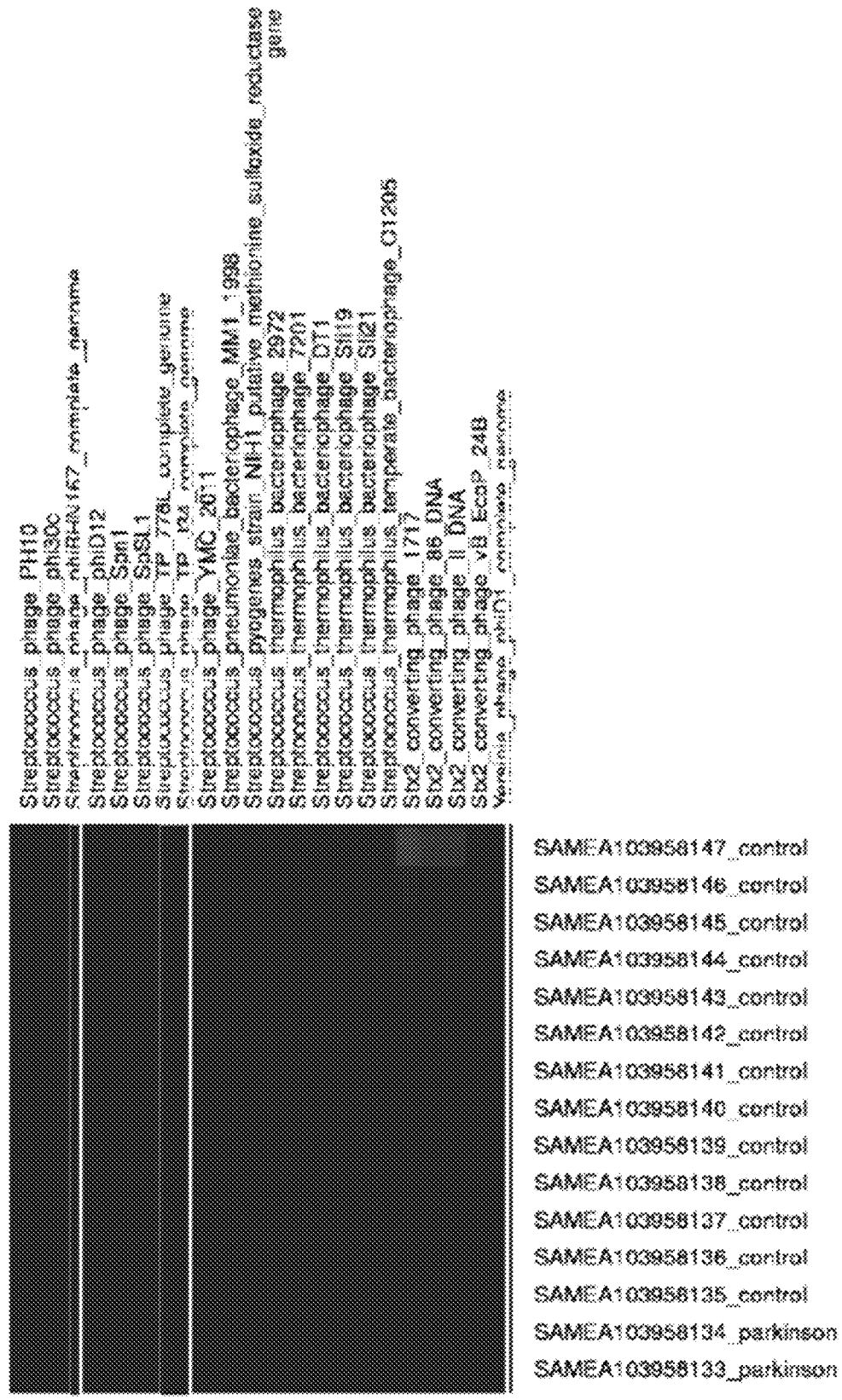
Figure 12B:
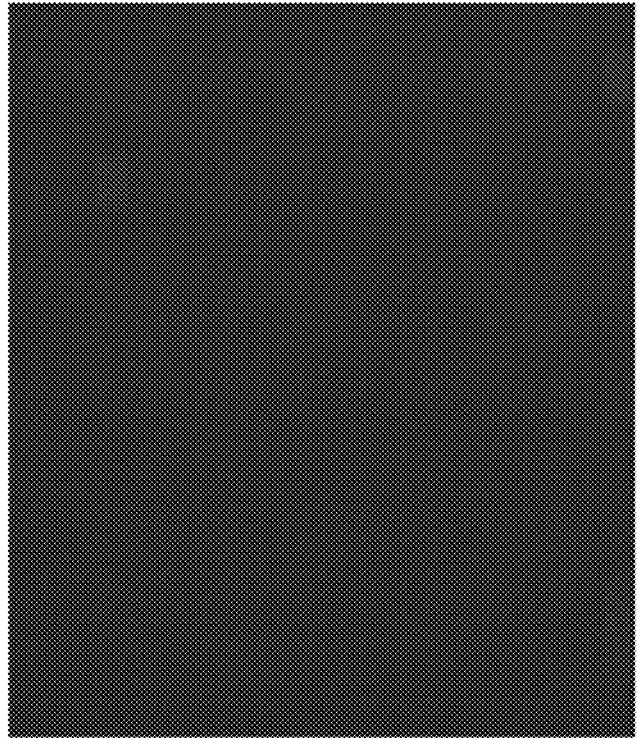
Figure 12B:
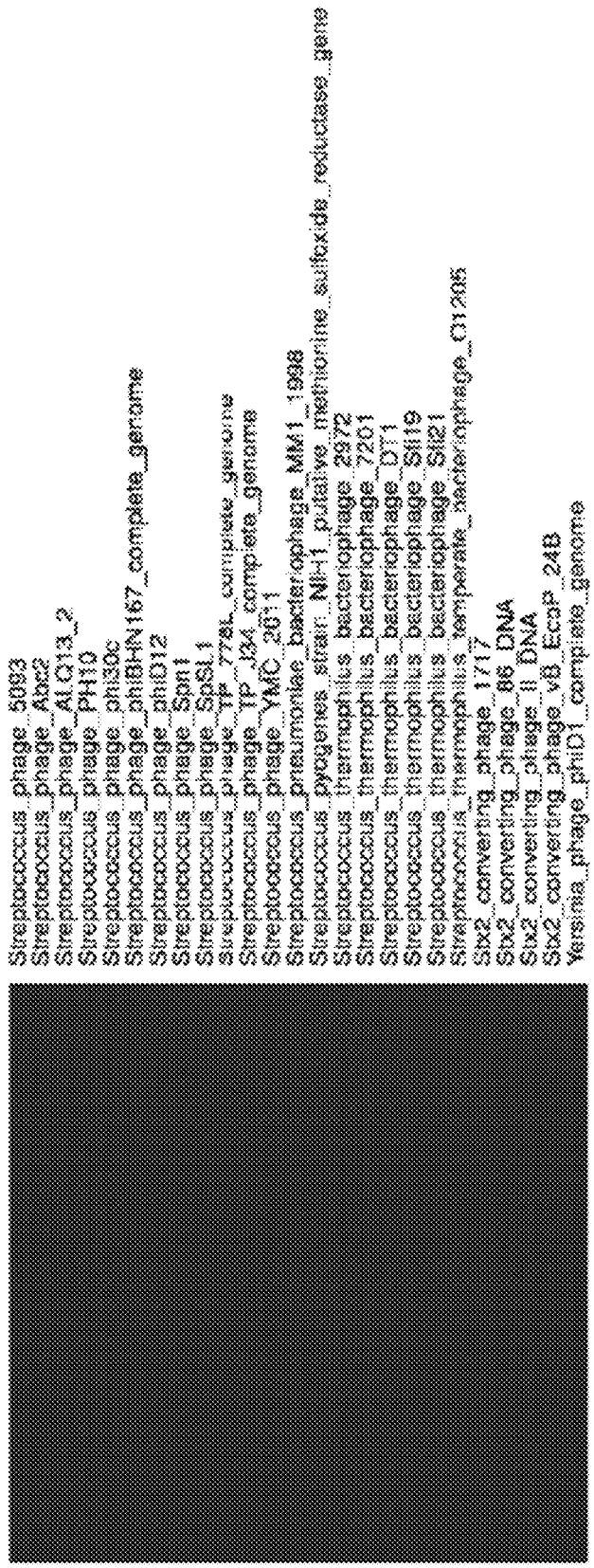
Figure 12B:
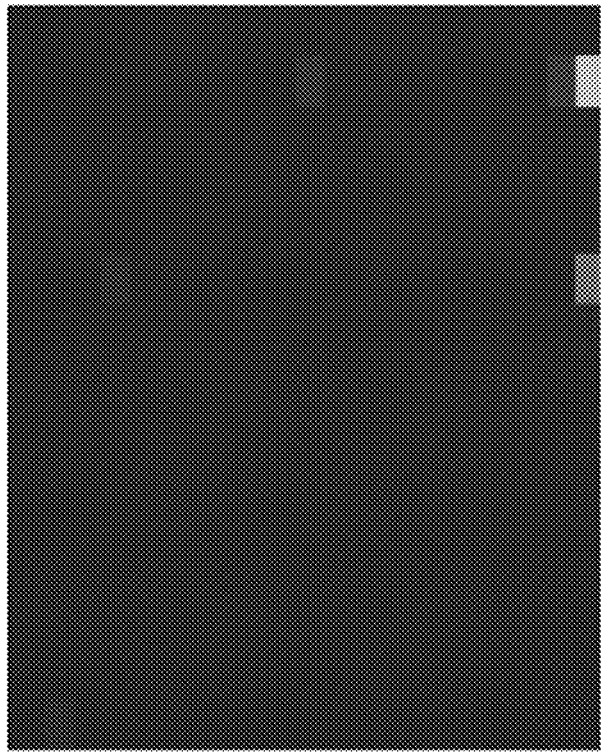
Figure 12B:
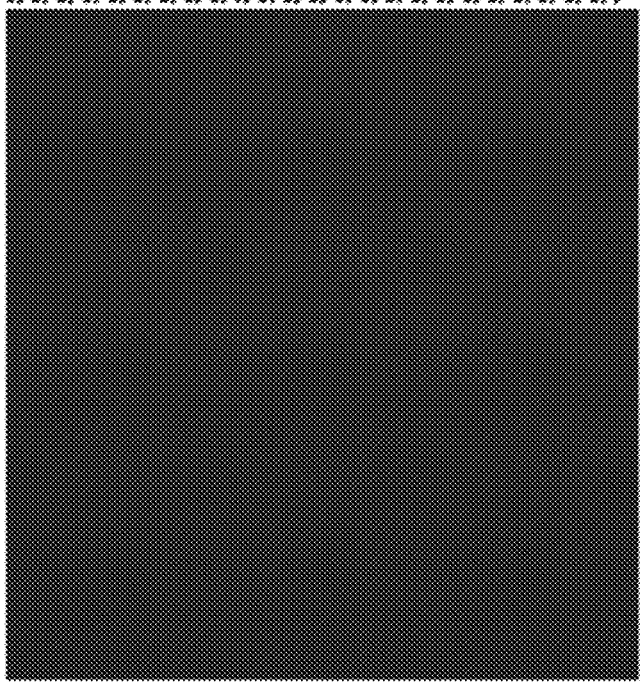
Figure 12C:
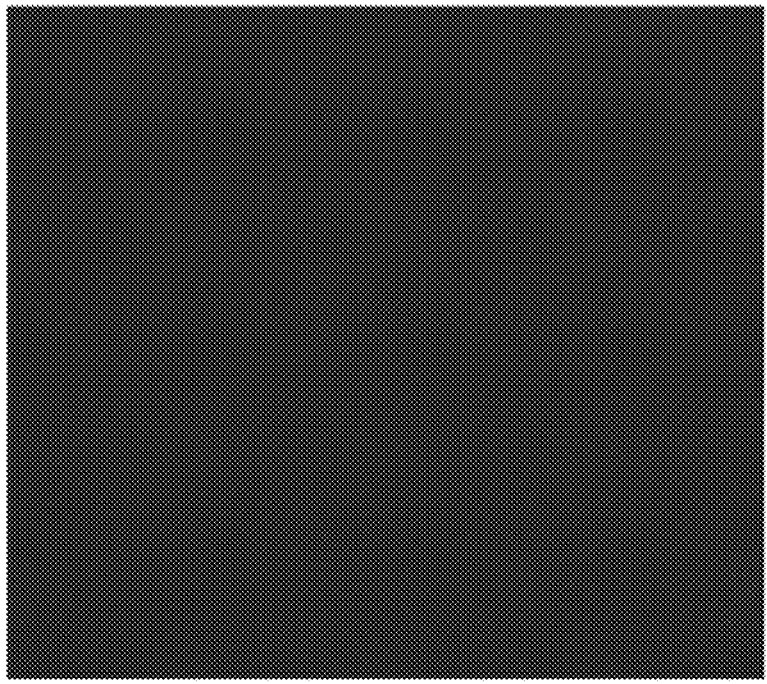
Figure 12C:
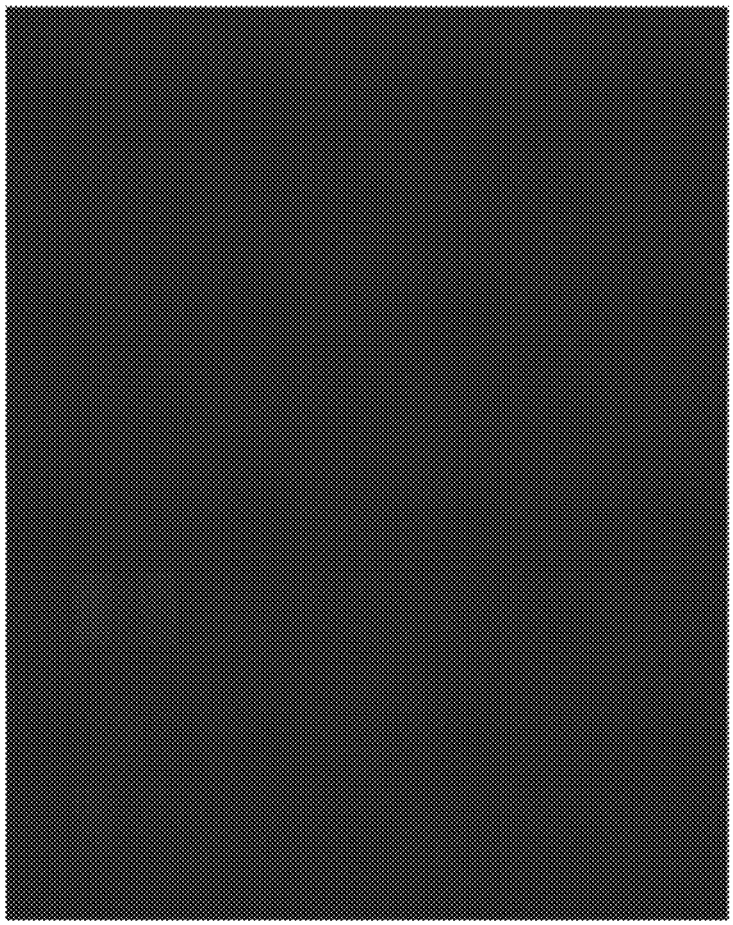
Figure 12C:
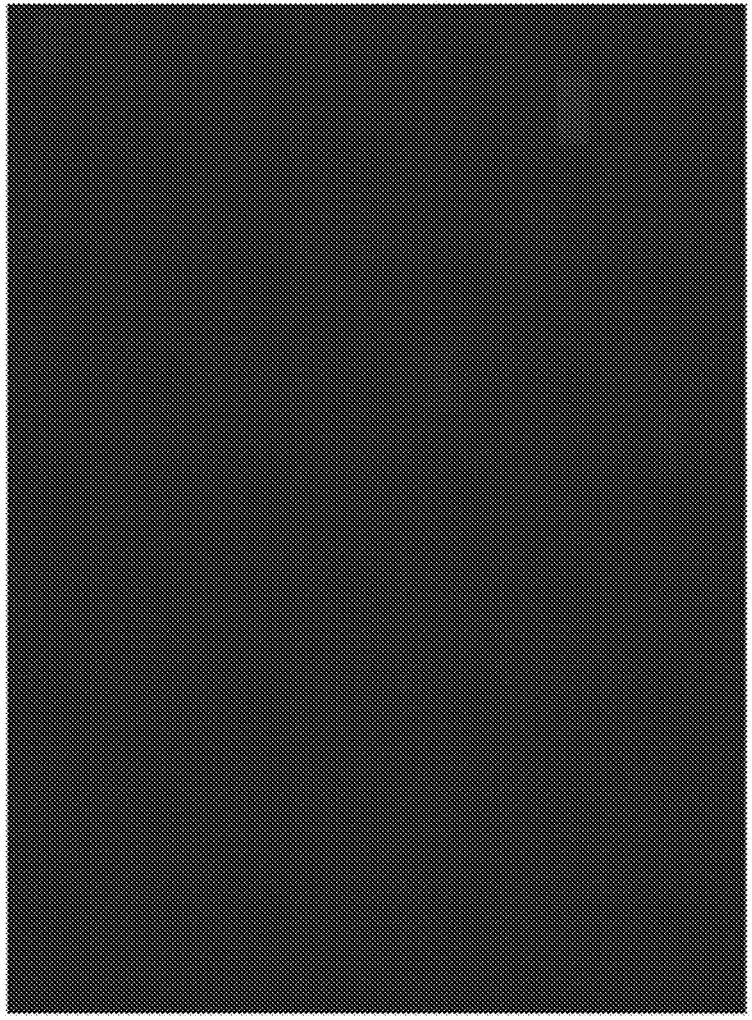
Figure 12C:
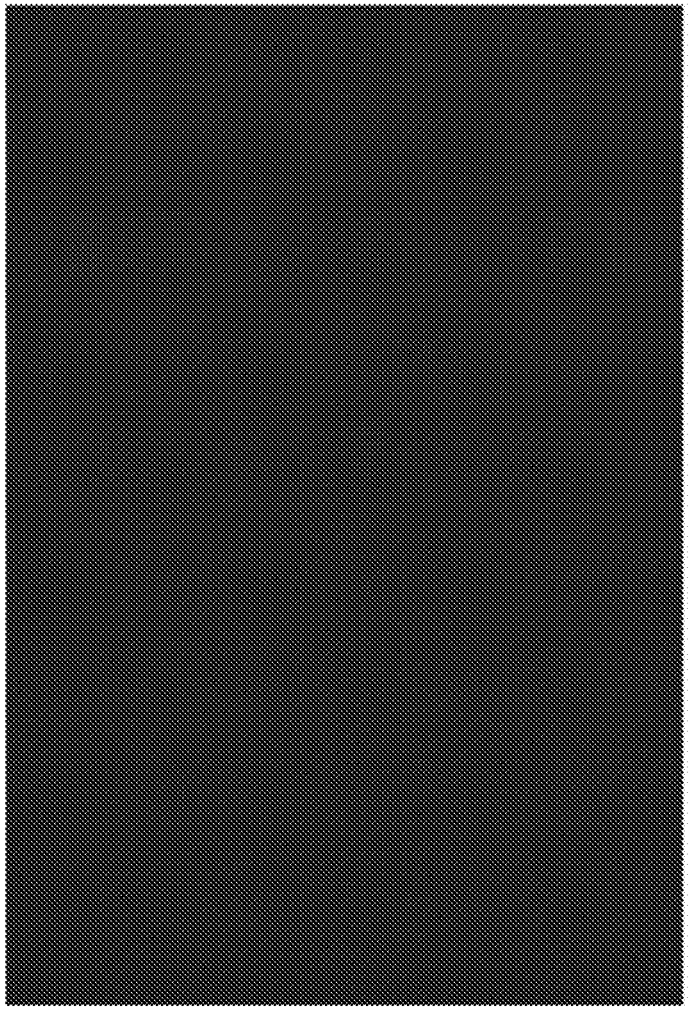
Figure 12D:
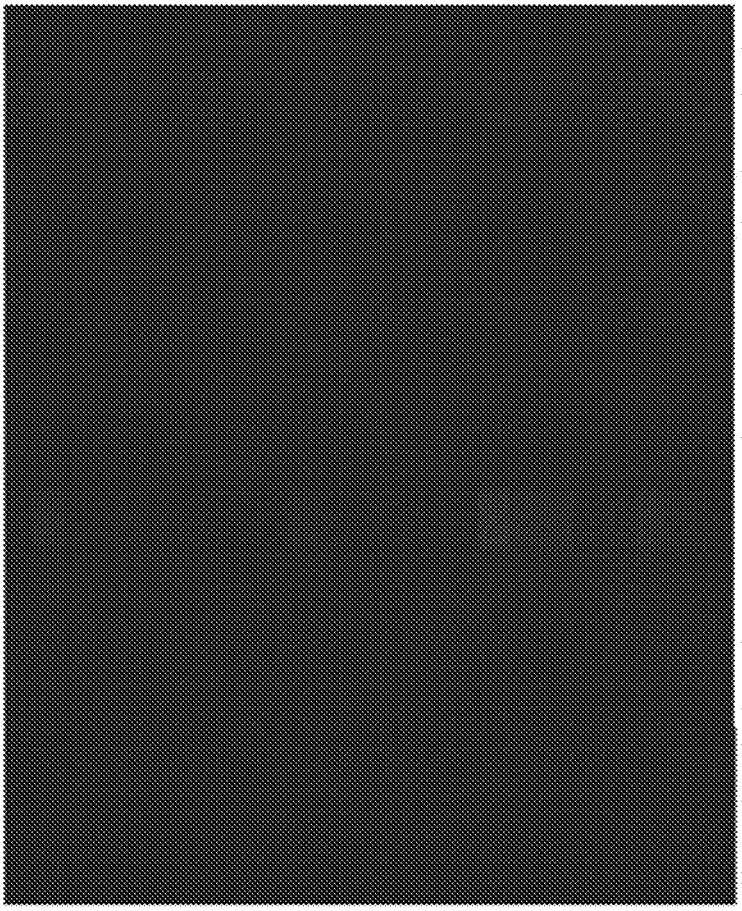
Figure 12D:
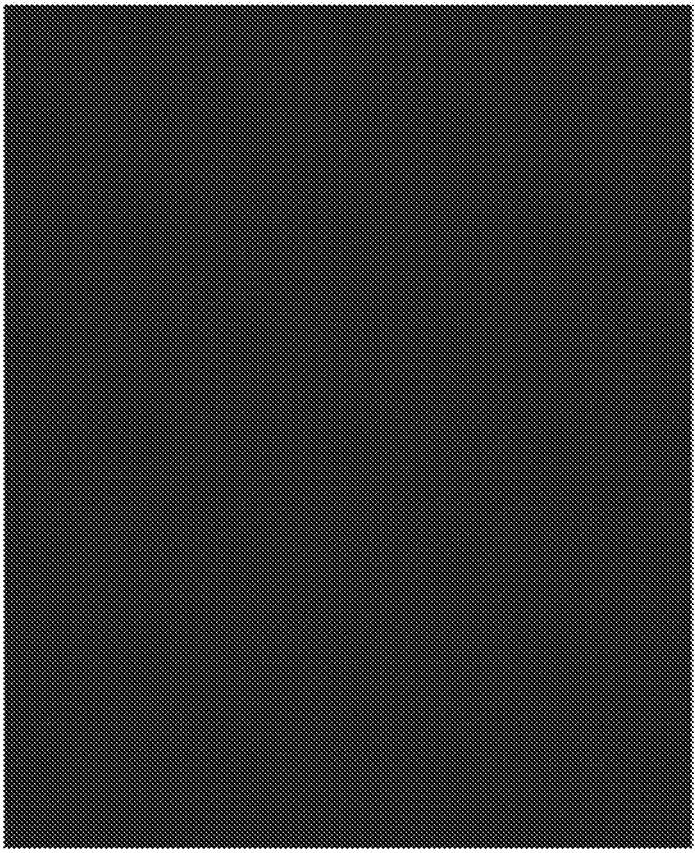
Figure 12D:
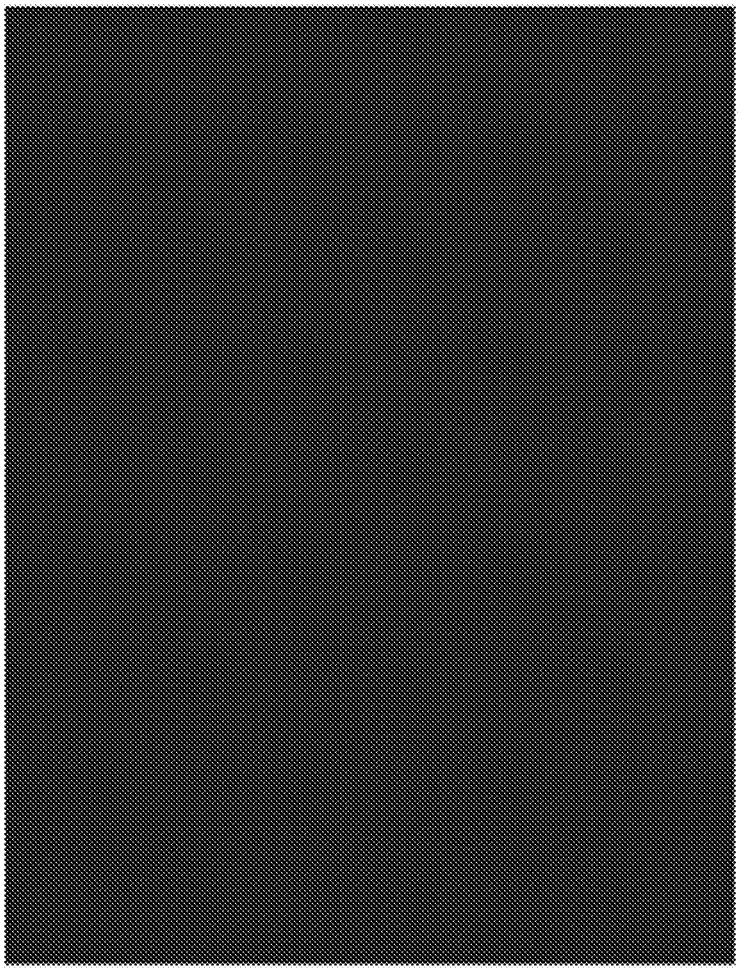
Figure 12E:
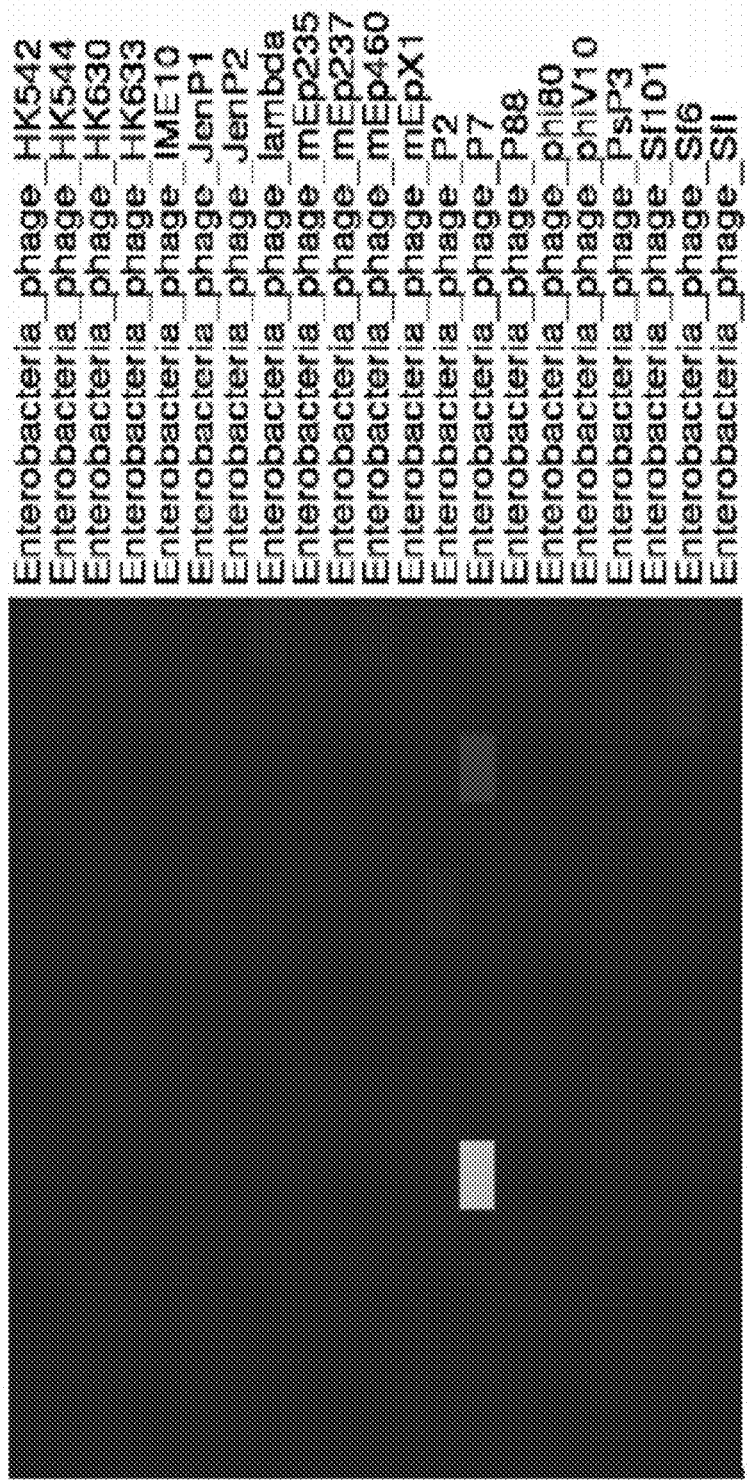
Figure 12E:
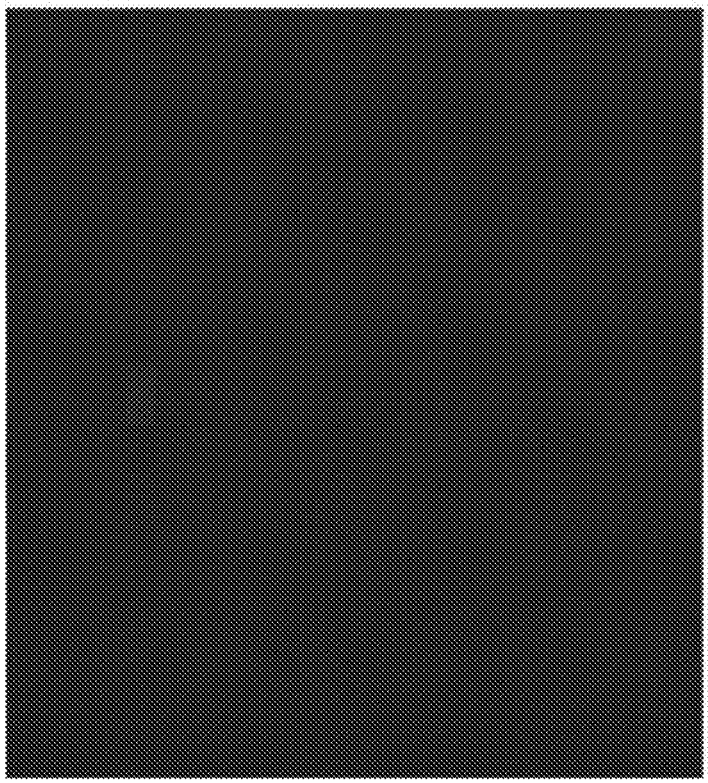
Figure 12E:
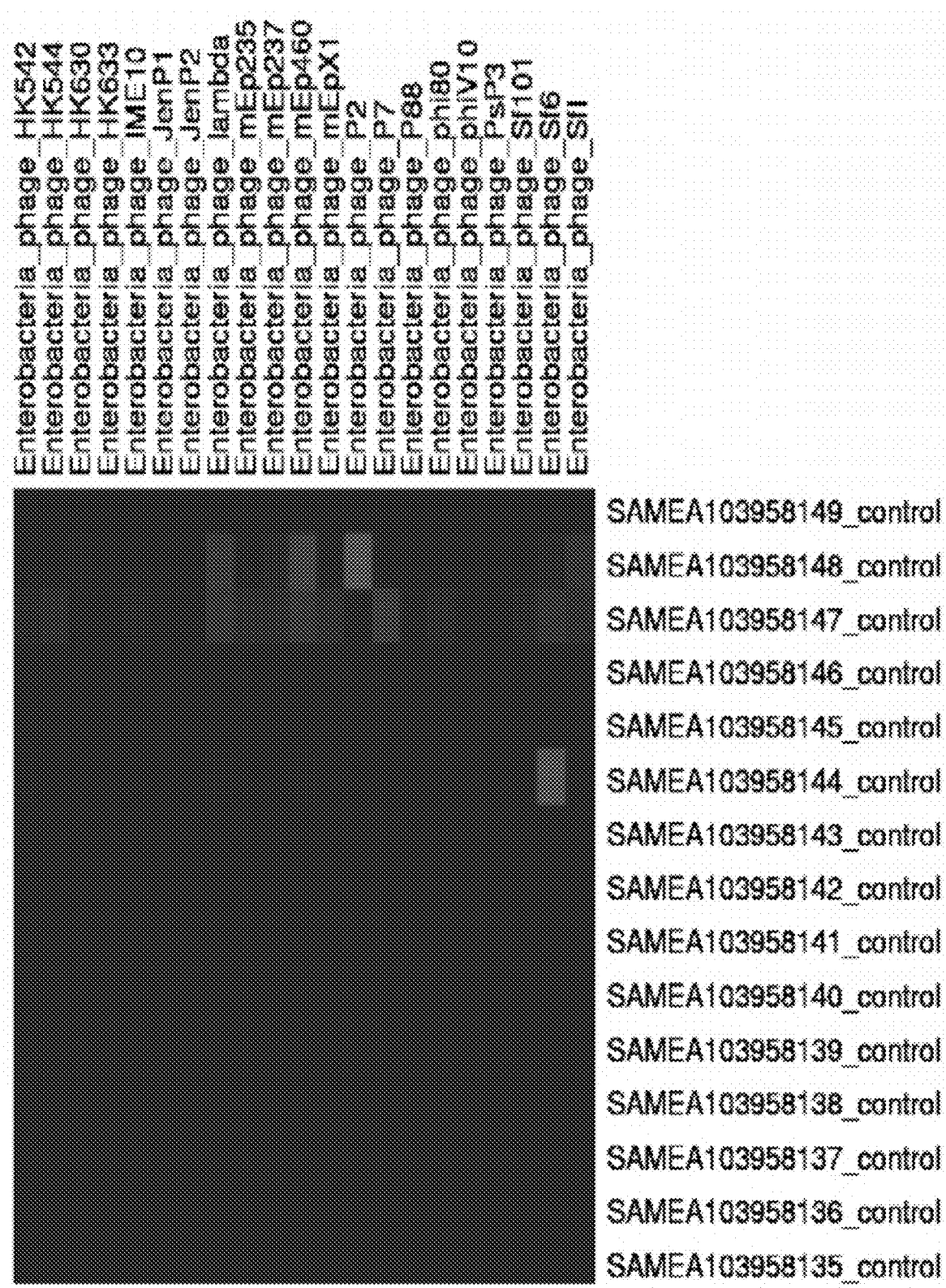
Figure 12E:
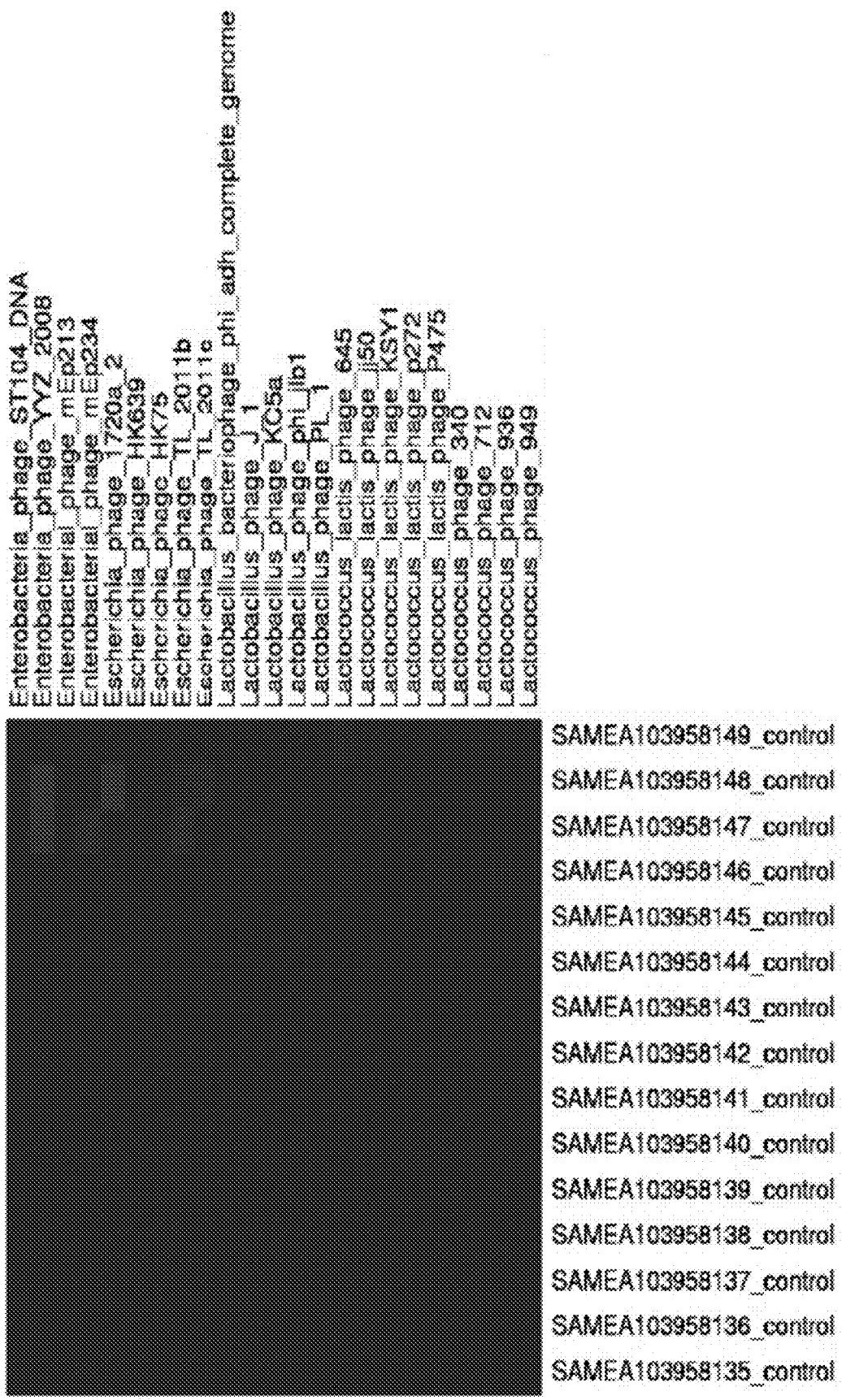
Figure 12G:
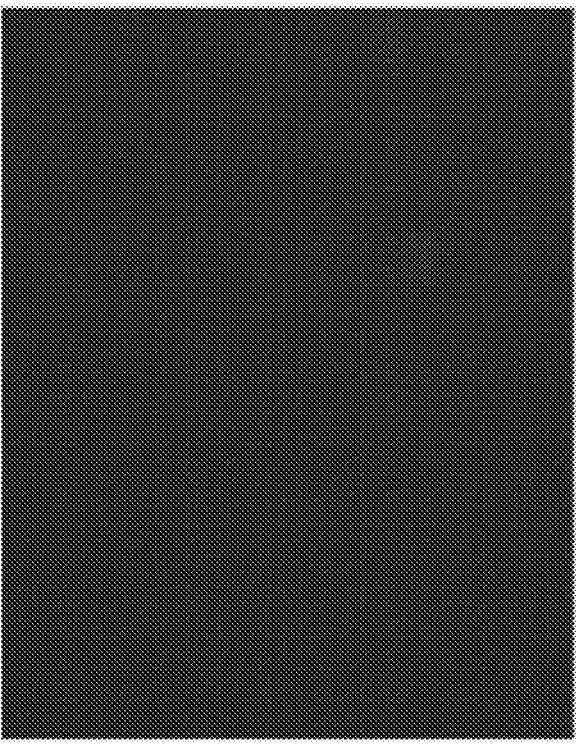
Figure 12G:
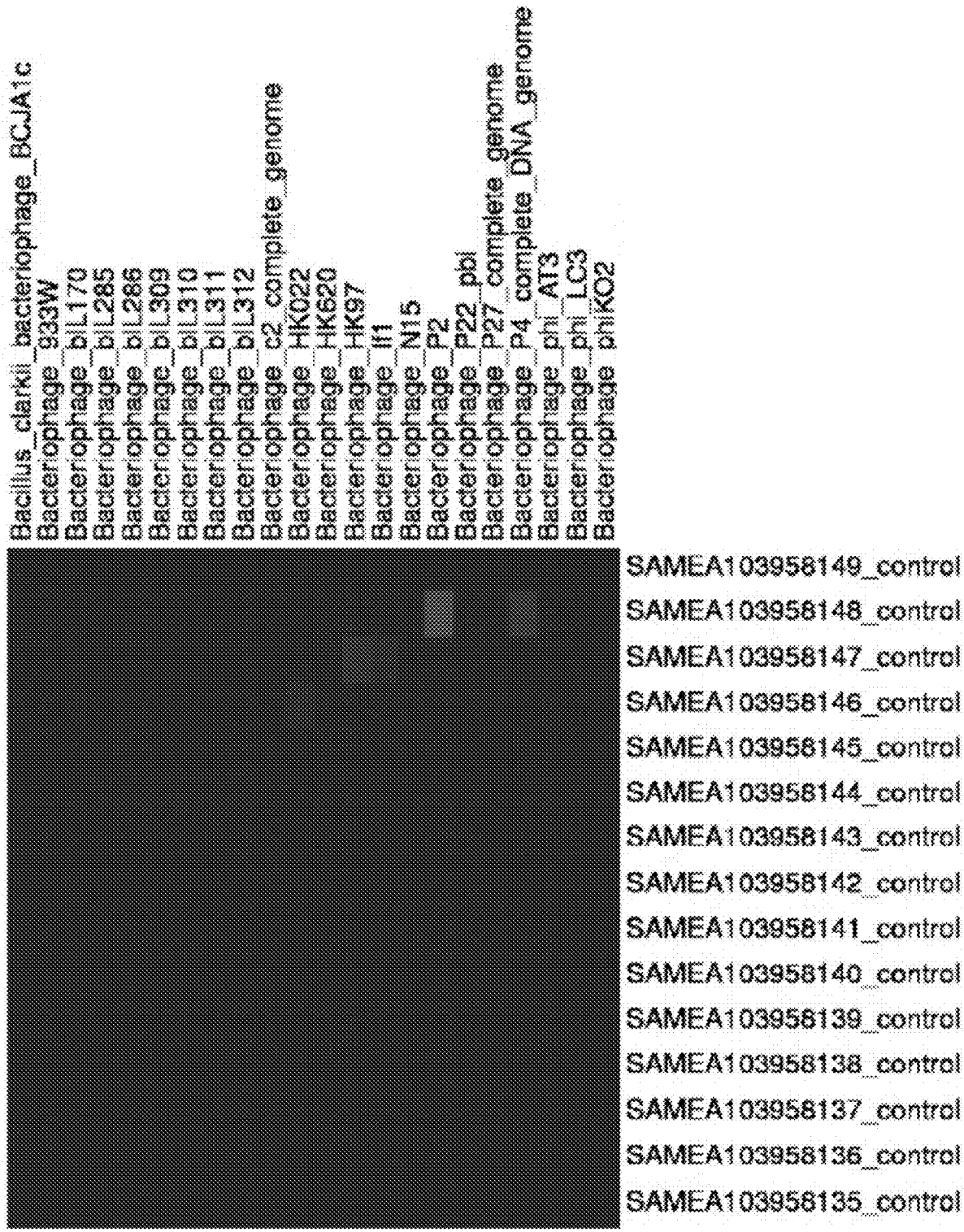
Figure 12H:
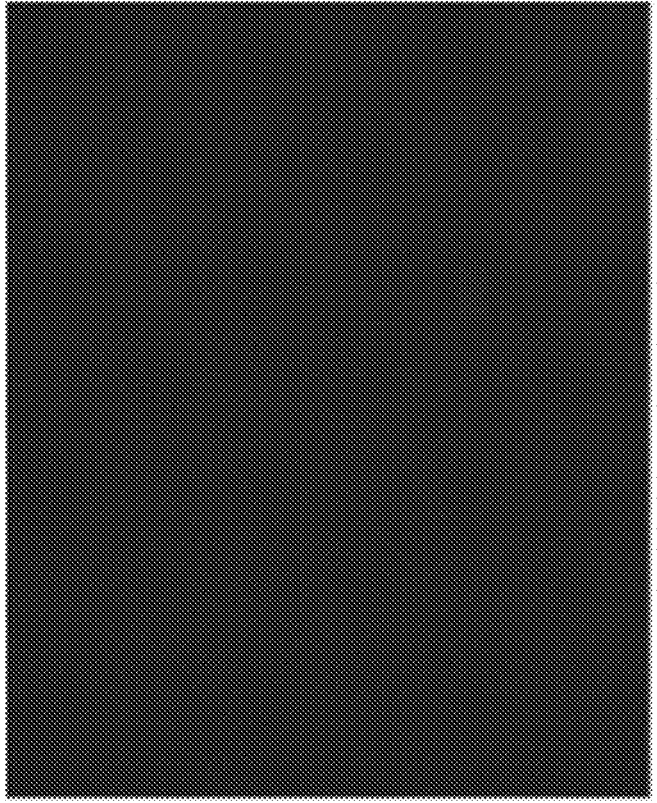
Figure 12I:
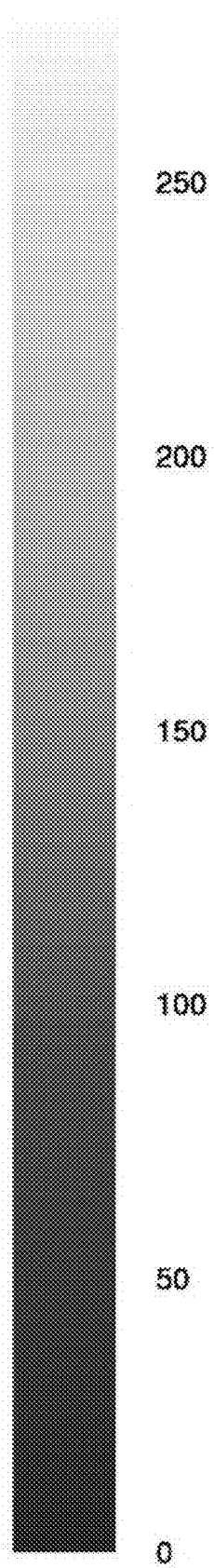
Figure 12J:
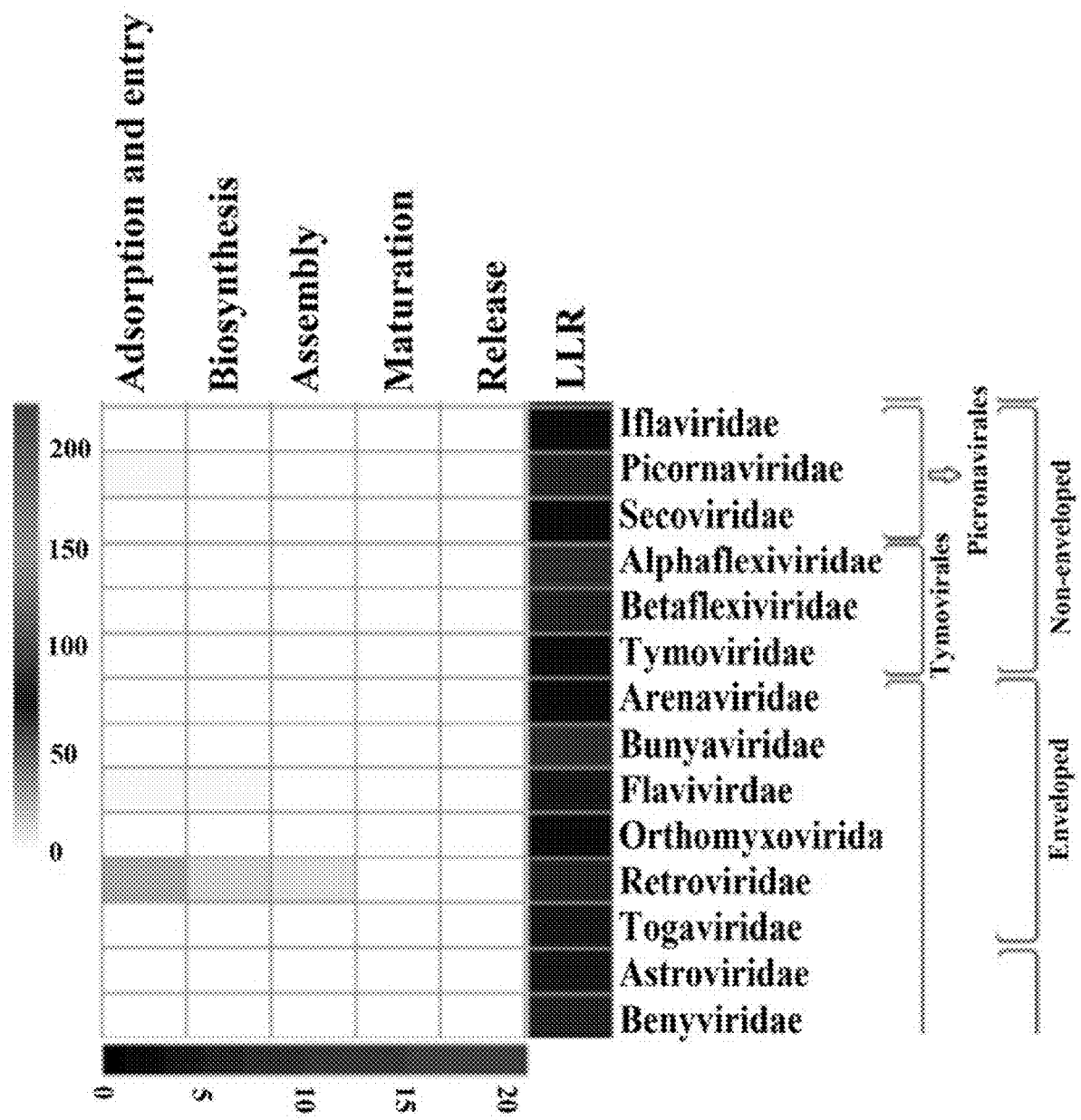
Figure 12J:
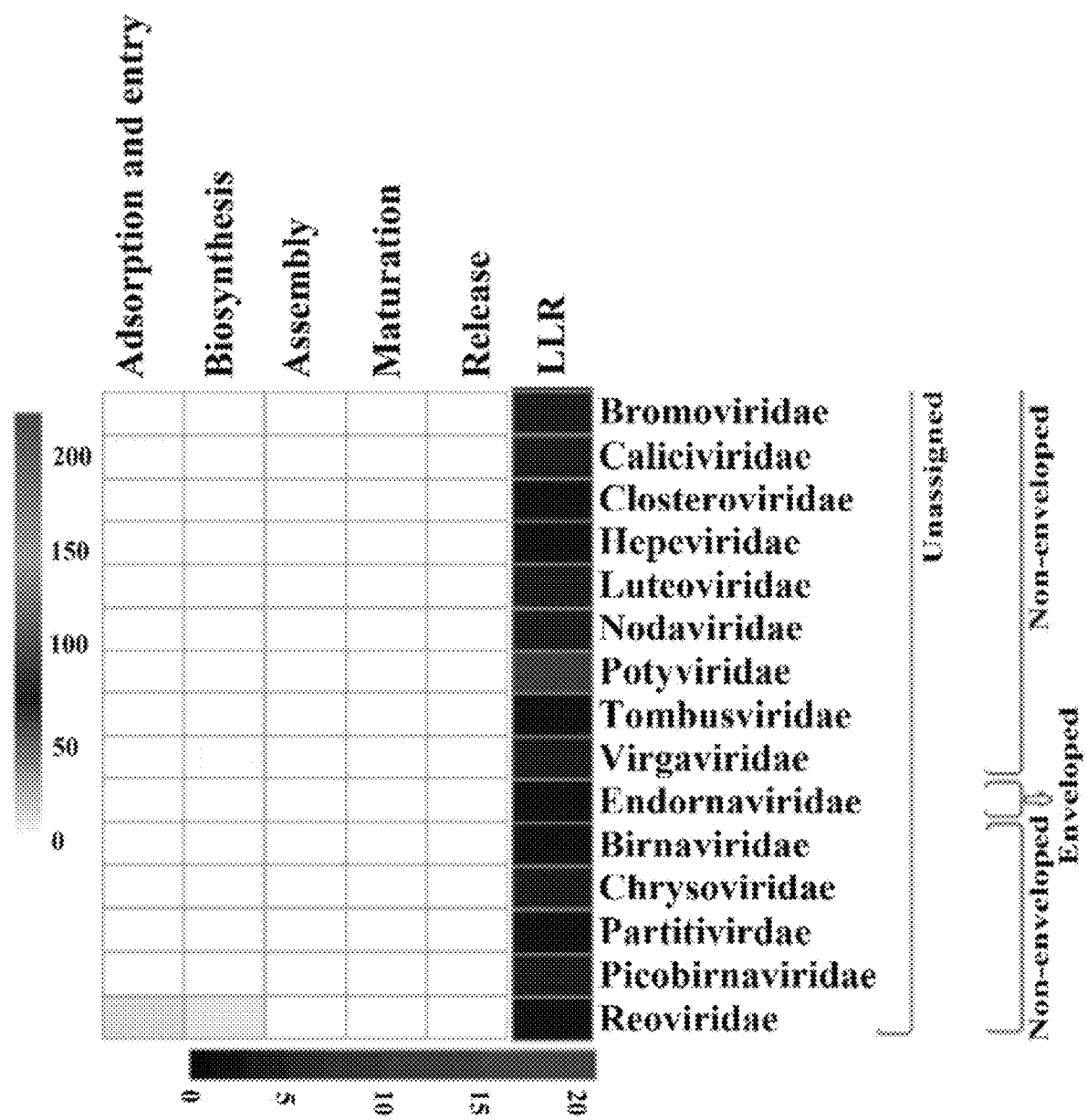
Figure 12J:
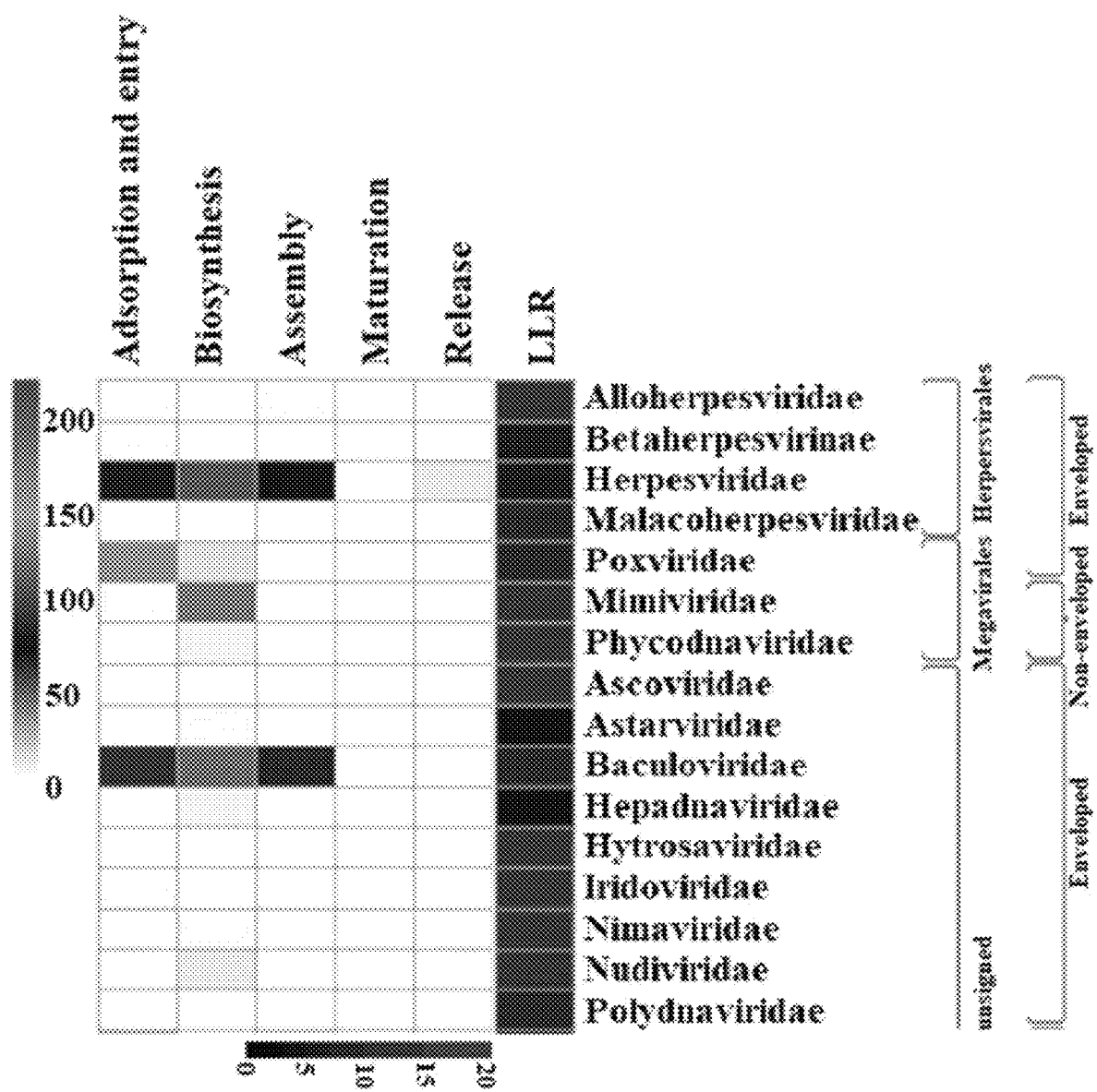
Figure 12J:
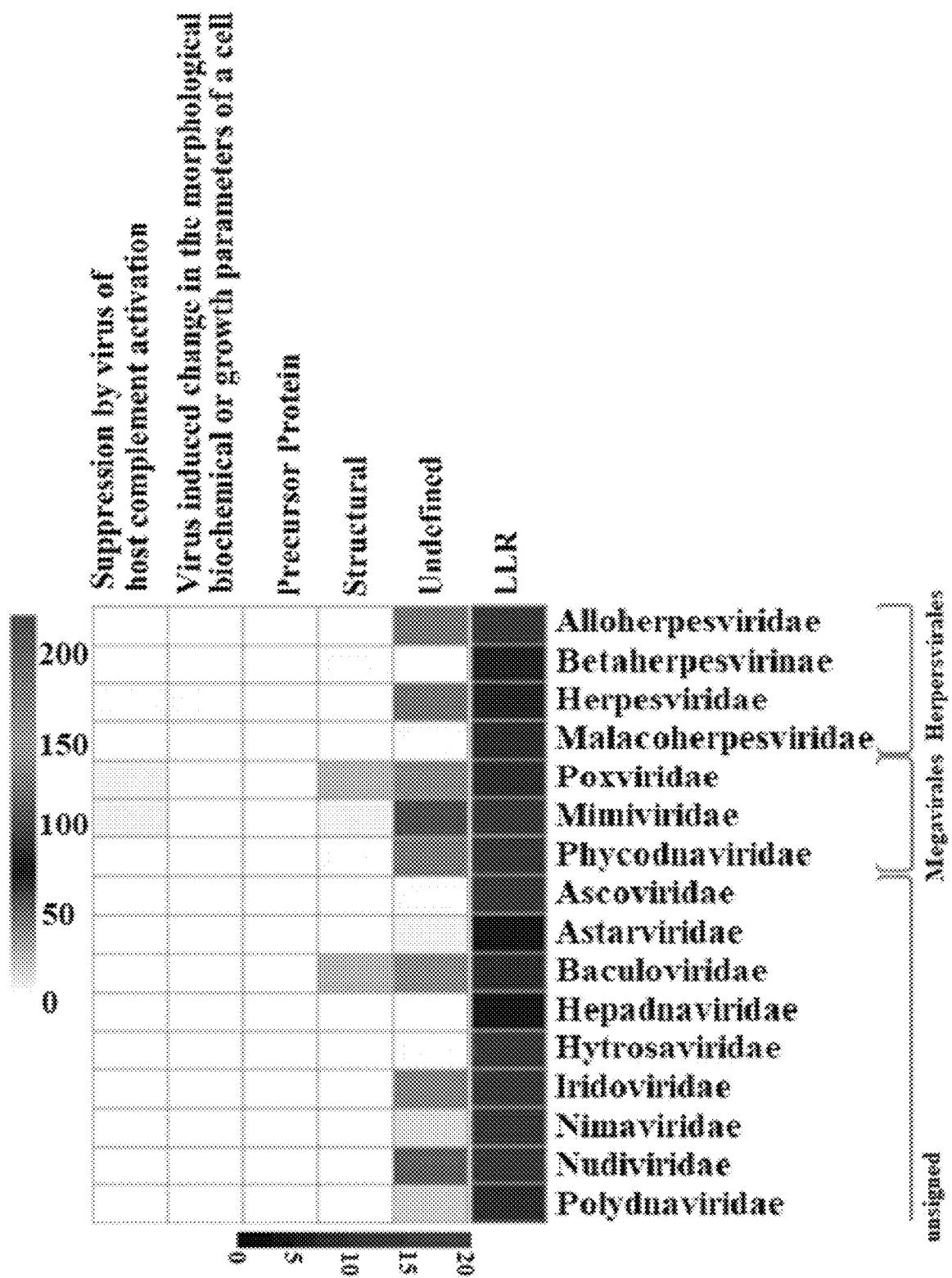
Figure 12J:
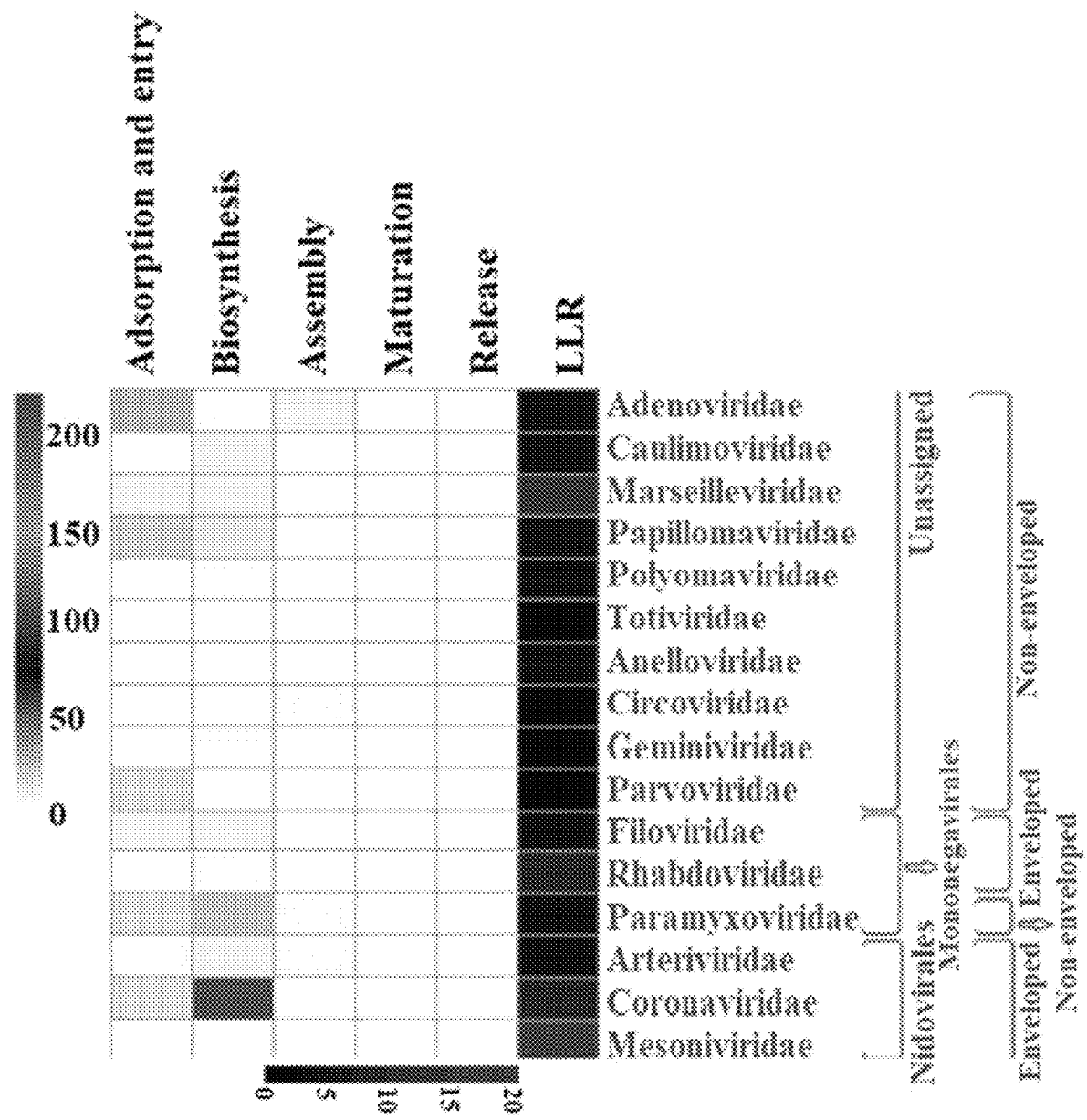
Figure 12J:
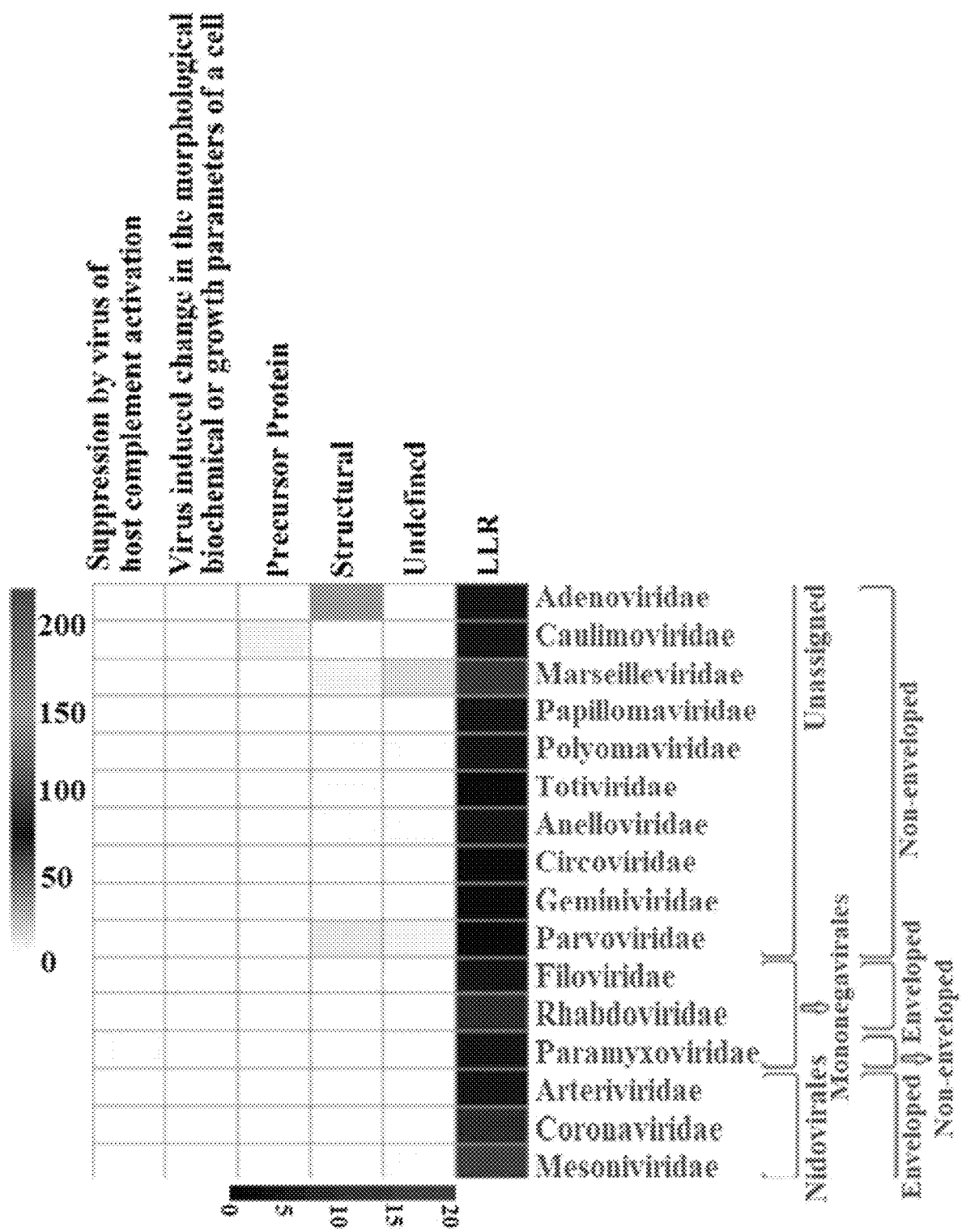

Among these, several short protein sequences were found to harbor a higher number of Q-rich domains than the longer ones. This indicates that the scores obtained in the analysis of protein sequences according to their prion-like characteristics do not correlate only with the size of a protein. The analysis of proteins with the known functions showed that the proteins involved in the replication of bacteriophage DNA and protein synthesis have the largest LLR scores. No direct correlation was observed between the functions of proteins containing PrDs and the LLR score. One of both highest and lowest LLR scores were obtained for the single-stranded DNA binding protein of *Listeria* bacteriophage LMSP-25 (LLR score, 45.89; Myoviridae) and the *Streptococcus* bacteriophage 5093 (LLR 1.97; Siphoviridae), respectively (FIGS. 8A and 8B).

Additionally, the inventors analyzed the proteome enrichment with PrDs in the bacteriophages of different bacteria. The highest enrichment rate, with at least five PrDs per proteome, was found among the bacteriophages of *Bacillus, Cronobacter, Lactobacillus, Synechococcus, Staphylococcus*, and other bacteria (FIGS. 10A-10D; Table 18).

TABLE 18

Correlation between the number of PrD per phage and the proteome size

| Phage name | # PrD per proteome |
|---|---|
| *Achromobacter_phage_JWAlpha* | 5 |
| *Acidianus_two-tailed_virus* | 6 |
| *Acinetobacter_phage_Acj61* | 5 |
| *Acinetobacter_phage_ZZ1* | 5 |
| *Aeromonas_phage_CC2* | 5 |
| *Aeromonas_phage_PX29* | 6 |
| *Aeromonas_virus_65* | 7 |
| *Bacillus_phage_AR9* | 6 |
| *Bacillus_phage_BCP78* | 13 |
| *Bacillus_phage_BCP8-2* | 5 |
| *Bacillus_phage_Bp8p-T* | 6 |
| *Bacillus_phage_Deep_Blue* | 5 |
| *Bacillus_phage_DirtyBetty* | 5 |
| *Bacillus_phage_Eldridge* | 7 |
| *Bacillus_phage_Gamma* | 5 |
| *Bacillus_phage_Hakuna* | 5 |
| *Bacillus_phage_JBP901* | 7 |
| *Bacillus_phage_Mater* | 7 |
| *Bacillus_phage_Megatron* | 5 |
| *Bacillus_phage_Moonbeam* | 8 |
| *Bacillus_phage_Nemo* | 5 |
| *Bacillus_phage_Nigalana* | 5 |
| *Bacillus_phage_NotTheCreek* | 8 |
| *Bacillus_phage_Phrodo* | 5 |
| *Bacillus_phage_SageFayge* | 5 |
| *Bacillus_phage_TsarBomba* | 7 |
| *Bacillus_virus_Agate* | 5 |
| *Bacillus_virus_Bastille* | 5 |
| *Bacillus_virus_Bobb* | 6 |
| *Bacillus_virus_Bp8pC* | 6 |
| *Bacillus_virus_G* | 9 |
| *Bacillus_virus_Pascal* | 5 |
| *Brucella_phage_Pr* | 10 |
| *Brucella_phage_Tb* | 13 |
| *Burkholderia_virus_Bcepil02* | 5 |
| *Campylobacter_virus_CP220* | 6 |
| *Campylobacter_virus_IBB35* | 5 |
| *Caulobacter_phage_Cr30* | 5 |
| *Cronobacter_phage_CR5* | 6 |
| *Cronobacter_phage_vB_CsaM_GAP32* | 12 |
| *Cyanophage* P-RSM3 | 6 |
| *Cyanophage_PP* | 5 |
| *Cyanophage_P-RSM1* | 5 |
| *Cyanophage_P-RSM6* | 11 |
| *Cyanophage_P-TIM40* | 15 |
| *Cyanophage_S-RIM32* | 6 |
| *Cyanophage_S-RIM50* | 6 |
| *Cyanophage_S-TIM5* | 7 |
| *Enterobacteria_phage_f1* | 5 |
| *Enterobacteria_phage_M13* | 13 |
| *Enterobacteria_phage_NJ01* | 5 |
| *Enterobacteria_phage_phiJLA23* | 5 |
| *Enterobacteria_phage_PRD1* | 15 |
| *Enterobacteria_phage_RB27* | 27 |
| *Enterobacteria_phage_RB51* | 5 |
| *Enterobacteria_phage_T4_sensu_lato* | 29 |
| *Enterobacteria_phage_vB_KleM-RaK2* | 17 |
| *Erwinia_phage_Ea35-70* | 13 |
| *Erwinia_phage_phiEa21-4* | 6 |
| *Erwinia_phage_PhiEaH1* | 6 |
| *Erwinia_phage_vB_EamM_Asesino* | 5 |
| *Erwinia_phage_vB_EamM_EarlPhillipIV* | 6 |
| *Erwinia_phage_vB_EamM_Huxley* | 6 |
| *Erwinia_phage_vB_EamM_Kwan* | 5 |
| *Erwinia_phage_vB_EamM_Phobos* | 5 |
| *Escherichia_phage_121Q* | 10 |
| *Escherichia_phage_172-1* | 7 |
| *Escherichia_phage_ECBP2* | 5 |
| *Escherichia_phage_KBNP1711* | 5 |
| *Escherichia_phage_PBECO_4* | 12 |
| *Escherichia_phage_T5* | 5 |
| *Escherichia_virus_AR1* | 6 |
| *Escherichia_virus_E41c* | 5 |
| *Escherichia_virus_KP26* | 6 |
| *Escherichia_virus_MS2* | 50 |
| *Escherichia_virus_phiEco32* | 6 |
| *Escherichia_virus_Rogue1* | 5 |
| *Klebsiella_phage_K64-1* | 14 |
| *Lactobacillus_phage_ATCC_8014-B2* | 5 |
| *Lactobacillus_phage_Lb338-1* | 6 |
| *Lactobacillus_phage_LfeInf* | 12 |
| *Lactobacillus_phage_LP65* | 7 |
| *Lactococcus_phage_1706* | 5 |
| *Lactococcus_phage_936_sensu_lato* | 13 |
| *Microcystis_aeruginosa_phage_Ma-LMM01* | 5 |
| *Mycobacterium_phage_Alice* | 5 |
| *Mycobacterium_phage_ET08* | 5 |
| *Mycobacterium_phage_Cali* | 5 |
| *Pectobacterium_bacteriophage_PM2* | 6 |
| *Phormidium_phage_Pf-WMP3* | 5 |
| *Prochlorococcus_phage_MED4-213* | 8 |
| *Prochlorococcus_phage_P-HM1* | 9 |
| *Prochlorococcus_phage_P-HM2* | 11 |
| *Prochlorococcus_phage_P-RSM4* | 13 |
| *Prochlorococcus_phage_P-SSM2* | 26 |
| *Prochlorococcus_phage_P-SSM3* | 10 |
| *Prochlorococcus_phage_P-SSM7* | 8 |
| *Prochlorococcus_phage_P-SSM5* | 7 |
| *Prochlorococcus_phage_P-TIM68* | 12 |
| *Prochlorococcus_phage_Syn1* | 10 |
| *Prochlorococcus_phage_Syn33* | 11 |
| *Pseudomonas_phage_201phi2-1* | 9 |
| *Pseudomonas_phage_EL* | 6 |
| *Pseudomonas_phage_OBP* | 9 |
| *Pseudomonas_phage_phi-2* | 6 |
| *Pseudomonas_phage_phiKZ* | 5 |
| *Pseudomonas_phage_PhiPA3* | 6 |
| *Ralstonia_phage_RSL2* | 9 |
| *Shigella_phage_SHFML-11* | 5 |
| *Staphylococcus_phage_812* | 13 |
| *Staphylococcus_phage_phi5967PVL* | 5 |
| *Staphylococcus_phage_phiBB-SEP1* | 7 |
| *Staphylococcus_phage_phiPLA-C1C* | 5 |
| *Staphylococcus_phage_Sb-1* | 5 |
| *Staphylococcus_phage_Slt* | 5 |
| *Staphylococcus_phage_Stau2* | 7 |
| *Staphylococcus_phage_Twort* | 7 |
| *Staphylococcus_phage_vB_SauM_Remus* | 6 |
| *Staphylococcus_phage_vB_SauM_Romulus* | 6 |
| *Staphylococcus_virus_A5W* | 5 |
| *Staphylococcus_virus_G1* | 6 |
| *Staphylococcus_virus_IME-SA1* | 6 |
| *Staphylococcus_virus_ISP* | 5 |
| *Staphylococcus_virus_JD7* | 5 |
| *Staphylococcus_virus_K* | 5 |
| *Staphylococcus_virus_MCE2014* | 5 |
| *Staphylococcus_virus_MSA6* | 6 |
| *Staphylococcus_virus_P4W* | 6 |
| *Staphylococcus_virus_S253* | 5 |
| *Staphylococcus_virus_SA11* | 7 |
| *Staphylococcus_virus_SA12* | 5 |
| *Staphylococcus_virus_Staph1N* | 5 |
| *Sulfolobus_virus_STSV1* | 5 |
| *Sulfolobus_virus_STSV2* | 5 |
| *Synechococcus_phage_ACG-2014b* | 45 |
| *Synechococcus_phage_ACG-2014c* | 30 |
| *Synechococcus_phage_ACG-2014d* | 114 |
| *Synechococcus_phage_ACG-2014e* | 18 |
| *Synechococcus_phage_ACG-2014f* | 173 |
| *Synechococcus_phage_ACG-2014g* | 6 |
| *Synechococcus_phage_ACG-2014h* | 8 |
| *Synechococcus_phage_ACG-2014i* | 12 |
| *Synechococcus_phage_ACG-2014j* | 27 |
| *Synechococcus_phage_metaG-MbCM1* | 11 |
| *Synechococcus_phage_S-CAM1* | 20 |
| *Synechococcus_phage_S-CAM8* | 27 |
| *Synechococcus_phage_S-CBP1* | 5 |
| *Synechococcus_phage_S-CRM01* | 7 |

TABLE 18-continued

Correlation between the number of
PrD per phage and the proteome size

| Phage name | # PrD per proteome |
|---|---|
| Synechococcus_phage_S-IOM18 | 12 |
| Synechococcus_phage_S-MbCM100 | 50 |
| Synechococcus_phage_S-PM2 | 13 |
| Synechococcus_phage_S-RIM2 | 46 |
| Synechococcus_phage_S-RIM8 | 36 |
| Synechococcus_phage_S-RSM4 | 6 |
| Synechococcus_phage_S-ShM2 | 18 |
| Synechococcus_phage_S-SM1 | 7 |
| Synechococcus_phage_S-SM2 | 6 |
| Synechococcus_phage_S-SSM4 | 18 |
| Synechococcus_phage_S-SSM5 | 9 |
| Synechococcus_phage_S-SSM7 | 16 |
| Synechococcus_phage_S-WAM1 | 9 |
| Synechococcus_phage_S-WAM2 | 8 |
| Synechococcus_phage_Syn19 | 24 |
| Synechococcus_phage_syn9 | 13 |
| Thermus_phage_phiYS40 | 6 |
| Vibrio_phage_ICP2 | 9 |
| Vibrio_phage_KVP40 | 7 |
| Yersinia_virus_PST | 5 |

However, the highest numbers of PrDs per proteome were found across *Prochlorococcus* and *Synechococcus* phages, whose hosts are represented by evolutionary ancient Cyanobacteria (FIGS. 10A-10D) (Schirrmeister et al. 2011). This finding along with the higher prevalence of PrDs in archaeal phages suggests a possible association of the presence of PrDs and "evolutionary age". Regardless, the enrichment of PrDs in the most abundant phages on Earth infecting marine *Prochlorococcus and Synechococcus suggests a possible particular role of these elements* (Sullivan et al., 2010).

To determine the potential correlations between the functions of PrD-containing proteins, bacteriophage families, and host organisms, the inventors generated a heatmap (FIG. 3) that showed that the highest LLRs were found among Myoviridae and Siphoviridae members of Moraxellaceae, Listeriaceae, and Pseudoalteromonadaceae, which were shown to be associated with replication of phage DNA, protein synthesis, and bacteriophage assembly. However, these data do not correspond to the frequency of PrD in bacteriophage proteomes. A vast majority of the bacteriophage PrD-containing proteins are involved in the interactions between a bacteriophage and bacterial cell wall, their attachment and penetration, and the release of progeny phages.

The majority of these bacteriophages containing more than five PrDs per one proteome was shown to belong to the Myoviridae family. Since the members of this family have larger proteomes compared with those of other bacteriophage families, a direct correlation between the number of PrDs per bacteriophage and the proteome (p<0.05) was found. At the same time, no correlations were observed within any bacteriophage family (FIG. 11). Notably, the particular enrichment with PrDs was found across the majority of Prochlorococcus and Synechococcus cyanophages identified as PrD carriers in this study.

Example 16: Analysis of Structural Domains Associated with to Bacteriophage PrDs In analyzing the functions of bacteriophage proteins with PrDs, the identified domains were clustered into five groups, according to the major steps during the process of bacteriophage interactions with its host cell (Marvin 1988). The proteins were grouped as follows, based on their functions during the interactions with the bacterial host cells (a) attachment and penetration, (b) replication of bacteriophage DNA and protein synthesis, (c) assembly, (d) release, and (e) unknown functions (Laemmli 1970; Marvin 1988; Zylicz et al., 1989; Rakhuba et al., 2010; Aksyuk and Rossmann 2011). The obtained correlations between the LLR scores, bacterial and bacteriophage families, and protein functions were analyzed. FIGS. 9A-9H display the results of such analysis.

The most abundant (2046 PrPs; medium LLR score 4.86) functional group was shown to be the attachment and penetration group, which included the proteins associated with the host cell binding and genome injection. The inventors identified receptor binding proteins, tail fiber proteins, peptidase_M23 baseplate wedge components, lysins, and other proteins known to have crucial functions in the various aspects of phage infection, including adsorption, peptidoglycan hydrolysis, cell wall penetration, and DNA ejection. However, the PrDs were predominantly found among tail component, tail fiber, and baseplate proteins (Rodríguez-Rubio et al., 2012, Stockdale et al., 2013). Furthermore, a PrD was identified in gp98/99 proteins that form the cell-puncturing device of *Mycobacterium* phages. Some of the identified proteins associated with surface structures, such as tail tube cap, are not involved in the direct contact with the bacterial cell, but they represent important structural components allowing the injection of DNA (Arisaka et al., 2003; Orlova 2012). The results of the heatmap analysis in FIGS. 9A-9H showed that Podoviridae belonging to the Mycobacteriaceae family and Myoviridae of Listeriaceae have the highest LLR score.

The second largest group was shown to contain 390 PrDs (medium LLR score, 7.93) involved in the replication of phage DNA and protein synthesis. The inventors identified several Erf proteins, essential for bacteriophage DNA recombination, proteins belonging to glycosyltransferase family protecting bacteriophage DNA from degradation, and single-strand binding proteins (Markine-Goriaynoff et al., 2004). Other identified proteins included those involved in the regulation of host cell metabolism, such as serine/threonine phosphatases (Howard-Varona et al., 2017). The highest average LLR score was obtained for the members of Myoviridae family of Moraxellaceae and Listeriaceae (FIGS. 9A-9H).

Following this, proteins with PrDs that are associated with the bacteriophage assembly in the host cells (170 proteins; medium LLR score, 6.16) were analyzed. These proteins were identified in all major families of Caudovirales. The highest average LLR score was obtained for the proteins of Myoviridae family of Moraxellaceae (FIGS. 9A-9H), which are also associated with the organization and maturation of bacteriophages, and those involved in the tail assembly and DNA packaging (Linderoth et al., 1994; Boudko et al., 2002; Aksyuk and Rossmann, 2011).

Fewer PrDs were identified in proteins that are involved in cell wall lysis and the release of bacteriophages from the host cells. This group contained only 105 proteins (medium LLR score, 5.13) and predominantly comprised lysins, including those with the amidase activity and proteins with peptidoglycan binding functions (hydrolases, D-ala-D-ala carboxypeptidase, endopeptidase CHAP domain protein, and others), which are involved in bacterial cell wall degradation, resulting in cell lysis and release of progeny viruses. They were predominantly detected among Siphoviridae infecting Streptococcaceae and Mycobacteriaceae.

The highest average LLR score was obtained in Myoviridae family of Moraxellaceae (FIGS. 9A-9H).

Finally, 2329 PrDs were identified among the proteins with the still unknown functions. Among these proteins in *Staphylococcus* bacteriophages belonging to the Siphoviridae family, the inventors identified Panton-Valentine leukocin (LukS-PV), a cytotoxin associated with the increased virulence of *Staphylococcus aureus*, which can induce a considerable tissue damage (Vandenesch et al., 2003).

Example 17: Bacterial Community Composition in PD

To explore the bacterial community structure in PD, shotgun metagenomics sequencing data of the faecal microbiome from 31 patients with PD and 28 control individuals were used (Bedarf, J. et al., 2017). The analysis was based on a study described in Bedarf et al. involving 31 PD patients and 28 gender- and age-matched non-Parkinsonian individuals (Bedarf, J. et al., 2017; Misof, B. et al., Science, Nov. 7, 2014, 346(6210):763-767). The patients had early-stage PD (onset of motor symptoms and diagnosis within the past year) not yet treated with L-DOPA, which is known to affect intestinal motility and possibly gut microbiota composition. Patients with chronic and inflammatory gastrointestinal diseases, including chronic constipation, and atypical and/or secondary parkinsonism, as well as those using laxatives, immunosuppressants, or antibiotics in the past three months were excluded. Although three PD patients and three control subjects were included despite the intake of antibiotics (up to three days) in a period of 28-34 days prior to faeces sampling, the omission of those cases from the analyses had no impact on the results (Bedarf, J. et al., 2017). The demographic parameters of study participants are presented in Table 30 (Bedarf, J. et al., 2017).

From the metagenomic data generated in the study of Bedarf, J. et al. described above, an analysis involving comparison of the phagobiota and its correlation with the bacterial component of GI microbiota between PD patients and non-Parkinsonian individuals was undertaken. The analysis was designed to reveal alterations in bacteriophage composition potentially associated with the initiation or progression of PD. Bacteria and phages with differential abundance in the PD and control group were identified. The identified phages were clustered according to their bacterial hosts. The phage/bacteria ratio was evaluated for each individual to allow for determination on whether shifts in bacterial composition resulted from phage infection or may reflect pathophysiological changes in PD patients affecting gut microbiota. Samples of the microbiota from each patient were subjected to sequencing and processing. DNA sequencing data were generated by Illumina Hiseq4000 paired-end shotgun sequencing. Short sequence reads were retrieved from NCBI SRA (see www.ncbi.nlm.nih.gov/bioproject/382085; Bedarf, J. et al., 2017). Sequences were quality-filtered to remove adaptor contamination, low-quality reads with minimum quality score cut-off of 20, sequences with <45 nucleotides, and human DNA. In the analysis of bacteria, sequences were grouped into OTUs with a 97% threshold of pairwise identity (Edgar, R. et al., 2010).

All reads were assembled de novo in each SRA file and the assembled contigs were tested against MetaPhlAn, which operates by mapping sequence reads to a database of predefined clade-specific marker genes, and HPviewer databases (Segata, N. et al., 2012; Hao, Yuhan, 2017). The resulting counts were normalized for total marker gene length and outliers, yielding profiles of the presence/absence and abundance of marker genes, and clade-relative abundance (Franzosa, E. et al., 2014).

HiSeq-mediated sequencing produced a total of 1,792,621,232 reads with an average of 30,383,411 reads per sample. Operational taxonomic units (OTUs) were defined as a set of sequence reads with a similarity cut-off of 97% (Schloss, P. et al., 2009).

The QIIME pipeline was used for quality filtering of bacterial and bacteriophage DNA sequences, chimera removal (by the USEARCH software), taxonomic assignment, and calculation of α-diversity, as previously described (Caporaso, J. et al., 2010; Cox, L. et al., 2014). Downstream data analysis and calculation of diversity metrics were performed in R3.3.2 using ggplot2 and phyloseq libraries; DESeq2 was used to calculate logarithm of fold change (Love, M. et al., 2014).

Bacterial and bacteriophage communities at the genus, family, and species levels were characterized based on α- and β-diversities. Calculation of the α-Diversity indices (ACE, Chao 1 richness estimator, Shannon, Simpson, and inverse Simpson) was performed using the phyloseq R library (McMurdie, P. J. et al., 2013). β-Diversity (similarity or difference in bacterial or bacteriophage composition between participants) was assessed based on Bray-Curtis dissimilarity computed using the "levelplot" package of the R software (www.r-project.org) and represented by PCoA (Pérez-Cobas, A. et al., 2012). Differences in α- and β-diversities between datasets were examined by ANOVA and PERMANOVA statistical tests; $p<0.05$ was considered statistically significant.

Differences in richness and diversity between PD and control groups were observed. The richness of bacterial species in the PD microbiome tended to decrease as evidenced by lower values of abundance-based coverage estimator (ACE; $p=0.483$) and Chao1 ($p=0.709$) compared to control). Differences in α-diversity indexes between the PD and control groups were also not statistically significant (Shannon: $p=0.241$; Simpson: $p=0.421$; inverse Simpson: $p=0.428$).

To evaluate possible differences in detail, β-diversity was assessed using the Bray-Curtis dissimilarity index and subjected the results to Principal Coordinate Analysis (PCoA), which revealed high similarity between PD and control samples based on the absence of statistically significant difference in bacterial diversity (Pérez-Cobas, A. et al., 2012; Suchodolski, J. et al., 2009).

The taxonomic composition of microbiome in the PD and control groups was analysed at the genus level. *Bacteroides* was the most abundant genus in both groups, and no statistically significant difference was detected in the presence of *Bifidobacterium, Eggerthella*, and *Adlercreutzia* species. However, a depletion of Prevotellaceae and Lachnospiraceae species was detected in PD patients. Furthermore, an analysis of less abundant families revealed reduced representation of Lactobacillaceae and Streptococcaceae in the PD group.

Example 18: Analysis of Bacteriophage Diversity in PD

Sequence reads were then used to investigate whether there was an overall gain or loss of diversity in bacteriophage composition between the groups (Dethlefsen, L. et al., 2008). A list of bacteriophages with nonzero signaling values is shown in Table 19 below.

TABLE 19

List of Bacteriophages with non-zero Signaling Values

Viruses|_|_|f__Myoviridae|g__Muvirus|s__Enterobacteria_phage_SfMu
Viruses|_|_|f__Myoviridae|g__Muvirus|s__*Escherichia*_phage_D108
Viruses|_|_|f__Myoviridae|g__P1virus|s__*Escherichia*_virus_P1
Viruses|_|_|f__Myoviridae|g__P2virus|s__Enterobacteria_phage_fiAA91-ss
Viruses|_|_|f__Myoviridae|g__P2virus|s__Enterobacteria_phage_P4
Viruses|_|_|f__Myoviridae|g__P2virus|s__*Escherichia*_virus_186
Viruses|_|_|f__Myoviridae|g__P2virus|s__*Escherichia*_virus_P2
Viruses|_|_|f__Myoviridae|g__P2virus|s__*Escherichia*_virus_P2
Viruses|_|_|f__Myoviridae|g__P2virus|s__*Pseudomonas*_phage_phiCTX
Viruses|_|_|f__Myoviridae|g__P2virus|s__*Ralstonia*_phage_RSA1
Viruses|_|_|f__Myoviridae|g__P2virus|s__*Salmonella*_phage_FSL_SP-004
Viruses|_|_|f__Myoviridae|g__P2virus|s__*Salmonella*_virus_PsP3
Viruses|_|_|f__Myoviridae|g__Schizot4virus|s__*Vibrio*_phage_VH7D
Viruses|_|_|f__Myoviridae|g__T4virus|s__*Aeromonas*_phage_phiAS5
Viruses|_|_|f__Myoviridae|g__T4virus|s__*Escherichia*_virus_ECML134
Viruses|_|_|f__Myoviridae|g__T4virus|s__*Yersinia*_virus_D1
Viruses|_|_|f__Myoviridae|g__undef|s__*Bacillus*_virus_G
Viruses|_|_|f__Myoviridae|g__undef|s__*Clostridium*_phage_c-st
Viruses|_|_|f__Myoviridae|g__undef|s__*Clostridium*_phage_phiMMP02
Viruses|_|_|f__Myoviridae|g__undef|s__*Clostridium*_phage_phiMMP03
Viruses|_|_|f__Myoviridae|g__undef|s__*Edwardsiella*_phage_eiAU
Viruses|_|_|f__Myoviridae|g__undef|s__*Edwardsiella*_phage_MSW-3
Viruses|_|_|f__Myoviridae|g__undef|s__Enterobacteria_phage_P88
Viruses|_|_|f__Myoviridae|g__undef|s__Enterobacteria_phage_phiP27
Viruses|_|_|f__Myoviridae|g__undef|s__Enterobacteria_phage_Sfl
Viruses|_|_|f__Myoviridae|g__undef|s__*Escherichia*_phage_PBECO_4
Viruses|_|_|f__Myoviridae|g__undef|s__*Lactobacillus*_phage_KC5a
Viruses|_|_|f__Myoviridae|g__undef|s__*Lactobacillus*_phage_LBR48
Viruses|_|_|f__Myoviridae|g__undef|s__*Lactobacillus*_phage_phi_jlb1
Viruses|_|_|f__Myoviridae|g__undef|s__*Lactobacillus*_phage_phiAQ113
Viruses|_|_|f__Myoviridae|g__undef|s__*Mycobacterium*_phage_Myrna
Viruses|_|_|f__Myoviridae|g__undef|s__*Salmonella*_phage_RE-2010
Viruses|_|_|f__Myoviridae|g__undef|s__*Shigella*_phage_SfII
Viruses|_|_|f__Myoviridae|g__undef|s__*Shigella*_phage_SfIV
Viruses|_|_|f__Myoviridae|g__undef|s__*Synechococcus*_phage_S-SSM7
Viruses|_|_|f__Podoviridae|g__Bcep22likevirus|s__*Burkholderia*_virus_Bcepmigl
Viruses|_|_|f__Podoviridae|g__Epsilon15virus|s__*Escherichia*_phage_phiV10
Viruses|_|_|f__Podoviridae|g__Epsilon15virus|s__*Escherichia*_phage_TL-2011b
Viruses|_|_|f__Podoviridae|g__Kp34virus|s__*Klebsiella*_virus_F19
Viruses|_|_|f__Podoviridae|g__Kp34virus|s__*Klebsiella*_virus_K244
Viruses|_|_|f__Podoviridae|g__Kp34virus|s__*Klebsiella*_virus_KP34
Viruses|_|_|f__Podoviridae|g__Kp34virus|s__*Klebsiella*_virus_SU503
Viruses|_|_|f__Podoviridae|g__Kp34virus|s__*Klebsiella*_virus_SU552A
Viruses|_|_|f__Podoviridae|g__P22virus|s__Enterobacteria_phage_CUS-3
Viruses|_|_|f__Podoviridae|g__P22virus|s__Enterobacteria_phage_ST104
Viruses|_|_|f__Podoviridae|g__P22virus|s__*Salmonella*_phage_epsilon34
Viruses|_|_|f__Podoviridae|g__P22virus|s__*Salmonella*_phage_g341c
Viruses|_|_|f__Podoviridae|g__P22virus|s__*Salmonella*_phage_HK620
Viruses|_|_|f__Podoviridae|g__P22virus|s__*Salmonella*_phage_ST160
Viruses|_|_|f__Podoviridae|g__P22virus|s__*Salmonella*_phage_vB_SemP
Viruses|_|_|f__Podoviridae|g__P22virus|s__*Salmonella*_virus_P22
Viruses|_|_|f__Podoviridae|q__P22virus|s__*Salmonella*_virus_P22
Viruses|_|_|f__Podoviridae|g__P22virus|s__*Shigella*_phage_Sf6
Viruses|_|_|f__Podoviridae|g__Sp6virus|s__*Escherichia*_virus_K1E
Viruses|_|_|f__Podoviridae|g__undef|s__Enterobacteria_phage_933W_
Viruses|_|_|f__Podoviridae|g__undef|s__Enterobacteria_phage_IME10
Viruses|_|_|f__Podoviridae|g__undef|s__Enterobacteria_phage_Sf101
Viruses|_|_|f__Podoviridae|g__undef|s__*Escherichia_coli*_O157
Viruses|_|_|f__Podoviridae|g__undef|s__*Escherichia*_phage_1720a-02
Viruses|_|_|f__Podoviridae|g__undef|s__*Escherichia*_phage_Pollock
Viruses|_|_|f__Podoviridae|g__undef|s__*Escherichia*_phage_TL-2011c
Viruses|_|_|f__Podoviridae|g__undef|s__*Lactococcus*_phage_KSY1
Viruses|_|_|f__Podoviridae|g__undef|s__*Salmonella*_phage_SPN9CC
Viruses|_|_|f__Podoviridae|g__undef|s__*Shigella*_phage_75/02_Stx
Viruses|_|_|f__Podoviridae|g__undef|s__*Shigella*_phage_POCJ13
Viruses|_|_|f__Podoviridae|g__undef|s__*Streptococcus*_phage_phi30c
Viruses|_|_|f__Podoviridae|g__undef|s__*Streptococcus*_phage_phi7917
Viruses|_|_|f__Podoviridae|g__undef|s__Stx2-converting_phage_86
Viruses|_|_|f__Siphoviridae|g__C2virus|s__*Lactococcus*_phage_blL67
Viruses|_|_|f__Siphoviridae|g__C2virus|s__*Lactococcus*_phage_c2
Viruses|_|_|f__Siphoviridae|g__Cjw1virus|s__*Mycobacterium*_phage_Toto
Viruses|_|_|f__Siphoviridae|g__D3virus|s__*Pseudomonas*_phage_D3
Viruses|_|_|f__Siphoviridae|g__D3virus|s__*Pseudomonas*_phage_PMG1
Viruses|_|_|f__Siphoviridae|g__Hk578virus|s__*Escherichia*_phage_HK578
Viruses|_|_|f__Siphoviridae|g__Hk578virus|s__*Escherichia*_virus_JL1
Viruses|_|_|f__Siphoviridae|g__Hk578virus|s__*Escherichia*_virus_SSL2009a
Viruses|_|_|f__Siphoviridae|g__Hk578virus|s__*Shigella*_phage_EP23
Viruses|_|_|f__Siphoviridae|g__Hk578virus|s__*Sodalis*_phage_SO1

TABLE 19-continued

List of Bacteriophages with non-zero Signaling Values

Viruses|_|_|f_Siphoviridae|g_Jerseyvirus|s_*Salmonella*_phage_SE2
Viruses|_|_|f_Siphoviridae|g_Lambdavirus|s_Enterobacteria_phage_BP-4795
Viruses|_|_|f_Siphoviridae|g_Lambdavirus|s_Enterobacteria_phage_cdtI
Viruses|_|_|f_Siphoviridae|g_Lambdavirus|s_Enterobacteria_phage_HK140
Viruses|_|_|f_Siphoviridae|g_Lambdavirus|s_Enterobacteria_phage_HK225
Viruses|_|_|f_Siphoviridae|g_Lambdavirus|s_Enterobacteria_phage_HK446
Viruses|_|_|f_Siphoviridae|g_Lambdavirus|s_Enterobacteria_phage_HK630
Viruses|_|_|f_Siphoviridae|g_Lambdavirus|s_Enterobacteria_phage_HK633
Viruses|_|_|f_Siphoviridae|g_Lambdavirus|s_Enterobacteria_phage_mEp043_c-1
Viruses|_|_|f_Siphoviridae|g_Lambdavirus|s_Enterobacteria_phage_mEp235
Viruses|_|_|f_Siphoviridae|g_Lambdavirus|s_Enterobacteria_phage_mEp237
Viruses|_|_|f_Siphoviridae|g_Lambdavirus|s_Enterobacteria_phage_mEp460
Viruses|_|_|f_Siphoviridae|g_Lambdavirus|s_Enterobacteria_phage_mEpX1
Viruses|_|_|f_Siphoviridae|g_Lambdavirus|s_Enterobacteria_phage_mEpX2
Viruses|_|_|f_Siphoviridae|g_Lambdavirus|s_Enterobacteria_phage_phi80
Viruses|_|_|f_Siphoviridae|g_Lambdavirus|s_Enterobacterial_phage_mEp213
Viruses|_|_|f_Siphoviridae|g_Lambdavirus|s_Enterobacterial_phage_mEp234
Viruses|_|_|f_Siphoviridae|g_Lambdavirus|s_Enterobacterial_phage_mEp390
Viruses|_|_|f_Siphoviridae|g_Lambdavirus|s_*Escherichia*_phage_HK639
Viruses|_|_|f_Siphoviridae|g_Lambdavirus|s_*Escherichia*_phage_HK75
Viruses|_|_|f_Siphoviridae|g_Lambdavirus|s_*Escherichia*_virus_HK022
Viruses|_|_|f_Siphoviridae|g_Lambdavirus|s_*Escherichia*_virus_HK97
Viruses|_|_|f_Siphoviridae|g_Lambdavirus|s_*Escherichia*_virus_Lambda
Viruses|_|_|f_Siphoviridae|g_Lambdavirus|s_*Escherichia*_virus_Lambda
Viruses|_|_|f_Siphoviridae|g_Lambdavirus|s_*Pseudomonas*_phage_MP42
Viruses|_|_|f_Siphoviridae|g_Lambdavirus|s_Stx2-converting_phage_1717
Viruses|_|_|f_Siphoviridae|g_Liefievirus|s_*Mycobacterium*_phage_Liefie
Viruses|_|_|f_Siphoviridae|g_N15virus|s_*Escherichia*_virus_N15
Viruses|_|_|f_Siphoviridae|g_Nonagvirus|s_*Escherichia*_virus_JenP1
Viruses|_|_|f_Siphoviridae|g_Nonagvirus|s_*Escherichia*_virus_JenP2
Viruses|_|_|f_Siphoviridae|g_Phietavirus|s_*Staphylococcus*_phage_B236
Viruses|_|_|f_Siphoviridae|g_Phifelvirus|s_*Enterococcus*_phage_phifl3
Viruses|_|_|f_Siphoviridae|g_Reyvirus|s_*Mycobacterium*_phage_Bongo
Viruses|_|_|f_Siphoviridae|g_Sfi11virus|s_*Streptococcus*_phage_2972
Viruses|_|_|f_Siphoviridae|g_Sfi11virus|s_*Streptococcus*_phage_858
Viruses|_|_|f_Siphoviridae|g_Sfi11virus|s_*Streptococcus*_phage_Alq132
Viruses|_|_|f_Siphoviridae|g_Sfi11virus|s_*Streptococcus*_phage_O1205
Viruses|_|_|f_Siphoviridae|g_Sfi11virus|s_*Streptococcus*_phage_Sfi11
Viruses|_|_|f_Siphoviridae|g_Sfi21dt1virus|s_*Streptococcus*_phage_7201
Viruses|_|_|f_Siphoviridae|g_Sfi21dt1virus|s_*Streptococcus*_phage_Abc2
Viruses|_|_|f_Siphoviridae|g_Sfi21dt1virus|s_*Streptococcus*_phage_DT1
Viruses|_|_|f_Siphoviridae|g_Sfi21dt1virus|s_*Streptococcus*_phage_Sfi19
Viruses|_|_|f_Siphoviridae|g_Sfi21dt1virus|s_*Streptococcus*_phage_Sfi21
Viruses|_|_|f_Siphoviridae|g_Sk1virus|s_*Lactococcus*_phage_712
Viruses|_|_|f_Siphoviridae|g_Sk1virus|s_*Lactococcus*_Phage_ASCC191
Viruses|_|_|f_Siphoviridae|g_Sk1virus|s_*Lactococcus*_Phage_ASCC273
Viruses|_|_|f_Siphoviridae|g_Sk1virus|s_*Lactococcus*_Phage_ASCC281
Viruses|_|_|f_Siphoviridae|g_Sk1virus|s_*Lactococcus*_Phage_ASCC465
Viruses|_|_|f_Siphoviridae|g_Sk1virus|s_*Lactococcus*_Phage_ASCC532
Viruses|_|_|f_Siphoviridae|g_Sk1virus|s_*Lactococcus*_phage_blBB29
Viruses|_|_|f_Siphoviridae|g_Sk1virus|s_*Lactococcus*_phage_blL170
Viruses|_|_|f_Siphoviridae|g_Sk1virus|s_*Lactococcus*_phage_CB13
Viruses|_|_|f_Siphoviridae|g_Sk1virus|s_*Lactococcus*_phage_CB14
Viruses|_|_|f_Siphoviridae|g_Sk1virus|s_*Lactococcus*_phage_CB19
Viruses|_|_|f_Siphoviridae|g_Sk1virus|s_*Lactococcus*_phage_CB20
Viruses|_|_|f_Siphoviridae|g_Sk1virus|s_*Lactococcus*_phage_jj50
Viruses|_|_|f_Siphoviridae|g_Sk1virus|s_*Lactococcus*_phage_P008
Viruses|_|_|f_Siphoviridae|g_Sk1virus|s_*Lactococcus*_phage_SK1
Viruses|_|_|f_Siphoviridae|g_Sk1virus|s_*Lactococcus*_phage_SL4
Viruses|_|_|f_Siphoviridae|g_T5virus|s_*Escherichia*_phage_Akfv33
Viruses|_|_|f_Siphoviridae|g_T5virus|s_*Escherichia*_phage_T5
Viruses|_|_|f_Siphoviridae|g_undef|s_*Bacillus*_phage_BCJA1c
Viruses|_|_|f_Siphoviridae|g_undef|s_*Bacteroides*_phage_B124-14
Viruses|_|_|f_Siphoviridae|g_undef|s_*Bacteroides*_phage_B40-8
Viruses|_|_|f_Siphoviridae|g_undef|s_*Clostridium*_phage_phiCD24-1
Viruses|_|_|f_Siphoviridae|g_undef|s_*Clostridium*_phage_vB_CpeS-CP51
Viruses|_|_|f_Siphoviridae|g_undef|s_Enterobacteria_phage_HK106
Viruses|_|_|f_Siphoviridae|g_undef|s_Enterobacteria_phage_HK542
Viruses|_|_|f_Siphoviridae|g_undef|s_Enterobacteria_phage_HK544
Viruses|_|_|f_Siphoviridae|g_undef|s_*Enterococcus*_phage_phiEf11
Viruses|_|_|f_Siphoviridae|g_undef|s_*Enterococcus*_phage_phiFL4A
Viruses|_|_|f_Siphoviridae|g_undef|s_*Escherichia*_phage_YD-2008.s
Viruses|_|_|f_Siphoviridae|g_undef|s_*Klebsiella*_phage_phiKO2
Viruses|_|_|f_Siphoviridae|g_undef|s_*Lactobacillus*_phage_J-1
Viruses|_|_|f_Siphoviridae|g_undef|s_*Lactobacillus*_phage_JCL1032
Viruses|_|_|f_Siphoviridae|g_undef|s_*Lactobacillus*_phage_Lc-Nu
Viruses|_|_|f_Siphoviridae|g_undef|s_*Lactobacillus*_phage_Lc-Nu
Viruses|_|_|f_Siphoviridae|g_undef|s_*Lactobacillus*_phage_LL-H TABLE 19-continued List of Bacteriophages with non-zero Signaling Values Viruses|_|_|f_Siphoviridae|g_undef|s_*Lactobacillus*_phage_phiadh
Viruses|_|_|f_Siphoviridae|g_undef|s_*Lactobacillus*_phage_PL-1
Viruses|_|_|f_Siphoviridae|g_undef|s_*Lactococcus*_phage_340
Viruses|_|_|f_Siphoviridae|g_undef|s_*Lactococcus*_phage_936_sensu_lato
Viruses|_|_|f_Siphoviridae|g_undef|s_*Lactococcus*_phage_936_sensu_lato
Viruses|_|_|f_Siphoviridae|g_undef|s_*Lactococcus*_phage_936_sensu_lato
Viruses|_|_|f_Siphoviridae|g_undef|s_*Lactococcus*_phage_936_sensu_lato
Viruses|_|_|f_Siphoviridae|g_undef|s_*Lactococcus*_phage_949
Viruses|_|_|f_Siphoviridae|g_undef|s_*Lactococcus*_phage_blL285
Viruses|_|_|f_Siphoviridae|g_undef|s_*Lactococcus*_phage_blL286
Viruses|_|_|f_Siphoviridae|g_undef|s_*Lactococcus*_phage_blL309
Viruses|_|_|f_Siphoviridae|g_undef|s_*Lactococcus*_phage_blL310
Viruses|_|_|f_Siphoviridae|g_undef|s_*Lactococcus*_phage_blL311
Viruses|_|_|f_Siphoviridae|g_undef|s_*Lactococcus*_phage_blL312
Viruses|_|_|f_Siphoviridae|g_undef|s_*Lactococcus*_phage_BK5-T
Viruses|_|_|f_Siphoviridae|g_undef|s_*Lactococcus*_phage_BM13
Viruses|_|_|f_Siphoviridae|g_undef|s_*Lactococcus*_phage_jm2
Viruses|_|_|f_Siphoviridae|g_undef|s_*Lactococcus*_phage_jm3
Viruses|_|_|f_Siphoviridae|g_undef|s_*Lactococcus*_phage_P162
Viruses|_|_|f_Siphoviridae|g_undef|s_*Lactococcus*_phage_P335_sensu_lato
Viruses|_|_|f_Siphoviridae|g_undef|s_*Lactococcus*_phage_P680
Viruses|_|_|f_Siphoviridae|g_undef|s_*Lactococcus*_phage_phi7
Viruses|_|_|f_Siphoviridae|g_undef|s_*Lactococcus*_phage_phiL47
Viruses|_|_|f_Siphoviridae|g_undef|s_*Lactococcus*_phage_phiLC3
Viruses|_|_|f_Siphoviridae|g_undef|s_*Lactococcus*_phage_r1t
Viruses|_|_|f_Siphoviridae|g_undef|s_*Lactococcus*_phage_Tuc2009
Viruses|_|_|f_Siphoviridae|g_undef|s_*Lactococcus*_phage_ul36
Viruses|_|_|f_Siphoviridae|g_undef|s_*Lactococcus*_phage_ul36
Viruses|_|_|f_Siphoviridae|g_undef|s_*Lactococcus*_phage_ul36
Viruses|_|_|f_Siphoviridae|g_undef|s_*Lactococcus*_phage_ul36
Viruses|_|_|f_Siphoviridae|g_undef|s_*Lactococcus*_phage_ul36
Viruses|_|_|f_Siphoviridae|g_undef|s_*Lactococcus*_phage_WRP3
Viruses|_|_|f_Siphoviridae|g_undef|s_*Leuconostoc*_phage_1-A4
Viruses|_|_|f_Siphoviridae|g_undef|s_*Leuconostoc*_phage_Lmd1
Viruses|_|_|f_Siphoviridae|g_undef|s_*Leuconostoc*_phage_P793
Viruses|_|_|f_Siphoviridae|g_undef|s_*Leuconostoc*_phage_phiLN04
Viruses|_|_|f_Siphoviridae|g_undef|s_*Microbacterium*_phage_Min1
Viruses|_|_|f_Siphoviridae|g_undef|s_*Mycobacterium*_phage_Nala
Viruses|_|_|f_Siphoviridae|g_undef|s_*Mycobacterium*_phage_Rakim
Viruses|_|_|f_Siphoviridae|g_undef|s_*Mycobacterium*_phage_Squirty
Viruses|_|_|f_Siphoviridae|g_undef|s_*Pseudomonas*_phage_F10
Viruses|_|_|f_Siphoviridae|g_undef|s_*Pseudomonas*_phage_JBD26
Viruses|_|_|f_Siphoviridae|g_undef|s_*Pseudomonas*_phage_phi297
Viruses|_|_|f_Siphoviridae|g_undef|s_*Salmonella*_phage_SPN3UB
Viruses|_|_|f_Siphoviridae|g_undef|s_*Salmonella*_phage_SSU5
Viruses|_|_|f_Siphoviridae|g_undef|s_*Salmonella*_phage_vB_SosS_Oslo
Viruses|_|_|f_Siphoviridae|g_undef|s_*Streptococcus*_phage_5093
Viruses|_|_|f_Siphoviridae|g_undef|s_*Streptococcus*_phage_M102AD
Viruses|_|_|f_Siphoviridae|g_undef|s_*Streptococcus*_phage_MM1
Viruses|_|_|f_Siphoviridae|g_undef|s_*Streptococcus*_phage_PH10
Viruses|_|_|f_Siphoviridae|g_undef|s_*Streptococcus*_phage_PH15
Viruses|_|_|f_Siphoviridae|g_undef|s_*Streptococcus*_phage_phiNJ2
Viruses|_|_|f_Siphoviridae|g_undef|s_*Streptococcus*_phage_SMP
Viruses|_|_|f_Siphoviridae|g_undef|s_*Streptococcus*_phage_SpSL1
Viruses|_|_|f_Siphoviridae|g_undef|s_*Streptococcus*_phage_TP-778L
Viruses|_|_|f_Siphoviridae|g_undef|s_*Streptococcus*_phage_TP-J34
Viruses|_|_|f_Siphoviridae|g_undef|s_*Streptococcus*_phage_YMC-2011
Viruses|_|_|f_Siphoviridae|g_undef|s_Temperate_phage_phiNIH1.1
Viruses|_|_|f_undef|g_undef|s_*Salmonella*_phage_ST64B
Viruses|_|_|f_Inoviridae|g_Inovirus|s_Enterobacteria_phage_If1
Viruses|_|_|f_Inoviridae|g_Inovirus|s_Enterobacteria_phage_Ike
Viruses|_|_|f_Inoviridae|g_Inovirus|s_*Pseudomonas*_phage_Pf1
Viruses|_|_|f_Inoviridae|g_undef|s_Uncultured_phage_WW-nAnB_strain_2
Viruses|_|_|f_Inoviridae|g_undef|s_Uncultured_phage_WW-nAnB_strain_3
Viruses|_|_|f_Phycodnaviridae|g_undef|s_*Aureococcus*_anophagefferens_virus
Viruses|_|_|f_undef|g_undef|s_Deep-sea_thermophilic_phage_D6E
Viruses|_|_|f_undef|g_undef|s_Enterobacteria_phage_YYZ-2008
Viruses|_|_|f_undef|g_undef|s_Organic_Lake_virophage
Viruses|_|_|f_undef|g_undef|s_*Rhizobium*_phage_RHEph10
Viruses|_|_|f_undef|g_undef|s_*Streptococcus*_phage_phi20c
Viruses|_|_|f_undef|g_undef|s_*Streptococcus*_phage_phiBHN167
Viruses|_|_|f_undef|g_undef|s_*Streptococcus*_phage_phiD12
Viruses|_|_|f_undef|g_undef|s_*Streptococcus*_phage_Spn1

Phagobiota richness was not statistically different between PD patients and control individuals, although a slight increase of ACE and decrease of Chao1 indexes in the PD group was detected (ACE: p=0.272; Chao1: p=0.797).

There was a tendency for reduced α-diversity in PD patients, as indicated by reduced Shannon (p=0.132), Simpson (p=0.963), and inverse Simpson (p=0.421) indexes (Mann-Whitney test), as compared with control. These results are consistent with a similar decreasing trend observed in bacterial richness and diversity among PD patients, suggesting that the reduced numbers of bacterial hosts may be related to the reduction of the associated bacteriophages.

β-Diversity of bacteriophages was analysed based on the Spearman's rank correlation coefficient and the Bray-Curtis dissimilarity index, which revealed statistically insignificant increase in β-diversity of phagobiota in PD (Spearman's test; p=0.731). Not surprisingly, PCoA of phagobiota revealed high similarity in bacteriophage diversity between PD and control groups, which showed no statistically significant difference.

PD is associated with lower bacterial diversity and richness (Scheperjans, F. et al., 2014). The analysis described herein revealed significant differences in the microbiota structure between PD patients and control individuals. Some previously overlooked alterations in the bacterial community at the family and genus levels were detected using the MetaPhlAn tool, which provides accurate microbial profiling and estimates relative abundance of microbial cells by mapping reads against a set of clade-specific marker sequences (McMurdie, P. J. et al., 2013). Alterations observed in PD patients included a decrease in certain members of Streptococcaceae and Lactobacillaceae families, such as Lactococcus and Lactobacillus, which are consistent with recent findings (Unger, M. et al., 2016). Different results shown in other studies may be explained by variations in analysis pipelines, bioinformatics tools, and study population, which can comprise patients at different disease stages receiving distinct therapeutic regimens that can potentially affect gut microbiota composition (Scheperjans, F. et al., 2014; Scheperjans, F. et al., 2016).

The comparative evaluation of phagobiota composition in control individuals and PD patients using HPviewer did not reveal changes in α- and β-diversities, which is in agreement with the study by Bedarf et al., who showed that the abundance of prophages was not altered in the PD group when using a different bioinformatic tool for viral metagenome analysis (Bedarf, J. et al., 2017; Hao, Yuhan et al., 2017). However, in this study PD phagobiota were characterized with total disappearance of certain bacteriophage groups, including those specific for *Bacillus, Enterobacteria, Lactococcus, Streptococcus*, and *Salmonella*. At the same time, some *Leuconostoc, Lactococcus*, and Enterobacteria phages absent in the control group were found in a subset of PD patients.

Analysis of relative abundance at the family level showed that Siphoviridae was the most abundant family in both PC and control groups. The second largest bacteriophage family in the PD group was Podoviridae followed by Myoviridae, whereas in control group the order was the opposite (p=0.017).

Example 19: Composition of Phagobiota at the Species and Analysis of Phage/Bacteria Ratio Compositional changes in the bacteriophage community were examined at the species level. To investigate phage diversity in the human gut, the abundance of phage species (relative abundance ≥0.01% detectable in at least two samples) were analysed individually for each sample. The data is shown in the form of heat maps presented in FIGS. 12A-12I. Notably, the sampling methods used in extracting total metagenomic DNA data included sampling phages which cover the bulk of the phagobiota (Waller, A. et al., 2014). Comparative analysis revealed under-representation of phages specific for *Enterobacteria* and *Salmonella* and over-representation of those specific for *Lactococcus* (phi7, CB13, jj50, biI67, and 645) in PD patients.

Figure 13A:
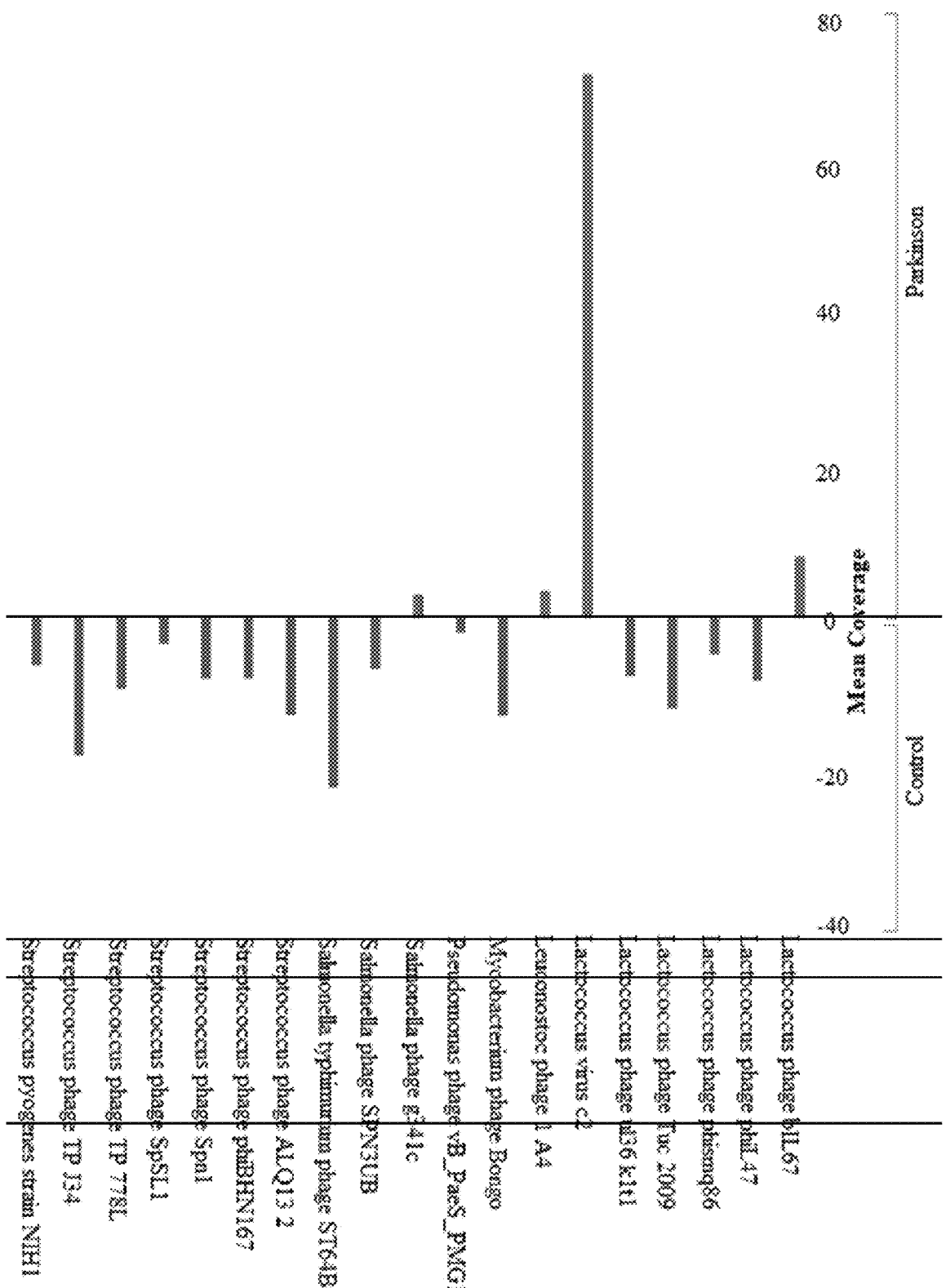
FIGS. 13A and 13B are bar graphs showing bacteriophage diversity in PD patients and healthy participants. The bar graphs show bacteriophage abundance at the genus level in the PD or control group (relative abundance≥0.01% found in at least two samples per group).
Figure 13B:
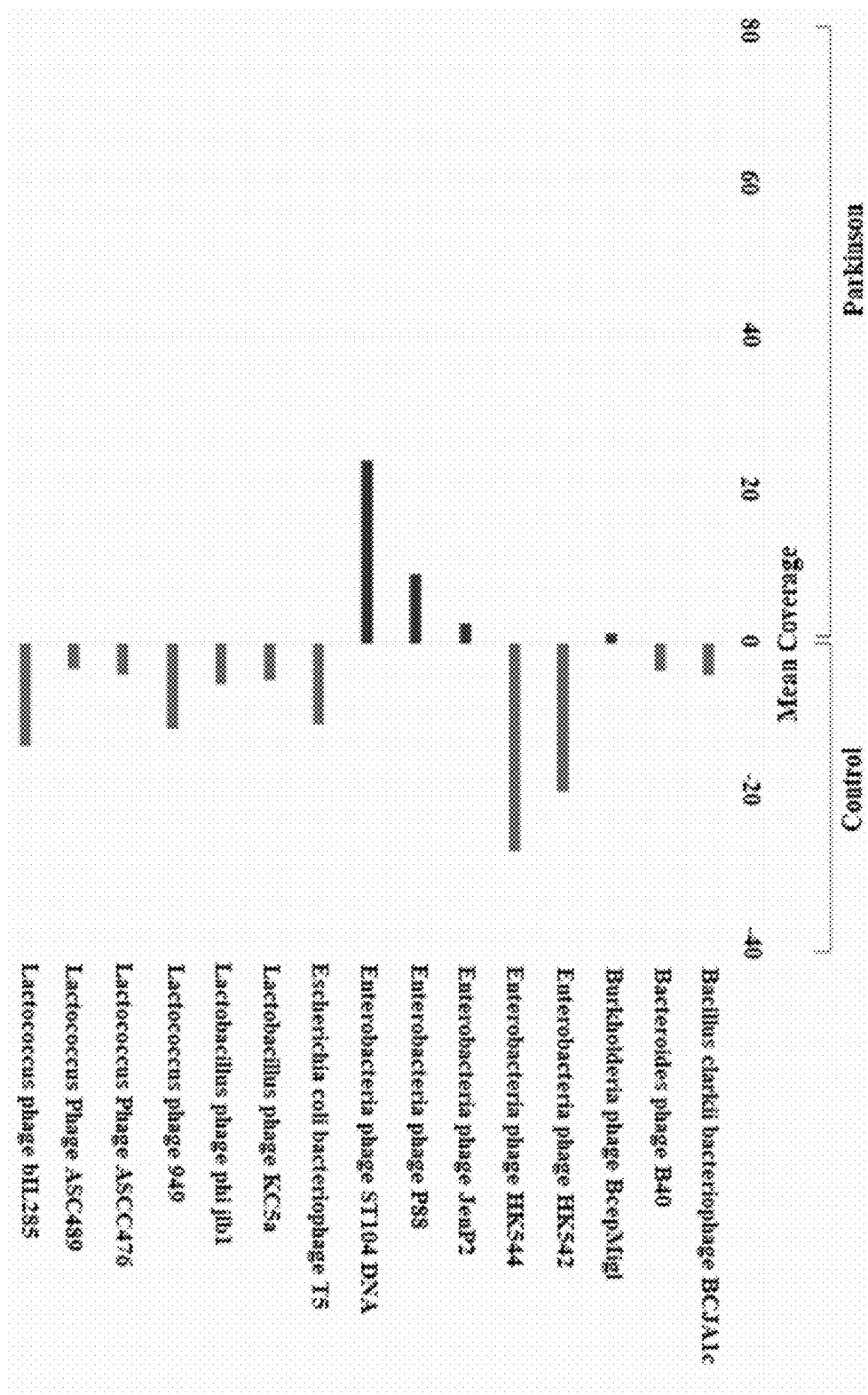
Figure 14A:
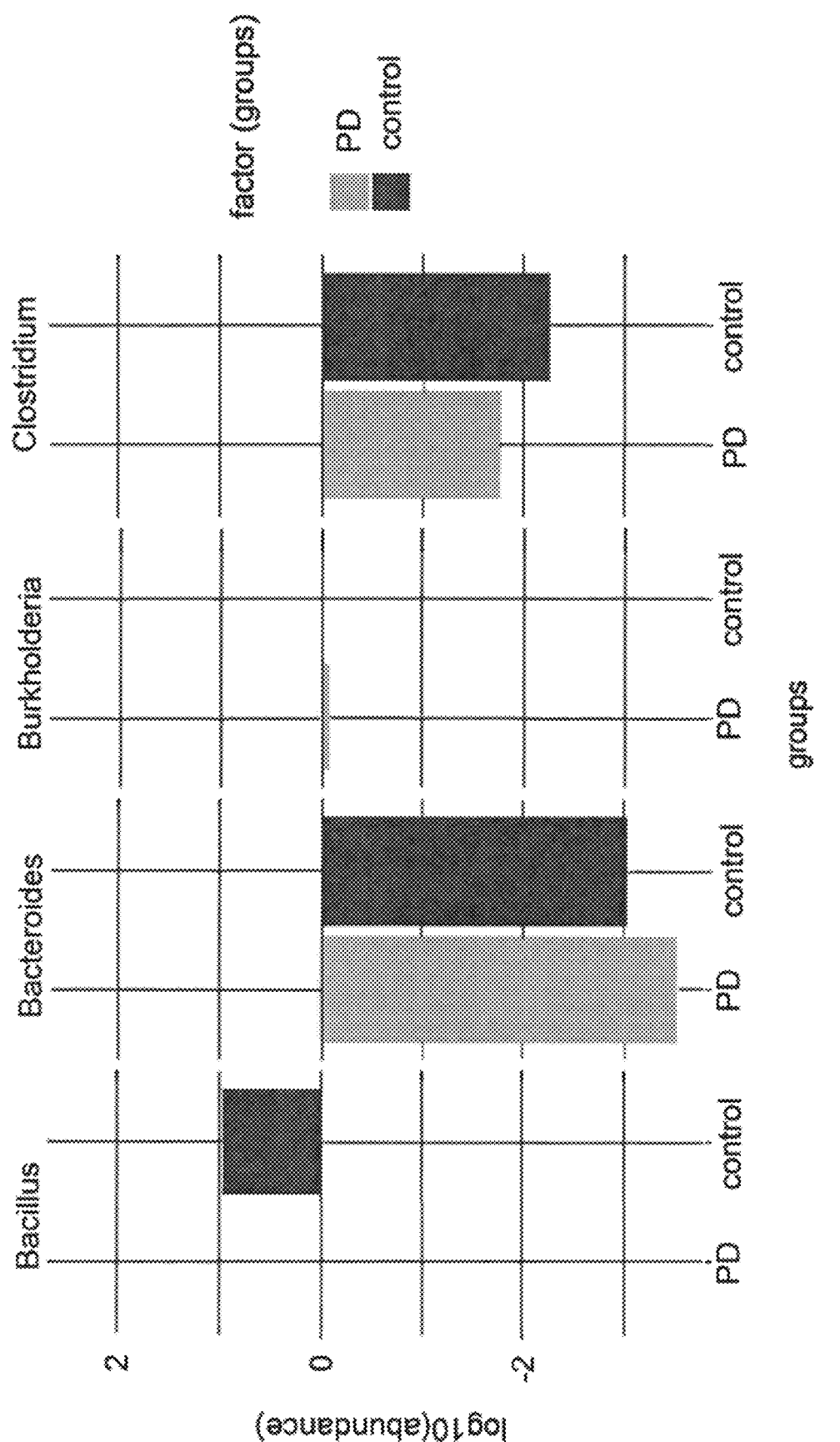
FIGS. 14A-14D show the phage/bacteria ratio in PD patients and healthy individuals. The ratio was calculated as phage abundance normalized to that of the respective bacterial hosts in each sample of the PD and control groups.
Figure 14B:
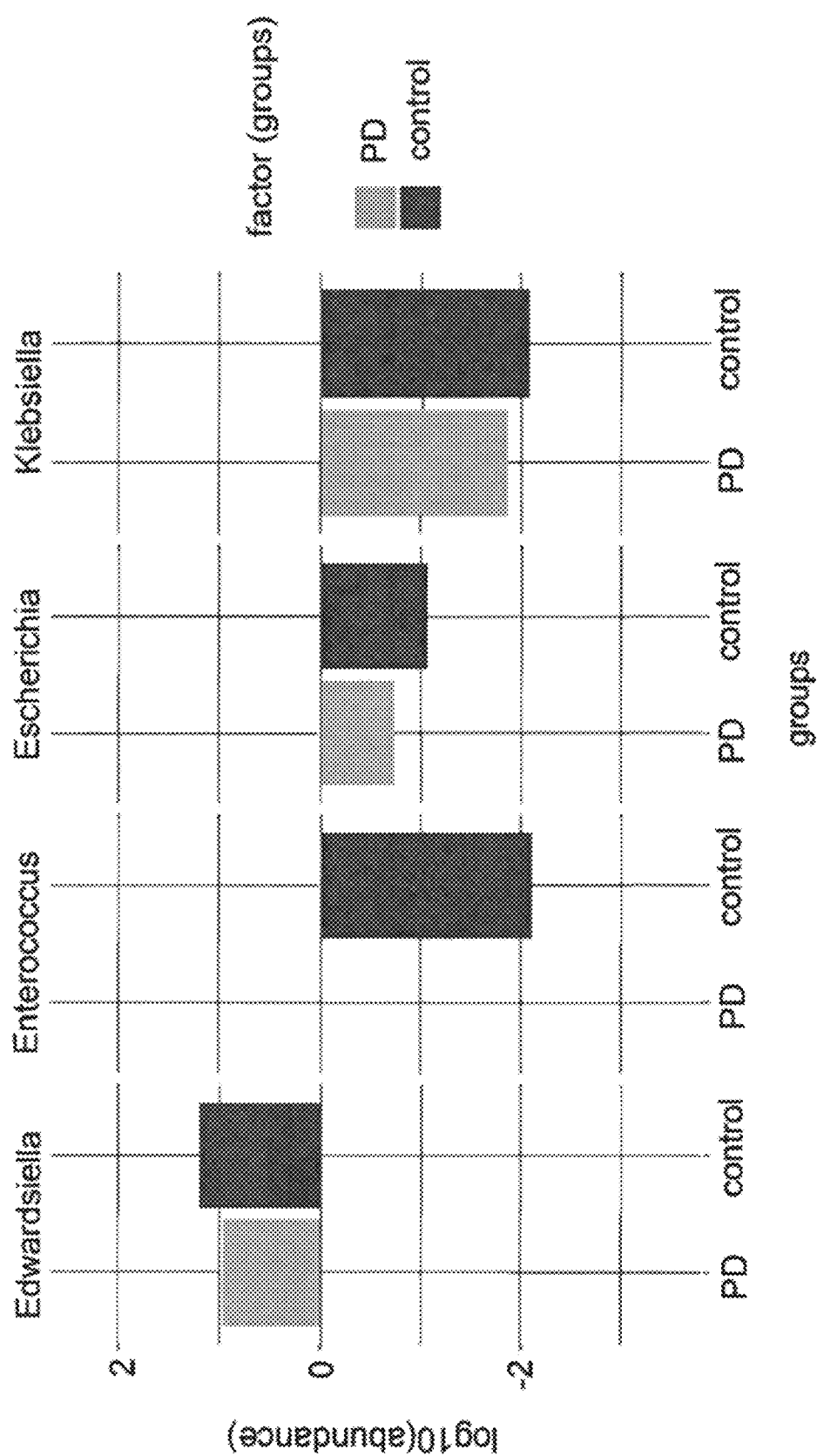
Figure 14C:
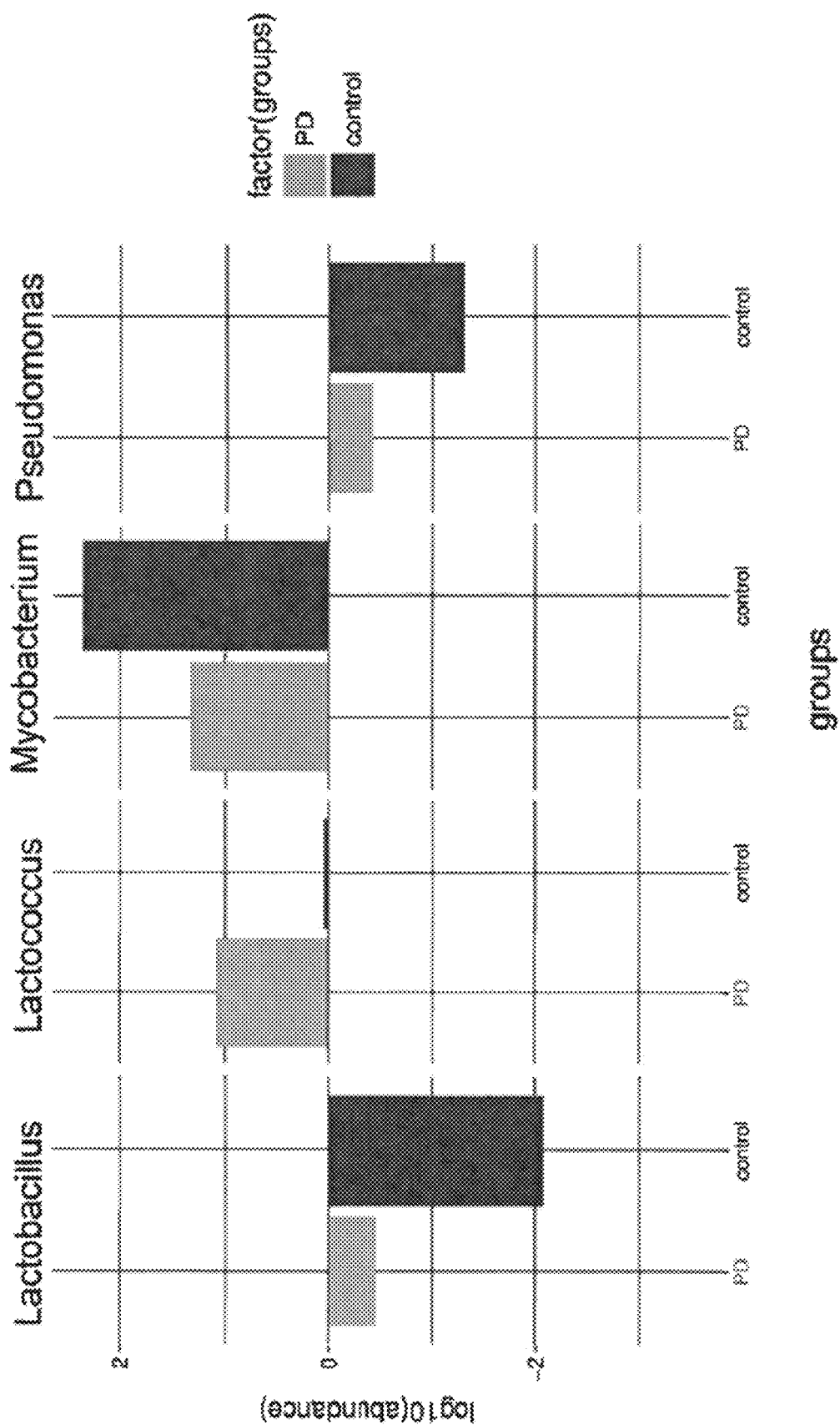
Figure 14D:
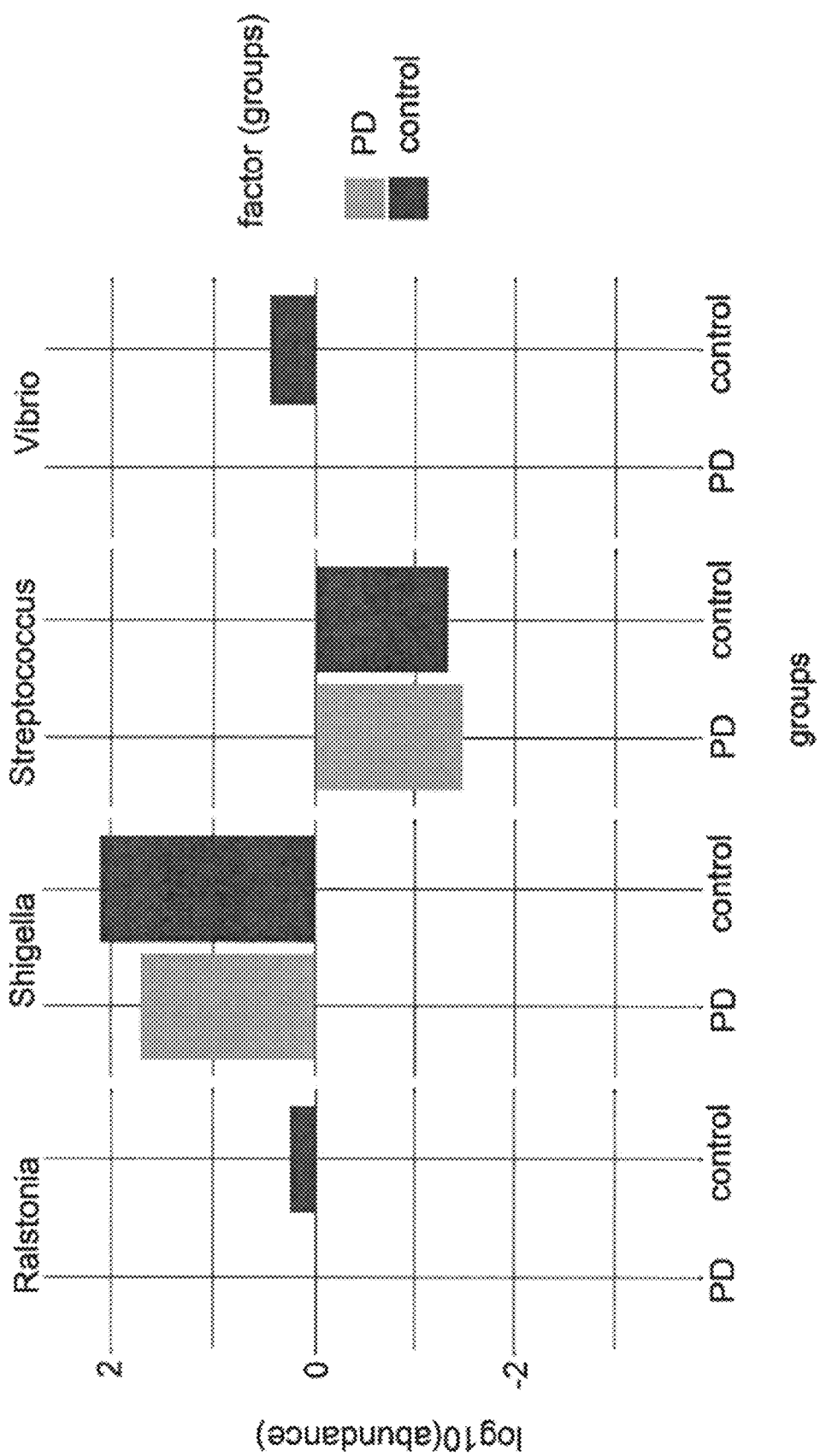

Species detectable only in one group (in at least two samples) were evaluated to assess the appearance or disappearance of individual bacteriophage species in comparison between one group versus the other. The data is shown in FIGS. 13A and 13B, as well as in Table 28. Significant changes include total disappearance of certain *Bacillus, Enterobacteria, Lactococcus Streptococcus*, and *Salmonella* phages, which belonged to the Siphoviridae family or were unclassified Caudovirales, as well as *Lactobacillus* phages of the Myoviridae family. At the same time, the appearance of certain *Leuconostoc, Lactococcus*, and Enterobacteria phages of the Siphoviridae family, Enterobacteria phages of the Myoviridae family, and *Salmonella* phages of the Podoviridae family was detected.

Finally, the ratio between phages and their bacterial hosts in the gut microbiome was analysed by calculating the phage/bacteria ratio in a manner defined as the 'lytic potential' (Waller, A. et al., 2014). Phages were clustered according to their bacterial hosts. The phage abundance was normalized to that of the respective hosts in each group. The data is shown in FIGS. 14A-14D. The obtained data were consistent with the trend of reduction in α- and β-diversity in both bacteriophages and bacteria among PD patients, which indicated stability of the phage/bacteria equilibrium across PD and control samples. However, some significant alterations in the phage/bacteria ratio in the PD group were identified, suggesting their association with PD.

In theory, a phage/bacteria ratio equal to one (or $\log 10^0$) indicates that a prophage is stably integrated within the host bacterial genome, which was observed in this study for *Bacillus* and *Vibrio* phages and the corresponding bacterial host in the PD group (Waller, A. et al., 2014). At the same time, the ratio less than one indicates that a prophage is most likely absent in the genomes of a part of the corresponding bacterial host population. Low phage/bacteria ratios were observed for *Bacteroides, Klebsiella, Clostridium*, and *Streptococcus*, which reflect low numbers of the corresponding phages and a high abundance of the host bacteria across both PD and control groups. A phage/bacteria ratio more than one suggests that the phage is at least partially present in the lytic phase. A phage/bacteria ratio more than one was observed for *Edwarsiella, Mycobacterium*, and *Shigella* in both PD and control groups without a statistically significant difference between the groups.

Example 20: Analysis of Lytic and Temperate *Lactococcus* Phages

Whole genome sequencing can produce results for both lytic and temperate phages, as methods used for metagenome DNA extraction isolate total phage DNA (Waller, A. et al., 2014). While analysing possible interplay between bacteria and phages, it is necessary to consider their mutual effects on the abundance to each other (Roossinck, M., 2011). For example, a high prevalence of certain prophage-harbouring bacteria should result in high numbers of the respective phages in metagenomics datasets, whereas increased abundance of certain lytic bacteriophages may be accompanied by a decrease of their bacterial hosts (Bryan, D. et al., 2016).

To investigate which *Lactococcus* phages are solely lytic and which are temperate (i.e., can undergo both lysogenic and lytic cycles), a detailed literature analysis was performed followed by clustering of *Lactococcus* phages into "temperate" or "lytic" groups, which is shown in Table 29 (Murphy, J. et al., 2016; Lyte, M. et al.).

Figure 15:
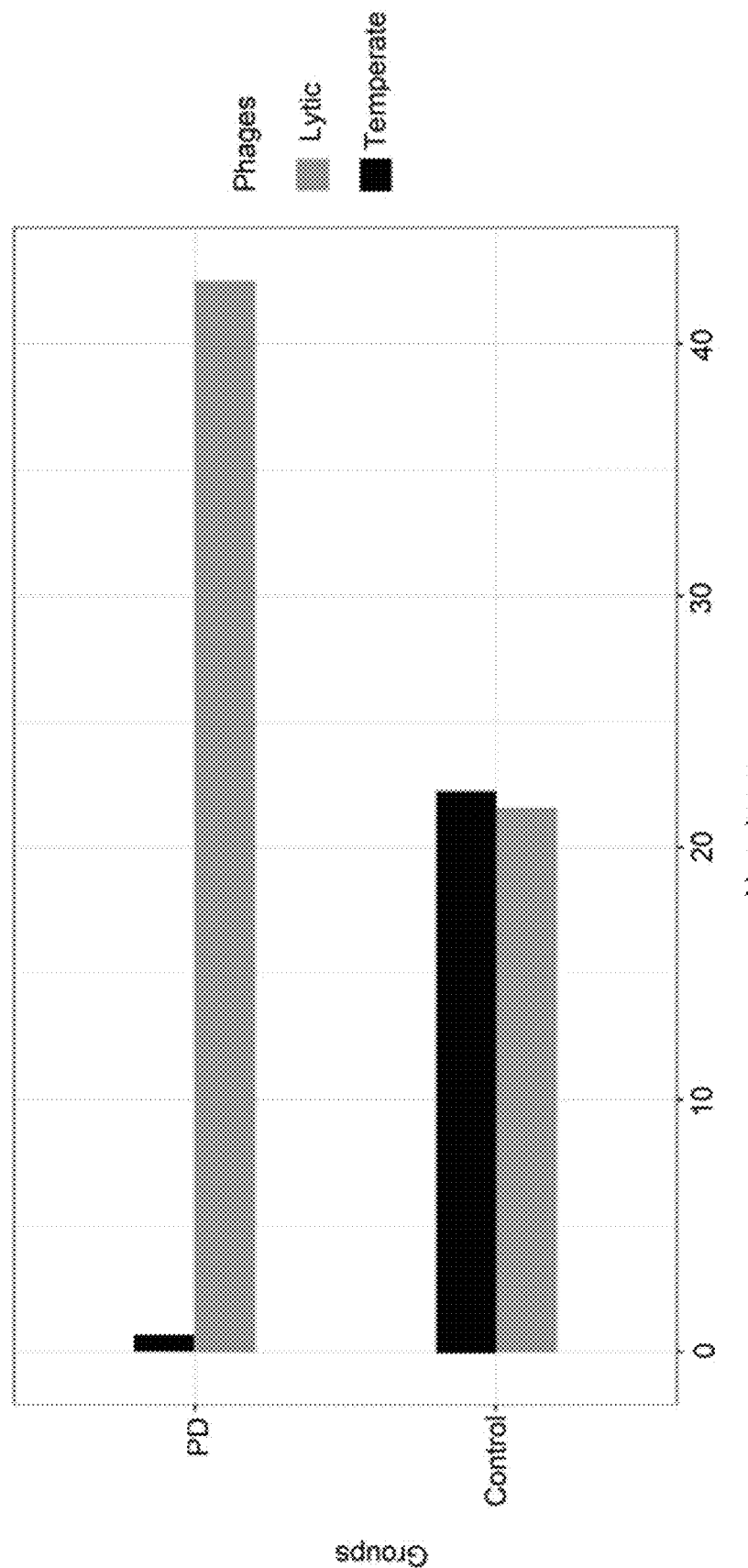
FIG. 15 shows the distribution of lytic and temperate *Lactococcus* bacteriophages in the PD and control groups. The graph in FIG. 15 shows the abundance of lytic and temperate lactococcus phages in each group.

A significant difference in the phage/bacterial ratio for *Lactococcus* was found in PD patients versus control subjects. The abundance of *Lactococcus* spp. decreased more than 10-fold in PD patients compared to control subjects, while the total number of phages was approximately the same. The data is shown in FIG. 15. The results show that lytic *Lactococcus* phages belonging to the 936 group were significantly overrepresented in PD patients. The results also indicate that the significant decrease of the abundance of *Lactococcus* spp. in PD is accompanied by under-representation of temperate and over-representation of lytic *Lactococcus* phages.

*Lactococcus* may play an important role in the metabolism of neurotransmitters, including dopamine, whose deficiency is a key pathological factor in the development of PD (Alkasir, R. et al., 2016; Özogul, F., 2011; Kuley, E. et al., 2011; Wall, R. et al., 2014). *Lactococcus* bacteria are important dopamine producers in the ENS and regulators of gut permeability. Depletion of *Lactococcus* due to high numbers of respective phages in PD patients may be associated with PD development that is directly linked to dopamine decrease (Madsen, K., 2012; Lyte, M. et al.)

Figure 16:
FIG. 16 shows the presence of *S. aureus* phages in the blood following bacteriophage administration to the animals with increased intestinal permeability.

To investigate a possible role of bacteriophages in the depletion of *Lactococcus* spp., all *Lactococcus* phages within each metagenome sample were divided into two clusters: strictly virulent (lytic), or temperate. Their distribution between PD patients and control individuals was compared (Murphy, J. et al., 2016; Chopin, A., 2001). The results in FIG. 16 indicate that in the control group, the abundance of the lytic and temperate phages was similar, whereas in the PD group, the majority of lactococcal phages were strictly virulent, are c2-like, and belong to group 936 (Murphy, J. et al., 2016). See also Table 29. Notably, the abundance of a majority of lytic *Lacotococcus* phages was higher in PD patients then in control individuals.

These data suggest that the striking depletion of *Lactococcus* spp. in PD patients could be caused by the appearance of lytic phages.

The decrease of the relative abundance of *Lactococcus* spp. in the PD group was observed herein for the first time. *Lactococcus* bacteria are considered as an important source of microbiota-derived neurochemicals, including dopamine which they produce in appreciable physiological amounts (Kuley, E. et al., 2011; Asano, Y. et al., 2012). A decrease in the production of intestinal dopamine may be associated with early gastrointestinal symptoms of PD and may be involved in triggering the neurodegenerative cascade of the disease (Houser, M. et al., 2017; Scheperjans, F., 2016).

Moreover, lactic acid bacteria, especially lactococci and lactobacilli, are known as important regulators of gut permeability (Wang, Y. et al., 2012; Madsen, K., 2012). Although intestinal permeability of the study participants was not evaluated, previous research indicates that PD is commonly associated with impaired barrier function (Wu, S. et al., 2015). Therefore, given the role of lactobacteria in intestinal dopamine production, their depletion in PD patients may contribute to triggering or aggravating PD symptoms through effects on intestinal permeability (Forsyth, C. et al., 2011).

*Lactococcus* phages may promote or trigger the onset of PD, as well as its gastrointestinal symptoms, associated with a lack of dopamine (Pfeiffer, R., 2003). Two possible scenarios can lead to the accumulation of lytic *Lactococcus* phages in the gut and depletion of their bacterial hosts (Mirzaei, M. et al., 2017). The first is a symptom of dysbiosis and the second is a result of environmental introduction of lytic *Lactococcus* phages, which are widely used in the food industry and can be found in a variety of dairy products, including milk, cheese, and yogurt (Mills, S. et al., 2013; Lyte, M. et al.) The impact of the latter factor is supported by the fact that the majority of lytic phages in PD patients are c2-like and 936-like lactococcal phages, both of which are most frequently isolated from dairy products (Marcó, M. et al., 2012; Rousseau, G. et al., 2009; Murphy, J. et al., 2013).

Example 21: Bacteriophages Circulation in Human Biologic Fluids

To mice with increased intestinal permeability, phages were orally administered daily (at a dose of $10^8$ CFU/day. Administration occurred over six days. Bacteriophages appeared in serum circulation. Such appearance upon oral administration has been shown for the first time by the present inventors. The data are presented in FIG. 16 and in Table 20 below.

TABLE 20

| | Amount of phages in blood circulation CFU/ml | |
| --- | --- | --- |
| Phage | Animals with increased intestinal permeability | Control animals |
| S. aureus | $10^3$ | 0 |
| Klebsiella spp | $10^2$ | 0 |
| E. coli | $10^2$ | 0 |
| Bacillus spp | $10^3$ | 0 |

Example 22: Inactivation of Bacteriophages by Nucleases and Proteases

Bacteriophages of *E. coli* (titer $10^7$) were inactivated by treatment with Deoxyribonuclease 10 mcg/ml (SIGMA-ALDRICH; 2000 Kunitz-units/ml) for 30 minutes or with Proteinase K (10 mcg/ml (Promega) 30 min. The degree of inactivation of bacteriophages is shown in Table 21. The results demonstrate that both DNAse I and Proteinase K treatment of bacteriophages reduces the titer to undetectable levels (as determined by Gratia's method, see Kropinski et al. "Enumeration of bacteriophages by double agar overlay plaque assay." Bacteriophages: Methods and Protocols, Volume 1: Isolation, Characterization, and Interactions, Humana Press, 2009, vol. 501, 69-76). As a control, when the original phage is added back, the titer increases. The data are shown in Table 21 below.

TABLE 21

| Sample | Phage titer (by Gratia's method) |
| --- | --- |
| E. coli and original phage | $4 \times 10^7$ |
| E. coli and DNAase I | $2 \times 10^5$ |
| E. coli and Proteinase K | $6 \times 10^4$ |

Example 23: Method for Diagnosing Diseases Based on Particularities of Phages Abundances in the Gut To explore the bacteriophage community structure in patients with different diseases, shotgun metagenomics sequencing data of the faecal microbiome was used.

The identified phages were clustered according to their bacterial hosts. To separate lytic phages from the temperate, samples of the microbiota from each patient were diluted in PBS and filtered through 0.22 mcm Millipore filter (Millipore Corp., Bedford, MA) and both fractions obtained following filtration were subjected to sequencing and processing. DNA sequencing data were generated by Illumina Hiseq4000 paired-end shotgun sequencing. Short sequence reads were retrieved from NCBI SRA (see www.ncbi.nlm.nih.gov/bioproject/382085; Bedarf., J. et al., 2017). Sequences were quality-filtered to remove adaptor contamination, low-quality reads with minimum quality score cut-off of 20, sequences with <45 nucleotides, and human DNA. In the analysis of bacteria, sequences were grouped into OTUs with a 97% threshold of pairwise identity (Edgar, R. et al., 2010).

All reads were assembled de novo in each SRA file and the assembled contigs were tested against MetaPhlAn, which operates by mapping sequence reads to a database of predefined clade-specific marker genes, and custom databases (Segata, N. et al., 2012; Hao, Yuhan, 2017). The resulting counts were normalized for total marker gene length and outliers, yielding profiles of the presence/absence and abundance of marker genes, and clade-relative abundance (Franzosa, E. et al., 2014).

The patient population and the results of the study participants are presented in Table 22 below.

TABLE 22

| Disease | Phage's particularities |
|---|---|
| Spinocerebellar ataxia | Increase in lytic phages of Myoviridae, Siphoviridae, Podoviridae |
| AD | Increase in lytic phages of Myoviridae, Siphoviridae, Podoviridae |
| PD | Increase in lytic Lacococcus phages |
| ALS | Increase in lytic phages of Myoviridae, Siphoviridae, Podoviridae |
| Multiple sclerosis | Increase in lytic phages of Myoviridae, Siphoviridae, Podoviridae |
| Diabetes I (at the initiation of seroconversion) | Decrease of *E. coli* phages' abundance Increase in Stx2 phages |

Example 24: Method for Diagnosing Diseases Based on Particularities of Phages Circulation in CSF For metagenomics analysis, DNA from patients with different diseases was extracted from 200 µl of cerebrospinal fluid (CSF) using the Qiagen blood DNA mini kit, according to manufacturer's instructions. For construction of metagenomics libraries, the Nextera XT (Illumina) technology was used. In brief, 2 ng of DNA was tagmented with 6 µl ATM for 5 min at 56° C. The reaction was terminated with 5 µl of NT buffer with the following incubation at 22C for 5 minutes. To obtain libraries, products were PCR amplified in the presence of a barcode for 24 cycles. To analyze the abundance of phages, data from metagenomics were analyzed with custom database. Table 23 below lists the bacteriophages that appeared in the CSF of a patient with the indicated disease.

TABLE 23

| Disease | Appearance of Phage's DNA in CSF |
|---|---|
| Spinocerebellar ataxia | *Acidithiobacillus* phage AcaML1 |
| AD | *Corynebacterium* phage |
| PD | Enterobacteria phage P7 |
| ALS | *Shigella* phage SflV |
| Multiple sclerosis | *Staphylococcus* phage StB2 *Acidithiobacillus* phage AcaML1 |
| Brain cancer | *Streptomyces* phage |

Example 25: Method for Treatment of Diseases by Inactivating Phages Circulating in Biological Fluids A patient with multiple sclerosis (from Example 24), with confirmed presence of *Staphylococcus* phage StB2 in CSF was treated with antibodies against *Staphylococcus* phage StB2. *Staphylococcus* phage StB2 was obtained from Human Microbiology Institute. Antibodies to *Staphylococcus* phage StB2 were obtained after hyperimmunization of a rabbit by the method according to "The guidelines for the production of antibodies in laboratory animals".

Antibodies were injected into the cerebrospinal fluid once.

The severity of the disease was measured with Expanded Disability Status Scale (EDSS) (Kurtzke J. F., "Rating neurologic impairment in multiple sclerosis: an expanded disability status scale (EDSS)" Neurology, 1983, 33(11): 1444-52). The data are shown in Table 24 below.

TABLE 24

| Status | EDSS |
|---|---|
| Before treatment | 9.5 |
| 7 days after treatment | 7.5 |

The data above indicate that the phage is eliminated from human biological fluids and may be used for treatment of diseases.

Example 26: Effect of Phages on the Proteome of Human Biological Fluids

To evaluate the effect of phages on human biological fluids, the proteome profile of the CSF was compared before and after treatment of bacteriophages. Bacteripophage treatment involved adding 1 mcl of *Listeria* P100 phage (phage concentration $10^6$ PFU/ml; possesses prion-like domain at Gp71 protein) to 1 ml of CSF. Following a one-hour exposure, proteins were analyzed with LC/MS analysis using nanoflow UPLC-MS/MS (Thermo Q Exactive HF Orbitrap) in which ultra high performance liquid chromatography was coupled to tandem mass spectrometry according to the manufacturer's instructions.

Data are presented in Table 25 below.

TABLE 25

| Accession Number | CSF#1 | CSF#1 + *Listeria* phage P100 |
|---|---|---|
| CO3_HUMAN | 103 | 78 |
| CO4B_HUMAN [3] | 47 | 33 |
| CERU_HUMAN | 45 | 34 |
| PTGDS_HUMAN | 22 | 34 |
| VTDB_HUMAN | 41 | 33 |
| ANGT_HUMAN | 32 | 18 |

TABLE 25-continued

| Accession Number | CSF#1 | CSF#1 + Listeria phage P100 |
|---|---|---|
| DKK3_HUMAN | 21 | 28 |
| CO7_HUMAN | 25 | 16 |
| AFAM_HUMAN | 29 | 12 |
| ECM1_HUMAN | 21 | 15 |
| C9JIZ6_HUMAN | 16 | 8 |
| A0A0U1RRJO_HUMAN | 23 | 11 |
| A0A059T5S9_9CAUD |  | 10 |
| A0A1W2PQ11_HUMAN | 15 | 8 |
| B2MG_HUMAN | 6 | 11 |
| B7ZKJ8_HUMAN | 10 | 5 |
| A0A0D9SEP4_HUMAN | 19 | 12 |
| J3KQ66_HUMAN | 16 | 8 |
| MIME_HUMAN | 14 | 8 |
| CBPE_HUMAN | 13 | 6 |
| ACTB_HUMAN | 5 | 2 |
| VTNC_HUMAN | 6 | 10 |
| LUM_HUMAN | 8 | 4 |
| ITIH2_HUMAN | 13 | 7 |
| T132A_HUMAN | 13 | 4 |
| H0YLB9_HUMAN | 11 | 4 |
| CO9_HUMAN | 9 | 2 |
| H7BY57_HUMAN | 6 | 2 |
| B0QYH5_HUMAN | 11 | 7 |
| NOV_HUMAN | 9 | 8 |
| PLTP_HUMAN | 4 | 3 |
| PON1_HUMAN | 7 | 4 |
| CADM3_HUMAN | 6 | 4 |
| PEBP1_HUMAN | 8 | 4 |
| PGRP2_HUMAN | 7 | 4 |
| SLIK1_HUMAN | 8 | 6 |
| CBG_HUMAN | 4 | 2 |
| PRDX2_HUMAN | 10 | 6 |
| APLP2_HUMAN | 6 | 4 |
| ATRN_HUMAN | 5 | 5 |
| PENK_HUMAN | 4 | 4 |
| IGHG2_HUMAN | 8 | 10 |
| B4DV12_HUMAN | 1 | 1 |
| C9J8Z4_HUMAN | 5 | 6 |
| CGRE1_HUMAN | 3 | 5 |
| IL6RB_HUMAN | 7 | 2 |
| ALDOC_HUMAN | 6 | 6 |
| CO1A1_HUMAN | 5 | 4 |
| LRC4B_HUMAN | 9 | 1 |
| NUCB1_HUMAN | 5 | 2 |
| Q30L74_9CAUD |  | 16 |
| A0A1B0GVD5_HUMAN | 6 | 1 |
| AGRL1_HUMAN | 6 | 3 |
| APOB_HUMAN | 6 | 2 |
| CO8B_HUMAN | 5 |  |
| ALS_HUMAN | 6 | 2 |
| A0A0A0MT71_HUMAN | 5 | 1 |
| A0A0A0MRJ7_HUMAN | 5 |  |
| LYVE1_HUMAN | 4 | 2 |
| CSPG2_HUMAN | 3 |  |
| NECT1_HUMAN | 3 |  |
| OMD_HUMAN | 4 |  |
| T132D_HUMAN | 4 |  |
| C1QA_HUMAN | 3 |  |
| Q30LA5_9CAUD |  | 4 |
| GOLM1_HUMAN | 3 |  |
| SCRG1_HUMAN | 3 |  |
| A0A059T753_9CAUD |  | 1 |
| A0A0C4DH07_HUMAN | 3 | 1 |
| E9PRU1_HUMAN | 3 |  |
| ENOG_HUMAN | 4 |  |
| F5GZA6_HUMAN |  | 3 |
| A0A059T8N0_9CAUD |  | 4 |
| A0A059T769_9CAUD |  | 3 |
| A0A059T8V6_9CAUD |  | 2 |
| A0A059T8P4_9CAUD |  | 2 |
| H3BP20_HUMAN | 2 |  |
| LRP1_HUMAN | 2 |  |
| PTPRF_HUMAN | 2 |  |

As it is seen, the presence of phages in human biological fluids alters the proteome in a manner that can be used both for the diagnostics as well as a determination of a cause of the diseases associated with an altered proteomic content of biological fluids.

Example 27. Phages in CSF of Patients with Different Effect of Phages on the Proteome of Human To examine the relationship between human gut phagobiome throughout infancy and type 1 diabetes (T1D), a cohort of infants genetically predisposed to T1D based on HLA risk genotyping was examined.

Stool samples were collected by participants' parents and stored in the household freezer (20° C.) until the next visit to the local study center; samples were then shipped on dry ice to the DIABIMMUNE Core Laboratory. The samples were then stored at 80° C. until shipping to the Broad Institute for DNA extraction. DNA extractions from stool were carried out using the QIAamp DNA Stool Mini Kit (QIAGEN, Inc., Valencia, CA, USA). Metagenomic data production and processing were performed as described previously (Consortium, 2012). In brief, library construction was performed (protocol available: hmpdacc.org/tools_protocols/tools_protocols.php). Libraries were sequenced on the Illumina HiSeq 2500 platform, targeting ~2.5 Gb of sequence per sample with 101 bp, paired-end reads. Contaminating human sequences were filtered-out using BMTagger, along with any reads less than 60 nt in length and low-quality reads (BWA-42 quality score).

Alterations were analyzed based on the time of seroconversion and the appearance of circulating autoantibodies. The results are shown in Table 26 below.

TABLE 26

| ID | | Age at collection | *Escherichia_coli* | Lytic *E. coli* phages |
|---|---|---|---|---|
| Patient 1 | T1D | 264 | 4.06693 | 118.8182 |
| Patient 1 | T1D | 399 | 0.61445 | 8.7204 |
| Patient 1 | T1D | 477 | 0 | 0 |
| Patient 1 | T1D | 527 | 0 | 0 |
| Patient 1 | T1D | 629 | 0 | 0 |
| Patient 1 | T1D | 1025 | 0 | 0 |
| Patient 2 | T1D | 237 | 6.06629 | 31.8032 |
| Patient 2 | T1D | 385 | 0.54745 | 12.3694 |
| Patient 2 | T1D | 509 | 1.41594 | 17.1696 |
| Patient 2 | T1D | 630 | 0.08631 | 0 |
| Patient 2 | T1D | 661 | 0.18194 | 4 |
| Patient 2 | T1D | 692 | 0.16473 | 1.7128 |
| Patient 2 | T1D | 938 | 1.31141 | 11.8639 |
| Patient 2 | T1D | 964 | 0.05684 | 0 |
| Patient 2 | T1D | 1027 | 0 | 0 |
| Patient 3 | T1D | 237 | 4.3633 | 20.0288 |
| Patient 3 | T1D | 366 | 5.23324 | 11.7656 |
| Patient 3 | T1D | 430 | 0.1145 | 8.9746 |
| Patient 3 | T1D | 520 | 0.00542 | 0 |
| Patient 3 | T1D | 562 | 0.13484 | 6.4881 |
| Patient 3 | T1D | 616 | 0.05929 | 0 |
| Patient 3 | T1D | 683 | 0.01071 | 0 |
| Patient 3 | T1D | 788 | 0 | 0 |
| Patient 3 | T1D | 844 | 0 | 0 |
| Patient 3 | T1D | 918 | 0 | 0 |
| Patient 3 | T1D | 1049 | 0 | 0 |
| Patient 4 | T1D | 208 | 0.90805 | 22.421 |
| Patient 4 | T1D | 249 | 0.00892 | 0 |
| Patient 4 | T1D | 355 | 0.12516 | 5.7532 |
| Patient 4 | T1D | 474 | 0 | 0 |
| Patient 4 | T1D | 508 | 0 | 0 |
| Control1 | Control | 303 | 8.3116 | 42.1067 |
| Control1 | Control | 457 | 14.15822 | 54.0621 |
| Control1 | Control | 638 | 12.05496 | 43.0056 |
| Control1 | Control | 853 | 4.10584 | 22.5666 |

TABLE 26-continued

| ID | | Age at collection | Escherichia_coli | Lytic E. coli phages |
|---|---|---|---|---|
| Control1 | Control | 1062 | 27.54601 | 67.6788 |
| Control2 | Control | 369 | 0.84121 | 3.2177 |
| Control2 | Control | 465 | 0 | 0 |
| Control2 | Control | 600 | 0.01177 | 8.5361 |
| Control2 | Control | 785 | 1.53232 | 20.2839 |
| Control2 | Control | 1040 | 0.11462 | 2.4807 |
| Control3 | Control | 352 | 0.97973 | 6.00267 |
| Control3 | Control | 504 | 0.29555 | 4.7438 |
| Control3 | Control | 606 | 0.14943 | 3.1645 |
| Control3 | Control | 747 | 0.11442 | 0 |
| Control3 | Control | 910 | 0.26751 | 3.221 |
| Control3 | Control | 1233 | 3.58098 | 35.7283 |
| Control4 | Control | 164 | 0.01667 | 0 |
| Control4 | Control | 290 | 0.22538 | 5.208 |
| Control4 | Control | 505 | 0.41986 | 4.7659 |
| Control4 | Control | 769 | 1.59332 | 10.1243 |
| Control4 | Control | 911 | 1.05013 | 5.673 |
| Control4 | Control | 1131 | 2.35271 | 14.2325 |

As it is seen there was a marked drop in *E. coli* in T1D progressors that was associated with an increase of a certail lytic *E. coli* phages (Stx2-converting phages; Enterobacteria phages; *E. coli* phages). These data point out that the alteration of the phages content might lead to depletion of *E. coli* that might be associated with an autoimmune disease.

Example 28. Bacteriophage can Enter the Bloodstream and Promote Release of Pathogen-Associated Molecular Patterns (PAMPs) to Systemic Circulation A study was performed to test whether the phages can increase cell free DNA and other PAMPs levels in systemic circulation. C57BL/6, one week old mice were administered bacteriophages orally with water. Each animal was used as its own control, with five animals in each group. Animals were treated daily with 2 mL of bacteriophage suspensions comprised of phages active against Enterobacteriaceae, Staphylococcaceae, Bacillaceae, Listeriaceae and Pseudomonadaceae by oro-gastric tube. Phages were also added to drinking water for the next days. The characteristics of the phages used in the study are shown in Table 27 below.

TABLE 27

| Bacteriophage | Bacterial host |
|---|---|
| *E. coli* phage | *E. coli* |
| Pseudomonas | *P. aeruginosa* |
| Staphylococcus phage | *S. aureus* |
| Bacillus phage | *Bacillus* spp. |
| Klebsiella phage | *Klebsielly* spp. |
| Listeria phage P100 | *L. monocytogenes* |
| Listeria phage 124 | *L. monocytogenes* |

Phage titers in blood were determined on days 0, 1, 2, 3 and 4. The presence of bacteriophages in the blood (every day) and in kidney (on the 4th day) of phages administration was detected by plating on LB agar plates (Sigma) with appropriate host bacteria.

Bacteriophages were chosen from different bacteriophage families including Myoviridae, Podoviridae, and Siphoviridae, Ligamenvirales and unclassified phages. Assuming phages frequently adhere to blood cells, erythrocytes obtained following separation of plasma were resuspended in sterile water and lyzed by osmotic shock freezing. The earliest recovery from mouse blood was for the *Klebsiella* phage with 3 log 10 PFU/ml was determined already at day 3, while all the other phages were recognized in circulation only at day 4. The highest phage titers on day four were for *Pseudomonas* phage with 5 log 10 PFU/ml at day 4.

The effect of phages on PAMPs and DNA levels in systemic circulation was studied at day 1. Then, an increase of circulating DNA, and particularly cell free bacterial DNA following bacteriophages treatment, was assayed by measuring the A260 value (SmartSpec Plus, BioRad) and by real-time PCR amplification (Thermofisher) of the 16S small-subunit rRNA gene. To evaluate extracullar DNA level, mouse plasma was filtered to remove bacterial contamination, followed by total DNA extraction from plasma using the Kit (Qiagen, Germany). The quantity of total DNA was measured at 260 nm and purity was assessed by the OD260/OD280 ratio. The extracted DNA was normalized to 50 ng/μl.

For the rtPCR, the following primers and reagents were used: 338F Primer: ACT CCT RCG GGA GGC AGC AG (SEQ ID NO: 3)

806R Primer: GGA CTA CCV GGG TAT CTA AT (SEQ ID NO: 4)

FAM-TAMRA/5-FAM/-TKA CCG CGG CTG CTG GCA C-/BHQ-1/(SEQ ID NO: 5)

The amplification process included initial denaturation at 95° C. for 2 min, 25 cycles of denaturation at 95° C. for 30 s, annealing at 55° C. for 30 s, elongation at 72° C. for 30 s, and final extension at 72° C. for 5 min.

Figure 17:
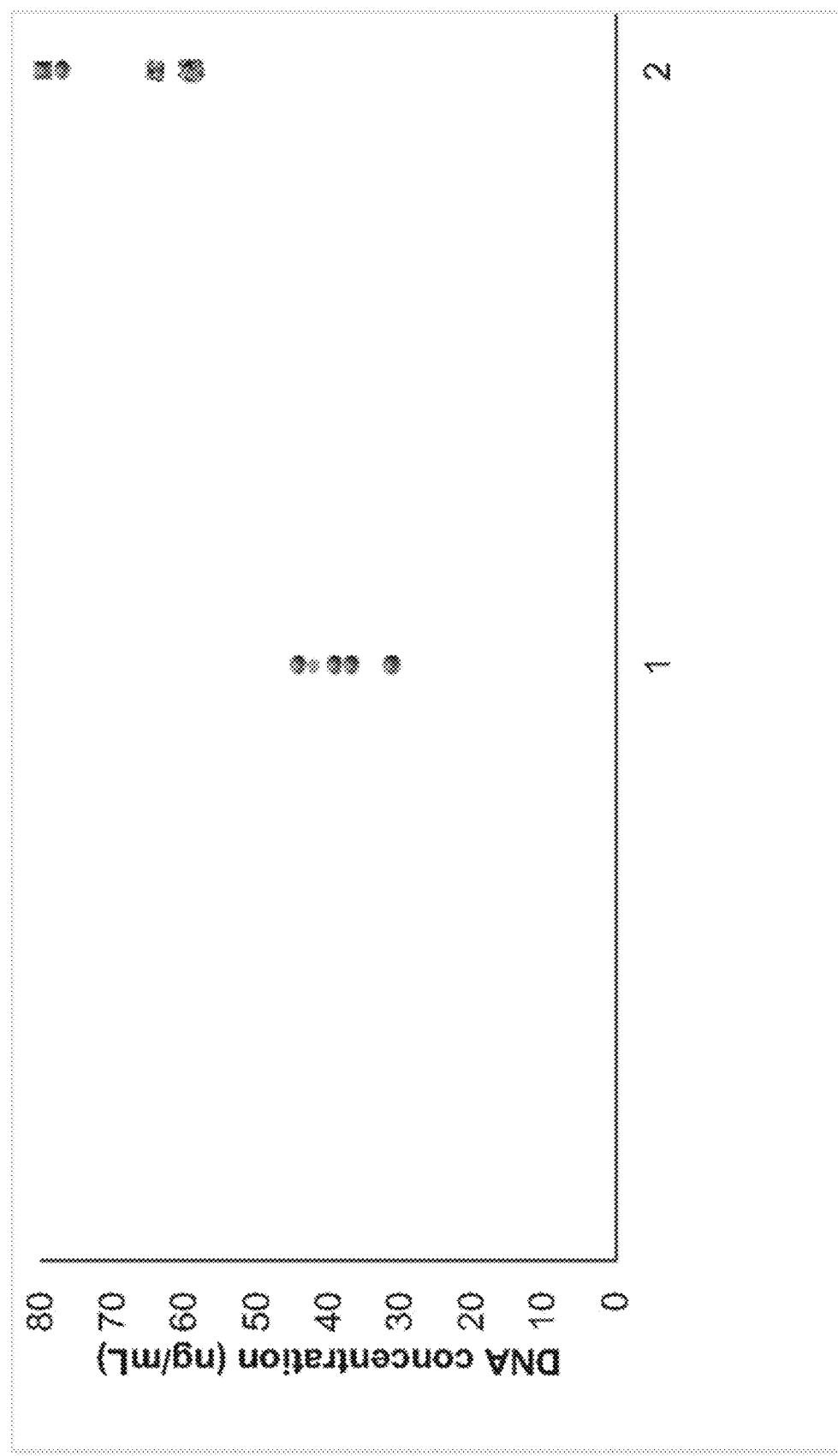
FIG. 17 shows the results of an assay in the form of a graph. The effect of oral bacteriophage administration on total cell-free circulating DNA was assayed. The Y axis shows the concentration of total cell-free circulating DNA in the plasma. On the X axis, "1" indicates before bacteriophage administration and "2" indicates 24 hours after phage challenge.

Significantly elevated total cell-free DNA concentrations were observed after 24 hours and over the following days following bacteriophage administration in all animals. The medium value for the cell-free circulating DNA in plasma was 72.8 ng/mL at 24 hours after bacteriophage administration, which was significantly higher as compared to the baseline of 38.8 ng/mL (n=5) (p=0.034) before bacteriophage administration. FIG. 17 shows the data in the form of a graph, where the Y axis shows the concentration of total cell-free circulating DNA in the plasma and, on the X axis, "1" indicates before bacteriophage administration and "2" indicates 24 hours after phage challenge.

To study levels of lipopolysaccharide (LPS), a Pyrochrome Limulus Amebocyte lysate kit (Associates of Cape Cod, Inc., East Falmouth, MA, USA) was used according to the manufacturer's instructions. Great care was taken to ensure aseptic collection and to avoid contamination with environmental LPS. Blood specimens were collected under pyrogen-free conditions and stored in LPS-free vials (Eppendorf, Germany). It was found that the animals had higher levels of plasma LPS after the bacteriophage challenge, with an average of 0.32±0.05 endotoxin units (EU)/mL as compared with an average of 0.06±0.03 EU/mL (p<0.05) before the treatment.

In conclusion, phage treatment unexpectedly increased plasma levels of PAMPs, including DNA, such as both bacterial-derived DNA and extracellular biofilm-derived DNA.

REFERENCES

1. Dalmasso, M., Hill, C. & Ross, R. Exploiting gut bacteriophages for human health. *Trends Microbiol.* 22, 399-405 (2014).
2. Natividad, J. & Verdu, E. Modulation of intestinal barrier by intestinal microbiota: Pathological and therapeutic implications. *Pharmacol. Res.* 69, 42-51 (2013).

3. Sommer, F. & Bäckhed, F. The gut microbiota—masters of host development and physiology. *Nat. Rev. Microbiol.* 11, 227-238 (2013).
4. Ashida, H., Ogawa, M., Kim, M., Mimuro, H. & Sasakawa, C. Bacteria and host interactions in the gut epithelial barrier. Nature Chemical Biology 8, 36-45 (2011).
5. Maes M, Kubera M, Leunis J C, Berk M. Increased IgA and IgM responses against gut commensals in chronic depression: further evidence for increased bacterial translocation or leaky gut. J Affect Disord. 2012; 141:55-62.
6. Tlaskalova-Hogenová H, Stepankova R, Kozakova H, Hudcovic T, Vannucci L, Tuckova L, Rossmann P, Hrncir T, Kverka M, Zakostelska Z, Klimesova K, Pribylova J, Bartova J, Sanchez D, Fundova P, Borovska D, Srutkova D, Zidek Z, Schwarzer M, Drastich P, Funda D. The role of gut microbiota (commensal bacteria) and the mucosal barrier in the pathogenesis of inflammatory and autoimmune diseases and cancer: contribution of germ-free and gnotobiotic animal models of human diseases. Cell Mol Immunol. 2011; 8:110-20.
7. Berk M, Williams L J, Jacka F N, O'Neil A, Pasco J A, Moylan S, Allen N B, Stuart A L, Hayley A C, Byrne M L, Maese M. So depression is an inflammatory disease, but where does the inflammation come from? BMC Med. 2013; .doi:10.1186/1741-7015-11-200.
8. Anderson G, Maes M. The gut-brain axis: the role of melatonin in linking psychiatric, inflammatory and neurodegenerative conditions. Adv Integr Med. 2015; 2:31-7.
9. Sulakvelidze, A., Alavidze, Z. & Morris, J. Bacteriophage Therapy. *Antimicrob. Agents Chemother.* 45, 649-659 (2001).
10. Wittebole, X., De Roock, S. & Opal, S. A historical overview of bacteriophage therapy as an alternative to antibiotics for the treatment of bacterial pathogens. *Virulence* 5, 226-235 (2013).
11. Blanco, L. P., Evans, M. L., Smith, D. R., Badtke, M. P., & Chapman, M. R. (2012). Diversity, biogenesis and function of microbial amyloids. *Trends microbial.* 20, 66-73. Doi: 10.1016/j.tim.2011.11.005
12. Yuan, A. H., Garrity, S. J., Nako, E., and Hochschild, A. (2014). Prion propagation can occur in a prokaryote and requires the ClpB chaperone. Elife, 3, e02949. DOI: 10.7554/eLife.02949
13. Lee, A. & Gilbert, R. Epidemiology of Parkinson Disease. Neurologic Clinics 34, 955-965 (2016).
14. Edwards, L., Pfeiffer, R., Quigley, E., Hofman, R. & Balluff, M. Gastrointestinal symptoms in Parkinson's disease. *Movement Disorders* 6, 151-156 (1991).
15. Agid, Y. Parkinson's disease: pathophysiology. *The Lancet* 337, 1321-1324 (1991).
16. Furukawa, Y. et al. Dystonia with motor delay in compound heterozygotes for GTP-cyclohydrolase I gene mutations. *Annals of Neurology* 44, 10-16 (1998).
17. Cookson, M. α-Synuclein and neuronal cell death. *Molecular Neurodegeneration* 4, 9 (2009).
18. Olanow, C. & Brundin, P. Parkinson's Disease and Alpha Synuclein: Is Parkinson's Disease a Prion-Like Disorder?. *Movement Disorders* 28, 31-40 (2013).
19. Volpicelli-Daley, L. et al. Exogenous α-Synuclein Fibrils Induce Lewy Body Pathology Leading to Synaptic Dysfunction and Neuron Death. *Neuron* 72, 57-71 (2011).
20. Klingelhoefer, L. & Reichmann, H. Pathogenesis of Parkinson disease—the gut—brain axis and environmental factors. *Nature Reviews Neurology* 11, 625-636 (2015).
21. Nails, M. Large-scale meta-analysis of genome-wide association data identifies six new risk loci for Parkinson's disease. *Nature Genetics* 46, 989-993 (2014).
22. Kalia, L. & Lang, A. Parkinson's disease. The Lancet 386, 896-912 (2015).
23. Ritz, B. et al. Traffic-Related Air Pollution and Parkinson's Disease in Denmark: A Case-Control Study. *Environmental Health Perspectives* 124, (2015).
24. Sampson, T. et al. Gut microbiota dysbiosis motor deficits and neuroinflammation in a model of Parkinson's Disease. *British Dental Journal* 221, 772-772 (2016).
25. Sharon, G., Sampson, T., Geschwind, D. & Mazmanian, S. The Central Nervous System and the Gut Microbiome. *Cell* 167, 915-932 (2016).
26. Jankovic, J. et al., Therapies in Parkinson's disease. *Curr. Opin. Neurol.* 25(4), 433-47 (2012).
27. Flemming, H. C. and Wingender, J. et al., *The Biofilm Matrix.* 8(9), 623-33 (2010).

TABLE 28

| Parkinson's | control | phages |
|---|---|---|
| 0 | 4.0622 | *Bacillus clarkii* bacteriophage BCJA1c |
| 0 | 3.5532 | *Bacteroides* phage B40 |
| 1.1393 | 0 | *Burkholderia* phage BcepMigl |
| 0 | 10.45304167 | *E. coli* phage T5 |
| 0 | 19.31180833 | Enterobacteria phage HK542 |
| 0 | 27.20690833 | Enterobacteria phage HK544 |
| 2.452975 | 0 | Enterobacteria phage JenP2 |
| 9.010375 | 0 | Enterobacteria phage P88 |
| 23.814225 | 0 | Enterobacteria phage ST104 DNA |
| 0 | 4.745875 | *Lactobacillus* phage KC5a |
| 0 | 5.245975 | *Lactobacillus* phage phi jlb1 |
| 0 | 11.0969 | *Lactococcus* phage 949 |
| 0 | 3.9605 | *Lactococcus* Phage ASCC476 |
| 0 | 3.300575 | *Lactococcus* Phage ASCC489 |
| 0 | 13.3778 | *Lactococcus* phage blL285 |
| 8.2135 | 0 | *Lactococcus* phage blL67 |
| 0 | 8.0831 | *Lactococcus* phage phiL47 |
| 0 | 4.699675 | *Lactococcus* phage phismq86 |
| 0 | 11.576875 | *Lactococcus* phage Tuc2009 |
| 71.184 | 0 | *Lactococcus* phage c2 |
| 0 | 7.5047 | *Lactococcus* phage ul36 k1t1 |
| 3.408875 | 0 | *Leuconostoc* phage 1 A4 |
| 0 | 12.5604 | *Mycobacterium* phage Bongo |
| 0 | 1.94795 | *Pseudomonas* phage vB_PaeS_PMG1 |
| 2.936975 | 0 | *Salmonella* phage g341c |
| 0 | 6.5828 | *Salmonella* phage SPN3UB |
| 0 | 21.63846667 | *Salmonella typhimurium* phage ST64B |
| 0 | 12.46025 | *Streptococcus* phage ALQ13 2 |
| 0 | 7.849025 | *Streptococcus* phage phiBHN167 |
| 0 | 7.846 | *Streptococcus* phage Spn1 |
| 0 | 3.37505 | *Streptococcus* phage SpSL1 |
| 0 | 9.1941 | *Streptococcus* phage TP 778L |
| 0 | 17.5454 | *Streptococcus* phage TP J34 |
| 0 | 6.07325 | *Streptococcus pyogenes* strain NIH1 |

TABLE 29

| Host Disease | Status | Control | PD |
|---|---|---|---|
| *Lactococcus lactis* phage 645 | Lytic | 0.653 | 0.317 |
| *Lactococcus lactis* phage jj50 | Lytic | 0.328 | 0.467 |
| *Lactococcus lactis* phage p272 | Lytic | 0.281 | 1.597 |
| *Lactococcus lactis* phage P475 | Lytic | 0.245 | 0.143 |
| *Lactococcus* phage 340 | Lytic | 0.175 | 0.035 |
| *Lactococcus* phage 712 | Lytic | 0.096 | 0.064 |
| *Lactococcus* phage 936 | Lytic | 0.362 | 0.402 |
| *Lactococcus* phage 949 | Lytic | 0.022 | 0 |
| *Lactococcus* Phage ASCC191 | Lytic | 0.508 | 0.310 |
| *Lactococcus* Phage ASCC273 | Lytic | 0.453 | 0.619 |
| *Lactococcus* Phage ASCC281 | Lytic | 0.037 | 0.046 |
| *Lactococcus* Phage ASCC284 | Lytic | 0.016 | 0.006 |
| *Lactococcus* Phage ASCC287 | Lytic | 0 | 0 |

TABLE 29-continued

| Host Disease | Status | Control | PD |
|---|---|---|---|
| *Lactococcus* Phage ASCC356 | Lytic | 0.050 | 0.043 |
| *Lactococcus* Phage ASCC365 | Lytic | 0 | 0 |
| *Lactococcus* Phage ASCC406 | Lytic | 0.023 | 0.050 |
| *Lactococcus* Phage ASCC465 | Lytic | 0.039 | 0.087 |
| *Lactococcus* Phage ASCC473 | Lytic | 0 | 0.018 |
| *Lactococcus* Phage ASCC476 | Lytic | 0.062 | 0 |
| *Lactococcus* Phage ASCC489 | Lytic | 0.029 | 0 |
| *Lactococcus* Phage ASCC532 | Lytic | 0.198 | 0.478 |
| *Lactococcus* Phage ASCC544 | Lytic | 0.053 | 0.041 |
| *Lactococcus* phage blBB29 | Lytic | 0.353 | 0.223 |
| *Lactococcus* phage blL67 | Lytic | 0 | 0.991 |
| *Lactococcus* phage CaseusJM1 | Lytic | 0.762 | 2.259 |
| *Lactococcus* phage CB13 | Lytic | 0.286 | 0.257 |
| *Lactococcus* phage CB14 | Lytic | 0.359 | 0.832 |
| *Lactococcus* phage CB19 | Lytic | 0.434 | 0.026 |
| *Lactococcus* phage CB20 | Lytic | 0.885 | 1.665 |
| *Lactococcus* phage fd13 | Lytic | 0.868 | 1.305 |
| *Lactococcus* phage jm2 | Lytic | 0.402 | 0.271 |
| *Lactococcus* phage jm3 | Lytic | 1.447 | 0.290 |
| *Lactococcus* phage P008 | Lytic | 0.308 | 0.445 |
| *Lactococcus* phage P162 | Lytic | 0.010 | 0 |
| *Lactococcus* phage P680 | Lytic | 4.363 | 1.884 |
| *Lactococcus* phage phi145 | Lytic | 1.979 | 4.703 |
| *Lactococcus* phage phi15 | Lytic | 0.925 | 1.293 |
| *Lactococcus* phage phi7 |  | 0.471 | 0.530 |
| *Lactococcus* phage phi93 | Lytic | 0.567 | 1.729 |
| *Lactococcus* phage phiL47 | Lytic | 0.029 | 0 |
| *Lactococcus* phage SK1833 | Lytic | 0.477 | 0.303 |
| *Lactococcus* phage SL4 | Lytic | 0.592 | 0.412 |
| *Lactococcus* phage WRP3 | Lytic | 0.016 | 0 |
| *Lactococcus* virus blL170 | Lytic | 0.498 | 0.172 |
| *Lactococcus* virus c2 | Lytic | 0 | 18.117 |
| *Lactococcus* phage blL286 | Lytic | 1.693 | 0.596 |

TABLE 30

| Parameter | Parkinson's Disease Group | Control Group | P value |
|---|---|---|---|
| Demographics | | | |
| n | 31 | 28 | |
| Age (years, mean ± SD) | 64.8 ± 9.5 | 65.6 ± 10.4 | 0.970 |
| Clinical Data | | | |
| UPDRS III (mean ± SD) | 12.6 ± 6.9 | 0 ± 0 | <0.001 |
| GIT symptoms incl. constipation (GSRS, mean ± SD) | 3.4 ± 2.9 | 2.2 ± 2.0 | 0.172 |
| Total serum bilirubin | 0.23 ± 0.03 | 0.23 ± 0.03 | 0.593 |
| Nutritional Habits | | | |
| Diet | | | |
| Omnivorous | 30 [96.8%] | 28 [100%] | |
| Vegetarian | 1 [3.2%] | 0 [0%] | |
| Probiotics | 4 [12.9%] | 1 [3.6%] | |
| Medication | | | |
| Amantadine | 26 [83.9%] | 0 [0%] | |
| Dopamine agonist | 11 [35.5%] | 0 [0%] | |
| MAO inhibitor | 28 [90.3%] | 0 [0%] | |
| L-DOPA | 0 [0%] | 0 [0%] | |
| Statin intake | 1 [3.2%] | 11 [39.3%] | |
| Metformin | 1 [3.2%] | 3 [10.7%] | |
| Acetylsalicylic acid | 2 [6.5%] | 7 [25.0%] | |
| Smoking | | | |
| No | 10 [32.3%] | 9 [32.1%] | |
| Yes | 5 [16.1%] | 4 [14.3%] | |
| Ex-smoker | 15 [48.4%] | 15 [53.6%] | |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for diagnosing a disease or determining a likelihood of a disease or predicting response to a treatment in a subject, said method comprising
   (i) performing quantitative and/or qualitative analysis of bacteriophages and/or component(s) thereof in microbiota and/or bodily fluid(s) and/or tissue(s) of the subject, wherein the quantitative and/or qualitative analysis of bacteriophages and/or component(s) thereof comprises quantitative and/or qualitative analysis of bacteriophage prion-like domains and/or quantitative and/or qualitative analysis of bacteriophage proteins comprising prion-like domains, and
   (ii) comparing the value(s) determined in step (i) to corresponding control value(s).

2. The method of claim 1, wherein the microbiota is selected from gastrointestinal (GI) microbiota, mucosal microbiota, skin microbiota, microbiota of respiratory system, microbiota of otorhinolaryngology, and microbiota of urinary tract.

3. The method of claim 1, wherein the quantitative and/or qualitative analysis of bacteriophage prion-like domains and/or of bacteriophage proteins comprising prion-like domains is performed using one or more methods selected from Western blot, ELISA, liquid biopsy, liquid chromatography and mass spectrometry (LC/MS) analysis, cultural microbiology methods, genetic methods, sequencing, proteomic methods, metagenomic methods, computational modeling and simulation methods, data analysis, microbiological methods, and prion-like protein modulation.

4. The method of claim 1, further comprising determining bacteriophage and bacterial ratio in microbiota and/or bodily fluid(s) and/or tissue(s) of the subject.

5. The method of claim 1, wherein the method further comprises inhibiting interaction of bacteria and bacteriophage(s) and/or inactivating or modifying bacteriophage(s) and/or inactivating or modifying bacteria harboring bacteriophage(s) in one or more of: microbiota of the subject, bodily fluid(s) of the subject, tissue(s) of the subject, a microbiota transplant, an organ transplant, food, drinking water, a probiotic composition, a prebiotic composition, water for washing, water for air humidification, air, or a habitat object of the subject.

* * * * *

SEQUENCE LISTING

```
<160> NUMBER OF SEQ ID NOS: 5

<210> SEQ ID NO 1
<211> LENGTH: 50
<212> TYPE: DNA
<213> ORGANISM: Artificial Sequence
<220> FEATURE:
<223> OTHER INFORMATION: Synthetic Primer for V3 and V4 region of 16S
      bacterial rRNA gene
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
<223> OTHER INFORMATION: Synthetic Primer for V3 and V4 region of 16S
      bacterial rRNA gene
```

```
<400> SEQUENCE: 2
gtctcgtggg ctcggagatg tgtataagag acaggactac hvgggtatct aatcc    55

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer 338F for V3-V4 region of 16S
      rRNA

<400> SEQUENCE: 3
actcctrcgg gaggcagcag    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer 806R for V3-V4 region of 16S
      rRNA

<400> SEQUENCE: 4
ggactaccvg ggtatctaat    20

<210> SEQ ID NO 5
<211> LENGTH: 19
<212> TYPE: DNA
<213> ORGANISM: Artificial Sequence
<220> FEATURE:
<223> OTHER INFORMATION: Synthetic Hydrolysis Probe

<400> SEQUENCE: 5
tkaccgcggc tgctggcac    19
```